United States Patent
Ioan et al.

(10) Patent No.: US 12,398,214 B2
(45) Date of Patent: Aug. 26, 2025

(54) BINDING AGENTS BINDING TO EpCAM AND CD137

(71) Applicants: Genmab A/S, Copenhagen V (DK); BioNTech SE, Mainz (DE)

(72) Inventors: Andreea Ioan, Utrecht (NL); Esther Cornelia Wilhelmina Breij, Utrecht (NL); Lars Guelen, Utrecht (NL); David P. E. Satijn, Utrecht (NL); Ugur Sahin, Mainz (DE); Alexander Muik, Mainz (DE); Kristina Nürmberger, Mainz (DE); Sina Fellermeier-Kopf, Mainz (DE); Bart-Jan De Kreuk, Utrecht (NL); Richard Hibbert, Utrecht (NL); Janine Schuurman, Utrecht (NL); Aran Frank Labrijn, Utrecht (NL)

(73) Assignees: Genmab A/S, Valby (DK); BioNTech SE, Mainz (DE)

( * ) Notice: Subject to any disclaimer, the term of this patent is extended or adjusted under 35 U.S.C. 154(b) by 0 days.

(21) Appl. No.: 18/184,120

(22) Filed: Mar. 15, 2023

(65) Prior Publication Data

US 2023/0295335 A1    Sep. 21, 2023

(30) Foreign Application Priority Data

Mar. 15, 2022    (WO) ................. PCT/EP2022/056734

(51) Int. Cl.
*C07K 16/30* (2006.01)
*C07K 16/28* (2006.01)

(52) U.S. Cl.
CPC .......... *C07K 16/30* (2013.01); *C07K 16/2878* (2013.01); *C07K 2317/31* (2013.01); *C07K 2317/92* (2013.01)

(58) Field of Classification Search
None
See application file for complete search history.

(56) References Cited

U.S. PATENT DOCUMENTS 7,648,703 B2    1/2010    Knick et al.

FOREIGN PATENT DOCUMENTS

| | | |
|---|---|---|
| AU | 2005232313 A1 | 12/2005 |
| EP | 1479696 A1 | 11/2004 |
| WO | WO/2001/048485 * | 7/2001 |
| WO | 2011131746 A2 | 10/2011 |
| WO | 2011147986 A1 | 12/2011 |
| WO | 2013060867 A2 | 5/2013 |
| WO | 2017182672 A1 | 10/2017 |
| WO | WO/2018/011421 * | 1/2018 |
| WO | 2019025545 A1 | 2/2019 |
| WO | 2022002038 A1 | 1/2022 |
| WO | WO 2022189667 | 9/2022 |

OTHER PUBLICATIONS

Wilkinson et al. (PLoS One 15(12):e0260954 (2021) (Year: 2021).*
Christian Klein et al: "Progress in overcoming the chain association issue in bispecif ic heterodimeric IgG antibodies", MABS, vol. 4, No. 6, Nov. 1, 2012 (Nov. 1, 2012), pp. 653-663.
Steffen Dickopf et al: "Format and geometries matter: Structure-based design defines the functionality of bispecific antibodies", Computational and Structural Biotechnology Journal, vol. 18, May 14, 2020 (May 14, 2020), pp. 1221-1227.
International Search Report and Written Opinion for International Application No. PCT/EP2022/056734, mailed Oct. 24, 2022, 18 pages.
International Search Report and Written Opinion for International Application No. PCT/EP2023/056513, mailed Aug. 3, 2023, 25 pages.
Gramer et al., Production of stable bispecific IgG1 y controlled Fab-arm exchange: Scalability from bench to large-scale manufacturing by application of standard approaches. mAbs, 2013, 5(6), pp. 962-973.
Labrijn et al., Efficient generation of stable bispecific IgG1 by controlled Fab-arm exchange. PNAS, 2013, 110(13), pp. 5145-5150.
Labrijn et al., Efficient Generation of Bispecific Murine Antibodies for Pre-Clinical Investigations in Syngeneic Rodent Models. Scientific Reports, 2017, 7: 2476.
International Search Report and Written Opinion of the International Searching Authority for PCT/EP2022/056734, dated Oct. 14, 2022 (13 pages).

* cited by examiner

*Primary Examiner* — Meera Natarajan
(74) *Attorney, Agent, or Firm* — Neal, Gerber & Eisenberg LLP

(57) ABSTRACT

The present invention provides a binding agent that binds to EpCAM and to CD137 which is useful to treat or prevent a tumor or cancer, or to prevent progression of a tumor or cancer.

24 Claims, 32 Drawing Sheets
Specification includes a Sequence Listing.

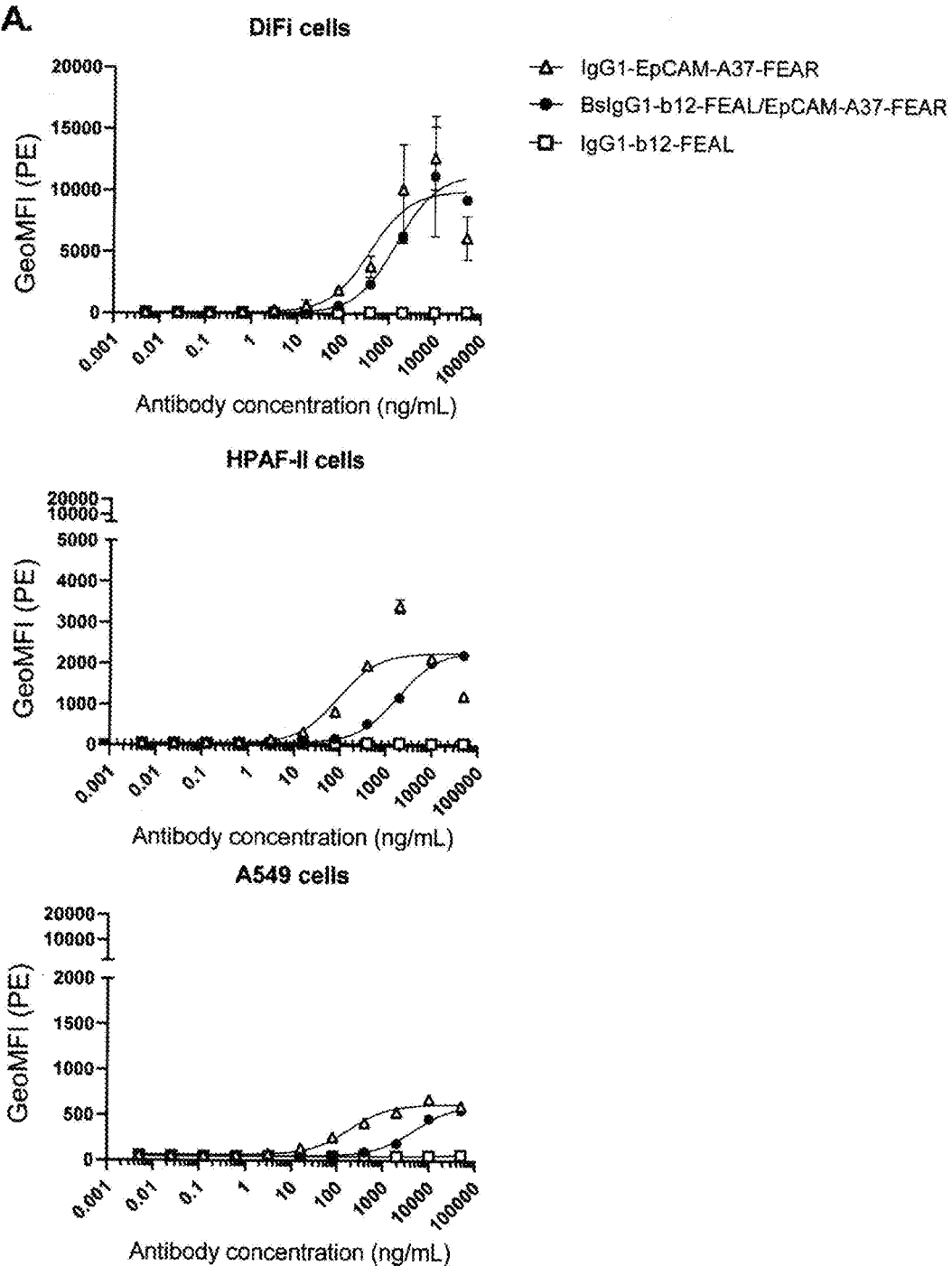

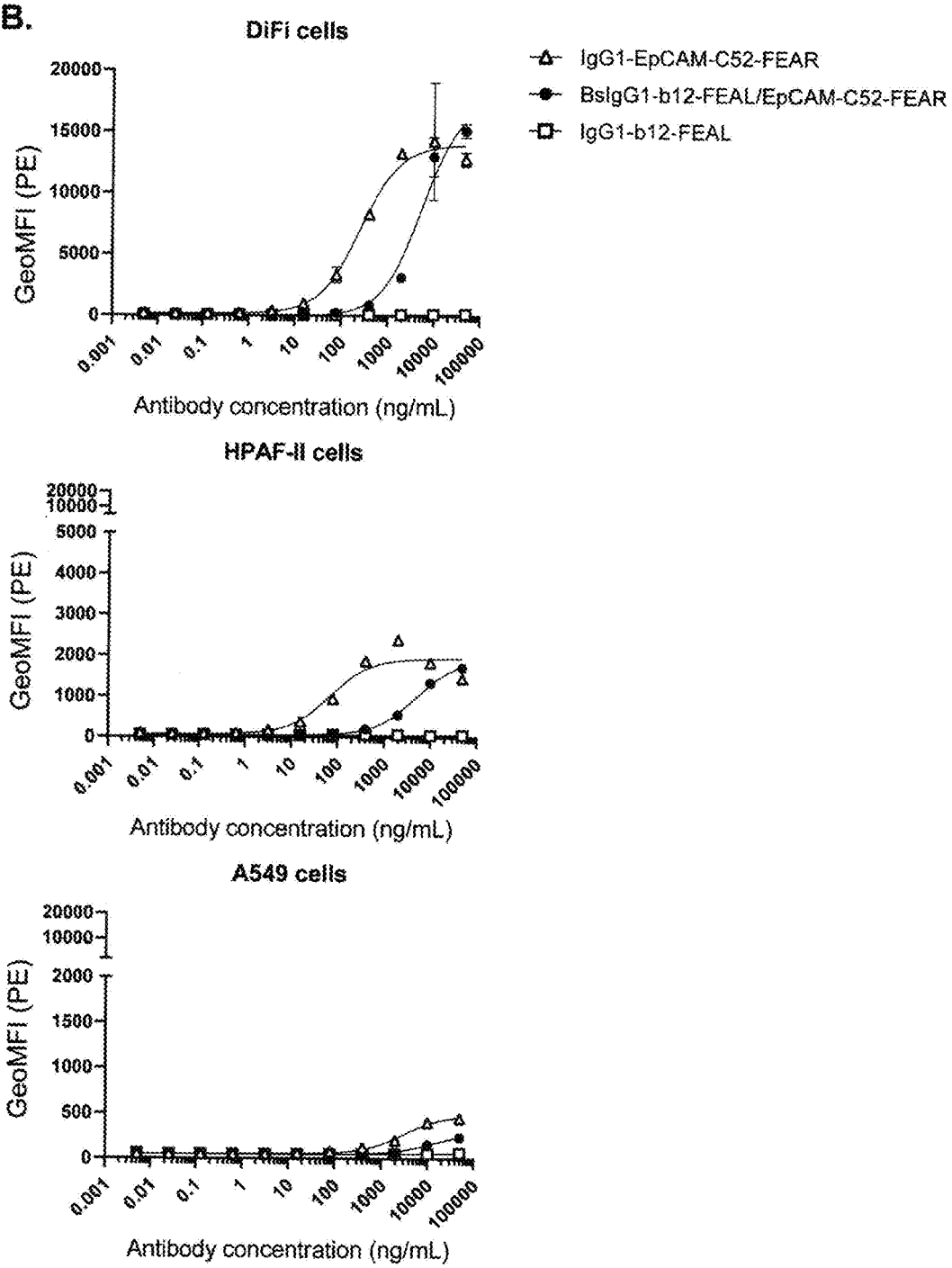

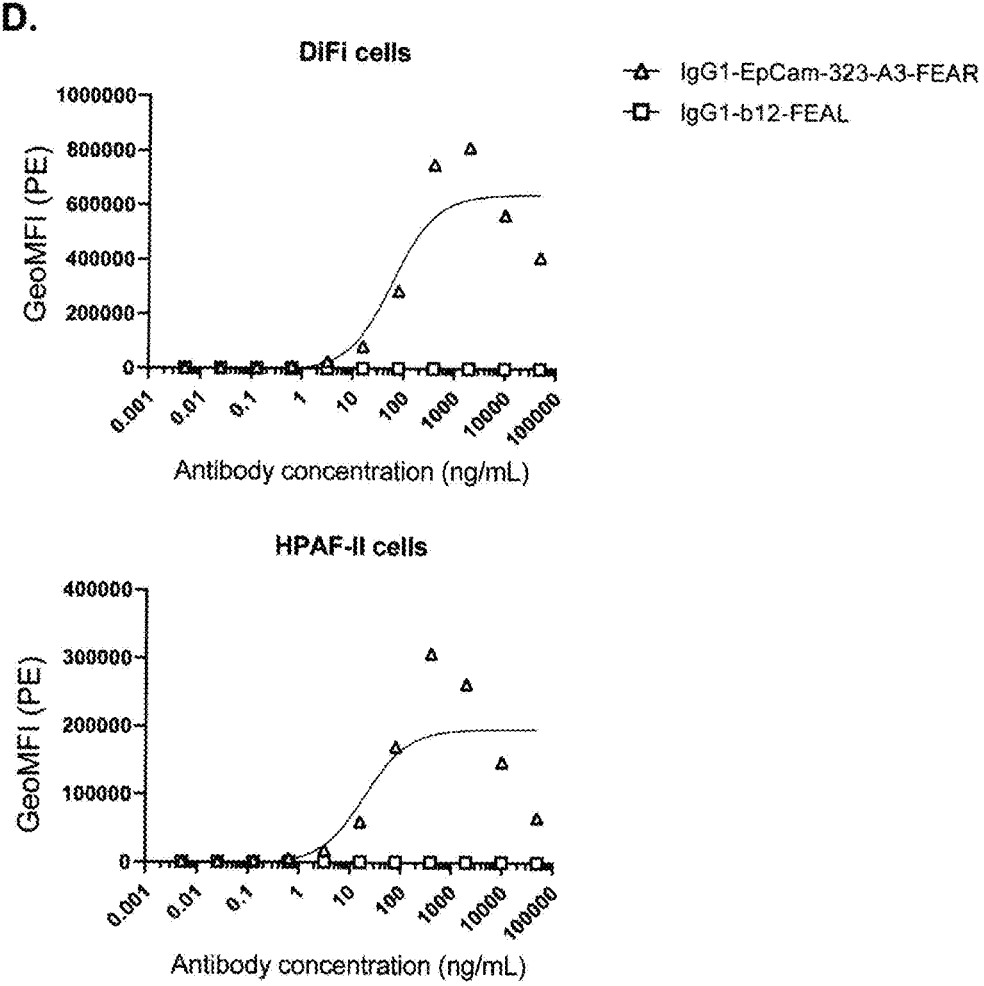

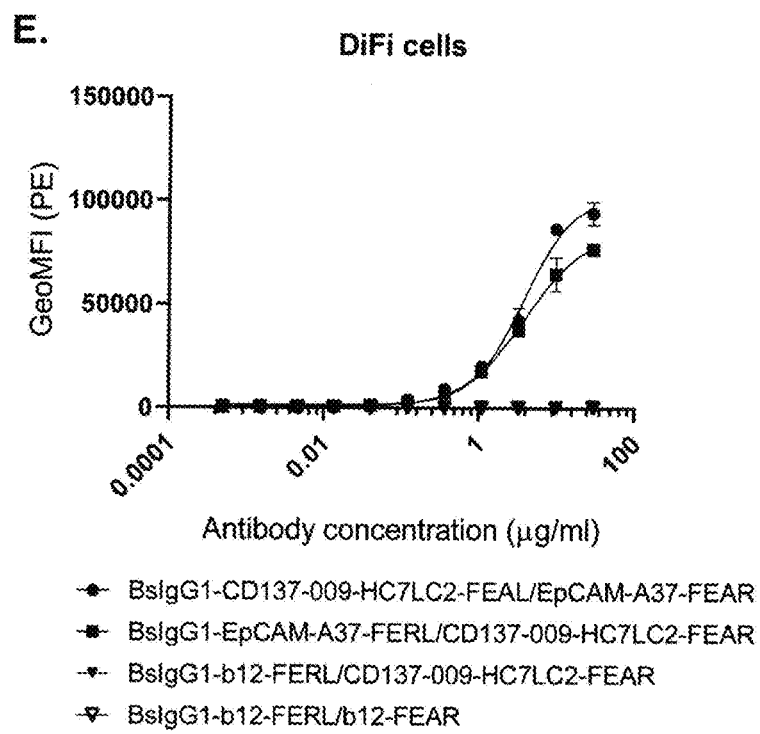

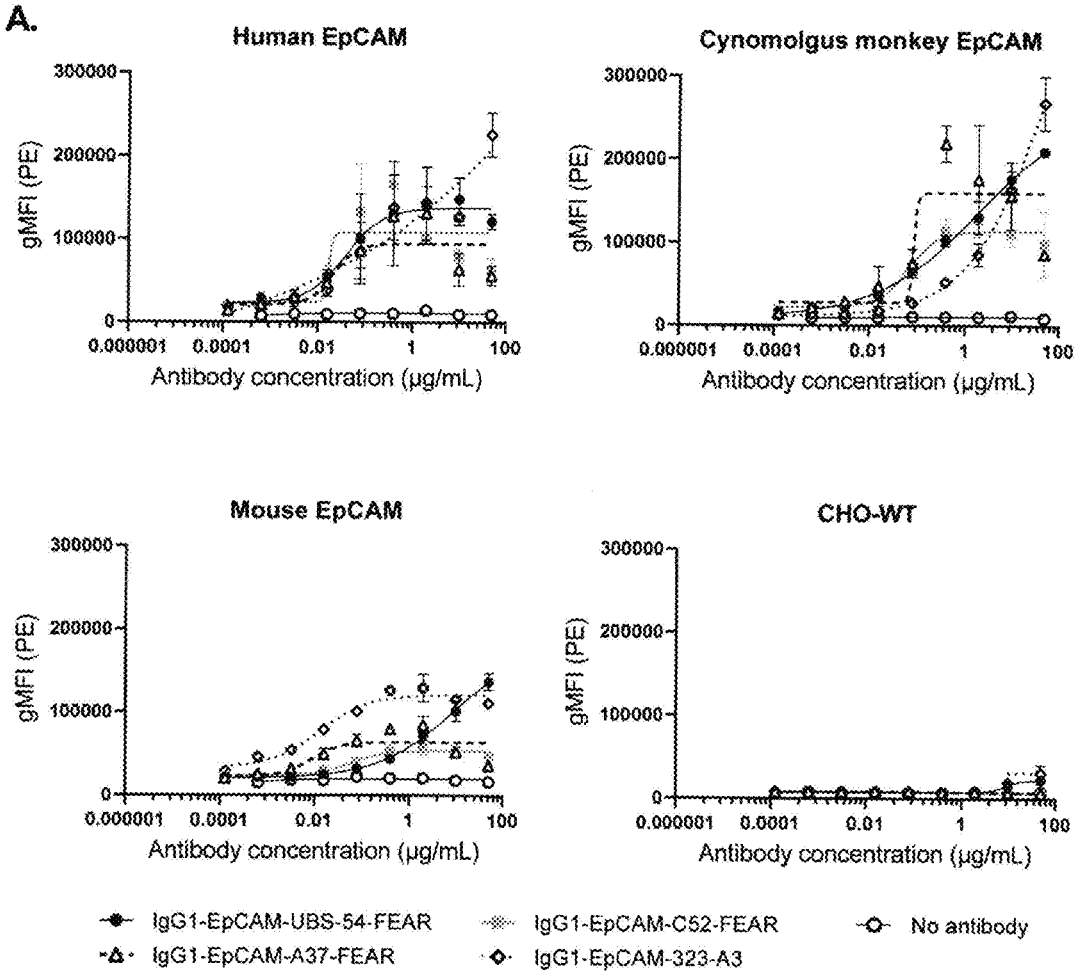

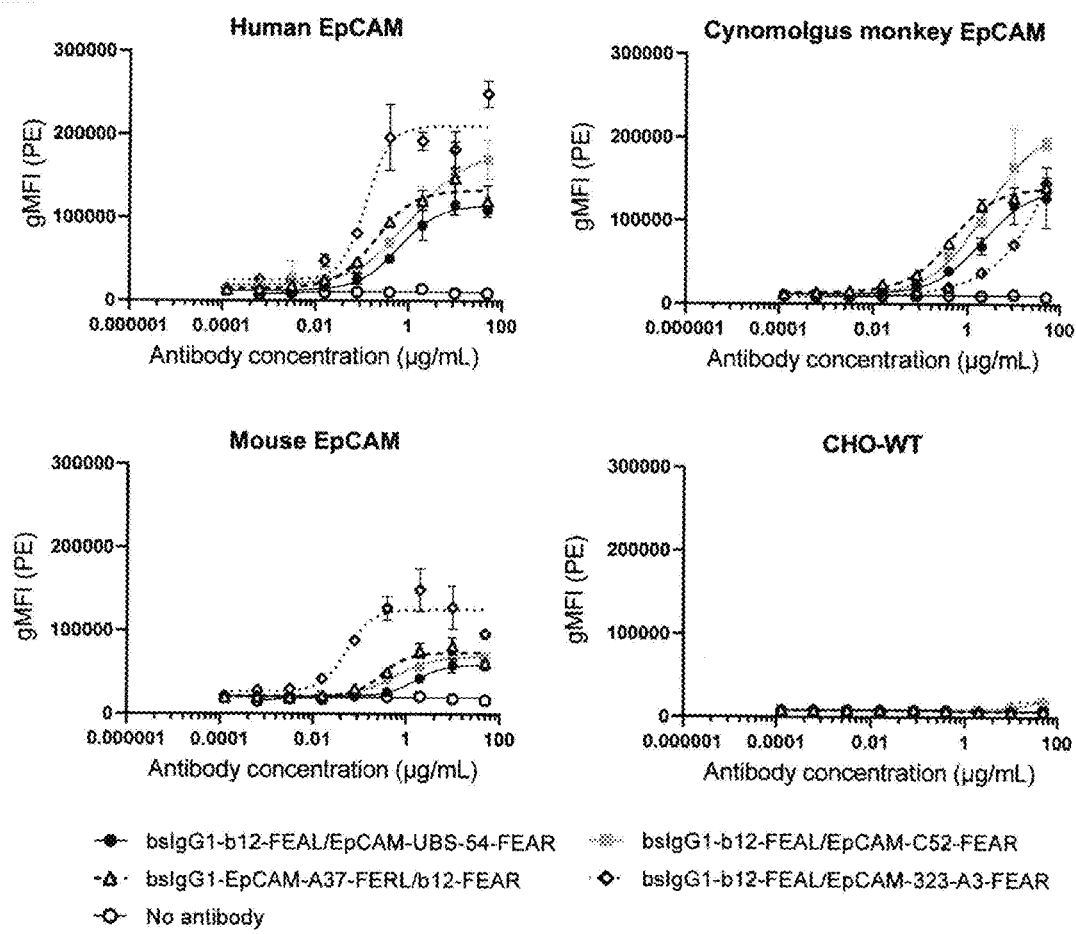

Fig. 5
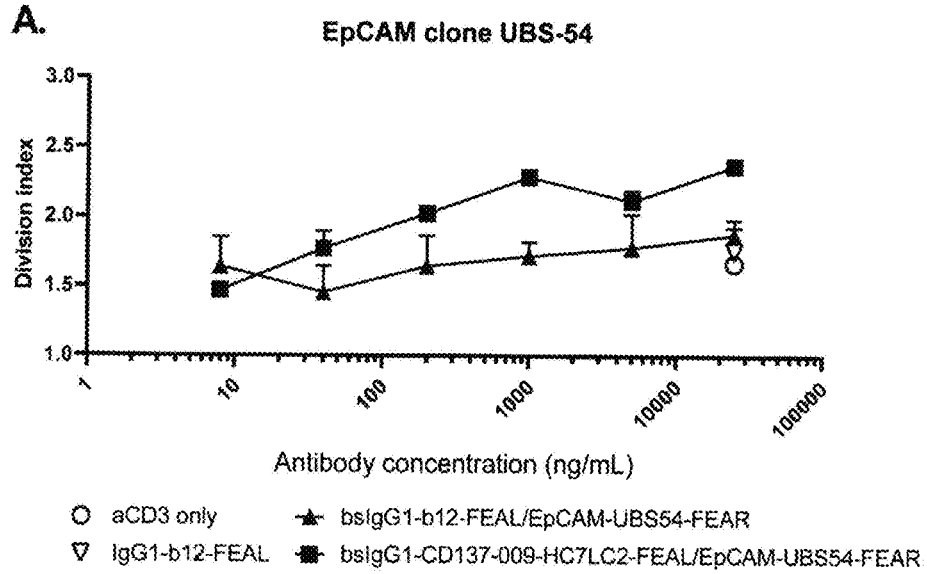
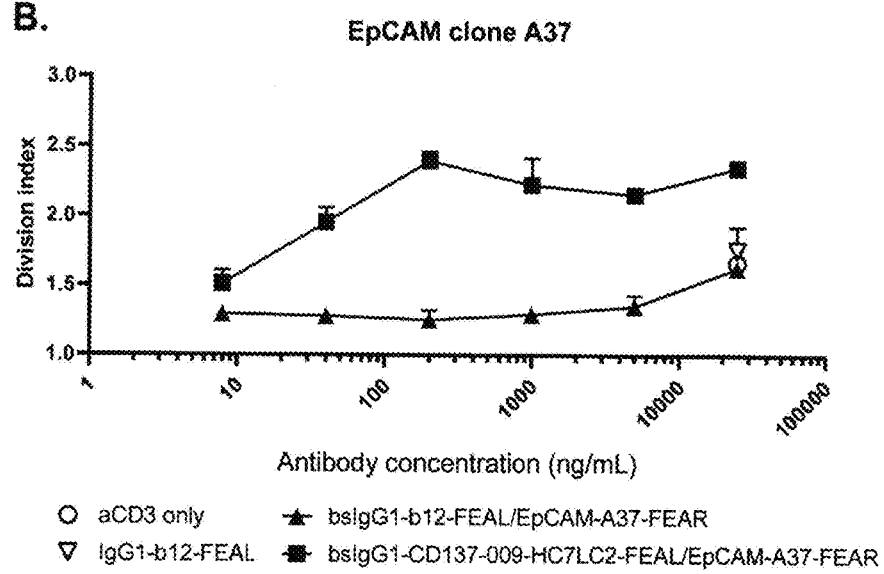

Fig. 5
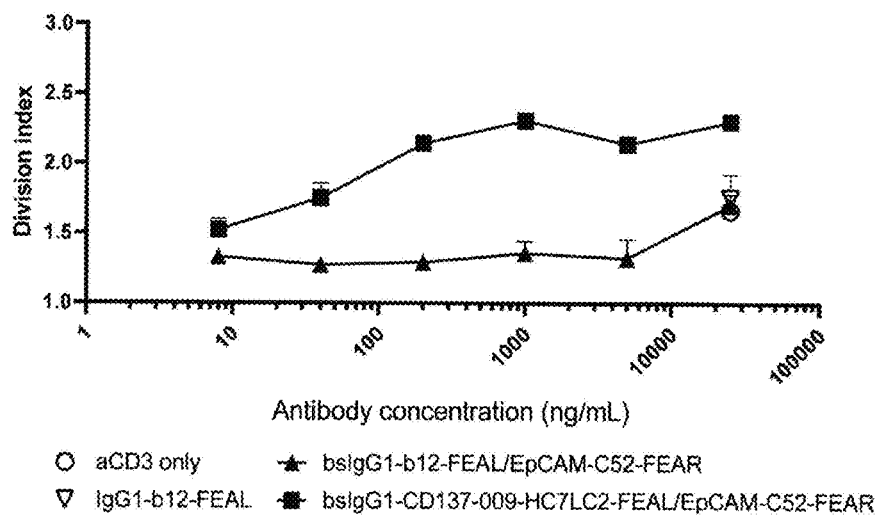
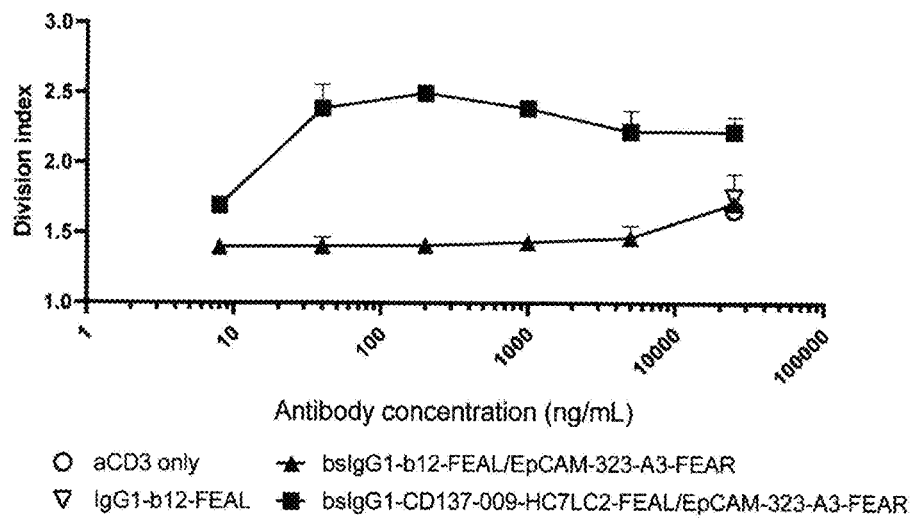

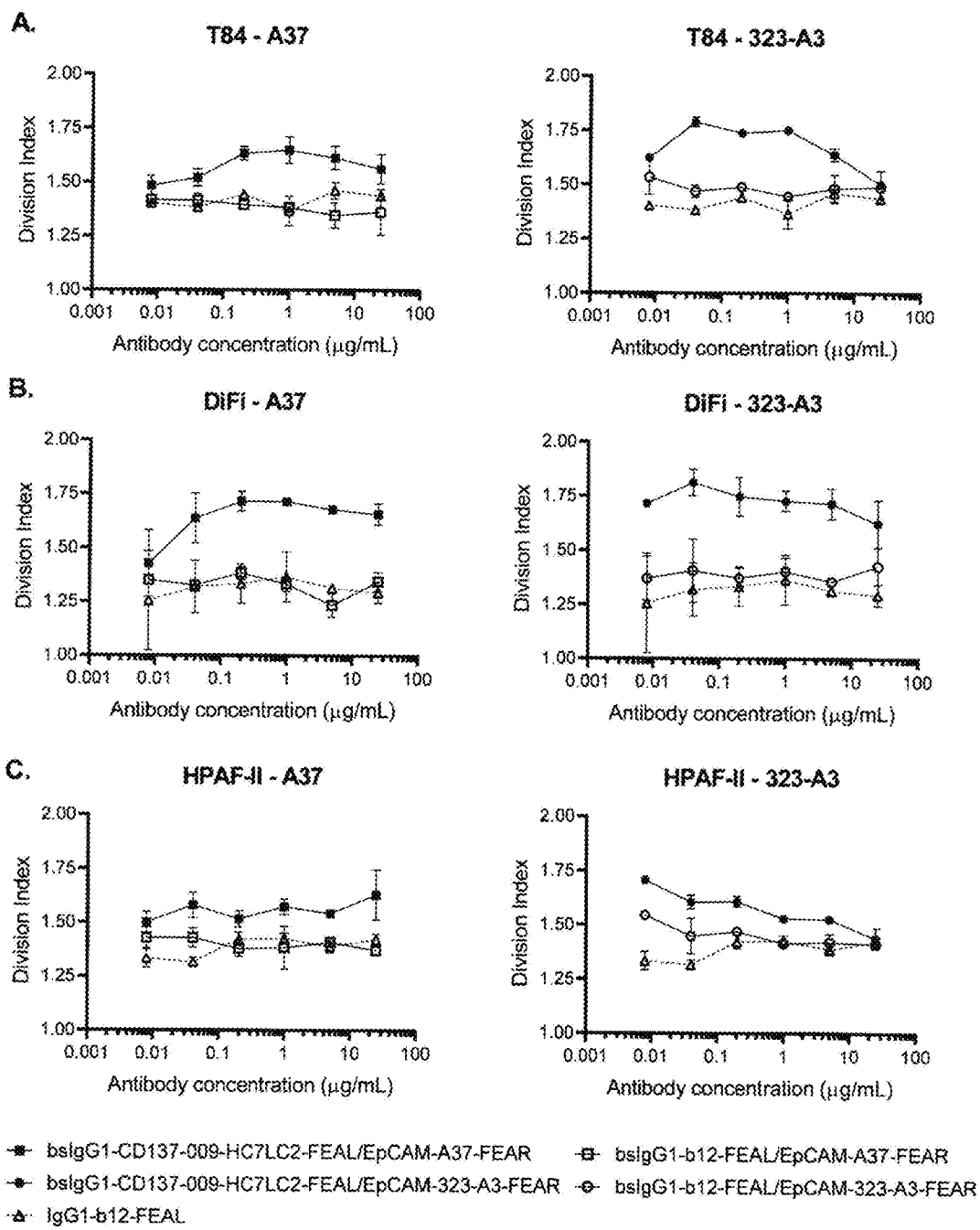

Fig. 10
A
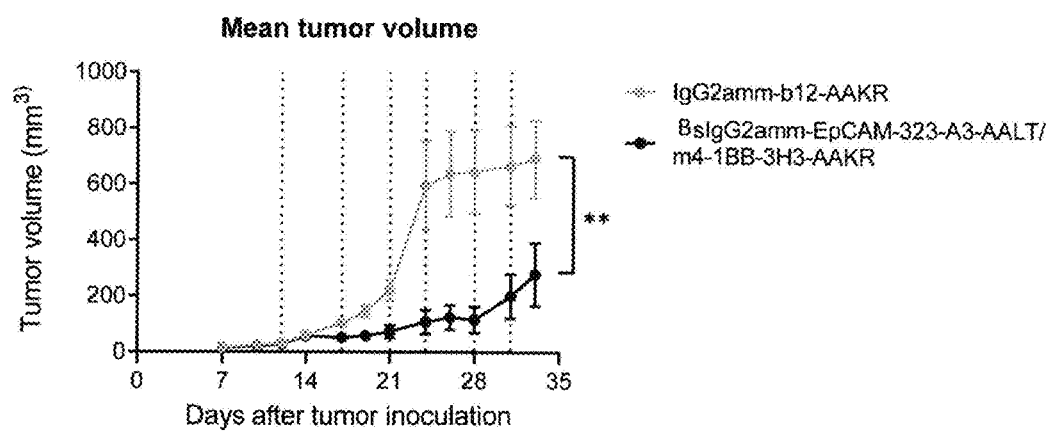
B
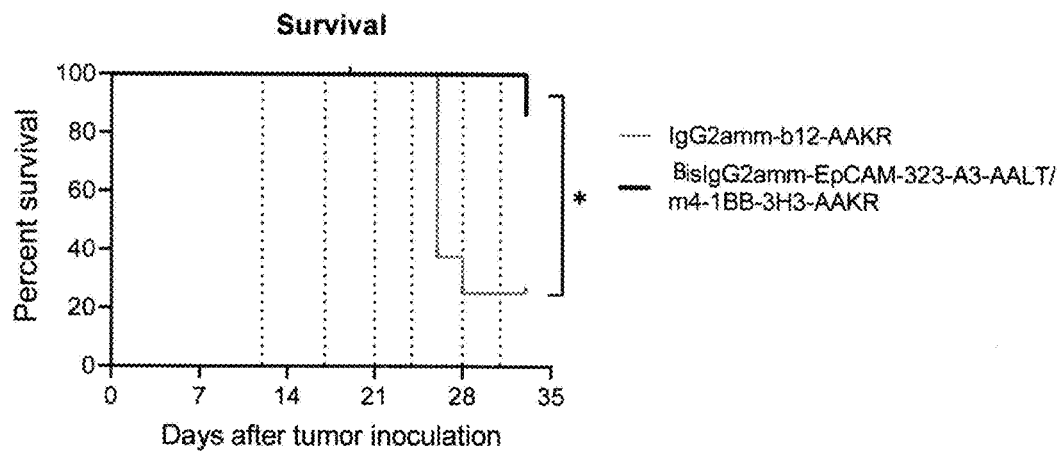

FIG. 17
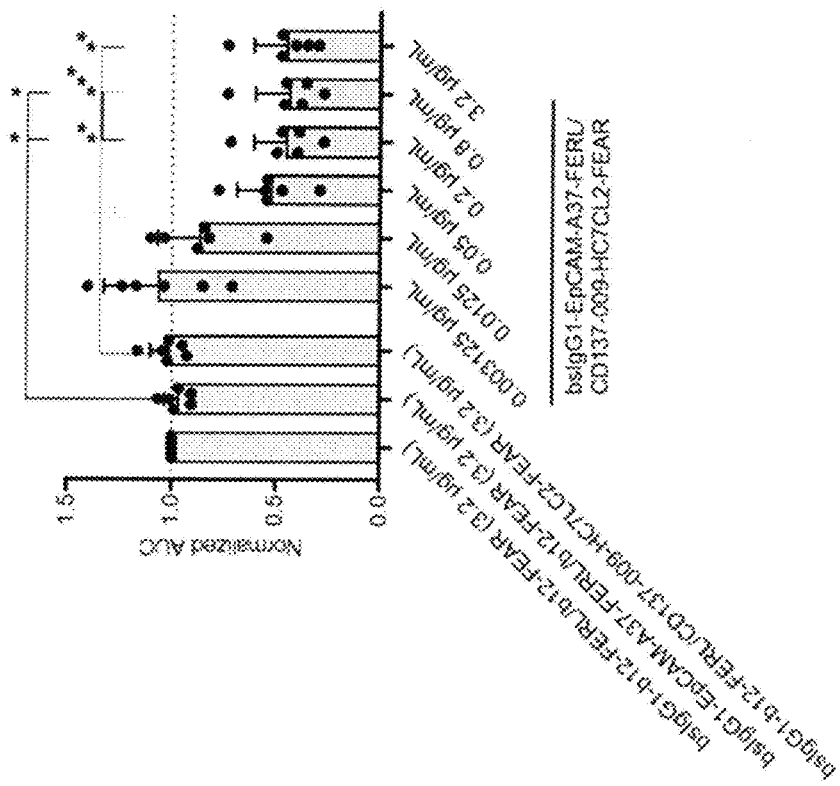
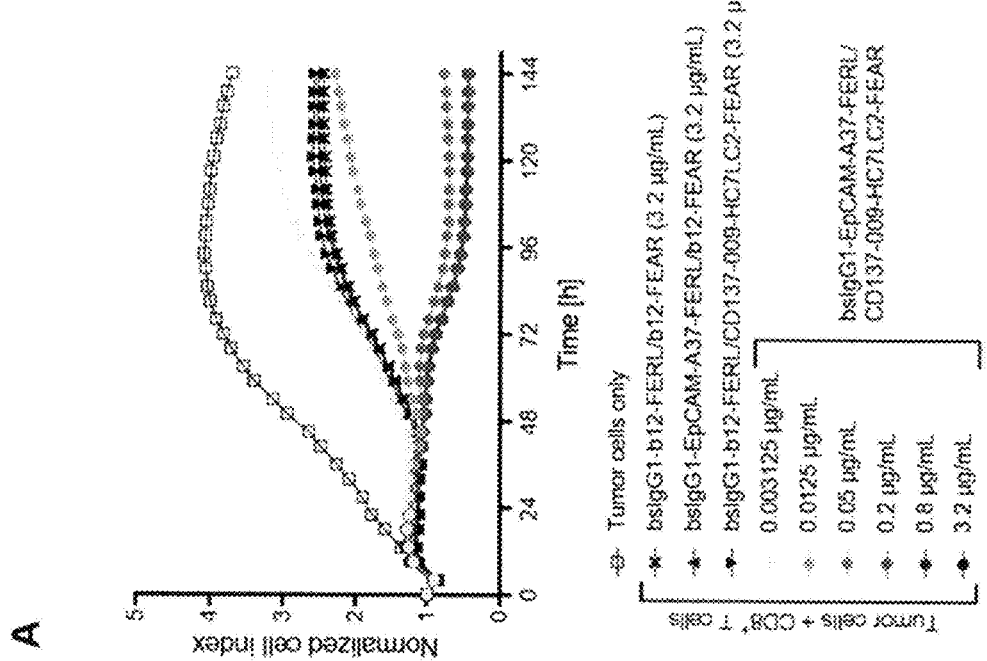

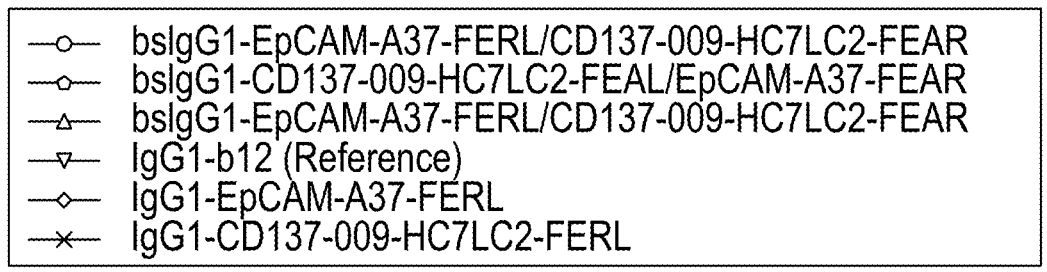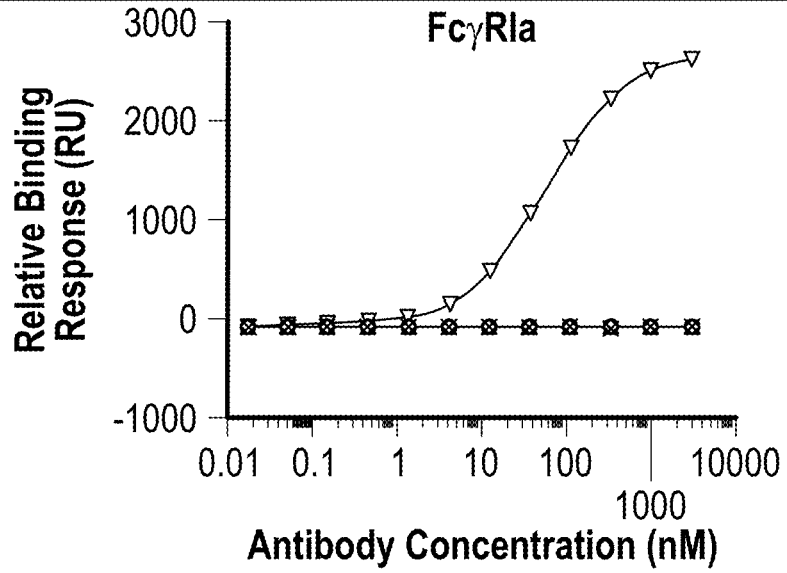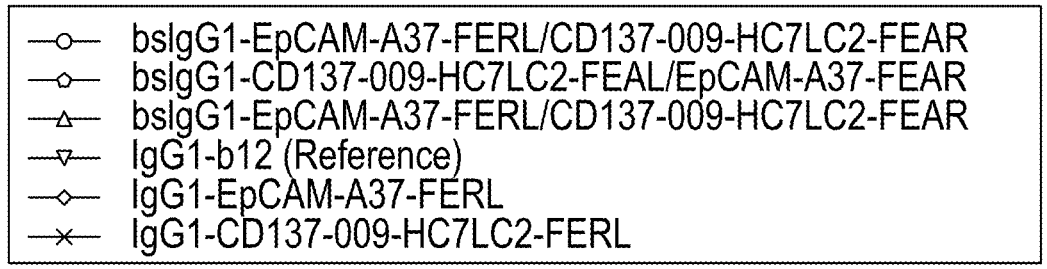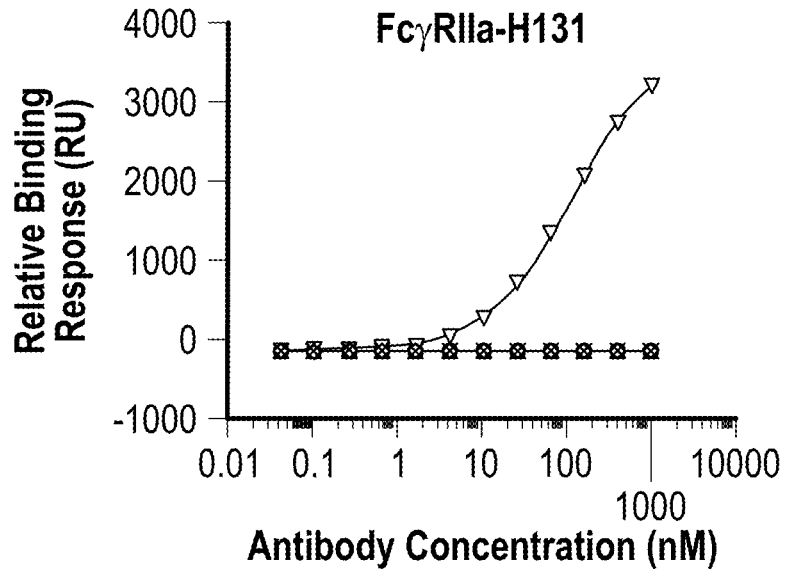
FIG. 18

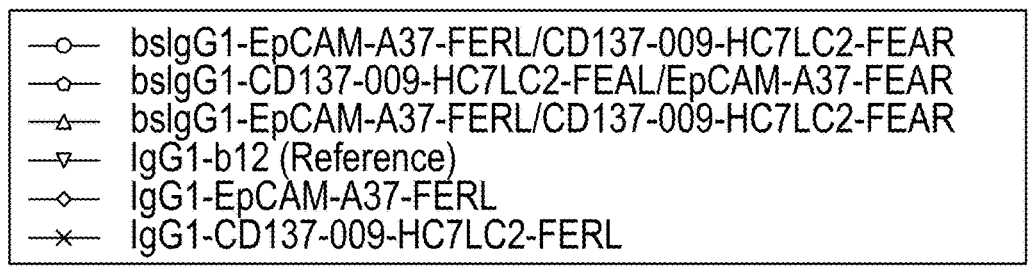
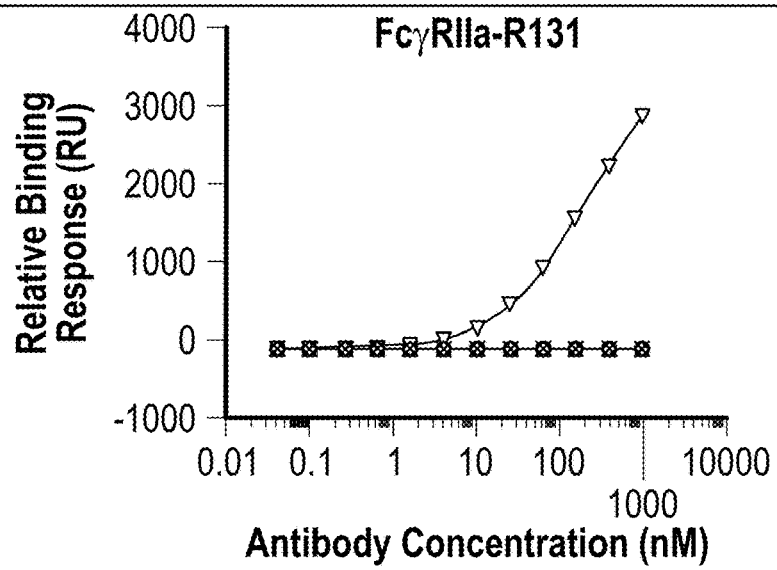
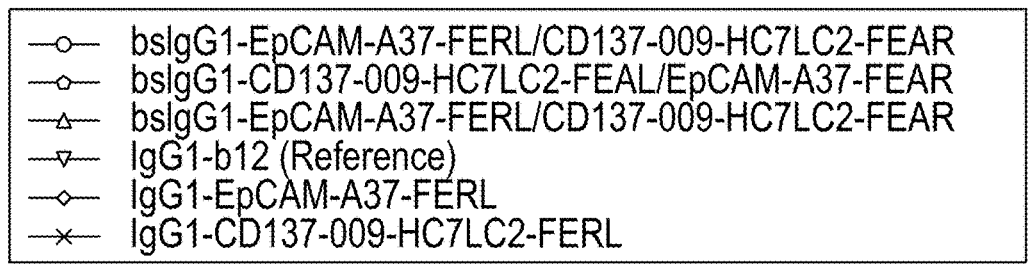
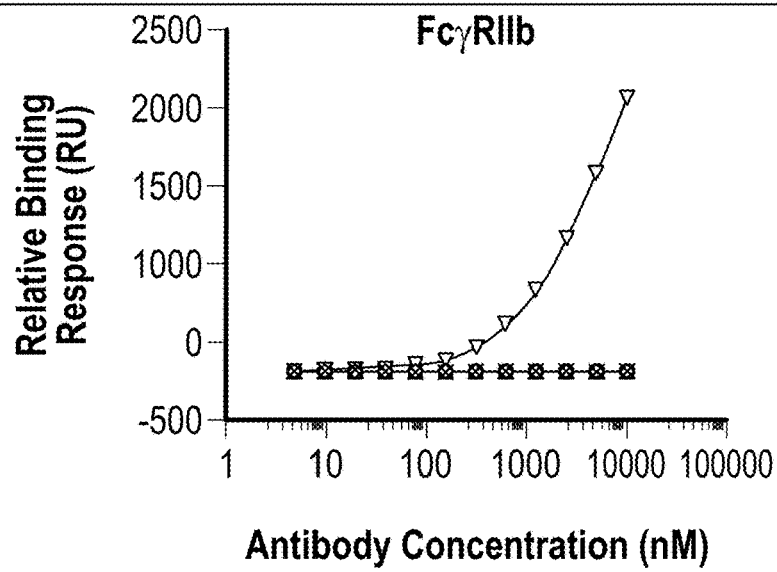
FIG. 18
(Continued)

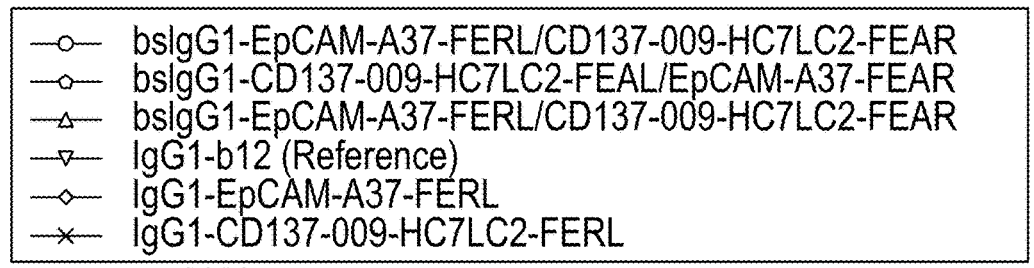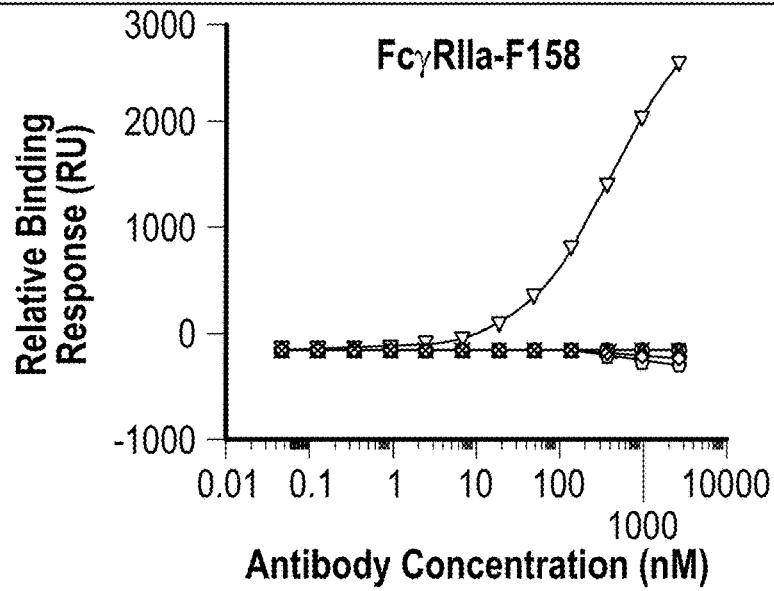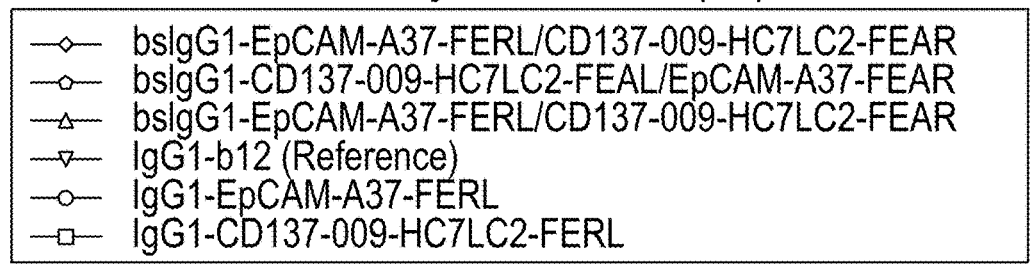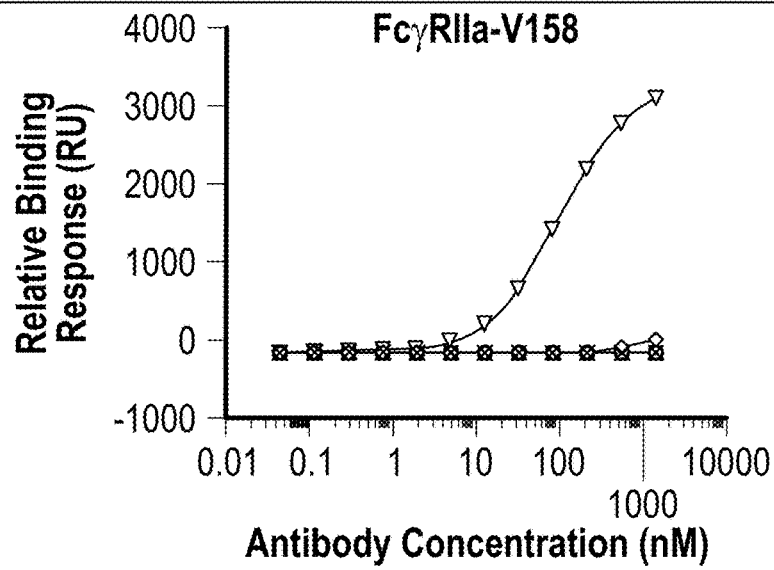
FIG. 18 (Continued)

BINDING AGENTS BINDING TO EpCAM AND CD137

CROSS-REFERENCE TO RELATED APPLICATIONS

This application claims priority to International Application Number PCT/EP2022/056734, which was filed on Mar. 15, 2022. The contents of the aforementioned application are incorporated herein by reference in their entireties.

SEQUENCE LISTING

The computer-readable Sequence Listing submitted on Mar. 15, 2023 and identified as follows: 121,625 bytes ST.26 XML document file named "028320-8051 Sequence Listing.xml," created Mar. 14, 2023, is incorporated herein by reference in its entirety.

TECHNICAL FIELD

The present invention relates to binding agents that bind to EpCAM and to CD137. Such binding agents are useful to treat or prevent a tumor or cancer.

BACKGROUND

Epithelial cell adhesion molecule (EpCAM) is a transmembrane glycoprotein mediating $Ca^{2+}$-independent homotypic cell-cell adhesion in epithelia. EpCAM is also involved in cell signaling, migration, proliferation, and differentiation. Additionally, EpCAM has oncogenic potential via its capacity to upregulate c-Myc, E-FABP, and cyclins A & E. EpCAM can be used as diagnostic marker for various cancers. Also, EpCAM appears to play a role in tumorigenesis and metastasis of carcinomas, and, thus, it can also act as a potential prognostic marker and as a potential target for immunotherapeutic strategies.

CD137 (4-1BB) is a member of the TNFR family and is a co-stimulatory molecule on CD8+ and CD4+ T cells, regulatory T cells (Tregs), Natural Killer (T) cells (NK[T] cells), B cells and neutrophils. On T cells, CD137 is not constitutively expressed, but induced upon T-cell receptor (TCR) activation (for example, on tumor infiltrating lymphocytes [TILs; Gros et al., J. Clin Invest 2014; 124(5): 2246-59]). Stimulation via its natural ligand 4-1BBL or agonist antibodies leads to signaling using TRAF-2 and TRAF-1 as adaptors. Early signaling by CD137 involves K63 poly-ubiquitination reactions that ultimately result in activation of the nuclear factor (NF)-κB and mitogen-activated protein (MAP)-kinase pathways. Signaling leads to increased T-cell co-stimulation, proliferation, cytokine production, maturation and prolonged CD8+ T-cell survival. Agonistic antibodies against CD137 have been shown to promote anti-tumor control by T cells in various pre-clinical models (Murillo et al., Clin Cancer Res 2008; 14(21):6895-906). Antibodies stimulating CD137 can induce survival and proliferation of T cells, thereby enhancing the anti-tumor immune response. Antibodies stimulating CD137 have been disclosed in the prior art, and include urelumab, a human IgG4 antibody (AU 2004279877) and utomilumab, a human IgG2 antibody (Fisher et al., 2012, Cancer Immunol. Immunother. 61: 1721-1733). There is a need for agents and methods to prevent or treat a tumor or cancer.

SUMMARY

In a first aspect, the present disclosure provides a binding agent comprising a first antigen-binding region binding to EpCAM and a second antigen-binding region binding to CD137.

In some embodiments, the EpCAM is human EpCAM. In some embodiments, the CD137 is human CD137. In some embodiments, human EpCAM comprises the sequence set forth in SEQ ID NO: 59. In some embodiments, human CD137 comprises the sequence set forth in SEQ ID NO: 62.

In some embodiments, said first antigen-binding region binding to EpCAM binds to EpCAM expressed on tumor cells.

In some embodiments, said first antigen-binding region binding to EpCAM comprises a heavy chain variable region (VH) comprising a HCDR3 sequence comprising the sequence as set forth in SEQ ID NO: 4. In some embodiments, said first antigen-binding region binding to EpCAM comprises a heavy chain variable region (VH) comprising a HCDR2 sequence comprising the sequence as set forth in SEQ ID NO: 3. In some embodiments, said first antigen-binding region binding to EpCAM comprises a heavy chain variable region (VH) comprising a HCDR1 sequence comprising the sequence as set forth in SEQ ID NO: 2. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 2, 3, and 4, respectively. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 64, 65, and 66, respectively. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 74, 3, and 66, respectively.

In some embodiments, said first antigen-binding region binding to EpCAM comprises a light chain variable region (VL) comprising a LCDR3 sequence comprising the sequence as set forth in SEQ ID NO: 8. In some embodiments, said first antigen-binding region binding to EpCAM comprises a light chain variable region (VL) comprising a LCDR2 sequence comprising the sequence as set forth in SEQ ID NO: 7. In some embodiments, said first antigen-binding region binding to EpCAM comprises a light chain variable region (VL) comprising a LCDR1 sequence comprising the sequence as set forth in SEQ ID NO: 6. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 6, 7, and 8, respectively. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 67, 68, and 8, respectively.

In some embodiments, said first antigen-binding region binding to EpCAM comprises a heavy chain variable region (VH) comprising a HCDR3 sequence and a light chain variable region (VL) comprising a LCDR3 sequence, wherein the HCDR3 sequence comprises the sequence as set forth in SEQ ID NO: 4, and the LCDR3 sequence comprises the sequence as set forth in SEQ ID NO: 8.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 6, 7, and 8, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 64, 65, and 66, respectively, and the LCDR1, LCDR2, and LCDR3 sequences comprise the sequences as set forth in SEQ ID NO: 67, 68, and 8, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 74, 3, and 66, respectively, and the LCDR1, LCDR2, and LCDR3 sequences comprise the sequences as set forth in SEQ ID NO: 6, 7, and 8, respectively.

In some embodiments, said first antigen-binding region binding to EpCAM comprises a heavy chain variable region (VH) comprising the HCDR1, HCDR2, and HCDR3 sequences of SEQ ID NO: 1 and/or a light chain variable region (VL) comprising the LCDR1, LCDR2, and LCDR3 sequences of SEQ ID NO: 5.

In some embodiments, said first antigen-binding region binding to EpCAM comprises a heavy chain variable region (VH) comprising a sequence having at least 80%, at least 85%, at least 90%, at least 95%, at least 97%, at least 99%, or 100% identity to the sequence as set forth in SEQ ID NO: 1.

In some embodiments, said first antigen-binding region binding to EpCAM comprises a heavy chain variable region (VH) comprising the sequence as set forth in SEQ ID NO: 1.

In some embodiments, said first antigen-binding region binding to EpCAM comprises a light chain variable region (VL) comprising a sequence having at least 80%, at least 85%, at least 90%, at least 95%, at least 97%, at least 99%, or 100% identity to the sequence as set forth in SEQ ID NO: 5.

In some embodiments, said first antigen-binding region binding to EpCAM comprises a light chain variable region (VL) comprising the sequence as set forth in SEQ ID NO: 5.

In some embodiments, said first antigen-binding region binding to EpCAM comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 1 and the VL comprises a sequence having at least 80%, at least 85%, at least 90%, at least 95%, at least 97%, at least 99%, or 100% identity to the sequence as set forth in SEQ ID NO: 5. In some embodiments, said first antigen-binding region binding to EpCAM comprises a heavy chain variable region (VH) and a light chain variable region (VL), wherein the VH comprises a sequence having at least at least 80% identity to the sequence as set forth in SEQ ID NO: 1 and the VL comprises a sequence having at least 80% identity to the sequence as set forth in SEQ ID NO: 5. In some embodiments, said first antigen-binding region binding to EpCAM comprises a heavy chain variable region (VH) and a light chain variable region (VL), wherein the VH comprises a sequence having at least at least 90% identity to the sequence as set forth in SEQ ID NO: 1 and the VL comprises a sequence having at least 90% identity to the sequence as set forth in SEQ ID NO: 5. In some embodiments, said first antigen-binding region binding to EpCAM comprises a heavy chain variable region (VH) and a light chain variable region (VL), wherein the VH comprises a sequence having at least at least 95% identity to the sequence as set forth in SEQ ID NO: 1 and the VL comprises a sequence having at least 95% identity to the sequence as set forth in SEQ ID NO: 5.

In some embodiments, said first antigen-binding region binding to EpCAM comprises a heavy chain variable region (VH) and a light chain variable region (VL), wherein the VH comprises the sequence as set forth in SEQ ID NO: 1 and the VL comprises the sequence as set forth in SEQ ID NO: 5.

In some embodiments, said first antigen-binding region binding to EpCAM comprises heavy and light chain variable regions of an antibody which competes for EpCAM binding with and/or has the specificity for EpCAM of an antibody comprising a heavy chain variable region (VH) and/or a light chain variable region (VL) as set forth above.

In some embodiments, said second antigen-binding region binding to CD137 comprises a heavy chain variable region (VH) comprising a HCDR3 sequence comprising the sequence as set forth in SEQ ID NO: 14. In some embodiments, said second antigen-binding region binding to CD137 comprises a heavy chain variable region (VH) comprising a HCDR2 sequence comprising the sequence as set forth in SEQ ID NO: 13. In some embodiments, said second antigen-binding region binding to CD137 comprises a heavy chain variable region (VH) comprising a HCDR1 sequence comprising the sequence as set forth in SEQ ID NO: 12. In some embodiments, said second antigen-binding region binding to CD137 comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 12, 13, and 14, respectively. In some embodiments, said second antigen-binding region binding to CD137 comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 69, 70, and 71, respectively. In some embodiments, said second antigen-binding region binding to CD137 comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 75, 13, and 71, respectively.

In some embodiments, said second antigen-binding region binding to CD137 comprises a light chain variable region (VL) comprising a LCDR3 sequence comprising the sequence as set forth in SEQ ID NO: 18. In some embodiments, said second antigen-binding region binding to CD137 comprises a light chain variable region (VL) comprising a LCDR2 sequence comprising the sequence as set forth in SEQ ID NO: 17. In some embodiments, said second antigen-binding region binding to CD137 comprises a light chain variable region (VL) comprising a LCDR1 sequence comprising the sequence as set forth in SEQ ID NO: 16. In some embodiments, said second antigen-binding region binding to CD137 comprises a light chain variable region (VL) comprising LCDR1, LCDR2, and LCDR3 sequences, wherein the LCDR1, LCDR2, and LCDR3 sequences comprise the sequences as set forth in SEQ ID NO: 16, 17 and 18, respectively. In some embodiments, said second antigen-binding region binding to CD137 comprises a light chain variable region (VL) comprising LCDR1, LCDR2, and LCDR3 sequences, wherein the LCDR1, LCDR2, and LCDR3 sequences comprise the sequences as set forth in SEQ ID NO: 72, 73 and 18, respectively.

In some embodiments, said second antigen-binding region binding to CD137 comprises a heavy chain variable region (VH) comprising a HCDR3 sequence and a light chain variable region (VL) comprising a LCDR3 sequence, wherein the HCDR3 sequence comprises the sequence as set forth in SEQ ID NO: 14, and the LCDR3 sequence comprises the sequence as set forth in SEQ ID NO: 18.

In some embodiments, said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments, said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 69, 70, and 71, respectively, and the LCDR1, LCDR2, and LCDR3 sequences comprises the sequences as set forth in SEQ ID NO: 72, 73 and 18, respectively.

In some embodiments, said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 75, 13, and 71, respectively, and the LCDR1, LCDR2, and LCDR3 sequences comprises the sequences as set forth in SEQ ID NO: 16, 17 and 18, respectively.

In some embodiments, said second antigen-binding region binding to CD137 comprises a heavy chain variable region (VH) comprising the HCDR1, HCDR2, and HCDR3 sequences of SEQ ID NO: 11 and/or a light chain variable region (VL) comprising the LCDR1, LCDR2, and LCDR3 sequences of SEQ ID NO: 15.

In some embodiments, said second antigen-binding region binding to CD137 comprises a heavy chain variable region (VH) comprising a sequence having at least 80%, at least 85%, at least 90%, at least 95%, at least 97%, at least 99%, or 100% identity to the sequence as set forth in SEQ ID NO: 11.

In some embodiments, said second antigen-binding region binding to CD137 comprises a heavy chain variable region (VH) comprising the sequence as set forth in SEQ ID NO: 11.

In some embodiments, said second antigen-binding region binding to CD137 comprises a light chain variable region (VL) comprising a sequence having at least 80%, at least 85%, at least 90%, at least 95%, at least 97%, at least 99%, or 100% identity to the sequence as set forth in SEQ ID NO: 15.

In some embodiments, said second antigen-binding region binding to CD137 comprises a light chain variable region (VL) comprising the sequence as set forth in SEQ ID NO: 15.

In some embodiments, said second antigen-binding region binding to CD137 comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 11 and the VL comprises a sequence having at least 80%, at least 85%, at least 90%, at least 95%, at least 97%, at least 99%, or 100% identity to the sequence as set forth in SEQ ID NO: 15. In some embodiments, said second antigen-binding region binding to CD137 comprises a heavy chain variable region (VH) and a light chain variable region (VL), wherein the VH comprises a sequence having at least at least 80% identity to the sequence as set forth in SEQ ID NO: 11 and the VL comprises a sequence having at least 80% identity to the sequence as set forth in SEQ ID NO: 15. In some embodiments, said second antigen-binding region binding to CD137 comprises a heavy chain variable region (VH) and a light chain variable region (VL), wherein the VH comprises a sequence having at least at least 90% identity to the sequence as set forth in SEQ ID NO: 11 and the VL comprises a sequence having at least 90% identity to the sequence as set forth in SEQ ID NO: 15. In some embodiments, said second antigen-binding region binding to CD137 comprises a heavy chain variable region (VH) and a light chain variable region (VL), wherein the VH comprises a sequence having at least at least 95% identity to the sequence as set forth in SEQ ID NO: 11 and the VL comprises a sequence having at least 95% identity to the sequence as set forth in SEQ ID NO: 15.

In some embodiments, said second antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

In some embodiments, said second antigen-binding region binding to CD137 comprises heavy and light chain variable regions of an antibody which competes for CD137 binding with and/or has the specificity for CD137 of an antibody comprising a heavy chain variable region and/or a light chain variable region as set forth above.

In some embodiments,
a) said first antigen-binding region binding to EpCAM comprises a heavy chain variable region (VH) comprising a HCDR3 sequence as set forth in SEQ ID NO: 4, and
b) said second antigen-binding region binding to CD137 comprises a heavy chain variable region (VH) comprising a HCDR3 sequence as set forth in SEQ ID NO: 14.

In some embodiments,
a) said first antigen-binding region binding to EpCAM comprises a light chain variable region (VL) comprising a LCDR3 sequence as set forth in SEQ ID NO: 8, and
b) said second antigen-binding region binding to CD137 comprises a light chain variable region (VL) comprising a LCDR3 sequence as set forth in SEQ ID NO: 18.

In some embodiments,
a) said first antigen-binding region binding to EpCAM comprises a heavy chain variable region (VH) comprising a HCDR3 sequence as set forth in SEQ ID NO: 4, and a light chain variable region (VL) comprising a LCDR3 sequence as set forth in SEQ ID NO: 8, and
b) said second antigen-binding region binding to CD137 comprises a heavy chain variable region (VH) comprising a HCDR3 sequence as set forth in SEQ ID NO: 14, and a light chain variable region (VL) comprising a LCDR3 sequence, as set forth in SEQ ID NO: 18.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 6, 7, and 8, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 64, 65, and 66, respectively, and the LCDR1, LCDR2, and LCDR3 sequences comprise the sequences as set forth in SEQ ID NO: 67, 68, and 8, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 69, 70, and 71, respectively, and the LCDR1, LCDR2, and LCDR3 sequences comprises the sequences as set forth in SEQ ID NO: 72, 73 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 74, 3, and 66, respectively, and the LCDR1, LCDR2, and LCDR3 sequences comprise the sequences as set forth in SEQ ID NO: 6, 7, and 8, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 75, 13, and 71, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising the HCDR1, HCDR2, and HCDR3 sequences of SEQ ID NO: 1 and a light chain variable region (VL) comprising the LCDR1, LCDR2, and LCDR3 sequences of SEQ ID NO: 5; and
b) said second antigen-binding region binding to CD137 comprises a heavy chain variable region (VH) comprising the HCDR1, HCDR2, and HCDR3 sequences of SEQ ID NO: 11 and a light chain variable region (VL) comprising the LCDR1, LCDR2, and LCDR3 sequences of SEQ ID NO: 15.

In some embodiments,
a) said first antigen-binding region binding to EpCAM comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 1 and the VL comprises an amino acid sequence having at least 80%, at least 85%, at least 90%, at least 95%, at least 97%, or at least 99% identity to the amino acid sequence as set forth in SEQ ID NO: 5; and
b) said second antigen-binding region binding to CD137 comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 11 and the VL comprises an amino acid sequence having at least 80%, at least 85%, at least 90%, at least 95%, at least 97%, or at least 99% identity to the amino acid sequence as set forth in SEQ ID NO: 15.

In some embodiments,
a) said first antigen-binding region binding to EpCAM comprises a heavy chain variable region (VH) and a light chain variable region (VL), wherein the VH comprises the sequence as set forth in SEQ ID NO: 1 and the VL comprises the sequence as set forth in SEQ ID NO: 5; and
b) said second antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

In some embodiments, said first antigen-binding region binding to EpCAM comprises heavy and light chain variable regions of an antibody which competes for EpCAM binding with and/or has the specificity for EpCAM of an antibody comprising a heavy chain variable region or a light chain variable region, or a combination thereof of a first antigen-binding region binding to EpCAM as set forth above and said second antigen-binding region binding to CD137 comprises heavy and light chain variable regions of an antibody which competes for CD137 binding with and/or has the specificity for CD137 of an antibody comprising a heavy chain variable region or a light chain variable region, or a combination thereof of a second antigen-binding region binding to CD137 as set forth above.

In some embodiments, a variable region comprises three complementarity determining regions (CDR1, CDR2, and CDR3) and four framework regions (FR1, FR2, FR3, and FR4).

In some embodiments, said complementarity determining regions and said framework regions are arranged from amino-terminus to carboxy-terminus in the following order: FR1, CDR1, FR2, CDR2, FR3, CDR3, FR4.

In some embodiments, the binding agent is in the format of a full-length antibody or an antibody fragment.

In some embodiments, the binding agent is a multispecific such as a bispecific binding agent.

In some embodiments, the binding agent is a multispecific such as a bispecific antibody.

In some embodiments, the binding agent comprises
(i) a first heavy chain variable region (VH) and a first light chain variable region (VL), wherein said first heavy chain variable region (VH) and said first light chain variable region (VL) form said first antigen-binding region binding to EpCAM; and
(ii) a second heavy chain variable region (VH) and a second light chain variable region (VL), wherein said second heavy chain variable region (VH) and said second light chain variable region (VL) form said second antigen-binding region binding to CD137.

In some embodiments, the binding agent comprises
i) a polypeptide comprising a first heavy chain variable region (VH) and a first heavy chain constant region (CH), and a polypeptide comprising a first light chain variable region (VL) and a first light chain constant region (CL), wherein said first heavy chain variable region (VH) and said first light chain variable region (VL) form said first antigen-binding region binding to EpCAM; and
ii) a polypeptide comprising a second heavy chain variable region (VH) and a second heavy chain constant region (CH), and a polypeptide comprising a second light chain variable region (VL) and a second light chain constant region (CL), wherein said second heavy chain variable region (VH) and said second light chain variable region (VL) form said second antigen-binding region binding to CD137.

In some embodiments, the binding agent is an antibody comprising a first binding arm comprising said first antigen-binding region binding to EpCAM and a second binding arm comprising said second antigen-binding region binding to CD137, wherein
the first binding arm comprises
i) a polypeptide comprising a first heavy chain variable region (VH) and a first heavy chain constant region (CH), and
ii) a polypeptide comprising a first light chain variable region (VL) and a first light chain constant region (CL); and the second binding arm comprises
iii) a polypeptide comprising a second heavy chain variable region (VH) and a second heavy chain constant region (CH), and
iv) a polypeptide comprising a second light chain variable region (VL) and a second light chain constant region (CL).

In some embodiments, the binding agent is an antibody comprising a first binding arm comprising said first antigen-binding region binding to EpCAM and a second binding arm comprising said second antigen-binding region binding to CD137, wherein
the first binding arm comprises
i) a first heavy chain comprising a first heavy chain variable region (VH) and a first heavy chain constant region (CH), and
ii) a first light chain comprising a first light chain variable region (VL) and a first light chain constant region (CL); and the second binding arm comprises
i) a second heavy chain comprising a second heavy chain variable region (VH) and a second heavy chain constant region (CH); and
ii) a second light chain comprising a second light chain variable region (VL) and a second light chain constant region (CL).

In some embodiments, the first binding arm is derived from a full-length antibody. In some embodiments, the first binding arm is derived from a monoclonal antibody. In some embodiments, the first binding arm is derived from a full-length IgG1, λ (lambda) or IgG1, κ (kappa) antibody. In some embodiments, the second binding arm is derived from a full-length antibody. In some embodiments, the second binding arm is derived from a monoclonal antibody. In some embodiments, the second binding arm is derived from a full-length IgG1, λ (lambda) or IgG1, κ (kappa) antibody. In some embodiments, the first and second binding arms are derived from full-length antibodies, such as from full-length IgG1, λ (lambda) or IgG1, κ (kappa) antibodies. In some embodiments, the first and second binding arms are derived from monoclonal antibodies.

In some embodiments, each of the first and second heavy chain constant regions (CHs) comprises one or more of a constant heavy chain 1 (CH1) region, a hinge region, a constant heavy chain 2 (CH2) region and a constant heavy chain 3 (CH3) region, preferably at least a hinge region, a CH2 region and a CH3 region.

In some embodiments, each of the first and second heavy chain constant regions (CHs) comprises a CH3 region and wherein the two CH3 regions comprise asymmetrical mutations.

In some embodiments, in said first heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and in said second heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and wherein said first and said second heavy chains are not substituted in the same positions.

In some embodiments, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain constant region (CH), and the amino acid in the position corresponding to F405 in a human IgG1 heavy chain according to EU numbering is L in said second heavy chain constant region (CH).

In some embodiments, said binding agent induces Fc-mediated effector function to a lesser extent compared to another antibody comprising the same first and second antigen binding regions and two heavy chain constant regions (CHs) comprising human IgG1 hinge, CH2 and CH3 regions.

In some embodiments, said first and second heavy chain constant regions (CHs) are modified so that the antibody induces Fc-mediated effector function to a lesser extent compared to an antibody which is identical except for comprising non-modified first and second heavy chain constant regions (CHs).

In some embodiments, each of said non-modified first and second heavy chain constant regions (CHs) comprises the amino acid sequence set forth in SEQ ID NO: 47.

In some embodiments, said Fc-mediated effector function is measured by binding to Fcγ receptors, binding to C1q, or induction of Fc-mediated crosslinking of Fcγ receptors.

In some embodiments, said Fc-mediated effector function is measured by binding to C1q.

In some embodiments, said first and second heavy chain constant regions have been modified so that binding of C1q to said antibody is reduced compared to a wild-type antibody, preferably reduced by at least 70%, at least 80%, at least 90%, at least 95%, at least 97%, or 100%, wherein C1q binding is preferably determined by ELISA.

In some embodiments, in at least one of said first and second heavy chain constant regions (CHs), one or more amino acids in the positions corresponding to positions L234, L235, D265, N297, P331, and G236 in a human IgG1 heavy chain according to EU numbering, are not L, L, D, N, P, and G, respectively.

In some embodiments, the positions corresponding to positions L234 and L235 in a human IgG1 heavy chain according to EU numbering are F and E, respectively, in said first and second heavy chains.

In some embodiments, the positions corresponding to positions L234, L235, and D265 in a human IgG1 heavy chain according to EU numbering are F, E, and A, respectively, in said first and/or second heavy chain constant regions (HCs) and/or the positions corresponding to positions L234, L235, and G236 in a human IgG1 heavy chain according to EU numbering are F, E, and R, respectively, in said first and/or second heavy chain constant regions (HCs).

In some embodiments,
(i) the positions corresponding to positions L234, L235, and D265 in a human IgG1 heavy chain according to EU numbering are F, E, and A, respectively, in both said first and second heavy chain constant regions;
(ii) the positions corresponding to positions L234, L235, and G236 in a human IgG1 heavy chain according to EU numbering are F, E, and R, respectively, in both said first and second heavy chain constant regions; or
(iii) the positions corresponding to positions L234, L235, and D265 in a human IgG1 heavy chain according to EU numbering are F, E, and A, respectively, in one of said first and second heavy chain constant regions and the positions corresponding to positions L234, L235, and G236 in a human IgG1 heavy chain according to EU numbering are F, E, and R, respectively, in the other of said first and second heavy chain constant regions.

In some embodiments, the positions corresponding to positions L234 and L235 in a human IgG1 heavy chain according to EU numbering of both the first and second heavy chain constant regions are F and E, respectively, and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein the position corresponding to F405 in a human IgG1 heavy chain according to EU numbering of the first heavy chain constant region is L, and the position corresponding to K409 in a human IgG1 heavy chain according to EU numbering of the second heavy chain constant region is R.

In some embodiments, the constant region of said first and/or second heavy chain comprises an amino acid sequence an amino acid sequence having at least 80%, at least 85%, at least 90%, at least 95%, at least 97%, or at least 99% identity to the amino acid sequence set forth in SEQ ID NO: 47.

In some embodiments,
a) the constant region of said first heavy chain comprises the amino acid sequence set forth in SEQ ID NO: 54; and
b) the constant region of said second heavy chain comprises the amino acid sequence set forth in SEQ ID NO: 52.

In some embodiments, said binding agent comprises a kappa (κ) light chain constant region.

In some embodiments, said binding agent comprises a lambda (λ) light chain constant region.

In some embodiments, said first light chain constant region is a kappa (κ) light chain constant region or a lambda (λ) light chain constant region.

In some embodiments, said second light chain constant region is a kappa (κ) light chain constant region or a lambda (λ) light chain constant region.

In some embodiments,
(i) said first light chain constant region and said second light chain constant region are kappa (κ) light chain constant regions,
(ii) said first light chain constant region and said second light chain constant region are lambda (λ) light chain constant regions,
(iii) said first light chain constant region is a kappa (κ) light chain constant region and said second light chain constant region is a lambda (λ) light chain constant region, or
(iv) said first light chain constant region is a lambda (λ) light chain constant region and said second light chain constant region is a kappa (κ) light chain constant region.

In some embodiments, the kappa (κ) light chain comprises an amino acid sequence having at least 80%, at least 85%, at least 90%, at least 95%, at least 97%, or at least 99% identity to the amino acid sequence set forth in SEQ ID NO:55.

In some embodiments, the lambda (λ) light chain comprises an amino acid sequence having at least 80%, at least 85%, at least 90%, at least 95%, at least 97%, or at least 99% identity to the amino acid sequence set forth in SEQ ID NO: 56.

In some embodiments, the binding agent is of an isotype selected from the group consisting of IgG1, IgG2, IgG3, and IgG4. In one embodiment, the isotype is selected from the group consisting of human IgG1, human IgG2, human IgG3 and human IgG4.

In some embodiments, the binding agent is a full-length IgG1 antibody.

In some embodiments, the binding agent is an antibody of the IgG1m(f) allotype.

In some embodiments, the binding agent is an antibody comprising a first binding arm comprising said first antigen-binding region binding to EpCAM and a second binding arm comprising said second antigen-binding region binding to CD137, wherein the first binding arm comprises
i) a polypeptide comprising a first heavy chain variable region (VH) and a first heavy chain constant region (CH), and
ii) a polypeptide comprising a first light chain variable region (VL) and a first light chain constant region (CL), wherein the first VH comprises first HCDR1, HCDR2, and HCDR3 sequences and the first VL comprises first LCDR1, LCDR2, and LCDR3 sequences, wherein the first HCDR1, HCDR2, and HCDR3 sequences comprise the sequences as set forth in SEQ ID NO: 2, 3, and 4, respectively, and the first LCDR1, LCDR2, and LCDR3 sequences comprise the sequences as set forth in SEQ ID NO: 6, 7, and 8, respectively;
and the second binding arm comprises
iii) a polypeptide comprising a second heavy chain variable region (VH) and a second heavy chain constant region (CH), and
iv) a polypeptide comprising a second light chain variable region (VL) and a second light chain constant region (CL),
wherein the second VH comprises second HCDR1, HCDR2, and HCDR3 sequences and the second VL comprises second LCDR1, LCDR2, and LCDR3 sequences, wherein the second HCDR1, HCDR2, and HCDR3 sequences comprise the sequences as set forth in SEQ ID NO: 12, 13, and 14, respectively, and the second LCDR1, LCDR2, and LCDR3 sequences comprise the sequences as set forth in SEQ ID NO: 16, 17, and 18, respectively;
wherein positions L234, L235, and G236 in a human IgG1 heavy chain according to EU numbering are F, E, and R, respectively, in the first CH and positions L234, L235, and D265 in a human IgG1 heavy chain according to EU numbering are F, E, and A in the second CH; and
wherein the amino acid in the position corresponding to F405 in a human IgG1 heavy chain according to EU numbering is L in the first CH and the amino acid in the position corresponding to K409 in a human IgG1 heavy chain according to EU numbering is R in the second CH.

In some embodiments, the binding agent comprises
i) a first heavy chain comprising an amino acid sequence having at least 80%, at least 85%, at least 90%, at least 95%, at least 97%, or at least 99% identity to the amino acid sequence set forth in SEQ ID NO: 9,
ii) a first light chain comprising an amino acid sequence having at least 80%, at least 85%, at least 90%, at least 95%, at least 97%, or at least 99% identity to the amino acid sequence set forth in SEQ ID NO: 10,
iii) a second heavy chain comprising an amino acid sequence having at least 80%, at least 85%, at least 90%, at least 95%, at least 97%, or at least 99% identity to the amino acid sequence set forth in SEQ ID NO: 19; and
iv) a second light chain comprising an amino acid sequence having at least 80%, at least 85%, at least 90%, at least 95%, at least 97%, or at least 99% identity to the amino acid sequence set forth in SEQ ID NO: 20.

In some embodiments, the binding agent comprises
i) a first heavy chain comprising the amino acid sequence set forth in SEQ ID NO: 9,
ii) a first light chain comprising the amino acid sequence set forth in SEQ ID NO: 10,
iii) a second heavy chain comprising the amino acid sequence set forth in SEQ ID NO: 19; and
iv) a second light chain comprising the amino acid sequence set forth in SEQ ID NO: 20.

In some embodiments, said first antigen-binding region binding to EpCAM comprises a heavy chain variable region (VH) comprising a HCDR3 sequence comprising the sequence as set forth in SEQ ID NO: 78. In some embodiments, said first antigen-binding region binding to EpCAM comprises a heavy chain variable region (VH) comprising a HCDR2 sequence comprising the sequence as set forth in SEQ ID NO: 77. In some embodiments, said first antigen-binding region binding to EpCAM comprises a heavy chain variable region (VH) comprising a HCDR1 sequence comprising the sequence as set forth in SEQ ID NO: 76. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 76, 77, and 78, respectively. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 82, 83, and 84, respectively. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 87, 77, and 84, respectively.

In some embodiments, said first antigen-binding region binding to EpCAM comprises a light chain variable region (VL) comprising a LCDR3 sequence comprising the sequence as set forth in SEQ ID NO: 81. In some embodiments, said first antigen-binding region binding to EpCAM comprises a light chain variable region (VL) comprising a LCDR2 sequence comprising the sequence as set forth in SEQ ID NO: 80. In some embodiments, said first antigen-binding region binding to EpCAM comprises a light chain variable region (VL) comprising a LCDR1 sequence comprising the sequence as set forth in SEQ ID NO: 79. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 79, 80, and 81, respectively. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 85, 86, and 81, respectively.

In some embodiments, said first antigen-binding region binding to EpCAM comprises a heavy chain variable region (VH) comprising a HCDR3 sequence and a light chain variable region (VL) comprising a LCDR3 sequence, wherein the HCDR3 sequence comprises the sequence as set forth in SEQ ID NO: 78, and the LCDR3 sequence comprises the sequence as set forth in SEQ ID NO: 81.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 76, 77, and 78, respectively, and the LCDR1, LCDR2, and LCDR3 sequences comprise the sequences as set forth in SEQ ID NO: 79, 80, and 81, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 82, 83, and 84, respectively, and the LCDR1, LCDR2, and LCDR3 sequences comprise the sequences as set forth in SEQ ID NO: 85, 86, and 81, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 87, 77, and 84, respectively, and the LCDR1, LCDR2, and LCDR3 sequences comprise the sequences as set forth in SEQ ID NO: 79, 80, and 81, respectively.

In some embodiments, said first antigen-binding region binding to EpCAM comprises a heavy chain variable region (VH) comprising the HCDR1, HCDR2, and HCDR3 sequences of SEQ ID NO: 21, positions 1 to 116 and/or a light chain variable region (VL) comprising the LCDR1, LCDR2, and LCDR3 sequences of SEQ ID NO: 22, positions 1 to 112.

In some embodiments, said first antigen-binding region binding to EpCAM comprises a heavy chain variable region (VH) comprising a sequence having at least 80%, at least 85%, at least 90%, at least 95%, at least 97%, at least 99%, or 100% identity to the sequence as set forth in SEQ ID NO: 21, positions 1 to 116.

In some embodiments, said first antigen-binding region binding to EpCAM comprises a heavy chain variable region (VH) comprising the sequence as set forth in SEQ ID NO: 21, positions 1 to 116.

In some embodiments, said first antigen-binding region binding to EpCAM comprises a light chain variable region (VL) comprising a sequence having at least 80%, at least 85%, at least 90%, at least 95%, at least 97%, at least 99%, or 100% identity to the sequence as set forth in SEQ ID NO: 22, positions 1 to 112.

In some embodiments, said first antigen-binding region binding to EpCAM comprises a light chain variable region (VL) comprising the sequence as set forth in SEQ ID NO: 22, positions 1 to 112.

In some embodiments, said first antigen-binding region binding to EpCAM comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 21, positions 1 to 116 and the VL comprises a sequence having at least 80%, at least 85%, at least 90%, at least 95%, at least 97%, at least 99%, or 100% identity to the sequence as set forth in SEQ ID NO: 22, positions 1 to 112. In some embodiments, said first antigen-binding region binding to EpCAM comprises a heavy chain variable region (VH) and a light chain variable region (VL), wherein the VH comprises a sequence having at least at least 80% identity to the sequence as set forth in SEQ ID NO: 21, positions 1 to 116 and the VL comprises a sequence having at least 80% identity to the sequence as set forth in SEQ ID NO: 22, positions 1 to 112. In some embodiments, said first antigen-binding region binding to EpCAM comprises a heavy chain variable region (VH) and a light chain variable region (VL), wherein the VH comprises a sequence having at least at least 90% identity to the sequence as set forth in SEQ ID NO: 21, positions 1 to 116 and the VL comprises a sequence having at least 90% identity to the sequence as set forth in SEQ ID NO: 22, positions 1 to 112. In some embodiments, said first antigen-binding region binding to EpCAM comprises a heavy chain variable region (VH) and a light chain variable region (VL), wherein the VH comprises a sequence having at least at least 95% identity to the sequence as set forth in SEQ ID NO: 21, positions 1 to 116 and the VL comprises a sequence having at least 95% identity to the sequence as set forth in SEQ ID NO: 22, positions 1 to 112.

In some embodiments, said first antigen-binding region binding to EpCAM comprises a heavy chain variable region (VH) and a light chain variable region (VL), wherein the VH comprises the sequence as set forth in SEQ ID NO: 21, positions 1 to 116 and the VL comprises the sequence as set forth in SEQ ID NO: 22, positions 1 to 112.

In some embodiments, said first antigen-binding region binding to EpCAM comprises heavy and light chain variable regions of an antibody which competes for EpCAM binding with and/or has the specificity for EpCAM of an antibody comprising a heavy chain variable region (VH) and/or a light chain variable region (VL) as set forth above.

In some embodiments, said second antigen-binding region binding to CD137 is as set forth above.

In some embodiments,
a) said first antigen-binding region binding to EpCAM comprises a heavy chain variable region (VH) comprising a HCDR3 sequence as set forth in SEQ ID NO: 78, and
b) said second antigen-binding region binding to CD137 comprises a heavy chain variable region (VH) comprising a HCDR3 sequence as set forth in SEQ ID NO: 14.

In some embodiments,
a) said first antigen-binding region binding to EpCAM comprises a light chain variable region (VL) comprising a LCDR3 sequence as set forth in SEQ ID NO: 81, and
b) said second antigen-binding region binding to CD137 comprises a light chain variable region (VL) comprising a LCDR3 sequence as set forth in SEQ ID NO: 18.

In some embodiments,
a) said first antigen-binding region binding to EpCAM comprises a heavy chain variable region (VH) comprising a HCDR3 sequence as set forth in SEQ ID NO: 78, and a light chain variable region (VL) comprising a LCDR3 sequence as set forth in SEQ ID NO: 81, and
b) said second antigen-binding region binding to CD137 comprises a heavy chain variable region (VH) comprising a HCDR3 sequence as set forth in SEQ ID NO: 14, and a light chain variable region (VL) comprising a LCDR3 sequence, as set forth in SEQ ID NO: 18.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 76, 77, and 78, respectively, and the LCDR1, LCDR2, and LCDR3 sequences comprise the sequences as set forth in SEQ ID NO: 79, 80, and 81, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 82, 83, and 84, respectively, and the LCDR1, LCDR2, and LCDR3 sequences comprise the sequences as set forth in SEQ ID NO: 85, 86, and 81, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 69, 70, and 71, respectively, and the LCDR1, LCDR2, and LCDR3 sequences comprises the sequences as set forth in SEQ ID NO: 72, 73 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 87, 77, and 84, respectively, and the LCDR1, LCDR2, and LCDR3 sequences comprise the sequences as set forth in SEQ ID NO: 79, 80, and 81, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 75, 13, and 71, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising the HCDR1, HCDR2, and HCDR3 sequences of SEQ ID NO: 21, positions 1 to 116 and a light chain variable region (VL) comprising the LCDR1, LCDR2, and LCDR3 sequences of SEQ ID NO: 22, positions 1 to 112; and
b) said second antigen-binding region binding to CD137 comprises a heavy chain variable region (VH) comprising the HCDR1, HCDR2, and HCDR3 sequences of SEQ ID NO: 11 and a light chain variable region (VL) comprising the LCDR1, LCDR2, and LCDR3 sequences of SEQ ID NO: 15.

In some embodiments,
a) said first antigen-binding region binding to EpCAM comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 21, positions 1 to 116 and the VL comprises an amino acid sequence having at least 80%, at least 85%, at least 90%, at least 95%, at least 97%, or at least 99% identity to the amino acid sequence as set forth in SEQ ID NO: 22, positions 1 to 112; and
b) said second antigen-binding region binding to CD137 comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 11 and the VL comprises an amino acid sequence having at least 80%, at least 85%, at least 90%, at least 95%, at least 97%, or at least 99% identity to the amino acid sequence as set forth in SEQ ID NO: 15.

In some embodiments,
a) said first antigen-binding region binding to EpCAM comprises a heavy chain variable region (VH) and a light chain variable region (VL), wherein the VH comprises the sequence as set forth in SEQ ID NO: 21, positions 1 to 116 and the VL comprises the sequence as set forth in SEQ ID NO: 22, positions 1 to 112; and
b) said second antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

In some embodiments, said first antigen-binding region binding to EpCAM comprises heavy and light chain variable regions of an antibody which competes for EpCAM binding with and/or has the specificity for EpCAM of an antibody comprising a heavy chain variable region or a light chain variable region, or a combination thereof of a first antigen-binding region binding to EpCAM as set forth above and said second antigen-binding region binding to CD137 comprises heavy and light chain variable regions of an antibody which competes for CD137 binding with and/or has the specificity for CD137 of an antibody comprising a heavy chain variable region or a light chain variable region, or a combination thereof of a second antigen-binding region binding to CD137 as set forth above.

In some embodiments, a variable region comprises three complementarity determining regions (CDR1, CDR2, and CDR3) and four framework regions (FR1, FR2, FR3, and FR4).

In some embodiments, said complementarity determining regions and said framework regions are arranged from amino-terminus to carboxy-terminus in the following order: FR1, CDR1, FR2, CDR2, FR3, CDR3, FR4.

In some embodiments, the binding agent is in the format of a full-length antibody or an antibody fragment.

In some embodiments, the binding agent is a multispecific such as a bispecific binding agent.

In some embodiments, the binding agent is a multispecific such as a bispecific antibody.

In some embodiments, the binding agent comprises
(i) a first heavy chain variable region (VH) and a first light chain variable region (VL), wherein said first heavy chain variable region (VH) and said first light chain variable region (VL) form said first antigen-binding region binding to EpCAM; and
(ii) a second heavy chain variable region (VH) and a second light chain variable region (VL), wherein said second heavy chain variable region (VH) and said second light chain variable region (VL) form said second antigen-binding region binding to CD137.

In some embodiments, the binding agent comprises
i) a polypeptide comprising a first heavy chain variable region (VH) and a first heavy chain constant region (CH), and a polypeptide comprising a first light chain variable region (VL) and a first light chain constant region (CL), wherein said first heavy chain variable region (VH) and said first light chain variable region (VL) form said first antigen-binding region binding to EpCAM; and
ii) a polypeptide comprising a second heavy chain variable region (VH) and a second heavy chain constant region (CH), and a polypeptide comprising a second light chain variable region (VL) and a second light chain constant region (CL), wherein said second heavy chain variable region (VH) and said second light chain variable region (VL) form said second antigen-binding region binding to CD137.

In some embodiments, the binding agent is an antibody comprising a first binding arm comprising said first antigen-binding region binding to EpCAM and a second binding arm comprising said second antigen-binding region binding to CD137, wherein the first binding arm comprises
i) a polypeptide comprising a first heavy chain variable region (VH) and a first heavy chain constant region (CH), and
ii) a polypeptide comprising a first light chain variable region (VL) and a first light chain constant region (CL); and the second binding arm comprises
iii) a polypeptide comprising a second heavy chain variable region (VH) and a second heavy chain constant region (CH), and
iv) a polypeptide comprising a second light chain variable region (VL) and a second light chain constant region (CL).

In some embodiments, the binding agent is an antibody comprising a first binding arm comprising said first antigen-binding region binding to EpCAM and a second binding arm comprising said second antigen-binding region binding to CD137, wherein the first binding arm comprises
i) a first heavy chain comprising a first heavy chain variable region (VH) and a first heavy chain constant region (CH), and
ii) a first light chain comprising a first light chain variable region (VL) and a first light chain constant region (CL); and the second binding arm comprises
i) a second heavy chain comprising a second heavy chain variable region (VH) and a second heavy chain constant region (CH); and
ii) a second light chain comprising a second light chain variable region (VL) and a second light chain constant region (CL).

In some embodiments, the first binding arm is derived from a full-length antibody. In some embodiments, the first binding arm is derived from a monoclonal antibody. In some embodiments, the first binding arm is derived from a full-length IgG1, λ (lambda) or IgG1, κ (kappa) antibody. In some embodiments, the second binding arm is derived from a full-length antibody. In some embodiments, the second binding arm is derived from a monoclonal antibody. In some embodiments, the second binding arm is derived from a full-length IgG1, λ (lambda) or IgG1, κ (kappa) antibody. In some embodiments, the first and second binding arms are derived from full-length antibodies, such as from full-length IgG1, λ (lambda) or IgG1, κ (kappa) antibodies. In some embodiments, the first and second binding arms are derived from monoclonal antibodies.

In some embodiments, each of the first and second heavy chain constant regions (CHs) comprises one or more of a constant heavy chain 1 (CH1) region, a hinge region, a constant heavy chain 2 (CH2) region and a constant heavy chain 3 (CH3) region, preferably at least a hinge region, a CH2 region and a CH3 region.

In some embodiments, each of the first and second heavy chain constant regions (CHs) comprises a CH3 region and wherein the two CH3 regions comprise asymmetrical mutations.

In some embodiments, in said first heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and in said second heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and wherein said first and said second heavy chains are not substituted in the same positions.

In some embodiments, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain constant region (CH), and the amino acid in the position corresponding to F405 in a human IgG1 heavy chain according to EU numbering is L in said second heavy chain constant region (CH).

In some embodiments, said binding agent induces Fc-mediated effector function to a lesser extent compared to another antibody comprising the same first and second antigen binding regions and two heavy chain constant regions (CHs) comprising human IgG1 hinge, CH2 and CH3 regions.

In some embodiments, said first and second heavy chain constant regions (CHs) are modified so that the antibody induces Fc-mediated effector function to a lesser extent compared to an antibody which is identical except for comprising non-modified first and second heavy chain constant regions (CHs).

In some embodiments, each of said non-modified first and second heavy chain constant regions (CHs) comprises the amino acid sequence set forth in SEQ ID NO: 47.

In some embodiments, said Fc-mediated effector function is measured by binding to Fcγ receptors, binding to C1q, or induction of Fc-mediated crosslinking of Fcγ receptors.

In some embodiments, said Fc-mediated effector function is measured by binding to C1q.

In some embodiments, said first and second heavy chain constant regions have been modified so that binding of C1q to said antibody is reduced compared to a wild-type antibody, preferably reduced by at least 70%, at least 80%, at least 90%, at least 95%, at least 97%, or 100%, wherein C1q binding is preferably determined by ELISA.

In some embodiments, in at least one of said first and second heavy chain constant regions (CHs), one or more amino acids in the positions corresponding to positions L234, L235, D265, N297, P331, and G236 in a human IgG1 heavy chain according to EU numbering, are not L, L, D, N, P, and G, respectively.

In some embodiments, the positions corresponding to positions L234 and L235 in a human IgG1 heavy chain according to EU numbering are F and E, respectively, in said first and second heavy chains.

In some embodiments, the positions corresponding to positions L234, L235, and D265 in a human IgG1 heavy chain according to EU numbering are F, E, and A, respectively, in said first and/or second heavy chain constant regions (HCs) and/or the positions corresponding to positions L234, L235, and G236 in a human IgG1 heavy chain according to EU numbering are F, E, and R, respectively, in said first and/or second heavy chain constant regions (HCs).

In some embodiments,
(i) the positions corresponding to positions L234, L235, and D265 in a human IgG1 heavy chain according to EU numbering are F, E, and A, respectively, in both said first and second heavy chain constant regions;
(ii) the positions corresponding to positions L234, L235, and G236 in a human IgG1 heavy chain according to EU numbering are F, E, and R, respectively, in both said first and second heavy chain constant regions; or
(iii) the positions corresponding to positions L234, L235, and D265 in a human IgG1 heavy chain according to EU numbering are F, E, and A, respectively, in one of said first and second heavy chain constant regions and the positions corresponding to positions L234, L235, and G236 in a human IgG1 heavy chain according to EU numbering are F, E, and R, respectively, in the other of said first and second heavy chain constant regions.

In some embodiments, the positions corresponding to positions L234 and L235 in a human IgG1 heavy chain according to EU numbering of both the first and second heavy chain constant regions are F and E, respectively, and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein the position corresponding to F405 in a human IgG1 heavy chain according to EU numbering of the first heavy chain constant region is L, and the position corresponding to K409 in a human IgG1 heavy chain according to EU numbering of the second heavy chain constant region is R.

In some embodiments, the constant region of said first and/or second heavy chain comprises an amino acid sequence an amino acid sequence having at least 80%, at least 85%, at least 90%, at least 95%, at least 97%, or at least 99% identity to the amino acid sequence set forth in SEQ ID NO: 47.

In some embodiments,
a) the constant region of said first heavy chain comprises the amino acid sequence set forth in SEQ ID NO: 54; and
b) the constant region of said second heavy chain comprises the amino acid sequence set forth in SEQ ID NO: 52.

In some embodiments, said binding agent comprises a kappa (κ) light chain constant region.

In some embodiments, said binding agent comprises a lambda (λ) light chain constant region.

In some embodiments, said first light chain constant region is a kappa (κ) light chain constant region or a lambda (λ) light chain constant region.

In some embodiments, said second light chain constant region is a kappa (κ) light chain constant region or a lambda (λ) light chain constant region.

In some embodiments,
(i) said first light chain constant region and said second light chain constant region are kappa (κ) light chain constant regions,
(ii) said first light chain constant region and said second light chain constant region are lambda (λ) light chain constant regions,
(iii) said first light chain constant region is a kappa (κ) light chain constant region and said second light chain constant region is a lambda (λ) light chain constant region, or
(iv) said first light chain constant region is a lambda (λ) light chain constant region and said second light chain constant region is a kappa (κ) light chain constant region.

In some embodiments, the kappa (κ) light chain comprises an amino acid sequence having at least 80%, at least 85%, at least 90%, at least 95%, at least 97%, or at least 99% identity to the amino acid sequence set forth in SEQ ID NO:55.

In some embodiments, the lambda (λ) light chain comprises an amino acid sequence having at least 80%, at least 85%, at least 90%, at least 95%, at least 97%, or at least 99% identity to the amino acid sequence set forth in SEQ ID NO: 56.

In some embodiments, the binding agent is of an isotype selected from the group consisting of IgG1, IgG2, IgG3, and IgG4. In one embodiment, the isotype is selected from the group consisting of human IgG1, human IgG2, human IgG3 and human IgG4.

In some embodiments, the binding agent is a full-length IgG1 antibody.

In some embodiments, the binding agent is an antibody of the IgG1m(f) allotype.

In some embodiments, the binding agent is an antibody comprising a first binding arm comprising said first antigen-binding region binding to EpCAM and a second binding arm comprising said second antigen-binding region binding to CD137, wherein
the first binding arm comprises
i) a polypeptide comprising a first heavy chain variable region (VH) and a first heavy chain constant region (CH), and
ii) a polypeptide comprising a first light chain variable region (VL) and a first light chain constant region (CL), wherein the first VH comprises first HCDR1, HCDR2, and HCDR3 sequences and the first VL comprises first LCDR1, LCDR2, and LCDR3 sequences, wherein the first HCDR1, HCDR2, and HCDR3 sequences comprise the sequences as set forth in SEQ ID NO: 76, 77, and 78, respectively, and the first LCDR1, LCDR2, and LCDR3 sequences comprise the sequences as set forth in SEQ ID NO: 79, 80, and 81, respectively;
and the second binding arm comprises
iii) a polypeptide comprising a second heavy chain variable region (VH) and a second heavy chain constant region (CH), and
iv) a polypeptide comprising a second light chain variable region (VL) and a second light chain constant region (CL),
wherein the second VH comprises second HCDR1, HCDR2, and HCDR3 sequences and the second VL comprises second LCDR1, LCDR2, and LCDR3 sequences, wherein the second HCDR1, HCDR2, and HCDR3 sequences comprise the sequences as set forth in SEQ ID NO: 12, 13, and 14, respectively, and the second LCDR1, LCDR2, and LCDR3 sequences comprise the sequences as set forth in SEQ ID NO: 16, 17, and 18, respectively;
wherein positions L234, L235, and G236 in a human IgG1 heavy chain according to EU numbering are F, E, and R, respectively, in the first CH and positions L234, L235, and D265 in a human IgG1 heavy chain according to EU numbering are F, E, and A in the second CH; and
wherein the amino acid in the position corresponding to F405 in a human IgG1 heavy chain according to EU numbering is L in the first CH and the amino acid in the position corresponding to K409 in a human IgG1 heavy chain according to EU numbering is R in the second CH.

In some embodiments, the binding agent comprises
i) a first heavy chain comprising an amino acid sequence having at least 80%, at least 85%, at least 90%, at least 95%, at least 97%, or at least 99% identity to the amino acid sequence set forth in SEQ ID NO: 21,
ii) a first light chain comprising an amino acid sequence having at least 80%, at least 85%, at least 90%, at least 95%, at least 97%, or at least 99% identity to the amino acid sequence set forth in SEQ ID NO: 22,
iii) a second heavy chain comprising an amino acid sequence having at least 80%, at least 85%, at least 90%, at least 95%, at least 97%, or at least 99% identity to the amino acid sequence set forth in SEQ ID NO: 19; and
iv) a second light chain comprising an amino acid sequence having at least 80%, at least 85%, at least 90%, at least 95%, at least 97%, or at least 99% identity to the amino acid sequence set forth in SEQ ID NO: 20.

In some embodiments, the binding agent comprises
i) a first heavy chain comprising the amino acid sequence set forth in SEQ ID NO: 21,
ii) a first light chain comprising the amino acid sequence set forth in SEQ ID NO: 22,
iii) a second heavy chain comprising the amino acid sequence set forth in SEQ ID NO: 19; and
iv) a second light chain comprising the amino acid sequence set forth in SEQ ID NO: 20.

In some embodiments, said first antigen-binding region binding to EpCAM comprises a light chain variable region (VL) comprising a LCDR3 sequence comprising the sequence as set forth in SEQ ID NO: 90. In some embodiments, said first antigen-binding region binding to EpCAM comprises a light chain variable region (VL) comprising a LCDR2 sequence comprising the sequence as set forth in SEQ ID NO: 89. In some embodiments, said first antigen-binding region binding to EpCAM comprises a light chain variable region (VL) comprising a LCDR1 sequence comprising the sequence as set forth in SEQ ID NO: 88. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 88, 89, and 90, respectively. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 91, 92, and 90, respectively.

In some embodiments, said first antigen-binding region binding to EpCAM comprises a heavy chain variable region (VH) comprising a HCDR3 sequence and a light chain variable region (VL) comprising a LCDR3 sequence, wherein the HCDR3 sequence comprises the sequence as set forth in SEQ ID NO: 4, and the LCDR3 sequence comprises the sequence as set forth in SEQ ID NO: 90.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 88, 89, and 90, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 64, 65, and 66, respectively, and the LCDR1, LCDR2, and LCDR3 sequences comprise the sequences as set forth in SEQ ID NO: 91, 92, and 90, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 74, 3, and 66, respectively, and the LCDR1, LCDR2, and LCDR3 sequences comprise the sequences as set forth in SEQ ID NO: 88, 89, and 90, respectively.

In some embodiments, said first antigen-binding region binding to EpCAM comprises a heavy chain variable region (VH) comprising the HCDR1, HCDR2, and HCDR3 sequences of SEQ ID NO: 25, positions 1 to 115 and/or a light chain variable region (VL) comprising the LCDR1, LCDR2, and LCDR3 sequences of SEQ ID NO: 26, positions 1 to 111.

In some embodiments, said first antigen-binding region binding to EpCAM comprises a heavy chain variable region (VH) comprising a sequence having at least 80%, at least 85%, at least 90%, at least 95%, at least 97%, at least 99%, or 100% identity to the sequence as set forth in SEQ ID NO: 25, positions 1 to 115.

In some embodiments, said first antigen-binding region binding to EpCAM comprises a heavy chain variable region (VH) comprising the sequence as set forth in SEQ ID NO: 25, positions 1 to 115.

In some embodiments, said first antigen-binding region binding to EpCAM comprises a light chain variable region (VL) comprising a sequence having at least 80%, at least 85%, at least 90%, at least 95%, at least 97%, at least 99%, or 100% identity to the sequence as set forth in SEQ ID NO: 26, positions 1 to 111.

In some embodiments, said first antigen-binding region binding to EpCAM comprises a light chain variable region (VL) comprising the sequence as set forth in SEQ ID NO: 26, positions 1 to 111.

In some embodiments, said first antigen-binding region binding to EpCAM comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 25, positions 1 to 115 and the VL comprises a sequence having at least 80%, at least 85%, at least 90%, at least 95%, at least 97%, at least 99%, or 100% identity to the sequence as set forth in SEQ ID NO: 26, positions 1 to 111. In some embodiments, said first antigen-binding region binding to EpCAM comprises a heavy chain variable region (VH) and a light chain variable region (VL), wherein the VH comprises a sequence having at least at least 80% identity to the sequence as set forth in SEQ ID NO: 25, positions 1 to 115 and the VL comprises a sequence having at least 80% identity to the sequence as set forth in SEQ ID NO: 26, positions 1 to 111. In some embodiments, said first antigen-binding region binding to EpCAM comprises a heavy chain variable region (VH) and a light chain variable region (VL), wherein the VH comprises a sequence having at least at least 90% identity to the sequence as set forth in SEQ ID NO: 25, positions 1 to 115 and the VL comprises a sequence having at least 90% identity to the sequence as set forth in SEQ ID NO: 26, positions 1 to 111. In some embodiments, said first antigen-binding region binding to EpCAM comprises a heavy chain variable region (VH) and a light chain variable region (VL), wherein the VH comprises a sequence having at least at least 95% identity to the sequence as set forth in SEQ ID NO: 25, positions 1 to 115 and the VL comprises a sequence having at least 95% identity to the sequence as set forth in SEQ ID NO: 26, positions 1 to 111.

In some embodiments, said first antigen-binding region binding to EpCAM comprises a heavy chain variable region (VH) and a light chain variable region (VL), wherein the VH comprises the sequence as set forth in SEQ ID NO: 25, positions 1 to 115 and the VL comprises the sequence as set forth in SEQ ID NO: 26, positions 1 to 111.

In some embodiments, said first antigen-binding region binding to EpCAM comprises heavy and light chain variable regions of an antibody which competes for EpCAM binding with and/or has the specificity for EpCAM of an antibody comprising a heavy chain variable region (VH) and/or a light chain variable region (VL) as set forth above.

In some embodiments, said second antigen-binding region binding to CD137 is as set forth above.

In some embodiments,
a) said first antigen-binding region binding to EpCAM comprises a light chain variable region (VL) comprising a LCDR3 sequence as set forth in SEQ ID NO: 90, and b) said second antigen-binding region binding to CD137 comprises a light chain variable region (VL) comprising a LCDR3 sequence as set forth in SEQ ID NO: 18.

In some embodiments,
a) said first antigen-binding region binding to EpCAM comprises a heavy chain variable region (VH) comprising a HCDR3 sequence as set forth in SEQ ID NO: 4, and a light chain variable region (VL) comprising a LCDR3 sequence as set forth in SEQ ID NO: 90, and
b) said second antigen-binding region binding to CD137 comprises a heavy chain variable region (VH) comprising a HCDR3 sequence as set forth in SEQ ID NO: 14, and a light chain variable region (VL) comprising a LCDR3 sequence, as set forth in SEQ ID NO: 18.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 88, 89, and 90, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 64, 65, and 66, respectively, and the LCDR1, LCDR2, and LCDR3 sequences comprise the sequences as set forth in SEQ ID NO: 91, 92, and 90, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 69, 70, and 71, respectively, and the LCDR1, LCDR2, and LCDR3 sequences comprises the sequences as set forth in SEQ ID NO: 72, 73 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 74, 3, and 66, respectively, and the LCDR1, LCDR2, and LCDR3 sequences comprise the sequences as set forth in SEQ ID NO: 88, 89, and 90, respectively; and b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 75, 13, and 71, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising the HCDR1, HCDR2, and HCDR3 sequences of SEQ ID NO: 25, positions 1 to 115 and a light chain variable region (VL) comprising the LCDR1, LCDR2, and LCDR3 sequences of SEQ ID NO: 26, positions 1 to 111; and
b) said second antigen-binding region binding to CD137 comprises a heavy chain variable region (VH) comprising the HCDR1, HCDR2, and HCDR3 sequences of SEQ ID NO: 11 and a light chain variable region (VL) comprising the LCDR1, LCDR2, and LCDR3 sequences of SEQ ID NO: 15.

In some embodiments,
a) said first antigen-binding region binding to EpCAM comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 25, positions 1 to 115 and the VL comprises an amino acid sequence having at least 80%, at least 85%, at least 90%, at least 95%, at least 97%, or at least 99% identity to the amino acid sequence as set forth in SEQ ID NO: 26, positions 1 to 111; and
b) said second antigen-binding region binding to CD137 comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 11 and the VL comprises an amino acid sequence having at least 80%, at least 85%, at least 90%, at least 95%, at least 97%, or at least 99% identity to the amino acid sequence as set forth in SEQ ID NO: 15.

In some embodiments,
a) said first antigen-binding region binding to EpCAM comprises a heavy chain variable region (VH) and a light chain variable region (VL), wherein the VH comprises the sequence as set forth in SEQ ID NO: 25, positions 1 to 115 and the VL comprises the sequence as set forth in SEQ ID NO: 26, positions 1 to 111; and
b) said second antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

In some embodiments, said first antigen-binding region binding to EpCAM comprises heavy and light chain variable regions of an antibody which competes for EpCAM binding with and/or has the specificity for EpCAM of an antibody comprising a heavy chain variable region or a light chain variable region, or a combination thereof of a first antigen-binding region binding to EpCAM as set forth above and said second antigen-binding region binding to CD137 comprises heavy and light chain variable regions of an antibody which competes for CD137 binding with and/or has the specificity for CD137 of an antibody comprising a heavy chain variable region or a light chain variable region, or a combination thereof of a second antigen-binding region binding to CD137 as set forth above.

In some embodiments, a variable region comprises three complementarity determining regions (CDR1, CDR2, and CDR3) and four framework regions (FR1, FR2, FR3, and FR4).

In some embodiments, said complementarity determining regions and said framework regions are arranged from amino-terminus to carboxy-terminus in the following order: FR1, CDR1, FR2, CDR2, FR3, CDR3, FR4.

In some embodiments, the binding agent is in the format of a full-length antibody or an antibody fragment.

In some embodiments, the binding agent is a multispecific such as a bispecific binding agent.

In some embodiments, the binding agent is a multispecific such as a bispecific antibody.

In some embodiments, the binding agent comprises
(i) a first heavy chain variable region (VH) and a first light chain variable region (VL), wherein said first heavy chain variable region (VH) and said first light chain variable region (VL) form said first antigen-binding region binding to EpCAM; and
(ii) a second heavy chain variable region (VH) and a second light chain variable region (VL), wherein said second heavy chain variable region (VH) and said second light chain variable region (VL) form said second antigen-binding region binding to CD137.

In some embodiments, the binding agent comprises
i) a polypeptide comprising a first heavy chain variable region (VH) and a first heavy chain constant region (CH), and a polypeptide comprising a first light chain variable region (VL) and a first light chain constant region (CL), wherein said first heavy chain variable region (VH) and said first light chain variable region (VL) form said first antigen-binding region binding to EpCAM; and
ii) a polypeptide comprising a second heavy chain variable region (VH) and a second heavy chain constant region (CH), and a polypeptide comprising a second light chain variable region (VL) and a second light chain constant region (CL), wherein said second heavy chain variable region (VH) and said second light chain variable region (VL) form said second antigen-binding region binding to CD137.

In some embodiments, the binding agent is an antibody comprising a first binding arm comprising said first antigen-binding region binding to EpCAM and a second binding arm comprising said second antigen-binding region binding to CD137, wherein the first binding arm comprises
i) a polypeptide comprising a first heavy chain variable region (VH) and a first heavy chain constant region (CH), and
ii) a polypeptide comprising a first light chain variable region (VL) and a first light chain constant region (CL); and the second binding arm comprises
iii) a polypeptide comprising a second heavy chain variable region (VH) and a second heavy chain constant region (CH), and
iv) a polypeptide comprising a second light chain variable region (VL) and a second light chain constant region (CL).

In some embodiments, the binding agent is an antibody comprising a first binding arm comprising said first antigen-binding region binding to EpCAM and a second binding arm comprising said second antigen-binding region binding to CD137, wherein the first binding arm comprises
i) a first heavy chain comprising a first heavy chain variable region (VH) and a first heavy chain constant region (CH), and
ii) a first light chain comprising a first light chain variable region (VL) and a first light chain constant region (CL); and the second binding arm comprises
i) a second heavy chain comprising a second heavy chain variable region (VH) and a second heavy chain constant region (CH); and
ii) a second light chain comprising a second light chain variable region (VL) and a second light chain constant region (CL).

In some embodiments, the first binding arm is derived from a full-length antibody. In some embodiments, the first binding arm is derived from a monoclonal antibody. In some embodiments, the first binding arm is derived from a full-length IgG1, λ (lambda) or IgG1, κ (kappa) antibody. In some embodiments, the second binding arm is derived from a full-length antibody. In some embodiments, the second binding arm is derived from a monoclonal antibody. In some embodiments, the second binding arm is derived from a full-length IgG1, λ (lambda) or IgG1, κ (kappa) antibody. In some embodiments, the first and second binding arms are derived from full-length antibodies, such as from full-length IgG1, λ (lambda) or IgG1, κ (kappa) antibodies. In some embodiments, the first and second binding arms are derived from monoclonal antibodies.

In some embodiments, each of the first and second heavy chain constant regions (CHs) comprises one or more of a constant heavy chain 1 (CH1) region, a hinge region, a constant heavy chain 2 (CH2) region and a constant heavy chain 3 (CH3) region, preferably at least a hinge region, a CH2 region and a CH3 region.

In some embodiments, each of the first and second heavy chain constant regions (CHs) comprises a CH3 region and wherein the two CH3 regions comprise asymmetrical mutations.

In some embodiments, in said first heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and in said second heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and wherein said first and said second heavy chains are not substituted in the same positions.

In some embodiments, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain constant region (CH), and the amino acid in the position corresponding to F405 in a human IgG1 heavy chain according to EU numbering is L in said second heavy chain constant region (CH).

In some embodiments, said binding agent induces Fc-mediated effector function to a lesser extent compared to another antibody comprising the same first and second antigen binding regions and two heavy chain constant regions (CHs) comprising human IgG1 hinge, CH2 and CH3 regions.

In some embodiments, said first and second heavy chain constant regions (CHs) are modified so that the antibody induces Fc-mediated effector function to a lesser extent compared to an antibody which is identical except for comprising non-modified first and second heavy chain constant regions (CHs).

In some embodiments, each of said non-modified first and second heavy chain constant regions (CHs) comprises the amino acid sequence set forth in SEQ ID NO: 47.

In some embodiments, said Fc-mediated effector function is measured by binding to Fcγ receptors, binding to C1q, or induction of Fc-mediated crosslinking of Fcγ receptors.

In some embodiments, said Fc-mediated effector function is measured by binding to C1q.

In some embodiments, said first and second heavy chain constant regions have been modified so that binding of C1q to said antibody is reduced compared to a wild-type antibody, preferably reduced by at least 70%, at least 80%, at least 90%, at least 95%, at least 97%, or 100%, wherein C1q binding is preferably determined by ELISA.

In some embodiments, in at least one of said first and second heavy chain constant regions (CHs), one or more amino acids in the positions corresponding to positions L234, L235, D265, N297, P331, and G236 in a human IgG1 heavy chain according to EU numbering, are not L, L, D, N, P, and G, respectively.

In some embodiments, the positions corresponding to positions L234 and L235 in a human IgG1 heavy chain according to EU numbering are F and E, respectively, in said first and second heavy chains.

In some embodiments, the positions corresponding to positions L234, L235, and D265 in a human IgG1 heavy chain according to EU numbering are F, E, and A, respectively, in said first and/or second heavy chain constant regions (HCs) and/or the positions corresponding to positions L234, L235, and G236 in a human IgG1 heavy chain according to EU numbering are F, E, and R, respectively, in said first and/or second heavy chain constant regions (HCs).

In some embodiments,
(i) the positions corresponding to positions L234, L235, and D265 in a human IgG1 heavy chain according to EU numbering are F, E, and A, respectively, in both said first and second heavy chain constant regions;
(ii) the positions corresponding to positions L234, L235, and G236 in a human IgG1 heavy chain according to EU numbering are F, E, and R, respectively, in both said first and second heavy chain constant regions; or
(iii) the positions corresponding to positions L234, L235, and D265 in a human IgG1 heavy chain according to EU numbering are F, E, and A, respectively, in one of said first and second heavy chain constant regions and the positions corresponding to positions L234, L235, and G236 in a human IgG1 heavy chain according to EU numbering are F, E, and R, respectively, in the other of said first and second heavy chain constant regions.

In some embodiments, the positions corresponding to positions L234 and L235 in a human IgG1 heavy chain according to EU numbering of both the first and second heavy chain constant regions are F and E, respectively, and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein the position corresponding to F405 in a human IgG1 heavy chain according to EU numbering of the first heavy chain constant region is L, and the position corresponding to K409 in a human IgG1 heavy chain according to EU numbering of the second heavy chain constant region is R.

In some embodiments, the constant region of said first and/or second heavy chain comprises an amino acid sequence an amino acid sequence having at least 80%, at least 85%, at least 90%, at least 95%, at least 97%, or at least 99% identity to the amino acid sequence set forth in SEQ ID NO: 47.

In some embodiments,
a) the constant region of said first heavy chain comprises the amino acid sequence set forth in SEQ ID NO: 54; and
b) the constant region of said second heavy chain comprises the amino acid sequence set forth in SEQ ID NO: 52.

In some embodiments, said binding agent comprises a kappa (κ) light chain constant region.

In some embodiments, said binding agent comprises a lambda (λ) light chain constant region.

In some embodiments, said first light chain constant region is a kappa (κ) light chain constant region or a lambda (λ) light chain constant region.

In some embodiments, said second light chain constant region is a kappa (κ) light chain constant region or a lambda (λ) light chain constant region.

In some embodiments,
(i) said first light chain constant region and said second light chain constant region are kappa (κ) light chain constant regions, (ii) said first light chain constant region and said second light chain constant region are lambda (λ) light chain constant regions, (iii) said first light chain constant region is a kappa (κ) light chain constant region and said second light chain constant region is a lambda (λ) light chain constant region, or (iv) said first light chain constant region is a lambda (λ) light chain constant region and said second light chain constant region is a kappa (κ) light chain constant region.

In some embodiments, the kappa (κ) light chain comprises an amino acid sequence having at least 80%, at least 85%, at least 90%, at least 95%, at least 97%, or at least 99% identity to the amino acid sequence set forth in SEQ ID NO:55.

In some embodiments, the lambda (λ) light chain comprises an amino acid sequence having at least 80%, at least 85%, at least 90%, at least 95%, at least 97%, or at least 99% identity to the amino acid sequence set forth in SEQ ID NO: 56.

In some embodiments, the binding agent is of an isotype selected from the group consisting of IgG1, IgG2, IgG3, and IgG4. In one embodiment, the isotype is selected from the group consisting of human IgG1, human IgG2, human IgG3 and human IgG4.

In some embodiments, the binding agent is a full-length IgG1 antibody.

In some embodiments, the binding agent is an antibody of the IgG1m(f) allotype.

In some embodiments, the binding agent is an antibody comprising a first binding arm comprising said first antigen-binding region binding to EpCAM and a second binding arm comprising said second antigen-binding region binding to CD137, wherein the first binding arm comprises i) a polypeptide comprising a first heavy chain variable region (VH) and a first heavy chain constant region (CH), and ii) a polypeptide comprising a first light chain variable region (VL) and a first light chain constant region (CL), wherein the first VH comprises first HCDR1, HCDR2, and HCDR3 sequences and the first VL comprises first LCDR1, LCDR2, and LCDR3 sequences, wherein the first HCDR1, HCDR2, and HCDR3 sequences comprise the sequences as set forth in SEQ ID NO: 2, 3, and 4, respectively, and the first LCDR1, LCDR2, and LCDR3 sequences comprise the sequences as set forth in SEQ ID NO: 88, 89, and 90, respectively;

and the second binding arm comprises iii) a polypeptide comprising a second heavy chain variable region (VH) and a second heavy chain constant region (CH), and iv) a polypeptide comprising a second light chain variable region (VL) and a second light chain constant region (CL), wherein the second VH comprises second HCDR1, HCDR2, and HCDR3 sequences and the second VL comprises second LCDR1, LCDR2, and LCDR3 sequences, wherein the second HCDR1, HCDR2, and HCDR3 sequences comprise the sequences as set forth in SEQ ID NO: 12, 13, and 14, respectively, and the second LCDR1, LCDR2, and LCDR3 sequences comprise the sequences as set forth in SEQ ID NO: 16, 17, and 18, respectively;

wherein positions L234, L235, and G236 in a human IgG1 heavy chain according to EU numbering are F, E, and R, respectively, in the first CH and positions L234, L235, and D265 in a human IgG1 heavy chain according to EU numbering are F, E, and A in the second CH; and wherein the amino acid in the position corresponding to F405 in a human IgG1 heavy chain according to EU numbering is L in the first CH and the amino acid in the position corresponding to K409 in a human IgG1 heavy chain according to EU numbering is R in the second CH.

In some embodiments, the binding agent comprises i) a first heavy chain comprising an amino acid sequence having at least 80%, at least 85%, at least 90%, at least 95%, at least 97%, or at least 99% identity to the amino acid sequence set forth in SEQ ID NO: 25, ii) a first light chain comprising an amino acid sequence having at least 80%, at least 85%, at least 90%, at least 95%, at least 97%, or at least 99% identity to the amino acid sequence set forth in SEQ ID NO: 26, iii) a second heavy chain comprising an amino acid sequence having at least 80%, at least 85%, at least 90%, at least 95%, at least 97%, or at least 99% identity to the amino acid sequence set forth in SEQ ID NO: 19; and iv) a second light chain comprising an amino acid sequence having at least 80%, at least 85%, at least 90%, at least 95%, at least 97%, or at least 99% identity to the amino acid sequence set forth in SEQ ID NO: 20.

In some embodiments, the binding agent comprises i) a first heavy chain comprising the amino acid sequence set forth in SEQ ID NO: 25, ii) a first light chain comprising the amino acid sequence set forth in SEQ ID NO: 26, iii) a second heavy chain comprising the amino acid sequence set forth in SEQ ID NO: 19; and iv) a second light chain comprising the amino acid sequence set forth in SEQ ID NO: 20.

In some embodiments, said first antigen-binding region binding to EpCAM comprises a heavy chain variable region (VH) comprising a HCDR3 sequence comprising the sequence as set forth in SEQ ID NO: 4. In some embodiments, said first antigen-binding region binding to EpCAM comprises a heavy chain variable region (VH) comprising a HCDR2 sequence comprising the sequence as set forth in SEQ ID NO: 93. In some embodiments, said first antigen-binding region binding to EpCAM comprises a heavy chain variable region (VH) comprising a HCDR1 sequence comprising the sequence as set forth in SEQ ID NO: 2. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 2, 93, and 4, respectively. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 64, 96, and 66, respectively. In some embodiments, said first antigen-binding region binding to EpCAM comprises a heavy chain variable region (VH) comprising HCDR1, HCDR2, and HCDR3 sequences, wherein the HCDR1, HCDR2, and HCDR3 sequences comprise the sequences as set forth in SEQ ID NO: 74, 93, and 66, respectively.

In some embodiments, said first antigen-binding region binding to EpCAM comprises a light chain variable region (VL) comprising a LCDR3 sequence comprising the sequence as set forth in SEQ ID NO: 8. In some embodiments, said first antigen-binding region binding to EpCAM comprises a light chain variable region (VL) comprising a LCDR2 sequence comprising the sequence as set forth in SEQ ID NO: 95. In some embodiments, said first antigen-binding region binding to EpCAM comprises a light chain variable region (VL) comprising a LCDR1 sequence comprising the sequence as set forth in SEQ ID NO: 94. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 94, 95, and 8, respectively. In some embodiments, said first antigen-binding region binding to EpCAM comprises a light chain variable region (VL) comprising LCDR1, LCDR2, and LCDR3 sequences, wherein the LCDR1, LCDR2 and LCDR3 sequences comprise the sequences as set forth in SEQ ID NO: 97, 98, and 8, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 93, and 4, respectively, and the LCDR1, LCDR2, and LCDR3 sequences comprise the sequences as set forth in SEQ ID NO: 94, 95, and 8, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 64, 96, and 66, respectively, and the LCDR1, LCDR2, and LCDR3 sequences comprise the sequences as set forth in SEQ ID NO: 97, 98, and 8, respectively.

In some embodiments, said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 74, 93, and 66, respectively, and the LCDR1, LCDR2, and LCDR3 sequences comprise the sequences as set forth in SEQ ID NO: 94, 95, and 8, respectively.

In some embodiments, said first antigen-binding region binding to EpCAM comprises a heavy chain variable region (VH) comprising the HCDR1, HCDR2, and HCDR3 sequences of SEQ ID NO: 27, positions 1 to 115 and/or a light chain variable region (VL) comprising the LCDR1, LCDR2, and LCDR3 sequences of SEQ ID NO: 28, positions 1 to 108.

In some embodiments, said first antigen-binding region binding to EpCAM comprises a heavy chain variable region (VH) comprising a sequence having at least 80%, at least 85%, at least 90%, at least 95%, at least 97%, at least 99%, or 100% identity to the sequence as set forth in SEQ ID NO: 27, positions 1 to 115.

In some embodiments, said first antigen-binding region binding to EpCAM comprises a heavy chain variable region (VH) comprising the sequence as set forth in SEQ ID NO: 27, positions 1 to 115.

In some embodiments, said first antigen-binding region binding to EpCAM comprises a light chain variable region (VL) comprising a sequence having at least 80%, at least 85%, at least 90%, at least 95%, at least 97%, at least 99%, or 100% identity to the sequence as set forth in SEQ ID NO: 28, positions 1 to 108.

In some embodiments, said first antigen-binding region binding to EpCAM comprises a light chain variable region (VL) comprising the sequence as set forth in SEQ ID NO: 28, positions 1 to 108.

In some embodiments, said first antigen-binding region binding to EpCAM comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 27, positions 1 to 115 and the VL comprises a sequence having at least 80%, at least 85%, at least 90%, at least 95%, at least 97%, at least 99%, or 100% identity to the sequence as set forth in SEQ ID NO: 28, positions 1 to 108. In some embodiments, said first antigen-binding region binding to EpCAM comprises a heavy chain variable region (VH) and a light chain variable region (VL), wherein the VH comprises a sequence having at least at least 80% identity to the sequence as set forth in SEQ ID NO: 27, positions 1 to 115 and the VL comprises a sequence having at least 80% identity to the sequence as set forth in SEQ ID NO: 28, positions 1 to 108. In some embodiments, said first antigen-binding region binding to EpCAM comprises a heavy chain variable region (VH) and a light chain variable region (VL), wherein the VH comprises a sequence having at least at least 90% identity to the sequence as set forth in SEQ ID NO: 27, positions 1 to 115 and the VL comprises a sequence having at least 90% identity to the sequence as set forth in SEQ ID NO: 28, positions 1 to 108. In some embodiments, said first antigen-binding region binding to EpCAM comprises a heavy chain variable region (VH) and a light chain variable region (VL), wherein the VH comprises a sequence having at least at least 95% identity to the sequence as set forth in SEQ ID NO: 27, positions 1 to 115 and the VL comprises a sequence having at least 95% identity to the sequence as set forth in SEQ ID NO: 28, positions 1 to 108.

In some embodiments, said first antigen-binding region binding to EpCAM comprises a heavy chain variable region (VH) and a light chain variable region (VL), wherein the VH comprises the sequence as set forth in SEQ ID NO: 27, positions 1 to 115 and the VL comprises the sequence as set forth in SEQ ID NO: 28, positions 1 to 108.

In some embodiments, said first antigen-binding region binding to EpCAM comprises heavy and light chain variable regions of an antibody which competes for EpCAM binding with and/or has the specificity for EpCAM of an antibody comprising a heavy chain variable region (VH) and/or a light chain variable region (VL) as set forth above.

In some embodiments, said second antigen-binding region binding to CD137 is as set forth above.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 93, and 4, respectively, and the LCDR1, LCDR2, and LCDR3 sequences comprise the sequences as set forth in SEQ ID NO: 94, 95, and 8, respectively; and b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 64, 96, and 66, respectively, and the LCDR1, LCDR2, and LCDR3 sequences comprise the sequences as set forth in SEQ ID NO: 97, 98, and 8, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 69, 70, and 71, respectively, and the LCDR1, LCDR2, and LCDR3 sequences comprises the sequences as set forth in SEQ ID NO: 72, 73 and 18, respectively.

In some embodiments,
a) said first antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 74, 93, and 66, respectively, and the LCDR1, LCDR2, and LCDR3 sequences comprise the sequences as set forth in SEQ ID NO: 94, 95, and 8, respectively; and
b) said second antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 75, 13, and 71, respectively, and the LCDR1, LCDR2, and LCDR3 sequences comprises the sequences as set forth in SEQ ID NO: 16, 17 and 18, respectively.

In some embodiments,
a) said first antigen-binding region binding to EpCAM comprises a heavy chain variable region (VH) comprising the HCDR1, HCDR2, and HCDR3 sequences of SEQ ID NO: 27, positions 1 to 115 and a light chain variable region (VL) comprising the LCDR1, LCDR2, and LCDR3 sequences of SEQ ID NO: 28, positions 1 to 108; and
b) said second antigen-binding region binding to CD137 comprises a heavy chain variable region (VH) comprising the HCDR1, HCDR2, and HCDR3 sequences of SEQ ID NO: 11 and a light chain variable region (VL) comprising the LCDR1, LCDR2, and LCDR3 sequences of SEQ ID NO: 15.

In some embodiments,
a) said first antigen-binding region binding to EpCAM comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 27, positions 1 to 115 and the VL comprises an amino acid sequence having at least 80%, at least 85%, at least 90%, at least 95%, at least 97%, or at least 99% identity to the amino acid sequence as set forth in SEQ ID NO: 28, positions 1 to 108; and
b) said second antigen-binding region binding to CD137 comprises a heavy chain variable region (VH) and a light chain variable region (VL), wherein the VH comprises an amino acid sequence having at least 80%, at least 85%, at least 90%, at least 95%, at least 97%, or at least 99% identity to the amino acid sequence as set forth in SEQ ID NO: 11 and the VL comprises an amino acid sequence having at least 80%, at least 85%, at least 90%, at least 95%, at least 97%, or at least 99% identity to the amino acid sequence as set forth in SEQ ID NO: 15.

In some embodiments,
a) said first antigen-binding region binding to EpCAM comprises a heavy chain variable region (VH) and a light chain variable region (VL), wherein the VH comprises the sequence as set forth in SEQ ID NO: 27, positions 1 to 115 and the VL comprises the sequence as set forth in SEQ ID NO: 28, positions 1 to 108; and
b) said second antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

In some embodiments, said first antigen-binding region binding to EpCAM comprises heavy and light chain variable regions of an antibody which competes for EpCAM binding with and/or has the specificity for EpCAM of an antibody comprising a heavy chain variable region or a light chain variable region, or a combination thereof of a first antigen-binding region binding to EpCAM as set forth above and said second antigen-binding region binding to CD137 comprises heavy and light chain variable regions of an antibody which competes for CD137 binding with and/or has the specificity for CD137 of an antibody comprising a heavy chain variable region or a light chain variable region, or a combination thereof of a second antigen-binding region binding to CD137 as set forth above.

In some embodiments, a variable region comprises three complementarity determining regions (CDR1, CDR2, and CDR3) and four framework regions (FR1, FR2, FR3, and FR4).

In some embodiments, said complementarity determining regions and said framework regions are arranged from amino-terminus to carboxy-terminus in the following order: FR1, CDR1, FR2, CDR2, FR3, CDR3, FR4.

In some embodiments, the binding agent is in the format of a full-length antibody or an antibody fragment.

In some embodiments, the binding agent is a multispecific such as a bispecific binding agent.

In some embodiments, the binding agent is a multispecific such as a bispecific antibody.

In some embodiments, the binding agent comprises
(i) a first heavy chain variable region (VH) and a first light chain variable region (VL), wherein said first heavy chain variable region (VH) and said first light chain variable region (VL) form said first antigen-binding region binding to EpCAM; and (ii) a second heavy chain variable region (VH) and a second light chain variable region (VL), wherein said second heavy chain variable region (VH) and said second light chain variable region (VL) form said second antigen-binding region binding to CD137.

In some embodiments, the binding agent comprises i) a polypeptide comprising a first heavy chain variable region (VH) and a first heavy chain constant region (CH), and a polypeptide comprising a first light chain variable region (VL) and a first light chain constant region (CL), wherein said first heavy chain variable region (VH) and said first light chain variable region (VL) form said first antigen-binding region binding to EpCAM; and ii) a polypeptide comprising a second heavy chain variable region (VH) and a second heavy chain constant region (CH), and a polypeptide comprising a second light chain variable region (VL) and a second light chain constant region (CL), wherein said second heavy chain variable region (VH) and said second light chain variable region (VL) form said second antigen-binding region binding to CD137.

In some embodiments, the binding agent is an antibody comprising a first binding arm comprising said first antigen-binding region binding to EpCAM and a second binding arm comprising said second antigen-binding region binding to CD137, wherein the first binding arm comprises i) a polypeptide comprising a first heavy chain variable region (VH) and a first heavy chain constant region (CH), and ii) a polypeptide comprising a first light chain variable region (VL) and a first light chain constant region (CL); and the second binding arm comprises iii) a polypeptide comprising a second heavy chain variable region (VH) and a second heavy chain constant region (CH), and iv) a polypeptide comprising a second light chain variable region (VL) and a second light chain constant region (CL).

In some embodiments, the binding agent is an antibody comprising a first binding arm comprising said first antigen-binding region binding to EpCAM and a second binding arm comprising said second antigen-binding region binding to CD137, wherein the first binding arm comprises i) a first heavy chain comprising a first heavy chain variable region (VH) and a first heavy chain constant region (CH), and ii) a first light chain comprising a first light chain variable region (VL) and a first light chain constant region (CL); and the second binding arm comprises i) a second heavy chain comprising a second heavy chain variable region (VH) and a second heavy chain constant region (CH); and ii) a second light chain comprising a second light chain variable region (VL) and a second light chain constant region (CL).

In some embodiments, the first binding arm is derived from a full-length antibody. In some embodiments, the first binding arm is derived from a monoclonal antibody. In some embodiments, the first binding arm is derived from a full-length IgG1, λ (lambda) or IgG1, κ (kappa) antibody. In some embodiments, the second binding arm is derived from a full-length antibody. In some embodiments, the second binding arm is derived from a monoclonal antibody. In some embodiments, the second binding arm is derived from a full-length IgG1, λ (lambda) or IgG1, κ (kappa) antibody. In some embodiments, the first and second binding arms are derived from full-length antibodies, such as from full-length IgG1, λ (lambda) or IgG1, κ (kappa) antibodies. In some embodiments, the first and second binding arms are derived from monoclonal antibodies.

In some embodiments, each of the first and second heavy chain constant regions (CHs) comprises one or more of a constant heavy chain 1 (CH1) region, a hinge region, a constant heavy chain 2 (CH2) region and a constant heavy chain 3 (CH3) region, preferably at least a hinge region, a CH2 region and a CH3 region.

In some embodiments, each of the first and second heavy chain constant regions (CHs) comprises a CH3 region and wherein the two CH3 regions comprise asymmetrical mutations.

In some embodiments, in said first heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and in said second heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and wherein said first and said second heavy chains are not substituted in the same positions.

In some embodiments, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain constant region (CH), and the amino acid in the position corresponding to F405 in a human IgG1 heavy chain according to EU numbering is L in said second heavy chain constant region (CH).

In some embodiments, said binding agent induces Fc-mediated effector function to a lesser extent compared to another antibody comprising the same first and second antigen binding regions and two heavy chain constant regions (CHs) comprising human IgG1 hinge, CH2 and CH3 regions.

In some embodiments, said first and second heavy chain constant regions (CHs) are modified so that the antibody induces Fc-mediated effector function to a lesser extent compared to an antibody which is identical except for comprising non-modified first and second heavy chain constant regions (CHs).

In some embodiments, each of said non-modified first and second heavy chain constant regions (CHs) comprises the amino acid sequence set forth in SEQ ID NO: 47.

In some embodiments, said Fc-mediated effector function is measured by binding to Fcγ receptors, binding to C1q, or induction of Fc-mediated crosslinking of Fcγ receptors.

In some embodiments, said Fc-mediated effector function is measured by binding to C1q.

In some embodiments, said first and second heavy chain constant regions have been modified so that binding of C1q to said antibody is reduced compared to a wild-type antibody, preferably reduced by at least 70%, at least 80%, at least 90%, at least 95%, at least 97%, or 100%, wherein C1q binding is preferably determined by ELISA.

In some embodiments, in at least one of said first and second heavy chain constant regions (CHs), one or more amino acids in the positions corresponding to positions L234, L235, D265, N297, P331, and G236 in a human IgG1 heavy chain according to EU numbering, are not L, L, D, N, P, and G, respectively.

In some embodiments, the positions corresponding to positions L234 and L235 in a human IgG1 heavy chain according to EU numbering are F and E, respectively, in said first and second heavy chains.

In some embodiments, the positions corresponding to positions L234, L235, and D265 in a human IgG1 heavy chain according to EU numbering are F, E, and A, respectively, in said first and/or second heavy chain constant regions (HCs) and/or the positions corresponding to positions L234, L235, and G236 in a human IgG1 heavy chain according to EU numbering are F, E, and R, respectively, in said first and/or second heavy chain constant regions (HCs).

In some embodiments,
(i) the positions corresponding to positions L234, L235, and D265 in a human IgG1 heavy chain according to EU numbering are F, E, and A, respectively, in both said first and second heavy chain constant regions;
(ii) the positions corresponding to positions L234, L235, and G236 in a human IgG1 heavy chain according to EU numbering are F, E, and R, respectively, in both said first and second heavy chain constant regions; or
(iii) the positions corresponding to positions L234, L235, and D265 in a human IgG1 heavy chain according to EU numbering are F, E, and A, respectively, in one of said first and second heavy chain constant regions and the positions corresponding to positions L234, L235, and G236 in a human IgG1 heavy chain according to EU numbering are F, E, and R, respectively, in the other of said first and second heavy chain constant regions.

In some embodiments, the positions corresponding to positions L234 and L235 in a human IgG1 heavy chain according to EU numbering of both the first and second heavy chain constant regions are F and E, respectively, and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein the position corresponding to F405 in a human IgG1 heavy chain according to EU numbering of the first heavy chain constant region is L, and the position corresponding to K409 in a human IgG1 heavy chain according to EU numbering of the second heavy chain constant region is R.

In some embodiments, the constant region of said first and/or second heavy chain comprises an amino acid sequence an amino acid sequence having at least 80%, at least 85%, at least 90%, at least 95%, at least 97%, or at least 99% identity to the amino acid sequence set forth in SEQ ID NO: 47.

In some embodiments,
a) the constant region of said first heavy chain comprises the amino acid sequence set forth in SEQ ID NO: 54; and
b) the constant region of said second heavy chain comprises the amino acid sequence set forth in SEQ ID NO: 52.

In some embodiments, said binding agent comprises a kappa (κ) light chain constant region.

In some embodiments, said binding agent comprises a lambda (λ) light chain constant region.

In some embodiments, said first light chain constant region is a kappa (κ) light chain constant region or a lambda (λ) light chain constant region.

In some embodiments, said second light chain constant region is a kappa (κ) light chain constant region or a lambda (λ) light chain constant region.

In some embodiments,
(i) said first light chain constant region and said second light chain constant region are kappa (κ) light chain constant regions,
(ii) said first light chain constant region and said second light chain constant region are lambda (λ) light chain constant regions,
(iii) said first light chain constant region is a kappa (κ) light chain constant region and said second light chain constant region is a lambda (λ) light chain constant region, or
(iv) said first light chain constant region is a lambda (λ) light chain constant region and said second light chain constant region is a kappa (κ) light chain constant region.

In some embodiments, the kappa (κ) light chain comprises an amino acid sequence having at least 80%, at least 85%, at least 90%, at least 95%, at least 97%, or at least 99% identity to the amino acid sequence set forth in SEQ ID NO:55.

In some embodiments, the lambda (λ) light chain comprises an amino acid sequence having at least 80%, at least 85%, at least 90%, at least 95%, at least 97%, or at least 99% identity to the amino acid sequence set forth in SEQ ID NO: 56.

In some embodiments, the binding agent is of an isotype selected from the group consisting of IgG1, IgG2, IgG3, and IgG4. In one embodiment, the isotype is selected from the group consisting of human IgG1, human IgG2, human IgG3 and human IgG4.

In some embodiments, the binding agent is a full-length IgG1 antibody.

In some embodiments, the binding agent is an antibody of the IgG1m(f) allotype.

In some embodiments, the binding agent is an antibody comprising a first binding arm comprising said first antigen-binding region binding to EpCAM and a second binding arm comprising said second antigen-binding region binding to CD137, wherein the first binding arm comprises
- i) a polypeptide comprising a first heavy chain variable region (VH) and a first heavy chain constant region (CH), and
- ii) a polypeptide comprising a first light chain variable region (VL) and a first light chain constant region (CL),
wherein the first VH comprises first HCDR1, HCDR2, and HCDR3 sequences and the first VL comprises first LCDR1, LCDR2, and LCDR3 sequences, wherein the first HCDR1, HCDR2, and HCDR3 sequences comprise the sequences as set forth in SEQ ID NO: 2, 93, and 4, respectively, and the first LCDR1, LCDR2, and LCDR3 sequences comprise the sequences as set forth in SEQ ID NO: 94, 95, and 8, respectively;
and the second binding arm comprises
- iii) a polypeptide comprising a second heavy chain variable region (VH) and a second heavy chain constant region (CH), and
- iv) a polypeptide comprising a second light chain variable region (VL) and a second light chain constant region (CL),
wherein the second VH comprises second HCDR1, HCDR2, and HCDR3 sequences and the second VL comprises second LCDR1, LCDR2, and LCDR3 sequences, wherein the second HCDR1, HCDR2, and HCDR3 sequences comprise the sequences as set forth in SEQ ID NO: 12, 13, and 14, respectively, and the second LCDR1, LCDR2, and LCDR3 sequences comprise the sequences as set forth in SEQ ID NO: 16, 17, and 18, respectively;
wherein positions L234, L235, and G236 in a human IgG1 heavy chain according to EU numbering are F, E, and R, respectively, in the first CH and positions L234, L235, and D265 in a human IgG1 heavy chain according to EU numbering are F, E, and A in the second CH; and
wherein the amino acid in the position corresponding to F405 in a human IgG1 heavy chain according to EU numbering is L in the first CH and the amino acid in the position corresponding to K409 in a human IgG1 heavy chain according to EU numbering is R in the second CH.

In some embodiments, the binding agent comprises
- i) a first heavy chain comprising an amino acid sequence having at least 80%, at least 85%, at least 90%, at least 95%, at least 97%, or at least 99% identity to the amino acid sequence set forth in SEQ ID NO: 27,
- ii) a first light chain comprising an amino acid sequence having at least 80%, at least 85%, at least 90%, at least 95%, at least 97%, or at least 99% identity to the amino acid sequence set forth in SEQ ID NO: 28,
- iii) a second heavy chain comprising an amino acid sequence having at least 80%, at least 85%, at least 90%, at least 95%, at least 97%, or at least 99% identity to the amino acid sequence set forth in SEQ ID NO: 19; and
- iv) a second light chain comprising an amino acid sequence having at least 80%, at least 85%, at least 90%, at least 95%, at least 97%, or at least 99% identity to the amino acid sequence set forth in SEQ ID NO: 20.

In some embodiments, the binding agent comprises
- i) a first heavy chain comprising the amino acid sequence set forth in SEQ ID NO: 27,
- ii) a first light chain comprising the amino acid sequence set forth in SEQ ID NO: 28,
- iii) a second heavy chain comprising the amino acid sequence set forth in SEQ ID NO: 19; and
- iv) a second light chain comprising the amino acid sequence set forth in SEQ ID NO: 20.

In a further aspect, the present disclosure provides a binding agent comprising a first binding arm comprising a first antigen-binding region and a first heavy chain constant region comprising a constant heavy chain 2 (CH2) region and a second binding arm comprising a second antigen-binding region and a second heavy chain constant region comprising a constant heavy chain 2 (CH2) region, wherein at least one of said first and second antigen-binding regions binds to EpCAM, and wherein the positions corresponding to positions L234, L235, and G236 in a human IgG1 heavy chain according to EU numbering are F, E, and R, respectively, in at least one of said first and second heavy chain constant regions.

In some embodiments, the positions corresponding to positions L234, L235, and G236 in a human IgG1 heavy chain according to EU numbering are F, E, and R, respectively, in said first and/or second heavy chain constant regions.

In some embodiments, the positions corresponding to positions L234, L235, and G236 in a human IgG1 heavy chain according to EU numbering are F, E, and R, respectively, in both of said first and/or second heavy chain constant regions.

In some embodiments, the positions corresponding to positions L234, L235, and G236 in a human IgG1 heavy chain according to EU numbering are F, E, and R, respectively, in one of said first or second heavy chain constant regions and the positions corresponding to positions L234, L235, and D265 in a human IgG1 heavy chain according to EU numbering are F, E, and A, respectively, in the other of said first or second heavy chain constant regions.

In some embodiments, both of said first and second antigen-binding regions binds to EpCAM.

In some embodiments, one of said first and second antigen-binding regions binds to EpCAM and the other of said first and second antigen-binding regions binds to an antigen other than EpCAM.

In some embodiments, one of said first and second antigen-binding regions binds to EpCAM and the other of said first and second antigen-binding regions binds to CD137.

In a further aspect, the present disclosure provides a binding agent comprising a first binding arm comprising a first antigen-binding region and a first heavy chain constant region comprising a constant heavy chain 2 (CH2) region and a second binding arm comprising a second antigen-binding region and a second heavy chain constant region comprising a constant heavy chain 2 (CH2) region, wherein at least one of said first and second antigen-binding regions binds to CD137, and wherein the positions corresponding to positions L234, L235, and G236 in a human IgG1 heavy chain according to EU numbering are F, E, and R, respectively, in at least one of said first and second heavy chain constant regions.

In some embodiments, the positions corresponding to positions L234, L235, and G236 in a human IgG1 heavy chain according to EU numbering are F, E, and R, respectively, in said first and/or second heavy chain constant regions.

In some embodiments, the positions corresponding to positions L234, L235, and G236 in a human IgG1 heavy chain according to EU numbering are F, E, and R, respectively, in both of said first and/or second heavy chain constant regions.

In some embodiments, the positions corresponding to positions L234, L235, and G236 in a human IgG1 heavy chain according to EU numbering are F, E, and R, respectively, in one of said first or second heavy chain constant regions and the positions corresponding to positions L234, L235, and D265 in a human IgG1 heavy chain according to EU numbering are F, E, and A, respectively, in the other of said first or second heavy chain constant regions.

In some embodiments, both of said first and second antigen-binding regions binds to CD137.

In some embodiments, one of said first and second antigen-binding regions binds to CD137 and the other of said first and second antigen-binding regions binds to an antigen other than CD137.

In some embodiments, one of said first and second antigen-binding regions binds to CD137 and the other of said first and second antigen-binding regions binds to EpCAM.

In some embodiments, said antigen-binding region binding to EpCAM and/or said antigen-binding region binding to CD137 is as described herein.

In some embodiments, the EpCAM is human EpCAM.

In some embodiments, said antigen-binding region binding to EpCAM binds to EpCAM expressed on tumor cells.

In some embodiments, said antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 6, 7, and 8, respectively.

In some embodiments, said antigen-binding region binding to EpCAM comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 1 and the VL comprises a sequence having at least 80%, at least 85%, at least 90%, at least 95%, at least 97%, at least 99%, or 100% identity to the sequence as set forth in SEQ ID NO: 5.

In some embodiments, said antigen-binding region binding to EpCAM comprises a heavy chain variable region (VH) and a light chain variable region (VL), wherein the VH comprises the sequence as set forth in SEQ ID NO: 1 and the VL comprises the sequence as set forth in SEQ ID NO: 5.

In some embodiments, the CD137 is human CD137.

In some embodiments, said antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments, said antigen-binding region binding to CD137 comprises a heavy chain variable region (VH) and a light chain variable region (VL), wherein the VH comprises a sequence having at least 80%, at least 85%, at least 90%, at least 95%, at least 97%, at least 99%, or 100% identity to the sequence as set forth in SEQ ID NO: 11 and the VL comprises a sequence having at least 80%, at least 85%, at least 90%, at least 95%, at least 97%, at least 99%, or 100% identity to the sequence as set forth in SEQ ID NO: 15.

In some embodiments, said antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

In some embodiments, the binding agent comprises an antigen-binding region binding to EpCAM and antigen-binding region binding to CD137, wherein
  a) said antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 6, 7, and 8, respectively; and
  b) said antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively.

In some embodiments, the binding agent is a bivalent binding agent.

In some embodiments, the binding agent comprises an Fc region.

In some embodiments, the binding agent is in the format of an antibody, e.g., a full-length antibody.

In some embodiments, the binding agent comprises a first binding arm comprising an antigen-binding region binding to EpCAM and a second binding arm comprising an antigen-binding region binding to CD137, wherein
  the first binding arm comprises
  i) a polypeptide comprising a first heavy chain variable region (VH) and a first heavy chain constant region (CH), and
  ii) a polypeptide comprising a first light chain variable region (VL) and a first light chain constant region (CL);
  and the second binding arm comprises
  iii) a polypeptide comprising a second heavy chain variable region (VH) and a second heavy chain constant region (CH), and
  iv) a polypeptide comprising a second light chain variable region (VL) and a second light chain constant region (CL).

In some embodiments,
the first VH comprises first HCDR1, HCDR2, and HCDR3 sequences and the first VL comprises first LCDR1, LCDR2, and LCDR3 sequences, wherein the first HCDR1, HCDR2, and HCDR3 sequences comprise the sequences as set forth in SEQ ID NO: 2, 3, and 4, respectively, and the first LCDR1, LCDR2, and LCDR3 sequences comprise the sequences as set forth in SEQ ID NO: 6, 7, and 8, respectively; and
the second VH comprises second HCDR1, HCDR2, and HCDR3 sequences and the second VL comprises second LCDR1, LCDR2, and LCDR3 sequences, wherein the second HCDR1, HCDR2, and HCDR3 sequences comprise the sequences as set forth in SEQ ID NO: 12, 13, and 14, respectively, and the second LCDR1, LCDR2, and LCDR3 sequences comprise the sequences as set forth in SEQ ID NO: 16, 17, and 18, respectively.

In some embodiments,
the first VH comprises an amino acid sequence having at least 80%, at least 85%, at least 90%, at least 95%, at least 97%, or at least 99% identity to the amino acid sequence as set forth in SEQ ID NO: 1 and the first VL comprises an amino acid sequence having at least 80%, at least 85%, at least 90%, at least 95%, at least 97%, or at least 99% identity to the amino acid sequence as set forth in SEQ ID NO: 5; and
the second VH comprises an amino acid sequence having at least 80%, at least 85%, at least 90%, at least 95%, at least 97%, or at least 99% identity to the amino acid sequence as set forth in SEQ ID NO: 11 and the second VL comprises an amino acid sequence having at least 80%, at least 85%, at least 90%, at least 95%, at least 97%, or at least 99% identity to the amino acid sequence as set forth in SEQ ID NO: 15.

In some embodiments,
the first VH comprises the amino acid sequence as set forth in SEQ ID NO: 1 and the first VL comprises the amino acid sequence as set forth in SEQ ID NO: 5; and
the second VH comprises the amino acid sequence as set forth in SEQ ID NO: 11 and the second VL comprises the amino acid sequence as set forth in SEQ ID NO: 15.

In some embodiments, each of the first and second heavy chain constant regions (CHs) comprises a CH3 region and wherein the two CH3 regions comprise asymmetrical mutations.

In some embodiments, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain constant region (CH), and the amino acid in the position corresponding to F405 in a human IgG1 heavy chain according to EU numbering is L in said second heavy chain constant region (CH).

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In some embodiments, the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein the position corresponding to F405 in a human IgG1 heavy chain according to EU numbering of the first heavy chain constant region is L, and the position corresponding to K409 in a human IgG1 heavy chain according to EU numbering of the second heavy chain constant region is R.

In a further aspect, the present disclosure provides a polynucleotide or a set of polynucleotides encoding the binding agent as set forth herein.

In a further aspect, the present disclosure provides a pharmaceutical composition comprising the binding agent as set forth herein or the polynucleotide as set forth herein.

In a further aspect, the present disclosure provides a method for treating a subject comprising administering to the subject the binding agent as set forth herein, the polynucleotide as set forth herein or the pharmaceutical composition as set forth herein.

In some embodiments, the method is a method for treating or preventing cancer in a subject.

In some embodiments, the subject is a human.

In a further aspect, the present disclosure provides the binding agent as set forth herein, the polynucleotide as set forth herein or the pharmaceutical composition as set forth herein for pharmaceutical use e.g. for use as a medicament.

In some embodiments, the binding agent as set forth herein, the polynucleotide as set forth herein or the pharmaceutical composition as set forth herein is for use in a therapeutic or prophylactic treatment of a disease or disorder.

In some embodiments, the disease or disorder is cancer.

In a further aspect, the present disclosure provides the binding agent as set forth herein, the polynucleotide as set forth herein or the pharmaceutical composition as set forth herein for treating or preventing cancer in a subject.

In some embodiments, the subject is a human.

BRIEF DESCRIPTION OF THE FIGURES

FIG. 1 shows the relative EpCAM expression on T84, DiFi, HPAF-II, NCI-N87, Calu-3, NCI-H747, and A549 tumor cell lines as determined by flow cytometry. Data shown is Δ geometric mean fluorescence intensity (gMFI) for each tumor cell line calculated as: Geomean fluorescence intensity (APC) of the EpCAM antibody-Geomean fluorescence (APC) of the non-binding control antibody.

FIG. 3: Binding of EpCAM antibodies to full length human, cynomolgus monkey or mouse EpCAM transfected into CHO-S cells.

Binding of monovalent and bivalent EpCAM antibodies was analysed using CHO-S cells transiently transfected with full length human, cynomolgus monkey or mouse EpCAM. As negative control, binding to non-transfected CHO-WT cells was evaluated. Data are presented as geomean fluorescence intensity (gMFI) R-PE values of two technical replicates±SD. A. Binding of IgG1-EpCAM-UBS-54-FEAR, IgG1-EpCAM-A37-FEAR, IgG1-EpCAM-052-FEAR and IgG1-EpCAM-343-A3. B. Binding of bsIgG1-b12-FEAL/EpCAM-UBS-54-FEAR, bsIgG1-EpCAM-A37-FERL/b12-FEAR, bsIgG1-b12-FEAL/EpCAM-052-FEAR, and bsIgG1-b12-FEAL/EpCAM-323-A3-FEAR.

Figure 4:
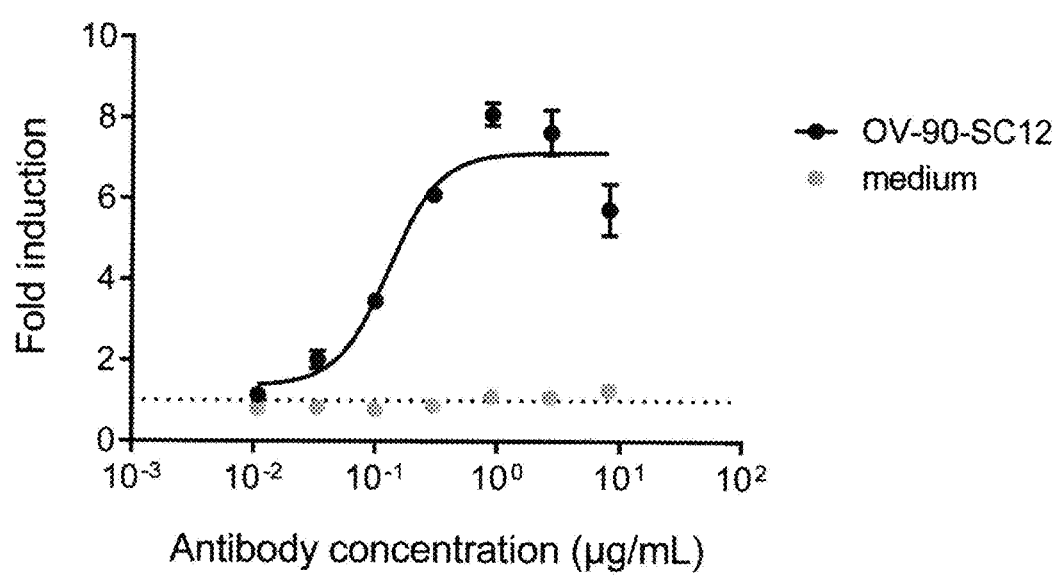

FIG. 4: Induction of 4-1BB-dependent luciferase activity by an EpCAMx4-1BB bispecific antibody in a cell-based reporter assay.

HEK293_NKF_h4-1BB_gfp_luc reporter cells were either co-cultured with EpCAM-expressing OV-90-SC12 cells, or cultured alone (medium), in the presence of serial dilutions of BsIgG1-CD137-005-FEAR/EpCAM-323-A3-FEAL overnight. Luciferase activity was quantified by luminescence measurements. Fold-induction of luciferase activity relative to cultures without antibody (dotted line) is shown. Error bars depict SD of duplicate wells. Data from one representative experiment out of three are shown.

FIG. 5: Enhancement of PBMC proliferation in vitro by EpCAMx4-1BB bispecific antibodies in PBMC-DiFi cell co-cultures.

EpCAMx4-1BB bispecific antibodies were tested in an in vitro PBMC proliferation assay using EpCAM-expressing DiFi cells in co-culture with CFSE-labeled PBMCs. Cells were cultured in the presence of anti-CD3 (0.1 µg/mL) with or without the addition of EpCAMx4-1BB or EpCAMxb12 bispecific antibodies or non-binding control IgG1-b12-FEAL at the indicated concentrations for 96 h. The number of CFSE-positive cells was extracted and used to calculate the division index. Data shown are the mean division index±SD of duplicate measurements obtained from one representative experiment. A. Division index of PBMC proliferation induced by bsIgG1-b12-FEAL/EpCAM-UBS54-FEAR (closed triangles) and bsIgG1-CD137-009-HC7LC2-FEAL/EpCAM-UBS54-FEAR (closed squares) antibodies. B. Division index of PBMC proliferation induced by bsIgG1-b12-FEAL/EpCAM-A37-FEAR (closed triangles) and bsIgG1-CD137-009-HC7LC2-FEAL/EpCAM-A37-FEAR (closed squares) antibodies. C. Division index of PBMC proliferation induced by bsIgG1-b12-FEAL/EpCAM-052-FEAR (closed triangles) and bsIgG1-CD137-009-HC7LC2-FEAL/EpCAM-052-FEAR (closed squares) antibodies. D. Division index of PBMC proliferation induced by bsIgG1-b12-FEAL/EpCAM-323-A3-FEAR (closed triangles) and bsIgG1-CD137-009-HC7LC2-FEAL/EpCAM-323-A3-FEAR (closed squares) antibodies.

Figure 6:
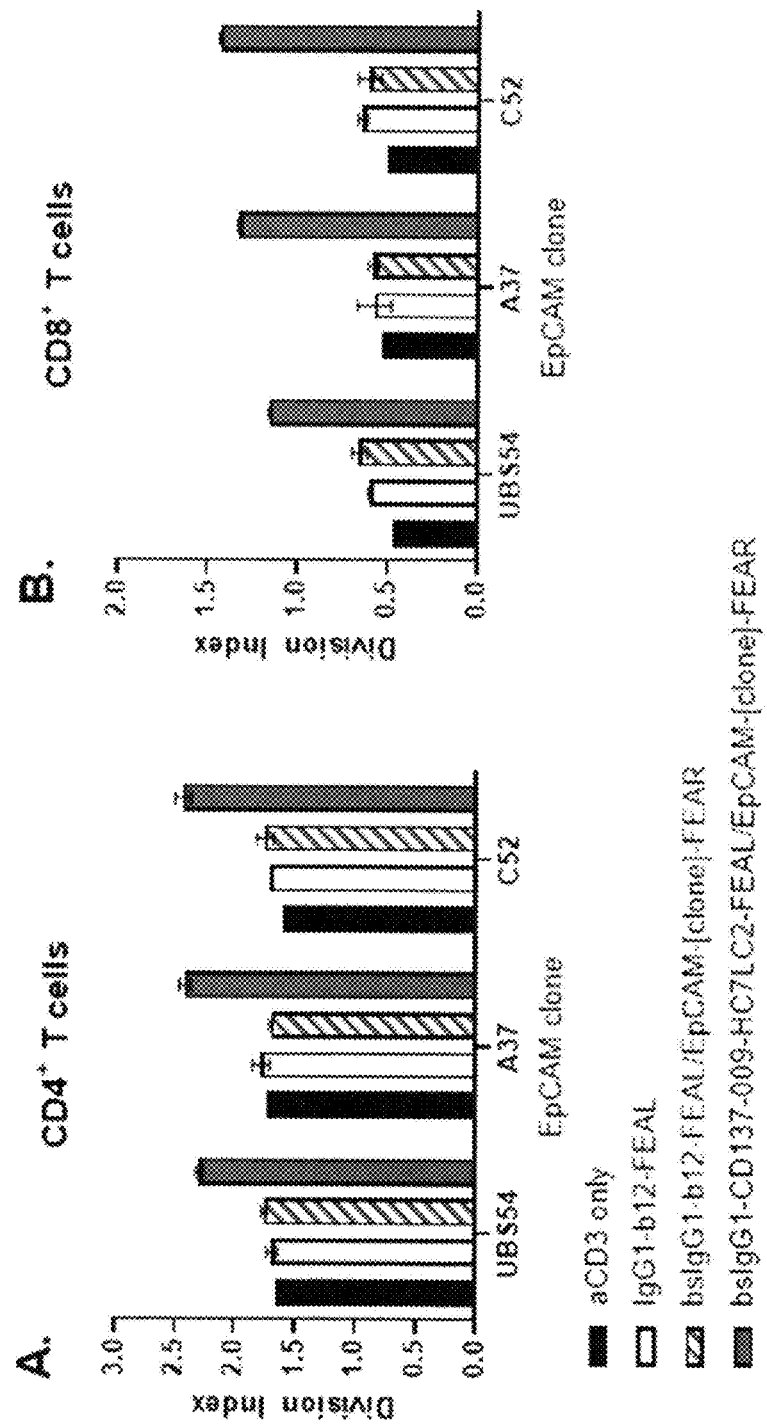

FIG. 6: Enhancement of CD4+ and CD8+ T-cell proliferation in vitro by EpCAMx4-1BB bispecific antibodies in PBMC-DiFi cell co-cultures.

EpCAMx4-1BB bispecific antibodies were tested in an in vitro T-cell proliferation assay using EpCAM-expressing DiFi cells in co-culture with CFSE-labeled PBMCs. Cells were cultured in the presence of anti-CD3 (0.1 µg/mL) with or without the addition of EpCAMx4-1BB (grey bars) or EpCAMxb12 (striped bars) bispecific antibodies (10 µg/mL) or non-binding control IgG1-b12-FEAL (10 µg/mL; open bars) for 96 h. The number of CFSE-positive cells was evaluated as a measure of absolute CD4+ (A) or CD8+ (B) T-cell counts by flow cytometry and the division index were calculated. Data shown are the mean division index±SD of duplicate measurements obtained from one representative experiment.

Figure 7:
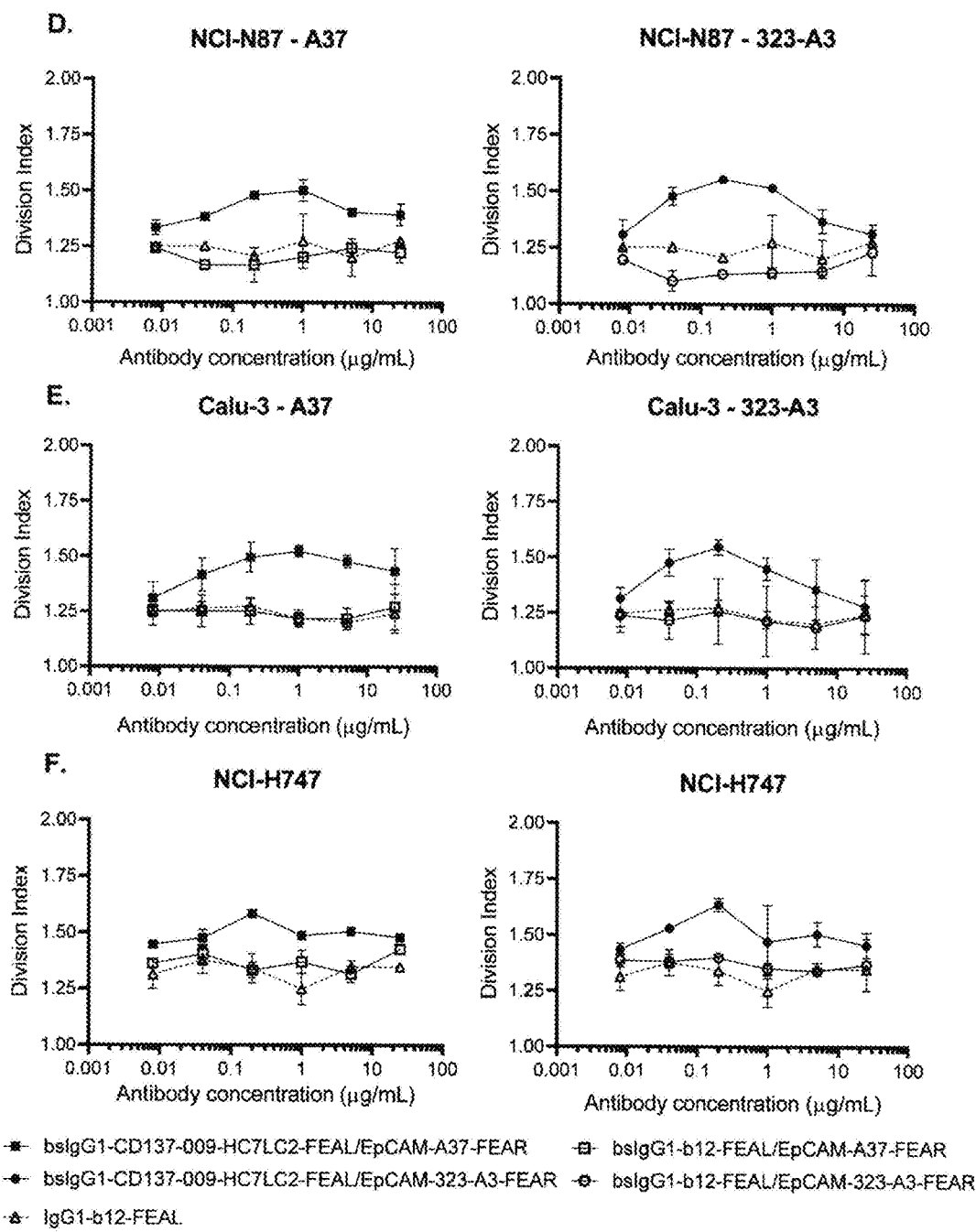

FIG. 7: Enhancement of PBMC proliferation in vitro by EpCAMx4-1BB bispecific antibodies in PBMC-tumor cell co-cultures using various tumor cell lines.

EpCAMx4-1BB bispecific antibodies were tested in an in vitro PBMC proliferation assay using EpCAM-expressing T84, DiFi, HPAF-II, NCI-N87, Calu-3 or NCI-H747 tumor cells in co-culture with CFSE-labeled PBMCs. Cells were cultured in the presence of anti-CD3 (0.1 µg/mL) and EpCAMx4-1BB or EpCAMxb12 bispecific antibodies or non-binding control IgG1-b12-FEAL at the indicated concentrations for 96 h. The number of CFSE-positive cells was evaluated as a measure of absolute PBMC counts by flow cytometry and the division index was calculated. Data shown are the mean division index±SD of duplicate measurements obtained from one representative experiment using (A) PBMC-T84 co-cultures, (B) PBMC-DiFi co-cultures, (C) PBMC-HPAF-II co-cultures, (D) PBMC-NCI-N87 co-cultures, (E) PBMC-Calu-3 co-cultures or (F) PBMC-NCI-H747 co-cultures.

Figure 8:
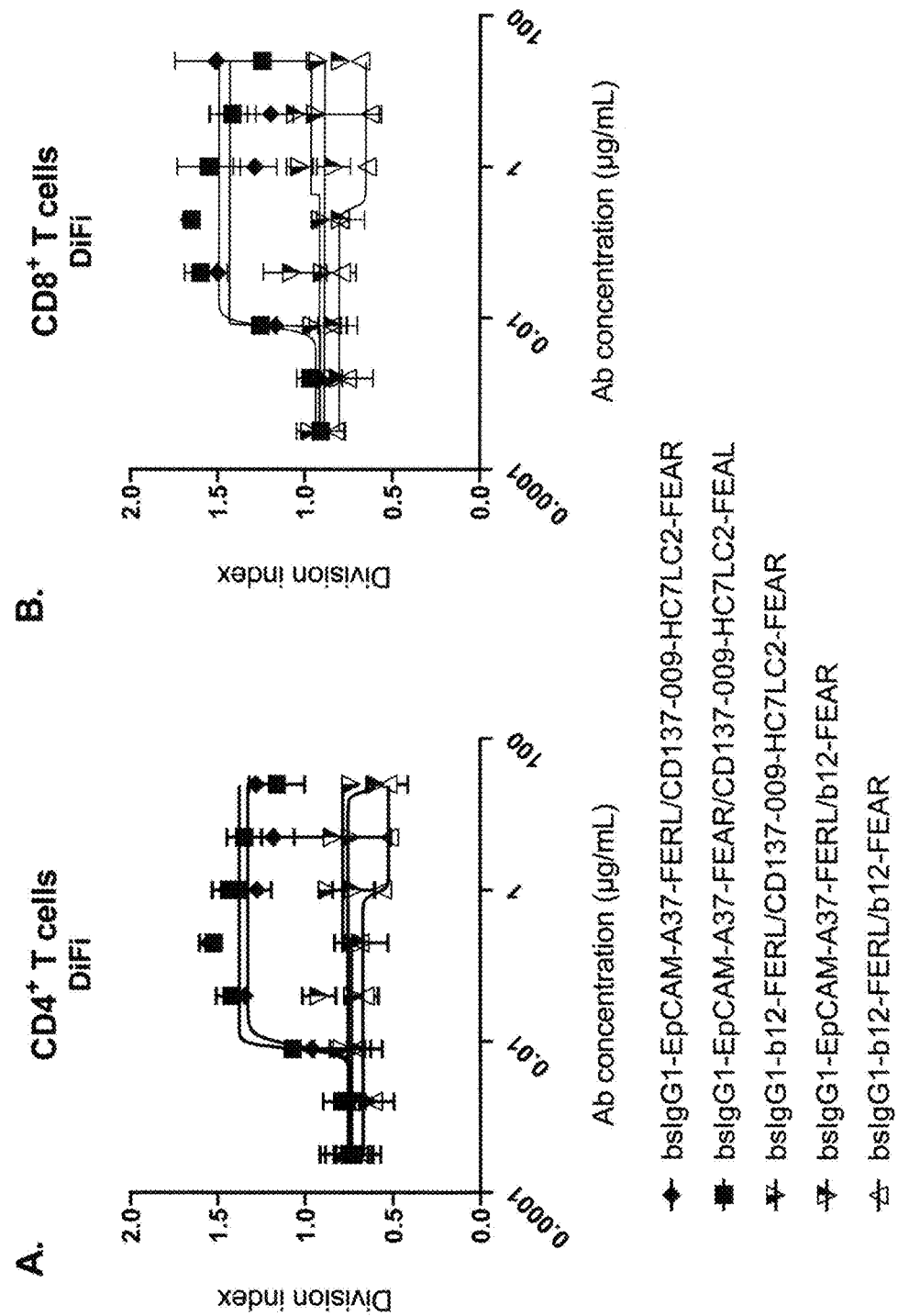

FIG. 8: Enhancement of human CD4+ and CD8+ T-cell in vitro proliferation in DiFi tumor cell co-cultures by EpCAMx4-1BB bispecific antibodies with Fc-domains containing inertness mutations.

EpCAMx4-1BB bispecific antibodies were tested in an in vitro PBMC proliferation assay using EpCAM-expressing DiFi tumor cells in co-culture with CFSE-labeled human PBMCs. Cells were cultured in the presence of anti-CD3 (0.1 µg/mL) and EpCAM-FERLx4-1BB-FEAR (closed diamonds), EpCAM-FEARx4-1BB-FEAL (closed squares), b12-FERLx4-1BB-FEAR (left-half-closed triangles), EpCAM-FERLxb12-FEAR (right-half-closed triangles) bispecific antibodies or non-binding control b12-FERLxb12-FEAR (open triangles) at the indicated concentrations for 96 h. The number of CFSE-positive (A) CD4+ and (B) CD8+ T cells was evaluated as a measure of absolute T-cell counts by flow cytometry and the division index was calculated. Data shown are non-linear 4-parameter variable slope fits of the mean division index±SD of duplicate measurements obtained from one representative experiment using PBMC-DiFi co-cultures.

Figure 9:
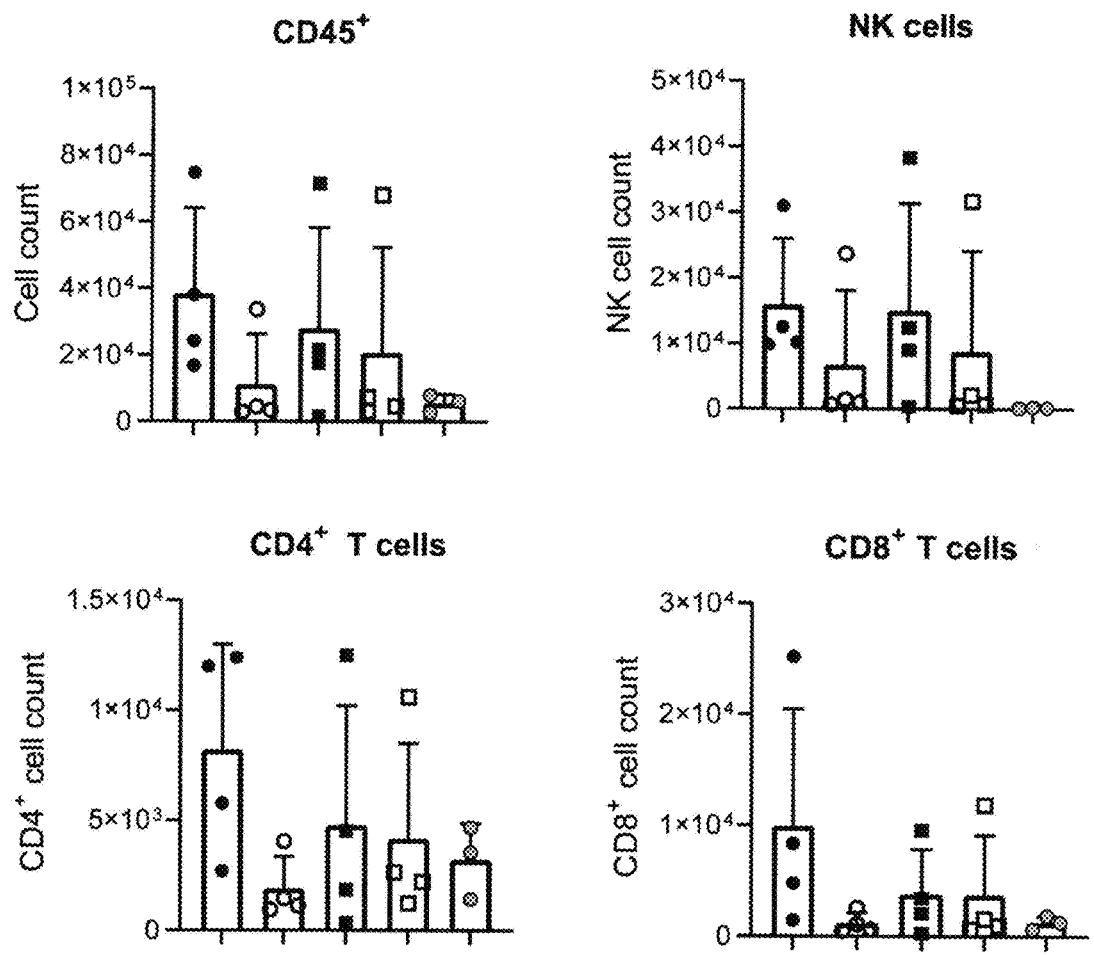

FIG. 9: Enhancement of tumor-infiltrating lymphocyte expansion by EpCAMx4-1BB bispecific antibodies in patient-derived tumor specimens ex vivo.

Tumor tissues resected from non-small cell lung cancer patients were cut into pieces of 1-2 mm$^3$ and cultured in the presence of IL-2 (50 U/mL) and 0.2-5 µg/mL BsIgG1-CD137-009-HC7LC2-FEAL/EpCAM-A37-FEAR or BsIgG1-CD137-009-HC7LC2-FEAL/EpCAM-323-A3-FEAR, or with IL-2 only (w/o Ab) for 14 days. IL-2 concentrations were reduced stepwise on days 7 and 10, to 33 U/mL and 15 U/mL, respectively. Absolute cell numbers after culture were determined by flow cytometry. Total TIL, NK cell, CD8+, and CD4+ T cell numbers are shown for cultures derived from one exemplary patient, out of two patients analyzed. Data from 3-4 individual replicates and average of replicates is shown. Error bars depict SD.

FIG. 10: Antitumor activity of an EpCAMx4-1BB bispecific antibody in hEpCAM mice bearing hEpCAM-overexpressing MC38 tumors.

Mice transgenic for human EpCAM protein (hEpCAM mice) were inoculated with 5×10$^5$ MC38 tumor cells overexpressing human EpCAM protein (MC38_hEpCAM). Treatment was commenced when tumors reached an average size of approximately 30 mm$^3$. Mice were treated intraperitoneally with 100 µg BsIgG2amm-EpCAM-323-A3-AALT/m4-1BB-3H3-AAKR or the negative control antibody IgG2amm-b12-AAKR on days 12, 17, 21, 24, 28, and 31 after tumor inoculation (vertical dotted lines). (A) Average tumor volumes per group are shown, error bars depict SEM. Growth curves contain last measured tumor volume of sacrificed mice (last observation carried forward). **, P<0.01; Two-Way repeated-measures ANOVA. (B) Percent survival. *, P<0.05; Log-rank (Mantel-Cox) test.

Figure 11:
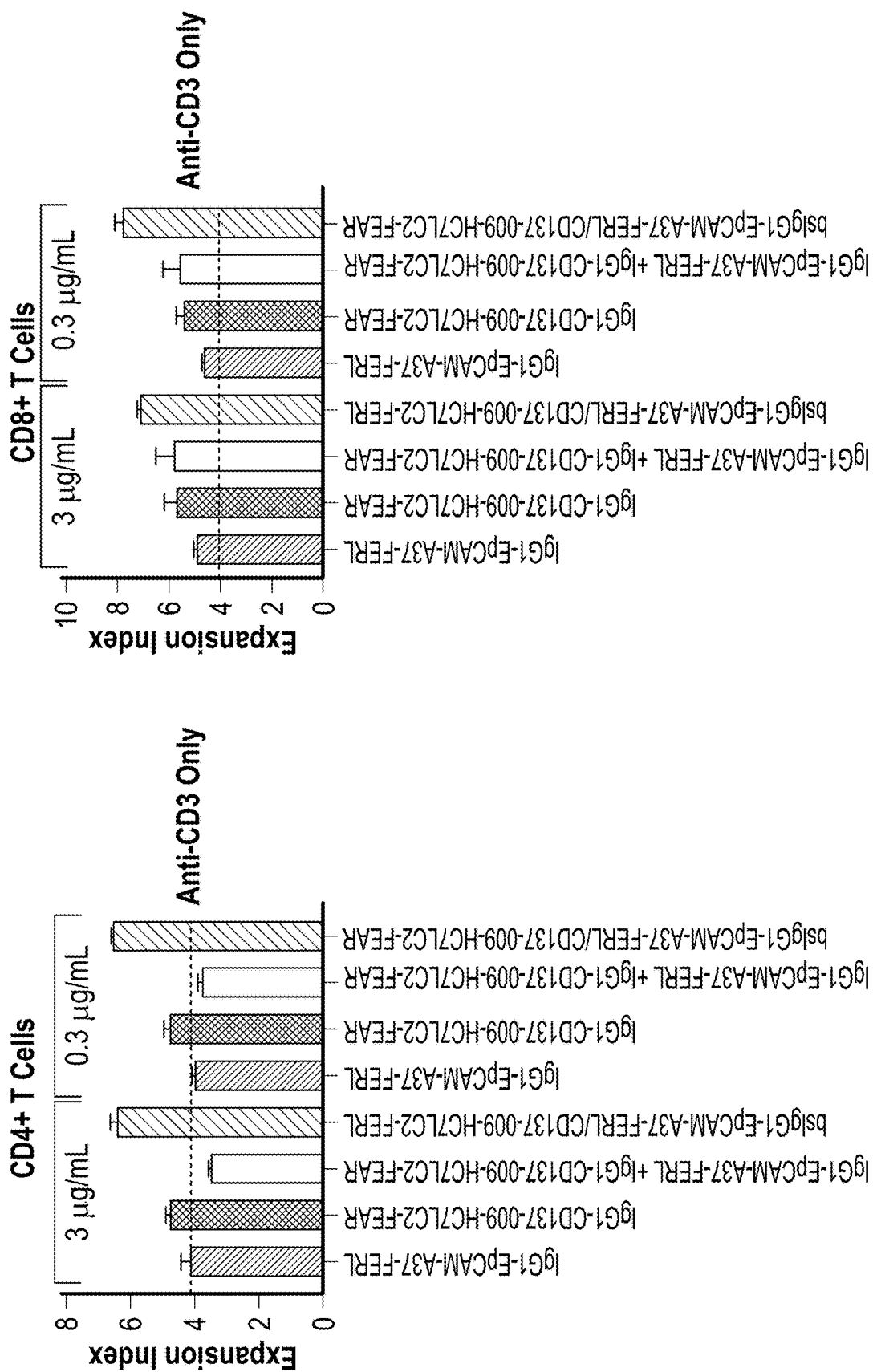

FIG. 11. Enhancement of human CD4+ and CD8+ T-cell proliferation in PBMC-DiFi tumor cell co-cultures by EpCAMx4-1BB bispecific antibodies in comparison to the combination of bivalent EpCAM- and 4-1BB-specific monoclonal antibodies.

Bispecific antibody bsIgG1-EpCAM-A37-FERL/CD137-009-HC7LC2-FEAR was compared to bivalent IgG1-EpCAM-A37-FERL and IgG1-CD137-009-HC7LC2-FEAR (either alone or in combination) in an in vitro PBMC proliferation assay using EpCAM-expressing DiFi tumor cells in co-culture with CellTrace Violet (CTV)-labeled human PBMCs. Cells were cultured in the presence of anti-CD3 (0.1 µg/mL; dotted line) and EpCAMx4-1BB, IgG1-EpCAM-A37-FERL and/or IgG1-CD137-009-HC7LC2-FEAR at the indicated concentrations for 96 h. CD4+ and CD8+ T proliferation was evaluated by flow cytometry analysis of CTV label dilution. Data shown are mean expansion index±SD of duplicate measurements obtained from one representative experiment.

Figure 12:
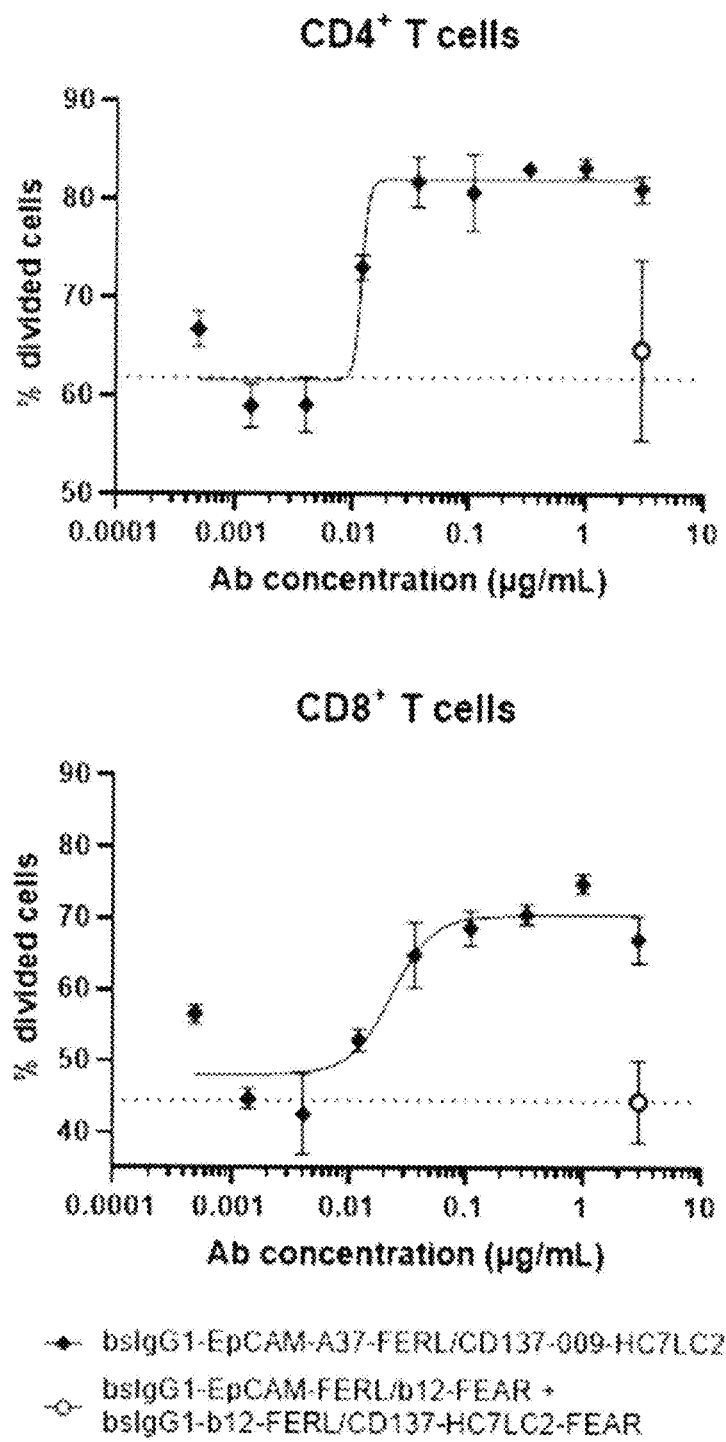

FIG. 12. Enhancement of human CD4+ and CD8+ T-cell proliferation in PBMC-DiFi tumor cell co-cultures by EpCAMx4-1BB bispecific antibodies in comparison to the combination of bsIgG1-EpCAM-A37-FERL/b12-FEAR and bsIgG1-b12-FERL/CD137-HC7LC2-FEAR.

Bispecific antibody bsIgG1-EpCAM-A37-FERL/CD137-009-HC7LC2-FEAR was compared to the combination of bsIgG1-EpCAM-A37-FERL/b12-FEAR and bsIgG1-b12-FERL/CD137-HC7LC2-FEAR in an in vitro PBMC proliferation assay using EpCAM-expressing DiFi tumor cells in co-culture with CTV-labeled human PBMCs. Cells were cultured in the presence of anti-CD3 (0.1 µg/mL; dotted line) and bsIgG1-EpCAM-A37-FERL/CD137-009-HC7LC2-FEAR or with the combination of bsIgG1-EpCAM-A37-FERL/b12-FEAR and bsIgG1-b12-FERL/CD137-HC7LC2-FEAR at the indicated concentrations for 96 h. CD4+ and CD8+ T proliferation was evaluated by flow cytometry analysis of CTV label dilution. Data shown are mean percentage divided cells±SD of duplicate measurements obtained from one representative experiment.

Figure 13:
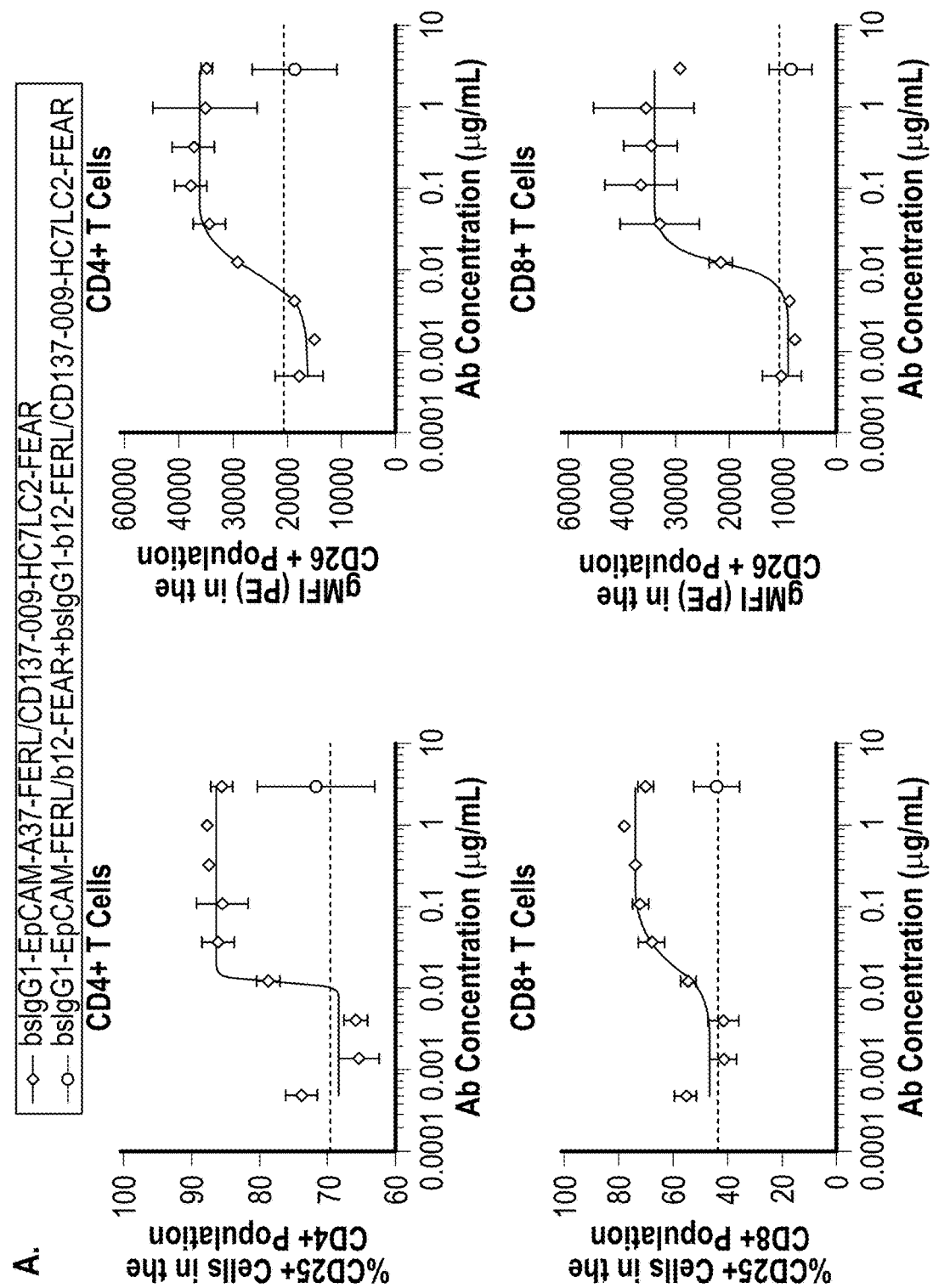
Figure 13:
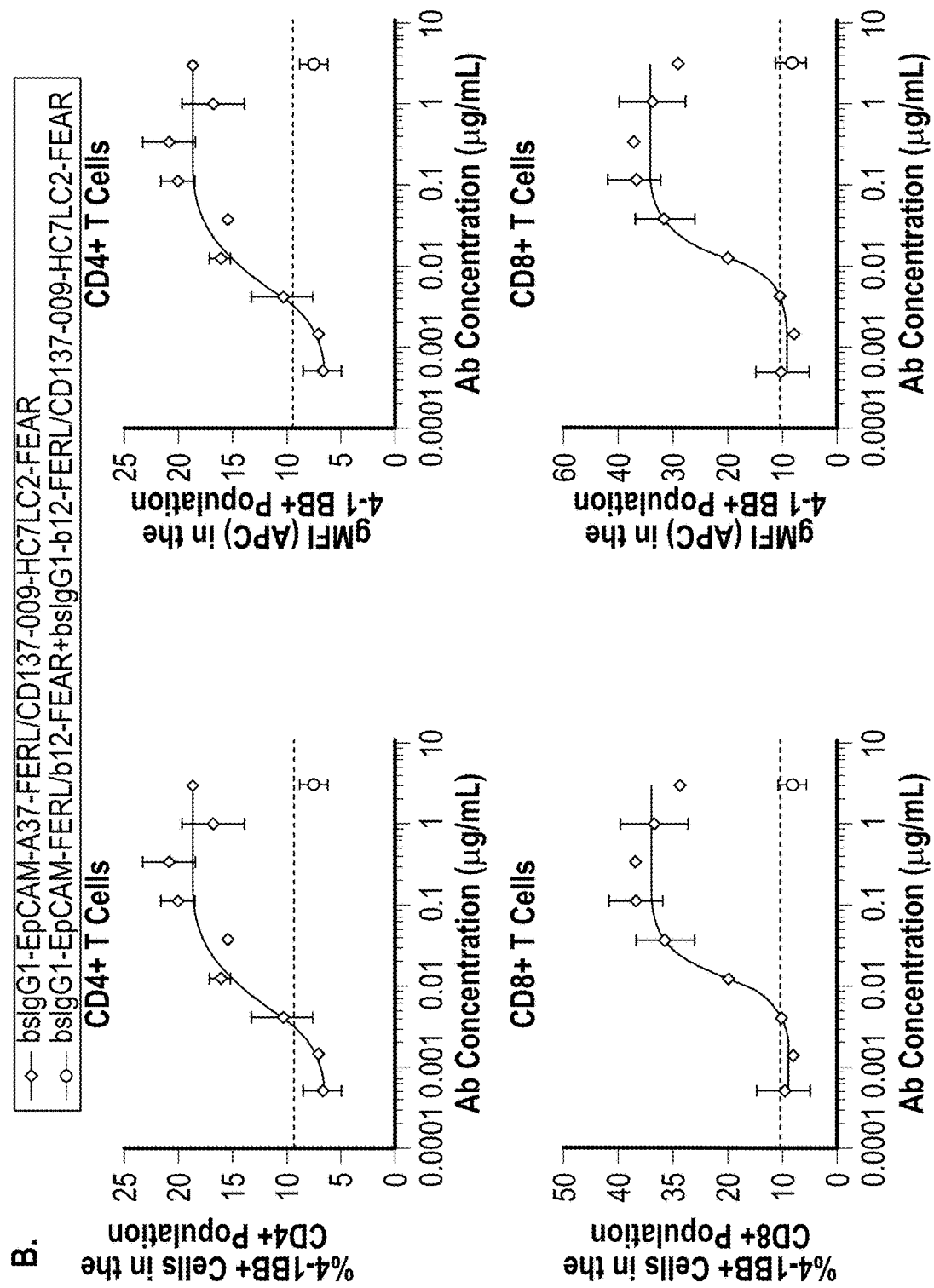

FIG. 13. Enhancement of human CD4+ and CD8+ T-cell activation in PBMC-DiFi tumor cell co-cultures by EpCAMx4-1BB bispecific antibodies in comparison to the combination of bsIgG1-EpCAM-A37-FERL/b12-FEAR and bsIgG1-b12-FERL/CD137-HC7LC2-FEAR.

EpCAMx4-1BB bispecific antibody bsIgG1-EpCAM-A37-FERL/CD137-009-HC7LC2-FEAR was compared to the combination of bsIgG1-EpCAM-A37-FERL/b12-FEAR and bsIgG1-b12-FERL/CD137-HC7LC2-FEAR in an in vitro PBMC proliferation assay using EpCAM-expressing DiFi tumor cells in co-culture with human PBMCs. Cells were cultured in the presence of anti-CD3 (0.1 µg/mL; dotted line) and bsIgG1-EpCAM-A37-FERL/CD137-009-HC7LC2-FEAR or with the combination of bsIgG1-EpCAM-A37-FERL/b12-FEAR and bsIgG1-b12-FERL/CD137-HC7LC2-FEAR at the indicated concentrations for 96 h. The percentage of CD4+ and CD8+ T cells expressing CD25 (A) or 4-1BB (B), as well as the geometric mean fluorescence intensity (FI) in the CD25+ or 4-1BB+ population was determined by flow cytometry. Data shown are mean±SD of duplicate measurements obtained from one representative experiment.

Figure 14:
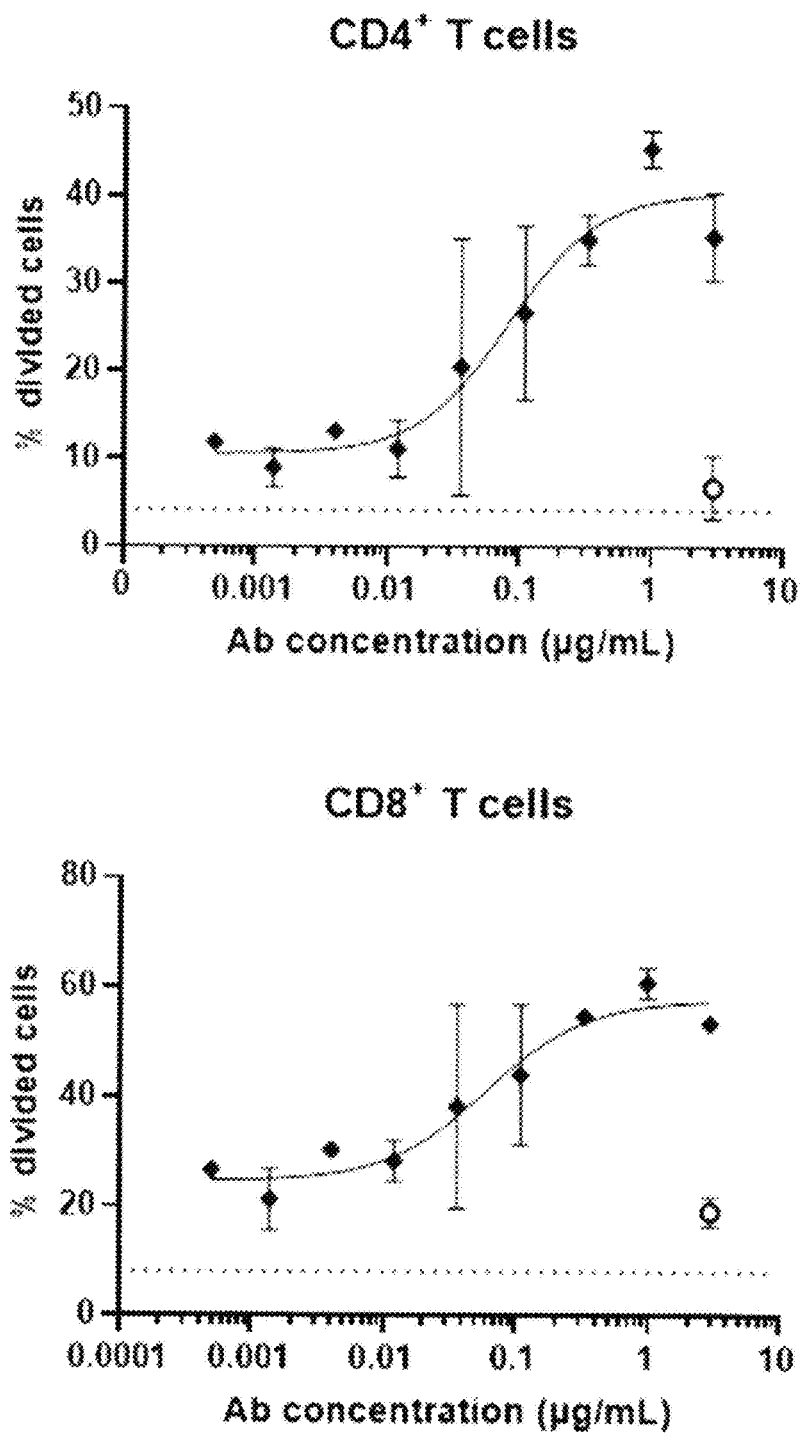

FIG. 14. Enhancement of human CD4+ and CD8+ T-cell proliferation in cancer patient-derived PBMC-DiFi tumor cell co-cultures by EpCAMx4-1BB bispecific antibodies in comparison to the combination of bsIgG1-EpCAM-A37-FERL/b12-FEAR and bsIgG1-b12-FERL/CD137-009-HC7LC2-FEAR.

EpCAMx4-1BB bispecific antibody bsIgG1-EpCAM-A37-FERL/CD137-009-HC7LC2-FEAR was compared to the combination of bsIgG1-EpCAM-A37-FERL/b12-FEAR and bsIgG1-b12-FERL/CD137-009-HC7LC2-FEAR in an in in vitro proliferation assay using EpCAM-expressing DiFi tumor cells in co-culture with CTV-labeled cancer patient-derived PBMC. Cells were cultured in the presence of anti-CD3 (0.1 µg/mL; dotted line) and bsIgG1-EpCAM-A37-FERL/CD137-009-HC7LC2-FEAR or with the combination of bsIgG1-EpCAM-A37-FERL/b12-FEAR and bsIgG1-b12-FERL/CD137-009-HC7LC2-FEAR at the indicated concentrations for 96 h. CD4+ and CD8+ T cell proliferation was evaluated by flow cytometry analysis of CTV label dilution. Data shown are mean percentage divided cells±SD of duplicate measurements obtained from one experiment.

Figure 15:
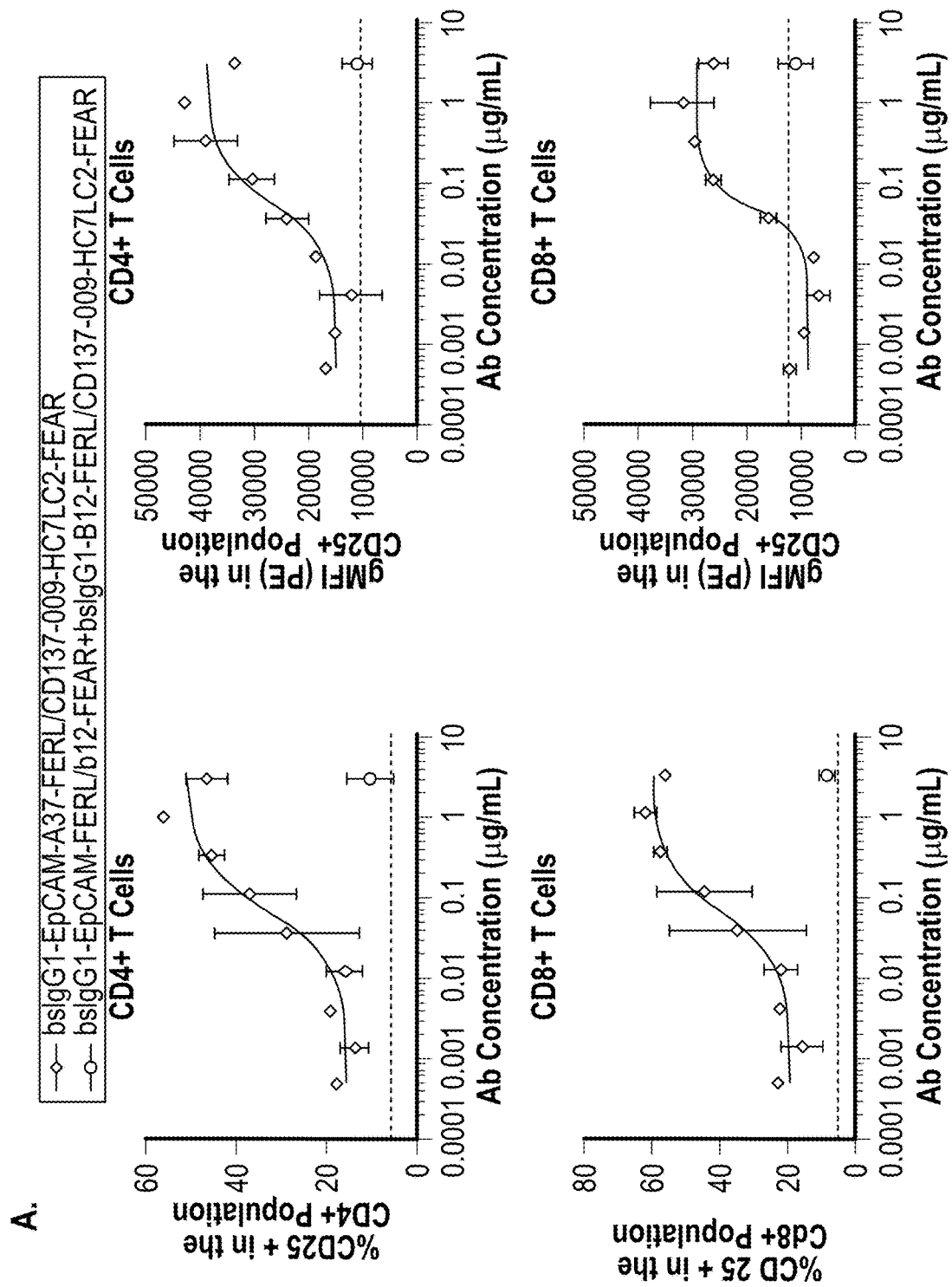
Figure 15:
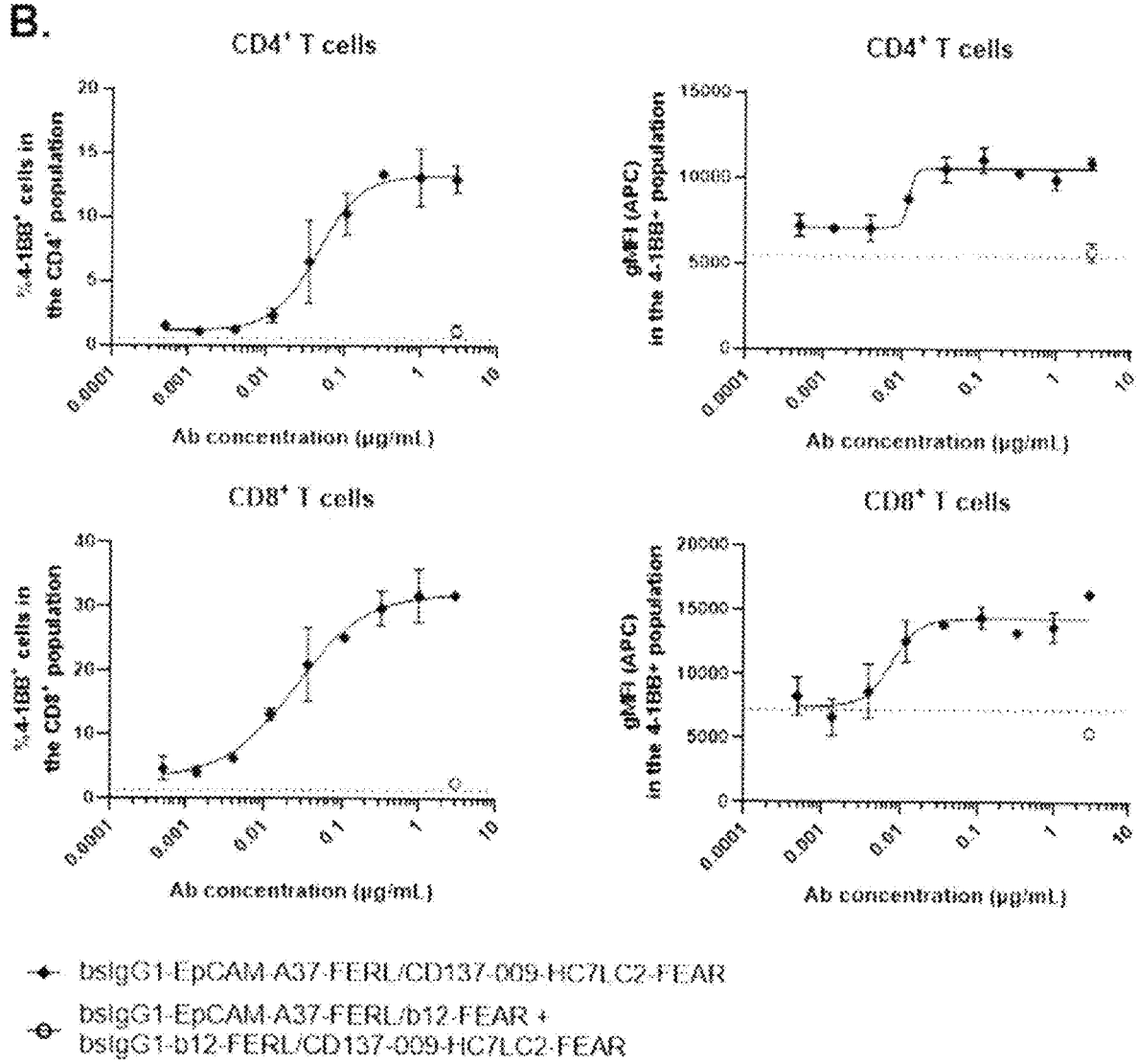

FIG. 15. Enhancement of human CD4+ and CD8+ T-cell activation in cancer patient-derived PBMC-DiFi tumor cell co-cultures by EpCAMx4-1BB bispecific antibodies in comparison to the combination of bsIgG1-EpCAM-A37-FERL/b12-FEAR and bsIgG1-b12-FERL/CD137-009-HC7LC2-FEAR.

EpCAMx4-1BB bispecific antibody bsIgG1-EpCAM-A37-FERL/CD137-009-HC7LC2-FEAR was compared to the combination of bsIgG1-EpCAM-A37-FERL/b12-FEAR and bsIgG1-b12-FERL/CD137-009-HC7LC2-FEAR in an in vitro proliferation assay using EpCAM-expressing DiFi tumor cells in co-culture with cancer patient-derived PBMCs. Cells were cultured in the presence of anti-CD3 (0.1 µg/mL; dotted line) and bsIgG1-EpCAM-A37-FERL/CD137-009-HC7LC2-FEAR or with the combination of bsIgG1-EpCAM-A37-FERL/b12-FEAR and bsIgG1-b12-FERL/CD137-009-HC7LC2-FEAR at the indicated concentrations for 96 h. The percentage of CD4+ and CD8+ T cells expressing CD25 (A) and 4-1BB (B), as well as the geometric mean fluorescence intensity (FI) in the CD25+ or 4-1BB+ population was determined by flow cytometry. Data shown are mean±SD of duplicate measurements obtained from one experiment.

Figure 16:
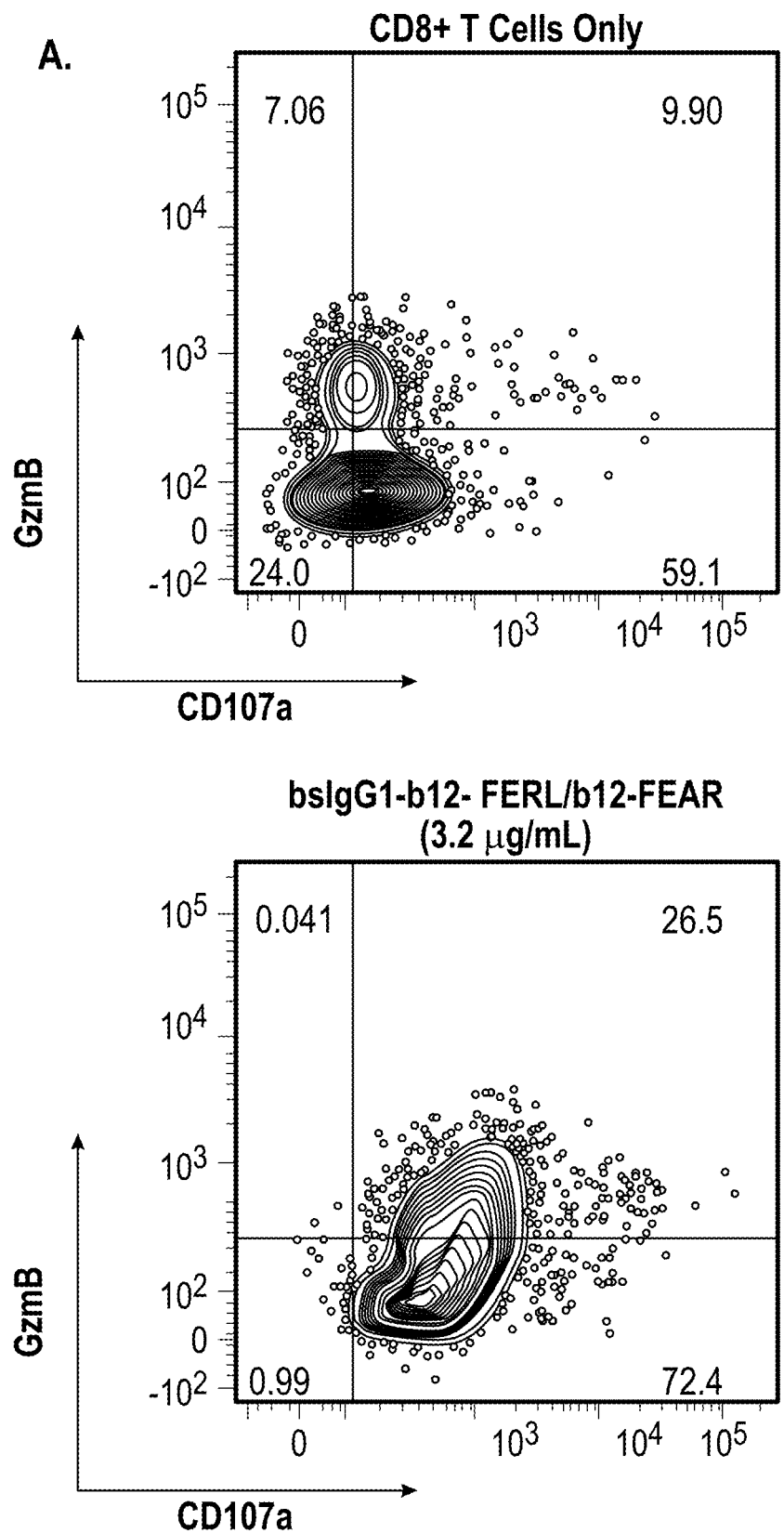
Figure 16:
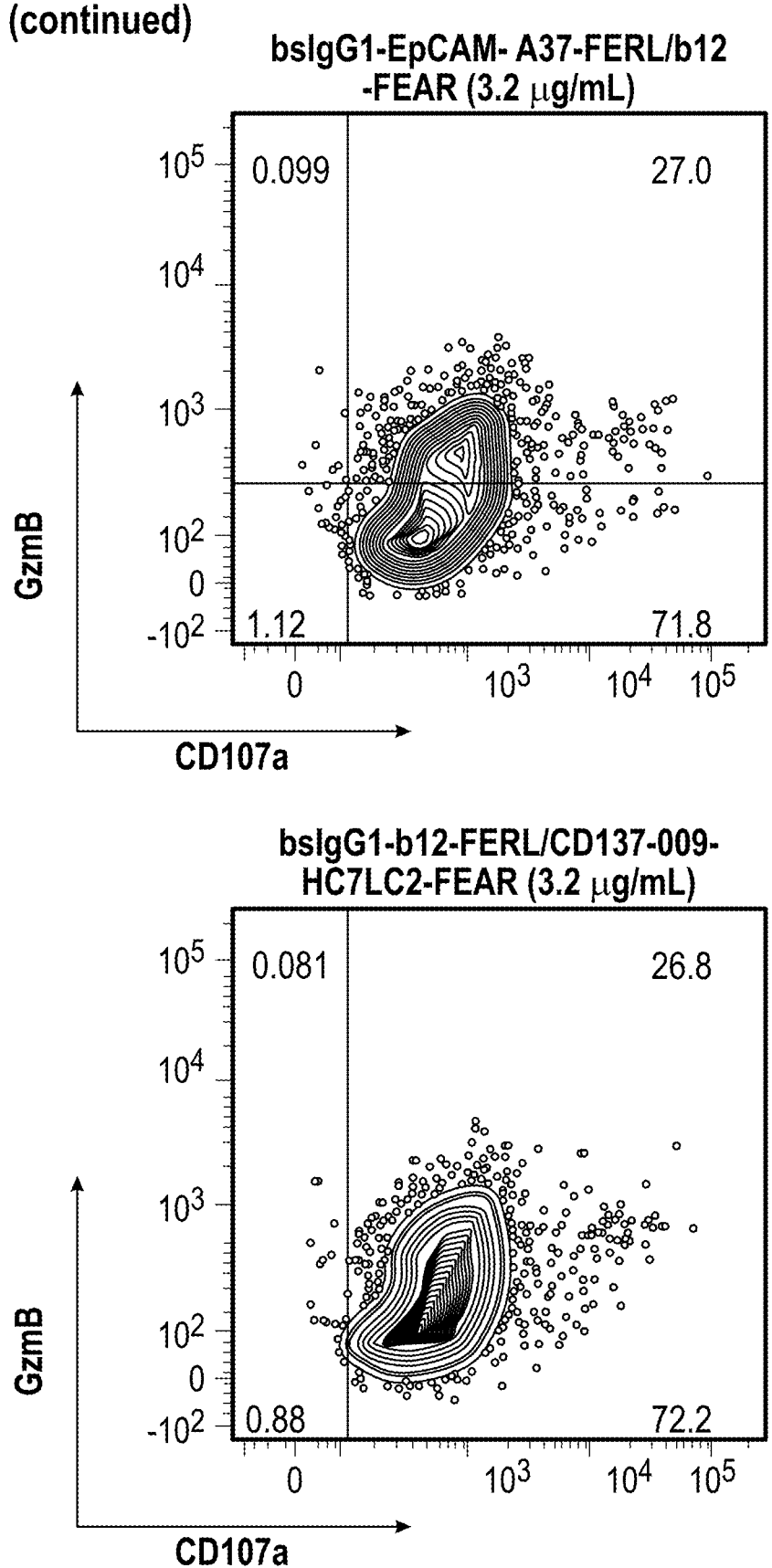
Figure 16:
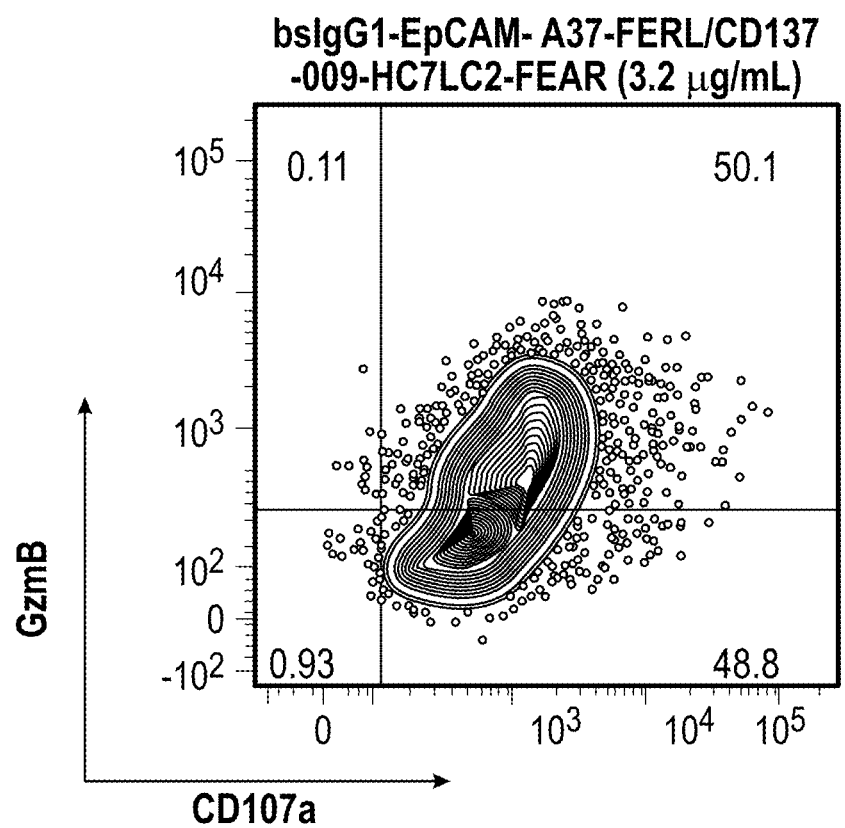
Figure 16:
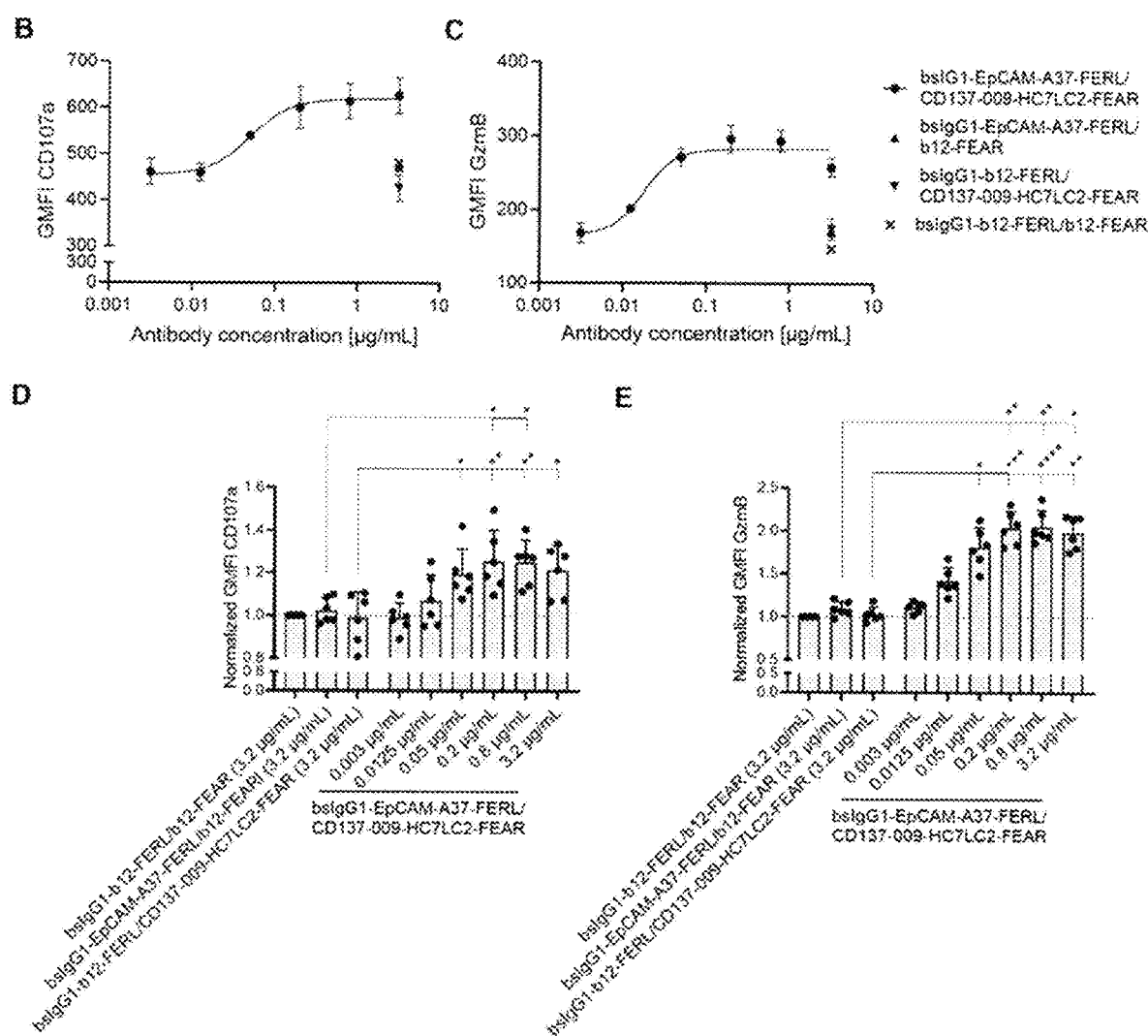

FIG. 16. An EpCAMx4-1BB bispecific antibody enhances CD107a and GzmB expression by CD8+ T cells PBMC-derived CD8+ T cells expressing a CLDN6-specific TCR were co-cultured with MDA-MB-231_hCLDN6_hEpCAM tumor cells for 2 d in the presence of bsIgG1-EpCAM-A37-FERL/CD137-009-HC7LC2-FEAR or control antibodies. CD107a and GzmB expression by CD8+ T cells were analyzed by flow cytometry. (A) Representative flow cytometry plots. (B-C) Dose-response curves of CD107a (C) and GzmB (D) expression levels. Data shown are average and SD of duplicate measurements from one of six donors tested. (D) Normalized CD107a and (E) GzmB expression levels (expression levels of bsIgG1-b12-FERL/b12-FEAR were set to 1 for each donor). Pooled data from six donors assessed in two independent experiments are shown. Error bars indicate SD. **, P<0.0001; *, P<0.001; **, P<0.01; *, P<0.05; Friedman test with Dunn's multiple comparisons test. GMFI=geometric mean fluorescence intensity; GzmB=granzyme B; PBMC= peripheral blood mononuclear cell; SD=standard deviation.

FIG. 17. An EpCAMx4-1BB bispecific antibody enhances CD8+ T-cell mediated cytotoxicity towards tumor cells
PBMC-derived CD8+ T cells expressing a CLDN6-specific TCR were co-cultured with MDA-MB-231_hCLDN6_ hEpCAM tumor cells for 5 to 6 d in the presence of bsIgG1-EpCAM-A37-FERL/CD137-009-HC7LC2-FEAR or control antibodies. Cell index values were derived from impedance measurements conducted at 2 to 3 h intervals. (A) Cell index curves in co-cultures from one representative donor are shown. Symbols represent average cell index values of duplicate wells. Data from every second impedance measurement (i.e., every 4 to 6 h) are shown for better visibility. (B) AUC analysis was performed using cell index data over the entire duration of the co-cultures. AUC of each treatment condition was normalized to bsIgG1-ctrl-b12-FERL/b12-FEAR-treated cultures from the same donor. Pooled data from all six donors assessed in two independent experiments are shown. Error bars indicate SD. *, P<0.001; , P<0.01; *, P<0.05; Friedman test with Dunn's multiple comparisons test.
AUC=area under the curve; PBMC=peripheral blood mononuclear cell; SD=standard deviation.

FIG. 18. Binding of EpCAMx4-1BB bispecific antibodies with different Fc-inertness mutations (FER/FEA, FEA/FEA, FER/FER) to FcγRs
The binding of EpCAMx4-1BB bispecific antibodies with various combinations of Fc-inertness mutations (FER/FEA, FEA/FEA, FER/FER), and the binding of monoclonal antibodies IgG1-EpCAM-A37-FERL and IgG1-CD137-009-HC7LC2-FEAR to immobilized human recombinant FcγR proteins was analyzed by SPR: FcγRIa, FcγRIIa-H131, FcγRIIa-R131, FcγRIIb, FcγRIIIa-F158, and FcγRIIIa-V158. The antibody IgG1-b12 (wild-type Fc) was included as a positive control for FcγR binding. The relative binding response in RU (response units) is measured by setting the sensorgram at 0 RU at the moment of SPR analyte injection. Each sample that was analyzed on an active surface was also analyzed on a parallel reference surface used for background correction. Shown are data of single measurements of one experiment.

DESCRIPTION OF THE SEQUENCES

TABLE 1

| SEQ ID NO: | Reference | Domain | Sequence |
|---|---|---|---|
| 1 | IgG1-EpCAM-A37-FERL | VH | QVQLVQSGAEVKKPGSSVRVSCKASGGTFSSYAISWVRQ APGQGLEWMGGIIPIFGTANYAQKFQGRVTITADESTSTA YMELSSLRSEDTAVYYCARDPFLHYWGQGTLVTVSS |
| 2 | IgG1-EpCAM-A37-FERL | VH_CDR1 | GGTFSSYA |
| 3 | IgG1-EpCAM-A37-FERL | VH_CDR2 | IIPIFGTA |
| 4 | IgG1-EpCAM-A37-FERL | VH_CDR3 | ARDPFLHY |
| 5 | IgG1-EpCAM-A37-FERL | VL | EIELTQSPGTLSLSPGERATLSCRASQTISNNYLAWYQQKR GQAPRLLIYAASSRATGIPDRFSGTGSGTDFTLTISRLEPED FAVYYCAQGELYPRQFGGGTKLEIK |
| 6 | IgG1-EpCAM-A37-FERL | VL_CDR1 | QTISNNY |
| 7 | IgG1-EpCAM-A37-FERL | VL_CDR2 | AAS |
| 8 | IgG1-EpCAM-A37-FERL | VL_CDR3 | AQGELYPRQ |
| 9 | IgG1-EpCAM-A37-FERL | Full heavy chain | QVQLVQSGAEVKKPGSSVRVSCKASGGTFSSYAISWVRQ APGQGLEWMGGIIPIFGTANYAQKFQGRVTITADESTSTA YMELSSLRSEDTAVYYCARDPFLHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICNV |

TABLE 1-continued

Sequences

| SEQ ID NO: | Reference | Domain | Sequence |
|---|---|---|---|
| | | | NHKPSNTKVDKRVEPKSCDKTHTCPPCPAPEFERGPSVFL FPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSREEMTKN QVSLTCLVKGFYPSDIAVEWESNGQPENNYKTTPPVLDSD GSFLLYSKLTVDKSRWQQGNVFSCSVMHEALHNHYTQKS LSLSPG |
| 10 | IgG1-EpCAM-A37-FEAR / IgG1-EpCAM-A37-FERL | Full light chain | EIELTQSPGTLSLSPGERATLSCRASQTISNNYLAWYQQKR GQAPRLLIYAASSRATGIPDRFSGTGSGTDFTLTISRLEPED FAVYYCAQGELYPRQFGGGTKLEIKRTVAAPSVFIFPPSDE QLKSGTASVVCLLNNFYPREAKVQWKVDNALQSGNSQES VTEQDSKDSTYSLSSTLTLSKADYEKHKVYACEVTHQGLSS PVTKSFNRGEC |
| 11 | IgG1-CD137-009-HC7LC2-FEAR | VH | EVQLVESGGGLVQPGRSLRLSCTASGFSLNDYWMSWVR QAPGKGLEWVGYIDVGGSLYYAASVKGRFTISRDDSKSIA YLQMNSLKTEDTAVYYCARGGLTYGFDLWGQGTLVTVSS |
| 12 | IgG1-CD137-009-HC7LC2-FEAR | VH_CDR1 | GFSLNDYW |
| 13 | IgG1-CD137-009-HC7LC2-FEAR | VH_CDR2 | IDVGGSL |
| 14 | IgG1-CD137-009-HC7LC2-FEAR | VH_CDR3 | ARGGLTYGFDL |
| 15 | IgG1-CD137-009-HC7LC2-FEAR | VL | DIVMTQSPSSLSASVGDRVTITCQASEDISSYLAWYQQKP GKAPKRLIYGASDLASGVPSRFSASGSGTDYTFTISSLQPED IATYYCHYYATISGLGVAFGGGTKVEIK |
| 16 | IgG1-CD137-009-HC7LC2-FEAR | VL_CDR1 | EDISSY |
| 17 | IgG1-CD137-009-HC7LC2-FEAR | VL_CDR2 | GAS |
| 18 | IgG1-CD137-009-HC7LC2-FEAR | VL_CDR3 | HYYATISGLGVA |
| 19 | IgG1-CD137-009-HC7LC2-FEAR | Full heavy chain | EVQLVESGGGLVQPGRSLRLSCTASGFSLNDYWMSWVR QAPGKGLEWVGYIDVGGSLYYAASVKGRFTISRDDSKSIA YLQMNSLKTEDTAVYYCARGGLTYGFDLWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFFLYSRLTVDKSRWQQGNVFSCSVMHEALHNHYT QKSLSLSPG |
| 20 | IgG1-CD137-009-HC7LC2-FEAR / IgG1-CD137-009-HC7LC2-FEAL | Full light chain | DIVMTQSPSSLSASVGDRVTITCQASEDISSYLAWYQQKP GKAPKRLIYGASDLASGVPSRFSASGSGTDYTFTISSLQPED IATYYCHYYATISGLGVAFGGGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTHQG LSSPVTKSFNRGEC |
| 21 | IgG1-EpCAM-323-A3-FEAL | Full heavy chain | QIQLVQSGPELKKPGETVKISCKASGYTFTNYGMNWVRQ ASGEGLKWMGWINTYTGEPTYGEDFKGRFAFSLETSAST AYLQINNLKNEDTATYFCARFGNYVDYWGQGTTLTVSSA STKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFLLYSKLTVDKSRWQQGNVFSCSVMHEALHNHYTQ KSLSLSPG |

TABLE 1-continued

Sequences

| SEQ ID NO: | Reference | Domain | Sequence |
|---|---|---|---|
| 22 | IgG1-EpCAM-323-A3/ IgG1-EpCAM-323-A3-FEAL / IgG1-EpCAM-323-A3-FEAR | Full light chain | DIVMTQAAFSNPVTLGTSASISCRSSKNLLHSNGITYLYWY LQKPGQSPHLLIYQMSNLASGVPDRFSSSGSGTDFTLRISR. VEAEDVGVYYCAQNLEIPRTFGGGTKLEIKRTVAAPSVFIF PPSDEQLKSGTASVVCLLNNFYPREAKVQWKVDNALQSG NSQESVTEQDSKDSTYSLSSTLTLSKADYEKHKVYACEVTH QGLSSPVTKSFNRGEC |
| 23 | IgG1-EpCAM-323-A3-FEAR | Full heavy chain | QIQLVQSGPELKKPGETVKISCKASGYTFTNYGMNWVRQ ASGEGLKWMGWINTYTGEPTYGEDFKGRFAFSLETSAST AYLQINNLKNEDTATYFCARFGNYVDYWGQGTTLTVSSA STKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFFLYSRLTVDKSRWQQGNVFSCSVMHEALHNHYT QKSLSLSPG |
| 24 | IgG1-EpCAM-323-A3 | Full heavy chain | QIQLVQSGPELKKPGETVKISCKASGYTFTNYGMNWVRQ ASGEGLKWMGWINTYTGEPTYGEDFKGRFAFSLETSAST AYLQINNLKNEDTATYFCARFGNYVDYWGQGTTLTVSSA STKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQ KSLSLSPG |
| 25 | IgG1-EpCAM-UBS-54-FEAR | Full heavy chain | QVQLVQSGAEVKKPGSSVRVSCKASGGTFSSYAISWVRQ APGQGLEWMGGIIPIFGTANYAQKFQGRVTITADESTSTA YMELSSLRSEDTAVYYCARDPFLHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICNV NHKPSNTKVDKRVEPKSCDKTHTCPPCPAPEFEGGPSVFL FPPKPKDTLMISRTPEVTCVVVAVSHEDPEVKFNWYDG VEVHNAKTKPREEQYNSTYRVVSVLTVLHQDWLNGKEYK CKVSNKALPAPIEKTISKAKGQPREPQVYTLPPSREEMTKN QVSLTCLVKGFYPSDIAVEWESNGQPENNYKTTPPVLDSD GSFFLYSRLTVDKSRWQQGNVFSCSVMHEALHNHYTQKS LSLSPG |
| 26 | IgG1-EpCAM-UBS-54-FEAR | Full light chain | EIELTQSPLSLPVTPGEPASISCRSSQSLLHSNGYNYLDWYL QKPGQSPQLLIYLGSNRASGVPDRFSGSGSGTDFTLKISRV EAEDVGVYYCMQALQTFTFGPGTKVEIKRTVAAPSVFIFP PSDEQLKSGTASVVCLLNNFYPREAKVQWKVDNALQSGN SQESVTEQDSKDSTYSLSSTLTLSKADYEKHKVYACEVTHQ GLSSPVTKSFNRGEC |
| 27 | IgG1-EpCAM-C52-FEAR | Full heavy chain | QVQLVQSGAEVKKPGASVKVSCKASGGTFSSYAISWVRQ APGQGLEWMGGIVPIFGTANYAQKFQGRVTITADESTST AYMELSSLRSEDTAVYYCARDPFLHYWGQGTLVTVSSAST KGPSVFPLAPSSKSTSGGTAALGCLVKDYFPEPVTVSWNS GALTSGVHTFPAVLQSSGLYSLSSVVTVPSSSLGTQTYICNV NHKPSNTKVDKRVEPKSCDKTHTCPPCPAPEFEGGPSVFL FPPKPKDTLMISRTPEVTCVVVAVSHEDPEVKFNWYVDG VEVHNAKTKPREEQYNSTYRVVSVLTVLHQDWLNGKEYK CKVSNKALPAPIEKTISKAKGQPREPQVYTLPPSREEMTKN QVSLTCLVKGFYPSDIAVEWESNGQPENNYKTTPPVLDSD GSFFLYSRLTVDKSRWQQGNVFSCSVMHEALHNHYTQKS LSLSPG |
| 28 | IgG1-EpCAM-C52-FEAR | Full light chain | EIELTQSPGTLSLSPGERATLSCRASQSVSSSYLAWYQQKP GQAPRLLIYGASSRATGIPDRFSGSGSGTDFTLTISRLEPED FAVYYCAQGELYPRQFGGGTKLDIKRTVAAPSVFIFPPSDE QLKSGTASVVCLLNNFYPREAKVQWKVDNALQSGNSQES VTEQDSKDSTYSLSSTLTLSKADYEKHKVYACEVTHQGLSS PVTKSFNRGEC |

TABLE 1-continued

Sequences

| SEQ ID NO: | Reference | Domain | Sequence |
|---|---|---|---|
| 29 | IgG1-EpCAM-A37-FEAR | Full heavy chain | QVQLVQSGAEVKKPGSSVRVSCKASGGTFSSYAISWVRQ APGQGLEWMGGIIPIFGTANYAQKFQGRVTITADESTSTA YMELSSLRSEDTAVYYCARDPFLHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICNV NHKPSNTKVDKRVEPKSCDKTHTCPPCPAPEFEGGPSVFL FPPKPKDTLMISRTPEVTCVVVAVSHEDPEVKFNWYVDG VEVHNAKTKPREEQYNSTYRVVSVLTVLHQDWLNGKEYK CKVSNKALPAPIEKTISKAKGQPREPQVYTLPPSREEMTKN QVSLTCLVKGFYPSDIAVEWESNGQPENNYKTTPPVLDSD GSFFLYSRLTVDKSRWQQGNVFSCSVMHEALHNHYTQKS LSLSPG |
| 30 | IgG1-CD137-009-HC7LC2-FEAL | Full heavy chain | EVQLVESGGGLVQPGRSLRLSCTASGFSLNDYWMSWVR QAPGKGLEWVGYIDVGGSLYYAASVKGRFTISRDDSKSIA YLQMNSLKTEDTAVYYCARGGLTYGFDLWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFLLYSKLTVDKSRWQQGNVFSCSVMHEALHNHYTQ KSLSLSPG |
| 31 | IgG1-CD137-009-FEAR | Full heavy chain | QSLEESGGRLVTPGTPLTLTCTVSGFSLNDYWMSWVRQA PGKGLEWIGYIDVGGSLYYASWAKGRFTISRTSTTVDLKM TSLTTEDTATYFCARGGLTYGFDLWGPGTLVTVSSASTKG PSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEFEGGPSVFLF PPKPKDTLMISRTPEVTCVVVAVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQ VSLTCLVKGFYPSDIAVEWESNGQPENNYKTTPPVLDSDG SFFLYSRLTVDKSRWQQGNVFSCSVMHEALHNHYTQKSL SLSPG |
| 32 | IgG1-CD137-009-FEAR | Full light chain | DIVMTQTPASVSEPVGGTVTINCQASEDISSYLAWYQQKP GQRPKRLIYGASDLASGVPSRFSASGSGTEYALTISDLESAD AATYYCHYYATISGLGVAFGGGTEVVVKRTVAAPSVFIFPP SDEQLKSGTASVVCLLNNFYPREAKVQWKVDNALQSGNS QESVTEQDSKDSTYSLSSTLTLSKADYEKHKVYACEVTHQG LSSPVTKSFNRGEC |
| 33 | IgG1-CD137-005-FEAR | Full heavy chain | QSVEESGGRLVTPGTPLTLTCTASGFTISDFHVTWVRQAP GKGLEWIGTIITSASTTAYATWARGRFTISKSSTTVNLKIVS PTTEDTATYFCARSTYTDTSGYYFDFWGQGTLVTVSSAST KGPSVFPLAPSSKSTSGGTAALGCLVKDYFPEPVTVSWNS GALTSGVHTFPAVLQSSGLYSLSSVVTVPSSSLGTQTYICNV NHKPSNTKVDKRVEPKSCDKTHTCPPCPAPEFEGGPSVFL FPPKPKDTLMISRTPEVTCVVVAVSHEDPEVKFNWYVDG VEVHNAKTKPREEQYNSTYRVVSVLTVLHQDWLNGKEYK CKVSNKALPAPIEKTISKAKGQPREPQVYTLPPSREEMTKN QVSLTCLVKGFYPSDIAVEWESNGQPENNYKTTPPVLDSD GSFFLYSRLTVDKSRWQQGNVFSCSVMHEALHNHYTQKS LSLSPG |
| 34 | IgG1-CD137-005-FEAR | Full light chain | AQVLTQTASPVSAAVGGTVIINCQSSQSIYNGNRLSWYQ QKPGQPPKLLIYSASTLASGVSSRFKGSGSGTQFTLAISDV QSDDAATYYCLGSYDCDSADCFAFGGGTEVVVERTVAAP SVFIFPPSDEQLKSGTASVVCLLNNFYPREAKVQWKVDNA LQSGNSQESVTEQDSKDSTYSLSSTLTLSKADYEKHKVYAC EVTHQGLSSPVTKSFNRGEC |
| 35 | IgG1-b12-FEAR | Full heavy chain | QVQLVQSGAEVKKPGASVKVSCQASGYRFSNFVIHWVR QAPGQRFEWMGWINPYNGNKEFSAKFQDRVTFTADTS ANTAYMELRSLRSADTAVYYCARVGPYSWDDSPQDNYY MDVWGKGTTVIVSSASTKGPSVFPLAPSSKSTSGGTAALG CLVKDYFPEPVTVSWNSGALTSGVHTFPAVLQSSGLYSLSS VVTVPSSSLGTQTYICNVNHKPSNTKVDKRVEPKSCDKTH TCPPCPAPEFEGGPSVFLFPPKPKDTLMISRTPEVTCVVVA |

TABLE 1-continued

Sequences

| SEQ ID NO: | Reference | Domain | Sequence |
|---|---|---|---|
| | | | VSHEDPEVKFNWYVDGVEVHNAKTKPREEQYNSTYRVVS VLTVLHQDWLNGKEYKCKVSNKALPAPIEKTISKAKGQPR EPQVYTLPPSREEMTKNQVSLTCLVKGFYPSDIAVEWESN GQPENNYKTTPPVLDSDGSFFLYSRLTVDKSRWQQGNVF SCSVMHEALHNHYTQKSLSLSPG |
| 36 | IgG1-b12-FEAL | Full heavy chain | QVQLVQSGAEVKKPGASVKVSCQASGYRFSNFVIHWVR QAPGQRFEWMGWINPYNGNKEFSAKFQDRVTFTADTS ANTAYMELRSLRSADTAVYYCARVGPYSWDDSPQDNYY MDVWGKGTTVIVSSASTKGPSVFPLAPSSKSTSGGTAALG CLVKDYFPEPVTVSWNSGALTSGVHTFPAVLQSSGLYSLSS VVTVPSSSLGTQTYICNVNHKPSNTKVDKRVEPKSCDKTH TCPPCPAPEFEGGPSVFLFPPKPKDTLMISRTPEVTCVVVA VSHEDPEVKFNWYVDGVEVHNAKTKPREEQYNSTYRVVS VLTVLHQDWLNGKEYKCKVSNKALPAPIEKTISKAKGQPR EPQVYTLPPSREEMTKNQVSLTCLVKGFYPSDIAVEWESN GQPENNYKTTPPVLDSDGSFLLYSKLTVDKSRWQQGNVF SCSVMHEALHNHYTQKSLSLSPG |
| 37 | IgG1-b12-FEAL / IgG1-b12-FEAR / IgG1-b12-FERL | Full light chain | EIVLTQSPGTLSLSPGERATFSCRSSHSIRSRRVAWYQHKP GQAPRLVIHGVSNRASGISDRFSGSGSGTDFTLTITRVEPE DFALYYCQVYGASSYTFGQGTKLERKRTVAAPSVFIFPPSD EQLKSGTASVVCLLNNFYPREAKVQWKVDNALQSGNSQE SVTEQDSKDSTYSLSSTLTLSKADYEKHKVYACEVTHQGLS SPVTKSFNRGEC |
| 38 | IgG1-b12-FERL | Full heavy chain | QVQLVQSGAEVKKPGASVKVSCQASGYRFSNFVIHWVR QAPGQRFEWMGWINPYNGNKEFSAKFQDRVTFTADTS ANTAYMELRSLRSADTAVYYCARVGPYSWDDSPQDNYY MDVWGKGTTVIVSSASTKGPSVFPLAPSSKSTSGGTAALG CLVKDYFPEPVTVSWNSGALTSGVHTFPAVLQSSGLYSLSS VVTVPSSSLGTQTYICNVNHKPSNTKVDKRVEPKSCDKTH TCPPCPAPEFERGPSVFLFPPKPKDTLMISRTPEVTCVVVD VSHEDPEVKFNWYVDGVEVHNAKTKPREEQYNSTYRVVS VLTVLHQDWLNGKEYKCKVSNKALPAPIEKTISKAKGQPR EPQVYTLPPSREEMTKNQVSLTCLVKGFYPSDIAVEWESN GQPENNYKTTPPVLDSDGSFLLYSKLTVDKSRWQQGNVF SCSVMHEALHNHYTQKSLSLSPG |
| 39 | IgG2amm-EpCAM-323-A3-AAKR | Full heavy chain | QIQLVQSGPELKKPGETVKISCKASGYTFTNYGMNWVRQ ASGEGLKWMGWINTYTGEPTYGEDFKGRFAFSLETSAST AYLQINNLKNEDTATYFCARFGNYVDYWGQGTTLTVSSA KTTAPSVYPLAPVCGDTTGSSVTLGCLVKGYFPEPVTLTW NSGSLSSGVHTFPAVLQSDLYTLSSSVTVTSSTWPSQSITC NVAHPASSTKVDKKIEPRGPTIKPCPPCKCPAPNAAGGPS VFIFPPKIKDVLMISLSPMVTCVVVDVSEDDPDVQISWFV NNVEVLTAQTQTHREDYNSTLRVVSALPIQHQDWMSGK EFKCKVNNKALPAPIERTISKPKGSVRAPQVYVLPPPEEEM TKKQVTLTCMVKDFMPEDIYVEWTNNGKTELNYKNTEPV LDSDGSYFMYSRLRVEKKNWVERNSYSCSVVHEGLHNHH TTKSFSRTPG |
| 40 | IgG2amm-EpCAM-323-A3-AAKR / IgG2amm-EpCAM-323-A3-AALT | Full light chain | DIVMTQAAFSNPVTLGTSASISCRSSKNLLHSNGITYLYWY LQKPGQSPHLLIYQMSNLASGVPDRFSSSGSGTDFTLRISR VEAEDVGVYYCAQNLEIPRTFGGGTKLEIKRADAAPTVSIF PPSSEQLTSGGASVVCFLNNFYPKDINVKWKIDGSERQNG VLNSWTDQDSKDSTYSMSSTLTLTKDEYERHNSYTCEATH KTSTSPIVKSFNRNEC |
| 41 | IgG2amm-EpCAM-323-A3-AALT | Full heavy chain | QIQLVQSGPELKKPGETVKISCKASGYTFTNYGMNWVRQ ASGEGLKWMGWINTYTGEPTYGEDFKGRFAFSLETSAST AYLQINNLKNEDTATYFCARFGNYVDYWGQGTTLTVSSA KTTAPSVYPLAPVCGDTTGSSVTLGCLVKGYFPEPVTLTW NSGSLSSGVHTFPAVLQSDLYTLSSSVTVTSSTWPSQSITC NVAHPASSTKVDKKIEPRGPTIKPCPPCKCPAPNAAGGPS VFIFPPKIKDVLMISLSPMVTCVVVDVSEDDPDVQISWFV NNVEVLTAQTQTHREDYNSTLRVVSALPIQHQDWMSGK EFKCKVNNKALPAPIERTISKPKGSVRAPQVYVLPPPEEEM TKKQVTLTCMVTDFMPEDIYVEWTNNGKTELNYKNTEPV LDSDGSYLMYSKLTVEKKNWVERNSYSCSVVHEGLHNHH TTKSFSRTPG |

TABLE 1-continued

Sequences

| SEQ ID NO: | Reference | Domain | Sequence |
|---|---|---|---|
| 42 | IgG2amm-m4-1BB-3H3-AAKR | Full heavy chain | EMQLVESGGGLVQPGRSMKLSCAGSGFTLSDYGVAWVR QAPKKGLEWVAYISYAGGTTYYRESVKGRFTISRDNAKSTL YLQMDSLRSEDTATYYCTIDGYGGYSGSHWYFDFWGPGT MVTVSSAKTTAPSVYPLAPVCGDTTGSSVTLGCLVKGYFP EPVTLTWNSGSLSSGVHTFPAVLQSDLYTLSSSVTVTSSTW PSQSITCNVAHPASSTKVDKKIEPRGPTIKPCPPCKCPAPN AAGGPSVFIFPPKIKDVLMISLSPMVTCVVVDVSEDDPDV QISWFVNNVEVLTAQTQTHREDYNSTLRVVSALPIQHQD WMSGKEFKCKVNNKALPAPIERTISKPKGSVRAPQVYVLP PPEEEMTKKQVTLTCMVKDFMPEDIYVEWTNNGKTELN YKNTEPVLDSDGSYFMYSRLRVEKKNWVERNSYSCSVVH EGLHNHHTTKSFSRTPG |
| 43 | IgG2amm-m4-1BB-3H3-AAKR | Full light chain | DIQMTQSPSLLSASVGDRVTLNCRTSQNVYKNLAWYQQK LGEAPKLLIYNANSLQAGIPSRFSGSGSGTDFTLTISSLQPE DVATYFCQQYYSGNTFGAGTNLELKRADAAPTVSIFPPSSE QLTSGGASVVCFLNNFYPKDINVKWKIDGSERQNGVLNS WTDQDSKDSTYSMSSTLTLTKDEYERHNSYTCEATHKTST SPIVKSFNRNEC |
| 44 | IgG2amm-b12-AALT | Full heavy chain | QVQLVQSGAEVKKPGASVKVSCQASGYRFSNFVIHWVR QAPGQRFEWMGWINPYNGNKEFSAKFQDRVTFTADTS ANTAYMELRSLRSADTAVYYCARVGPYSWDDSPQDNYY MDVWGKGTTVIVSSAKTTAPSVYPLAPVCGDTTGSSVTL GCLVKGYFPEPVTLTWNSGSLSSGVHTFPAVLQSDLYTLSS SVTVTSSTWPSQSITCNVAHPASSTKVDKKIEPRGPTIKPC PPCKCPAPNAAGGPSVFIFPPKIKDVLMISLSPMVTCVVV DVSEDDPDVQISWFVNNVEVLTAQTQTHREDYNSTLRVV SALPIQHQDWMSGKEFKCKVNNKALPAPIERTISKPKGSV RAPQVYVLPPPEEEMTKKQVTLTCMVTDFMPEDIYVEWT NNGKTELNYKNTEPVLDSDGSYLMYSKLTVEKKNWVERN SYSCSVVHEGLHNHHTTKSFSRTPG |
| 45 | IgG2amm-b12-AALT / IgG2amm-b12-AAKR | Full light chain | EIVLTQSPGTLSLSPGERATFSCRSSHSIRSRRVAWYQHKP GQAPRLVIHGVSNRASGISDRFSGSGSGTDFTLTITRVEPE DFALYYCQVYGASSYTFGQGTKLERKADAAPTVSIFPPSS EQLTSGGASVVCFLNNFYPKDINVKWKIDGSERQNGVLN SWTDQDSKDSTYSMSSTLTLTKDEYERHNSYTCEATHKTS TSPIVKSFNRNEC |
| 46 | IgG2amm-b12-AAKR | Full heavy chain | QVQLVQSGAEVKKPGASVKVSCQASGYRFSNFVIHWVR QAPGQRFEWMGWINPYNGNKEFSAKFQDRVTFTADTS ANTAYMELRSLRSADTAVYYCARVGPYSWDDSPQDNYY MDVWGKGTTVIVSSAKTTAPSVYPLAPVCGDTTGSSVTL GCLVKGYFPEPVTLTWNSGSLSSGVHTFPAVLQSDLYTLSS SVTVTSSTWPSQSITCNVAHPASSTKVDKKIEPRGPTIKPC PPCKCPAPNAAGGPSVFIFPPKIKDVLMISLSPMVTCVVV DVSEDDPDVQISWFVNNVEVLTAQTQTHREDYNSTLRVV SALPIQHQDWMSGKEFKCKVNNKALPAPIERTISKPKGSV RAPQVYVLPPPEEEMTKKQVTLTCMVKDFMPEDIYVEWT NNGKTELNYKNTEPVLDSDGSYFMYSRLRVEKKNWVERN SYSCSVVHEGLHNHHTTKSFSRTPG |
| 47 | IgG1 constant region | | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQ KSLSLSPG |
| 48 | IgG1-FEA constant region | with FEA substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFFLYSKLTVDKSRWQQGNVFSCSVMHEALHNHYT QKSLSLSPG |

TABLE 1-continued

Sequences

| SEQ ID NO: | Reference | Domain | Sequence |
|---|---|---|---|
| 49 | IgG1-FER constant region | with FER substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFERGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQ KSLSLSPG |
| 50 | IgG1-F405L constant region | with F405L substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFLLYSKLTVDKSRWQQGNVFSCSVMHEALHNHYTQ KSLSLSPG |
| 51 | IgG1-K409R constant region | with K409R substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFFLYSRLTVDKSRWQQGNVFSCSVMHEALHNHYTQ KSLSLSPG |
| 52 | IgG1-FEAR constant region | with FEA substitution and with K409R substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFFLYSRLTVDKSRWQQGNVFSCSVMHEALHNHYT QKSLSLSPG |
| 53 | IgG1-FEAL constant region | with FEA substitution and with F405L substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFEGGPS VFLFPPKPKDTLMISRTPEVTCVVVAVSHEDPEVKFNWYV DGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLD SDGSFLLYSKLTVDKSRWQQGNVFSCSVMHEALHNHYTQ KSLSLSPG |
| 54 | IgG1-FERL constant region | with FER substitution and with F405 substitution (bold) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEFERGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFLLYSKLTVDKSRWQQGNVFSCSVMHEALHNHYTQ KSLSLSPG |
| 55 | kappa light chain constant region | constant region of human kappa light chain | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC |
| 56 | lambda light chain constant region | constant region of human lambda light chain | GQPKAAPSVTLFPPSSEELQANKATLVCLISDFYPGAVTVA WKADSSPVKAGVETTTPSKQSNNKYAASSYLSLTPEQWK SHRSYSCQVTHEGSTVEKTVAPTECS |

TABLE 1-continued

Sequences

| SEQ ID NO: | Reference | Domain | Sequence |
|---|---|---|---|
| 57 | IgG2amm-AAKR | with AAKR substitution substitution (bold) | AKTTAPSVYPLAPVCGDTTGSSVTLGCLVKGYFPEPVTLT WNSGSLSSGVHTFPPAVLQSDLYTLSSSVTVTSSTWPSQSIT CNVAHPASSTKVDKKIEPRGPTIKPCPPCKCPAPNAAGGP SVFIFPPKIKDVLMISLSPMVTCVVVDVSEDDPDVQISWFV NNVEVLTAQTQTHREDYNSTLRVVSALPIQHQDWMSGK EFKCKVNNKALPAPIERTISKPKGSVRAPQVYVLPPPEEEM TKKQVTLTCMVKDFMPEDIYVEWTNNGKTELNYKNTEPV LDSDGSYFMYSRLRVEKKNWVERNSYSCSVVHEGLHNHH TTKSFSRTPG |
| 58 | IgG2amm-AALT | with AALT substitution substitution (bold) | AKTTAPSVYPLAPVCGDTTGSSVTLGCLVKGYFPEPVTLT WNSGSLSSGVHTFPPAVLQSDLYTLSSSVTVTSSTWPSQSIT CNVAHPASSTKVDKKIEPRGPTIKPCPPCKCPAPNAAGGP SVFIFPPKIKDVLMISLSPMVTCVVVDVSEDDPDVQISWFV NNVEVLTAQTQTHREDYNSTLRVVSALPIQHQDWMSGK EFKCKVNNKALPAPIERTISKPKGSVRAPQVYVLPPPEEEM TKKQVTLTCMVTDFMPEDIYVEWTNNGKTELNYKNTEPV LDSDGSYLMYSKLTVEKKNWVERNSYSCSVVHEGLHNHH TTKSFSRTPG |
| 59 | Human EpCAM | Full length protein sequence with signal peptide (bold) | MAPPQVLAFGLLLAAATATFAAAQEECVCENYKLAVNCF VNNNRQCQCTSVGAQNTVICSKLAAKCLVMKAEMNGSK LGRRAKPEGALQNNDGLYDPDCDESGLFKAKQCNGTSM CWCVNTAGVRRTDKDTEITCSERVRTYWIIIELKHKAREKP YDSKSLRTALQKEITTRYQLDPKFITSILYENNVITIDLVQNS SQKTQNDVDIADVAYYFEKDVKGESLFHSKKMDLTVNGE QLDLDPGQTLIYYVDEKAPEFSMQGLKAGVIAVIVVVVIAV VAGIVVLVISRKKRMAKYEKAEIKEMGEMHRELNA |
| 60 | Cynomolgus monkey EpCAM | Full length protein sequence with signal peptide (bold) | MAPPQVLAFGLLLAAATASFAAAQKECVCENYKLAVNCF LNDNGQCQCTSIGAQNTVLCSKLAAKCLVMKAEMNGSK LGRRAKPEGALQNNDGLYDPDCDESGLFKAKQCNGTSTC WCVNTAGVRRTDKDTEITCSERVRTYWIIIELKHKAREKPY DVQSLRTALEEAIKTRYQLDPKFITNILYEDNVITIDLVQNSS QKTQNDVDIADVAYYFEKDVKGESLFHSKKMDLRVNGEQ LDLDPGQTLIYYVDEKAPEFSMQGLKAGVIAVIVVVVIAIV AGIVVLVISRKKRMAKYEKAEIKEMGEIHRELNA |
| 61 | Mouse EpCAM | Full length protein sequence with signal peptide (bold) | MAGPQALAFGLLLAVVTATLAAAQRDCVCDNYKLATSCS LNEYGECQCTSYGTQNTVICSKLASKCLAMKAEMTHSKG RRIKPEGAIQNNDGLYDPDCDEQGLFKAKQCNGTATCWC VNTAGVRRTDKDTEITCSERVRTYWIIIELKHKERESPYDH QSLQTALQEAFTSRYKLNQKFIKNIMYENNVITIDLMQNSS QKTQDDVDIADVAYYFEKDVKGESLFHSSKSMDLRVNGE PLDLDPGQTLIYYVDEKAPEFSMQGLTAGIIAVIVVVSLAVI AGIVVLVISTRKKSAKYEKAEIKEMGEIHRELNA |
| 62 | Human 4-1BB | Full length protein sequence with signal peptide (bold) | MGNSCYNIVATLLLVLNFERTRSLQDPCSNCPAGTFCDN NRNQICSPCPPNSFSSAGGQRTCDICRQCKGVFRTRKECS STSNAECDCTPGFHCLGAGCSMCEQDCKQGQELTKKGCK DCCFGTFNDQKRGICRPWTNCSLDGKSVLVNGTKERDVV CGPSPADLSPGASSVTPPAPAREPGHSPQIISFFLALTSTAL LFLLFFLTLRFSVVKRGRKKLLYIFKQPFMRPVQTTQEEDGC SCRFPEEEEGGCEL |
| 63 | Cynomolgus monkey 4-1BB | Full length protein sequence with signal peptide (bold) | MGNSCYNIVATLLLVLNFERTRSLQDLCSNCPAGTFCDN NRSQICSPCPPNSFSSAGGQRTCDICRQCKGVFKTRKECSS TSNAECDCISGYHCLGAECSMCEQDCKQGQELTKKGCKD CCFGTFNDQKRGICRPWTNCSLDGKSVLVNGTKERDVVC GPSPADLSPGASSATPPAPAREPGHSPQIIFFLALTSTVVLF LLFFLVLRFSVVKRSRKKLLYIFKQPFMRPVQTTQEEDGCSC RFPEEEEGGCEL |
| 64 | IgG1-EpCAM-A37-FERL | VH_CDR1 | SYAIS |
| 65 | IgG1-EpCAM-A37-FERL | VH_CDR2 | GIIPIFGTANYAQKFQG |
| 66 | IgG1-EpCAM-A37-FERL | VH_CDR3 | DPFLHY |
| 67 | IgG1-EpCAM-A37-FERL | VL_CDR1 | RASQTISNNYLA |

TABLE 1-continued

Sequences

| SEQ ID NO: | Reference | Domain | Sequence |
|---|---|---|---|
| 68 | IgG1-EpCAM-A37-FERL | VL_CDR2 | AASSRAT |
| 69 | IgG1-CD137-009-HC7LC2-FEAR | VH_CDR1 | DYWMS |
| 70 | IgG1-CD137-009-HC7LC2-FEAR | VH_CDR2 | YIDVGGSLYYAASVKG |
| 71 | IgG1-CD137-009-HC7LC2-FEAR | VH_CDR3 | GGLTYGFDL |
| 72 | IgG1-CD137-009-HC7LC2-FEAR | VL_CDR1 | QASEDISSYLA |
| 73 | IgG1-CD137-009-HC7LC2-FEAR | VL_CDR2 | GASDLAS |
| 74 | IgG1-EpCAM-A37-FERL | VH_CDR1 | SYA |
| 75 | IgG1-CD137-009-HC7LC2-FEAR | VH_CDR1 | DYW |
| 76 | | VH_CDR1 | GYTFTNYG |
| 77 | | VH_CDR2 | INTYTGEP |
| 78 | | VH_CDR3 | ARFGNYVDY |
| 79 | | VL_CDR1 | KNLLHSNGITY |
| 80 | | VL_CDR2 | QM |
| 81 | | VL_CDR3 | AQNLEIPRT |
| 82 | | VH_CDR1 | NYGMN |
| 83 | | VH_CDR2 | WINTYTGEPTYGEDFKG |
| 84 | | VH_CDR3 | FGNYVDY |
| 85 | | VL_CDR1 | RSSKNLLHSNGITYLY |
| 86 | | VL_CDR2 | QMSNLAS |
| 87 | | VH_CDR1 | NYG |
| 88 | | VL_CDR1 | QSLLHSNGYNY |
| 89 | | VL_CDR2 | LG |
| 90 | | VL_CDR3 | MQALQTFT |
| 91 | | VL_CDR1 | RSSQSLLHSNGYNYLD |
| 92 | | VL_CDR2 | LGSNRAS |
| 93 | | VH_CDR2 | IVPIFGTA |
| 94 | | VL_CDR1 | QSVSSSY |
| 95 | | VL_CDR2 | GA |
| 96 | | VH_CDR2 | GIVPIFGTANYAQKFQG |
| 97 | | VL_CDR1 | RASQSVSSSYLA |
| 98 | | VL_CDR2 | GASSRAT |

DETAILED DESCRIPTION OF THE INVENTION

Although the present disclosure is further described in more detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

In the following, the elements of the present disclosure will be described in more detail. These elements are listed with specific embodiments, however, it should be understood that they may be combined in any manner and in any number to create additional embodiments. The variously described examples and preferred embodiments should not be construed to limit the present disclosure to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kolbl, Eds., Helvetica Chimica Acta, CH-4010 Basel, Switzerland, (1995).

The practice of the present disclosure will employ, unless otherwise indicated, conventional chemistry, biochemistry, cell biology, immunology, and recombinant DNA techniques which are explained in the literature in the field (cf., e.g., Organikum, Deutscher Verlag der Wissenschaften, Berlin 1990; Streitwieser/Heathcook, "Organische Chemie", VCH, 1990; Beyer/Walter, "Lehrbuch der Organischen Chemie", S. Hirzel Verlag Stuttgart, 1988; Carey/Sundberg, "Organische Chemie", VCH, 1995; March, "Advanced Organic Chemistry", John Wiley & Sons, 1985; Rompp Chemie Lexikon, Falbe/Regitz (Hrsg.), Georg Thieme Verlag Stuttgart, New York, 1989; Molecular Cloning: A Laboratory Manual, 2nd Edition, J. Sambrook et al. eds., Cold Spring Harbor Laboratory Press, Cold Spring Harbor 1989.

All methods described herein can be performed in any suitable order unless otherwise indicated herein or otherwise clearly contradicted by the context. The use of any and all examples, or exemplary language (e.g., "such as"), provided herein is intended merely to better illustrate the present disclosure and does not pose a limitation on the scope of the present disclosure otherwise claimed. No language in the specification should be construed as indicating any non-claimed element essential to the practice of the present disclosure.

Recitation of ranges of values herein is merely intended to serve as a shorthand method of referring individually to each separate value falling within the range. Unless otherwise indicated herein, each individual value is incorporated into the specification as if it were individually recited herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

In the following, definitions will be provided which apply to all aspects of the present disclosure. The following terms have the following meanings unless otherwise indicated. Any undefined terms have their art recognized meanings.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a", "an" and "the" and similar references used in the context of describing the present disclosure (especially in the context of the claims) are to be construed to cover both the singular and the plural, unless otherwise indicated herein or clearly contradicted by the context.

Where used herein, "and/or" is to be taken as specific disclosure of each of the two specified features or components with or without the other. For example, "X and/or Y" is to be taken as specific disclosure of each of (i) X, (ii) Y, and (iii) X and Y, just as if each is set out individually herein.

In the context of the present disclosure, the term "about" denotes an interval of accuracy that the person of ordinary skill will understand to still ensure the technical effect of the feature in question. The term typically indicates deviation from the indicated numerical value by ±5%, ±4%, ±3%, ±2%, ±1%, ±0.9%, ±0.8%, ±0.7%, ±0.6%, ±0.5%, ±0.4%, ±0.3%, ±0.2%, ±0.1%, ±0.05%, and for example±0.01%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect.

The term "binding agent" in the context of the present disclosure refers to any agent capable of binding to desired antigens. In certain embodiments of the present disclosure, the binding agent is an antibody, antibody fragment, or construct thereof. The binding agent may also comprise synthetic, modified or non-naturally occurring moieties, in particular non-peptide moieties. Such moieties may, for example, link desired antigen-binding functionalities or regions such as antibodies or antibody fragments. In one embodiment, the binding agent is a synthetic construct comprising antigen-binding CDRs or variable regions.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies.

The structure of immunoglobulins has been well characterized. See, e.g., Fundamental Immunology Ch. 7 (Paul, W., ed., $2^{nd}$ ed. Raven Press, N.Y. (1989)). Briefly, immunoglobulins generally comprise several chains, typically two identical heavy chains and two identical light chains which are linked via disulfide bonds. These chains are primarily composed of immunoglobulin domains or regions, such as the $V_L$ or VL (variable light chain) domain/region, $C_L$ or CL (constant light chain) domain/region, $V_H$ or VH (variable heavy chain) domain/region, and the CH or CH (constant heavy chain) domains/regions $C_H1$ (CH1), $C_H2$ (CH2), $C_H3$ (CH3), and $C_H4$ (CH4). The heavy chain constant region typically is comprised of three domains, CH1, CH2, and CH3. The hinge region is the region between the CH1 and CH2 domains of the heavy chain and is highly flexible. Disulfide bonds in the hinge region are part of the interactions between two heavy chains in an IgG molecule. Each light chain typically is comprised of a VL and a CL. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules using DomainGapAlign (Lefranc M P., Nucleic Acids Research 1999; 27:209-212 and Ehrenmann F, Kaas Q. and Lefranc M.-P. Nucleic Acids Res., 38, D301-307 (2010); see also internet http address www.imgt.org. However, it should be understood that the present disclosure is not limited to CDR sequences only determined according to the IMGT rules. Thus, the HCDR1, HCDR2, and HCDR3 sequences of a heavy chain variable region (VH), e.g., SEQ ID NO: 1 or SEQ ID NO: 11, or the LCDR1, LCDR2, and LCDR3 sequences of a light chain variable region (VL), e.g., SEQ ID NO: 5 or SEQ ID NO: 15, shall encompass those CDR sequences which are determined by any method for determining CDR sequences, for example according to the IMGT rules or the Kabat rules. In addition, sequences shall also be included that represent an overlap of CDR sequences that are determined by different methods for determining CDR sequences, e.g., according to the IMGT rules and the Kabat rules.

The following table shows the results of determining CDR sequences according to the IMGT rules and the Kabat rules in relation to SEQ ID NO: 1 and SEQ ID NO: 5 or SEQ ID NO: 11 and SEQ ID NO: 15, and also shows the overlap of the determined CDR sequences.

| | IMGT | Kabat | Overlap |
|---|---|---|---|
| | CDR sequences of SEQ ID NO: 1 [SEQ ID NOs in brackets] | | |
| HCDR1 | GGTFSSYA [2] | SYAIS [64] | SYA [74] |
| HCDR2 | IIPIFGTA [3] | GIIPIFGTANYAQKFQG [65] | IIPIFGTA [3] |
| HCDR3 | ARDPFLHY [4] | DPFLHY [66] | DPFLHY [66] |
| | CDR sequences of SEQ ID NO: 5 [SEQ ID Nos in brackets] | | |
| LCDR1 | QTISNNY [6] | RASQTISNNYLA [67] | QTISNNY [6] |
| LCDR2 | AAS [7] | AASSRAT [68] | AAS [7] |
| LCDR3 | AQGELYPRQ [8] | AQGELYPRQ [8] | AQGELYPRQ [8] |
| | CDR sequences of SEQ ID NO: 11 [SEQ ID NOs in brackets] | | |
| HCDR1 | GFSLNDYW [12] | DYWMS [69] | DYW [75] |
| HCDR2 | IDVGGSL [13] | YIDVGGSLYYAASVKG [70] | IDVGGSL [13] |
| HCDR3 | ARGGLTYGFDL [14] | GGLTYGFDL [71] | GGLTYGFDL [71] |
| | CDR sequences of SEQ ID NO: 15 [SEQ ID Nos in brackets] | | |
| LCDR1 | EDISSY [16] | QASEDISSYLA [72] | EDISSY [16] |
| LCDR2 | GAS [17] | GASDLAS [73] | GAS [17] |
| LCDR3 | HYYATISGLGVA [18] | HYYATISGLGVA [18] | HYYATISGLGVA [18] |

The following table shows the results of determining CDR sequences according to the IMGT rules and the Kabat rules in relation to SEQ ID NO: 21 and SEQ ID NO: 22, and also shows the overlap of the determined CDR sequences.

| | IMGT | Kabat | Overlap |
|---|---|---|---|
| | CDR sequences of SEQ ID NO: 21 [SEQ ID NOs in brackets] | | |
| HCDR1 | GYTFTNYG [76] | NYGMN [82] | NYG [87] |
| HCDR2 | INTYTGEP [77] | WINTYTGEPTYGEDFKG [83] | INTYTGEP [77] |
| HCDR3 | ARFGNYVDY [78] | FGNYVDY [84] | FGNYVDY [84] |

| IMGT | Kabat | Overlap |
|---|---|---|

CDR sequences of SEQ ID NO: 22 [SEQ ID Nos in brackets]

| | | |
|---|---|---|
| LCDR1 KNLLHSNGITY [79] | RSSKNLLHSNGITYLY [85] | KNLLHSNGITY [79] |
| LCDR2 QM [80] | QMSNLAS [86] | QM [80] |
| LCDR3 AQNLEIPRT [81] | AQNLEIPRT [81] | AQNLEIPRT [81] |

The following table shows the results of determining CDR sequences according to the IMGT rules and the Kabat rules in relation to SEQ ID NO: 25 and SEQ ID NO: 26, and also shows the overlap of the determined CDR sequences.

| IMGT | Kabat | Overlap |
|---|---|---|

CDR sequences of SEQ ID NO: 25 [SEQ ID NOs in brackets]

| | | |
|---|---|---|
| HCDR1 GGTFSSYA [2] | SYAIS [64] | SYA [74] |
| HCDR2 IIPIFGTA [3] | GIIPIFGTANYAQKFQG [65] | IIPIFGTA [3] |
| HCDR3 ARDPFLHY [4] | DPFLHY [66] | DPFLHY [66] |

CDR sequences of SEQ ID NO: 26 [SEQ ID Nos in brackets]

| | | |
|---|---|---|
| LCDR1 QSLLHSNGYNY [88] | RSSQSLLHSNGYNYLD [91] | QSLLHSNGYNY [88] |
| LCDR2 LG [89] | LGSNRAS [92] | LG [89] |
| LCDR3 MQALQTFT [90] | MQALQTFT [90] | MQALQTFT [90] |

The following table shows the results of determining CDR sequences according to the IMGT rules and the Kabat rules in relation to SEQ ID NO: 27 and SEQ ID NO: 28, and also shows the overlap of the determined CDR sequences.

| IMGT | Kabat | Overlap |
|---|---|---|

CDR sequences of SEQ ID NO: 27 [SEQ ID NOs in brackets]

| | | |
|---|---|---|
| HCDR1 GGTFSSYA [2] | SYAIS [64] | SYA [74] |
| HCDR2 IVPIFGTA [93] | GIVPIFGTANYAQKFQG [96] | IVPIFGTA [93] |
| HCDR3 ARDPFLHY [4] | DPFLHY [66] | DPFLHY [66] |

CDR sequences of SEQ ID NO: 28 [SEQ ID Nos in brackets]

| | | |
|---|---|---|
| LCDR1 QSVSSSY [94] | RASQSVSSSYLA [97] | QSVSSSY [94] |
| LCDR2 GA [95] | GASSRAT [98] | GA [95] |
| LCDR3 AQGELYPRQ [8] | AQGELYPRQ [8] | AQGELYPRQ [8] |

Unless otherwise stated or contradicted by context, reference to amino acid positions in the constant regions in the present disclosure is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "amino acid" and "amino acid residue" may herein be used interchangeably, and are not to be understood limiting amino acids are organic compounds containing amine (—NH$_2$) and carboxyl (—COOH) functional groups, along with a side chain (R group) specific to each amino acid. In the context of the present disclosure, amino acids may be classified based on structure and chemical characteristics. Thus, classes of amino acids may be reflected in one or both of the following tables:

TABLE 2

Main classification based on structure and general chemical characterization of R group

| Class | Amino acid |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Alternative Physical and Functional Classifications of Amino Acid Residues

| Class | Amino acid |
|---|---|
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Substitution of one amino acid for another may be classified as a conservative or non-conservative substitution. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. In the context of the present disclosure, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues. Naturally occurring amino acids may also be generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

The term "amino acid corresponding to position . . . ." and similar expressions as used herein refer to an amino acid position number in a human IgG1 heavy chain Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present disclosure.

The term "antibody" (Ab) in the context of the present disclosure refers to an immunoglobulin molecule, a fragment of an immunoglobulin molecule, or a derivative of either thereof, which has the ability to specifically bind to an antigen (in particular an epitope on an antigen), typically under physiological conditions, preferably with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). In particular, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3 (or CDR-H1, CDR-H2 and CDR-H3), the CDRs of a VL are termed LCDR1, LCDR2 and LCDR3 (or CDR-L1, CDR-L2 and CDR-L3). The variable regions of the heavy and light chains contain a binding domain that interacts with an antigen. The constant regions of an antibody comprise the heavy chain constant region (CH) and the light chain constant region (CL), wherein CH can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and components of the complement system such as C1q. Antibodies can be intact immunoglobulins derived from natural sources or from recombinant sources and can be immunoactive portions of intact immunoglobulins. Antibodies are typically tetramers of immunoglobulin molecules. Antibodies may exist in a variety of forms including, for example, polyclonal antibodies, monoclonal antibodies, Fv, Fab and F(ab)$_2$, as well as single chain antibodies and humanized antibodies.

The variable regions of the heavy and light chains of the immunoglobulin molecule contain a binding domain that interacts with an antigen. The terms "binding region" and "antigen-binding region" are used herein interchangeably and refer to the region which interacts with the antigen and comprises both a VH region and a VL region. An antibody as used herein comprises not only monospecific antibodies, but also multispecific antibodies which comprise multiple, such as two or more, e.g., three or more, different antigen-binding regions.

As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the VL, VH, CL and CH1 domains, or a monovalent antibody as described in WO 2007/059782 (Genmab); (ii) F(ab')$_2$ fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody; (v) a dAb fragment (Ward et al., Nature 341, 544-546 (1989)), which consists essentially of a VH domain and also called domain antibodies (Holt et al; Trends Biotechnol. 2003 November; 21(11):484-90); (vi) camelid or Nanobody molecules (Revets et al; Expert Opin Biol Ther. 2005 January; 5(1):111-24); and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present disclosure, exhibiting different biological properties and utility. These and other useful antibody fragments in the context of the present disclosure, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques.

An antibody as generated can possess any isotype. As used herein, the term "isotype" refers to the immunoglobulin class (for instance IgG (such as IgG1, IgG2, IgG3, IgG4), IgD, IgA (such as IgA1, IgA2), IgE, IgM, or IgY) that is encoded by heavy chain constant region genes. When a particular isotype, e.g. IgG1, is mentioned herein, the term is not limited to a specific isotype sequence, e.g. a particular IgG1 sequence, but is used to indicate that the antibody is closer in sequence to that isotype, e.g. IgG1, than to other isotypes. Thus, e.g. an IgG1 antibody disclosed herein may be a sequence variant of a naturally-occurring IgG1 antibody, including variations in the constant regions.

IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

The term "multispecific antibody" in the context of the present disclosure refers to an antibody having at least two different antigen-binding regions defined by different antibody sequences. In some embodiments, said different antigen-binding regions bind different epitopes on the same antigen. However, in preferred embodiments, said different antigen-binding regions bind different target antigens. In one embodiment, the multispecific antibody is a "bispecific antibody" or "bs". A multispecific antibody, such as a bispecific antibody, can be of any format, including any of the bispecific or multispecific antibody formats described herein below.

The prefixes BisG1 and bsIgG1 are used interchangeably herein for bispecific antibodies.

The term "full-length" when used in the context of an antibody indicates that the antibody is not a fragment, but contains all of the domains of the particular isotype normally found for that isotype in nature, e.g. the VH, CH1, CH2, CH3, hinge, VL and CL domains for an IgG1 antibody.

The term "human antibody", as used herein, is intended to include antibodies having variable and framework regions derived from human germline immunoglobulin sequences and a human immunoglobulin constant domain. The human antibodies disclosed herein may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another non-human species, such as a mouse, have been grafted onto human framework sequences.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generically for different kinds of modifications of antibodies, and processes for antibody engineering are well-known for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody may be performed by other methods than those described herein. Chimeric monoclonal antibodies for therapeutic applications in humans are developed to reduce anticipated antibody immunogenicity of non-human antibodies, e.g. rodent antibodies. They may typically contain non-human (e.g. murine or rabbit) variable regions, which are specific for the antigen of interest, and human constant antibody heavy and light chain domains. The terms "variable region" or "variable domain" as used in the context of chimeric antibodies, refer to a region which comprises the CDRs and framework regions of both the heavy and light chains of an immunoglobulin, as described below.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO 92/22653 and EP 0 629 240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

As used herein, a protein which is "derived from" another protein, e.g., a parent protein, means that one or more amino acid sequences of the protein are identical or similar to one or more amino acid sequences in the other or parent protein. For example, in an antibody, binding arm, antigen-binding region, constant region, or the like which is derived from another or a parent antibody, binding arm, antigen-binding region, or constant region, one or more amino acid sequences are identical or similar to those of the other or parent antibody, binding arm, antigen-binding region, or constant region. Examples of such one or more amino acid sequences include, but are not limited to, those of the VH and VL CDRs and/or one or more or all of the framework regions, VH, VL, CL, hinge, or CH regions. For example, a humanized antibody can be described herein as "derived from" a non-human parent antibody, meaning that at least the VL and VH CDR sequences are identical or similar to the VH and VL CDR sequences of said non-human parent antibody. A chimeric antibody can be described herein as being "derived from" a non-human parent antibody, meaning that typically the VH and VL sequences may be identical or similar to those of the non-human parent antibody. Another example is a binding arm or an antigen-binding region which may be described herein as being "derived from" a particular parent antibody, meaning that said binding arm or antigen-binding region typically comprises identical or similar VH and/or VL CDRs, or VH and/or VL sequences to the binding arm or antigen-binding region of said parent antibody. As described elsewhere herein, however, amino acid modifications such as mutations can be made in the CDRs, constant regions or elsewhere in the antibody, binding arm, antigen-binding region or the like, to introduce desired characteristics. When used in the context of one or more sequences derived from a first or parent protein, a "similar" amino acid sequence preferably has a sequence identity of at least about 50%, such as at least about 60%, at least about 70%, at least about 80%, at least about 90%, at least about 95%, or at least about 97%, 98% or 99%.

Non-human antibodies can be generated in a number of different species, such as mouse, rabbit, chicken, guinea pig, llama and goat.

Monoclonal antibodies can be produced by a variety of techniques, including conventional monoclonal antibody methodology, e.g., the standard somatic cell hybridization technique of Kohler and Milstein, Nature 256: 495 (1975). Other techniques for producing monoclonal antibodies can be employed, e.g., viral or oncogenic transformation of B-lymphocytes or phage display techniques using libraries of antibody genes, and such methods are well known to a person skilled in the art.

Hybridoma production in such non-human species is a very well-established procedure Immunization protocols and techniques for isolation of splenocytes of immunized animals/non-human species for fusion are known in the art. Fusion partners (e.g., murine myeloma cells) and fusion procedures are also known.

When used herein, unless contradicted by context, the term "Fab-arm" or "arm" refers to one heavy chain-light chain pair and is used interchangeably with "half molecules" herein.

The term "binding arm comprising an antigen-binding region" means an antibody molecule or fragment that comprises an antigen-binding region. Thus, a binding arm can comprise, e.g., the six VH and VL CDR sequences, the VH and VL sequences, a Fab or Fab' fragment, or a Fab-arm.

When used herein, unless contradicted by context, the term "Fc region" refers to an antibody region consisting of the two Fc sequences of the heavy chains of an immunoglobulin, wherein said Fc sequences comprise at least a hinge region, a CH2 domain, and a CH3 domain. In one embodiment, the term "Fc region", as used herein, refers to a region comprising, in the direction from the N- to C-terminal end of the antibody, at least a hinge region, a CH2 region and a CH3 region. An Fc region of the antibody may mediate the binding of the immunoglobulin to host tissues or factors, including various cells of the immune system (such as effector cells) and components of the complement system.

In the context of the present disclosure, the term "induce Fc-mediated effector function to a lesser extent" used in relation to an antibody, including a multispecific antibody, means that the antibody induces Fc-mediated effector functions, such function in particular being selected from the list of IgG Fc receptor (FcgammaR, FcγR) binding, C1q binding, ADCC or CDC, to a lesser extent compared to a human IgG1 antibody comprising (i) the same CDR sequences, in particular comprising the same first and second antigen-binding regions, as said antibody and (ii) two heavy chains comprising human IgG1 hinge, CH2 and CH3 regions.

Fc-mediated effector function may be measured by binding to FcγRs, binding to C1q, or induction of Fc-mediated cross-linking via FcγRs.

The term "hinge region" as used herein refers to the hinge region of an immunoglobulin heavy chain. Thus, for example, the hinge region of a human IgG1 antibody corresponds to amino acids 216-230 according to the EU numbering as set forth in Kabat (Kabat, E. A. et al., Sequences of proteins of immunological interest. 5th Edition—US Department of Health and Human Services, NIH publication No. 91-3242, pp 662,680,689 (1991). However, the hinge region may also be any of the other subtypes as described herein.

The term "CH1 region" or "CH1 domain" as used herein refers to the CH1 region of an immunoglobulin heavy chain. Thus, for example, the CH1 region of a human IgG1 antibody corresponds to amino acids 118-215 according to the EU numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example, the CH2 region of a human IgG1 antibody corresponds to amino acids 231-340 according to the EU numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus, for example, the CH3 region of a human IgG1 antibody corresponds to amino acids 341-447 according to the EU numbering as set forth in Kabat (ibid). However, the CH3 region may also be any of the other subtypes as described herein.

The term "monovalent antibody" means in the context of the present disclosure that an antibody molecule is capable of binding a single molecule of the antigen, and thus is not capable of antigen cross-linking.

An "EpCAM antibody" or "anti-EpCAM antibody" is an antibody as described above, which binds specifically to the antigen EpCAM.

A "CD137 antibody" or "anti-CD137 antibody" is an antibody as described above, which binds specifically to the antigen CD137.

An "EpCAMxCD137 antibody" or "anti-EpCAMxCD137 antibody" is a bispecific antibody, which comprises two different antigen-binding regions, one of which binds specifically to the antigen EpCAM and one of which binds specifically to the antigen CD137.

The term "biosimilar" (e.g., of an approved reference product/biological drug) as used herein refers to a biologic product that is similar to the reference product based on data from (a) analytical studies demonstrating that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is approved and intended to be used and for which approval is sought (e.g., that there are no clinically meaningful differences between the biological product and the reference product in terms of the safety, purity, and potency of the product). In some embodiments, the biosimilar biological product and reference product utilizes the same mechanism or mechanisms of action for the condition or conditions of use prescribed, recommended, or suggested in the proposed labeling, but only to the extent the mechanism or mechanisms of action are known for the reference product. In some embodiments, the condition or conditions of use prescribed, recommended, or suggested in the labeling proposed for the biological product have been previously approved for the reference product. In some embodiments, the route of administration, the dosage form, and/or the strength of the biological product are the same as those of the reference product. A biosimilar can be, e.g., a presently known antibody having the same primary amino acid sequence as a marketed antibody, but may be made in different cell types or by different production, purification, or formulation methods.

As used herein, the terms "binding" or "capable of binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when determined using Bio-Layer Interferometry (BLI) or, for instance, when determined using surface plasmon resonance (SPR) technology in a BIAcore 3000 instrument using the antigen as the ligand and the antibody as the analyte. The antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein) other than the predetermined antigen or a closely related antigen. The amount with which the affinity is higher is dependent on the $K_D$ of the antibody, so that when the $K_D$ of the antibody is very low (that is, the antibody is highly specific), then the degree to which the affinity for the antigen is lower than the affinity for a non-specific antigen may be at least 10,000-fold.

The term "$k_d$" ($sec^{-1}$), as used herein, refers to the dissociation rate constant of a particular antibody-antigen interaction. Said value is also referred to as the $k_{off}$ value.

The term "$K_D$" (M), as used herein, refers to the dissociation equilibrium constant of a particular antibody-antigen interaction.

Two antibodies have the "same specificity" if they bind to the same antigen and to the same epitope. Whether an antibody to be tested recognizes the same epitope as a certain antigen-binding antibody, i.e., the antibodies bind to the same epitope, may be tested by different methods well known to a person skilled in the art.

The competition between the antibodies can be detected by a cross-blocking assay. For example, a competitive ELISA assay may be used as a cross-blocking assay. E.g., target antigen may be coated on the wells of a microtiter plate and antigen-binding antibody and candidate competing test antibody may be added. The amount of the antigen-binding antibody bound to the antigen in the well indirectly correlates with the binding ability of the candidate competing test antibody that competes therewith for binding to the same epitope. Specifically, the larger the affinity of the candidate competing test antibody is for the same epitope, the smaller the amount of the antigen-binding antibody bound to the antigen-coated well. The amount of the antigen-binding antibody bound to the well can be measured by labeling the antibody with detectable or measurable labeling substances.

An antibody competing for binding to an antigen with another antibody, e.g., an antibody comprising heavy and light chain variable regions as described herein, or an antibody having the specificity for an antigen of another antibody, e.g., an antibody comprising heavy and light chain variable regions as described herein, may be an antibody comprising variants of said heavy and/or light chain variable regions as described herein, e.g. modifications in the CDRs and/or a certain degree of identity as described herein.

An "isolated multispecific antibody" as used herein is intended to refer to a multispecific antibody which is substantially free of other antibodies having different antigenic specificities (for instance an isolated bispecific antibody that specifically binds to EpCAM and CD137 is substantially free of monospecific antibodies that specifically bind to EpCAM or CD137).

The term "monoclonal antibody" as used herein refers to a preparation of antibody molecules of single molecular composition. A monoclonal antibody composition displays a single binding specificity and affinity for a particular epitope.

When used herein the term "heterodimeric interaction between the first and second CH3 regions" refers to the interaction between the first CH3 region and the second CH3 region in a first-CH3/second-CH3 heterodimeric antibody.

When used herein the term "homodimeric interactions of the first and second CH3 regions" refers to the interaction between a first CH3 region and another first CH3 region in a first-CH3/first-CH3 homodimeric antibody and the interaction between a second CH3 region and another second CH3 region in a second-CH3/second-CH3 homodimeric antibody.

When used herein the term "homodimeric antibody" refers to an antibody comprising two first Fab-arms or half-molecules, wherein the amino acid sequence of said Fab-arms or half-molecules is the same.

When used herein the term "heterodimeric antibody" refers to an antibody comprising a first and a second Fab-arm or half-molecule, wherein the amino acid sequence of said first and second Fab-arms or half-molecules are different. In particular, the CH3 region, or the antigen-binding region, or the CH3 region and the antigen-binding region of said first and second Fab-arms/half-molecules are different.

The term "reducing conditions" or "reducing environment" refers to a condition or an environment in which a substrate, such as a cysteine residue in the hinge region of an antibody, is more likely to become reduced than oxidized.

The present disclosure also describes multispecific antibodies, such as bispecific antibodies, comprising functional variants of the VL regions, VH regions, or one or more CDRs of the bispecific antibodies of the examples. A functional variant of a VL, VH, or CDR used in the context of a bispecific antibody still allows each antigen-binding region of the bispecific antibody to retain at least a substantial proportion (at least about 50%, 60%, 70%, 80%, 90%, 95% or more) of the affinity and/or the specificity/selectivity of the parent bispecific antibody and in some cases such a bispecific antibody may be associated with greater affinity, selectivity and/or specificity than the parent bispecific antibody.

Such functional variants typically retain significant sequence identity to the parent bispecific antibody. The percent identity between two sequences is a function of the number of identical positions shared by the sequences (i.e., % homology=#of identical positions/total #of positions× 100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

In the context of the present disclosure, unless otherwise indicated, the following notations are used to describe a mutation: i) substitution of an amino acid in a given position is written as e.g. K409R which means a substitution of a lysine in position 409 of the protein with an arginine; and ii) for specific variants the specific three or one letter codes are used, including the codes Xaa and X to indicate any amino acid residue. Thus, the substitution of lysine with arginine in position 409 is designated as: K409R, and the substitution of lysine with any amino acid residue in position 409 is designated as K409X. In case of deletion of lysine in position 409 it is indicated by K409*.

Exemplary variants include those which differ from the VH and/or VL and/or CDRs of the parent sequences mainly by conservative substitutions; for example, 12, such as 11, 10, 9, 8, 7, 6, 5, 4, 3, 2 or 1 of the substitutions in the variant are conservative amino acid residue replacements.

In the context of the present disclosure, conservative substitutions may be defined by substitutions within the classes of amino acids as defined in tables 2 and 3.

Functional variants of antibody sequences described herein such as VL regions, or VH regions, or antibody sequences having a certain degree of homology or identity to antibody sequences described herein such as VL regions, or VH regions preferably comprise modifications or variations in the non-CDR sequences, while the CDR sequences preferably remain unchanged.

The term "EpCAM" as used herein, refers to epithelial cell adhesion molecule, also referred to as DIAR5, EGP-2, EGP314, EGP40, ESA, HNPCC8, KS1/4, KSA, M4S1, MIC18, MK-1, TACSTD1, TROP1, BerEp4, MOC-31, Ber-Ep4. EpCAM is believed to have many different roles, and appears to play a role in cell adhesion and cancer. In one embodiment, EpCAM is human EpCAM, having UniProt accession number P16422. The sequence of human EpCAM is also shown in SEQ ID NO: 59. Amino acids 1-23 of SEQ ID NO: 59 correspond to the signal peptide of human EpCAM; while amino acids 24-265 of SEQ ID NO: 59 correspond to the extracellular domain of human EpCAM; and the remainder of the protein, i.e. from amino acids 266-288 and 289-314 of SEQ ID NO: 59 are transmembrane and cytoplasmic domain, respectively.

The term "CD137" as used herein, refers to CD137 (4-1BB), also referred to as tumor necrosis factor receptor superfamily member 9 (TNFRSF9), which is the receptor for the ligand TNFSF9/4-1BBL. CD137 (4-1BB) is believed to be involved in T-cell activation. Other synonyms for CD137 include, but are not limited to, 4-1BB ligand receptor, CDw137, T-cell antigen 4-1BB homolog and T-cell antigen ILA. In one embodiment, CD137 (4-1BB) is human CD137 (4-1BB), having UniProt accession number Q07011. The sequence of human CD137 is also shown in SEQ ID NO: 37 Amino acids 1-23 of SEQ ID NO: 37 correspond to the signal peptide of human CD137; while amino acids 24-186 of SEQ ID NO: 37 correspond to the extracellular domain of human CD137; and the remainder of the protein, i.e. from amino acids 187-213 and 214-255 of SEQ ID NO: 37 are transmembrane and cytoplasmic domain, respectively.

"Treatment cycle" is herein defined as the time period, within the effects of separate dosages of the binding agent add on due to the pharmacodynamics of the binding agent, or in other words the time period after the subject's body is essentially cleared from the administrated binding agent. Multiple small doses in a small time window, e.g. within 2-24 few hours, such as 2-12 hours or on the same day, might be equal to a larger single dose.

In the present context, the term "treatment", "treating" or "therapeutic intervention" relates to the management and care of a subject for the purpose of combating a condition such as a disease or disorder.

The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications. In one embodiment, "treatment" refers to the administration of an effective amount of a therapeutically active binding agent, such as of a therapeutically active antibody, of the present disclosure with the purpose of easing, ameliorating, arresting or eradicating (curing) symptoms or disease states.

The response to treatment as well as the resistance to, failure to respond to and/or relapse from treatment with a binding agent of the present disclosure may be determined according to the Response Evaluation Criteria in Solid Tumors; version 1.1 (RECIST Criteria v1.1).

The "best overall response" is the best response recorded from the start of the treatment until disease progression/recurrence (the smallest measurements recorded since the treatment started will be used as the reference for PD). Subjects with CR or PR are considered to be objective response. Subjects with CR, PR or SD are considered to be in disease control. Subjects with NE are counted as non-responders. The best overall response is the best response recorded from the start of the treatment until disease progression/recurrence (the smallest measurements recorded since the treatment started will be used as the reference for PD). Subjects with CR, PR or SD are considered to be in disease control. Subjects with NE are counted as non-responders.

"Duration of response (DOR)" only applies to subjects whose confirmed best overall response is CR or PR and is defined as the time from the first documentation of objective tumor response (CR or PR) to the date of first PD or death due to underlying cancer.

"Progression-free survival (PFS)" is defined as the number of days from Day 1 in Cycle 1 to the first documented progression or death due to any cause.

"Overall survival (OS)" is defined as the number of days from Day 1 in Cycle 1 to death due to any cause. If a subject is not known to have died, then OS will be censored at the latest date the subject was known to be alive (on or before the cut-off date).

In the context of the present disclosure, the term "treatment regimen" refers to a structured treatment plan designed to improve and maintain health.

The term "effective amount" or "therapeutically effective amount" refers to an amount effective, at dosages and for periods of time necessary, to achieve a desired therapeutic result. A therapeutically effective amount of a binding agent, such as an antibody, like a multispecific antibody or monoclonal antibody, may vary according to factors such as the disease state, age, sex, and weight of the individual, and the ability of the binding agent to elicit a desired response in the individual. A therapeutically effective amount is also one in which any toxic or detrimental effects of the binding agent or a fragment thereof, are outweighed by the therapeutically beneficial effects. In the case that a reaction in a patient is insufficient with an initial dose, higher doses (or effectively higher doses achieved by a different, more localized route of administration) may be used. In case that unwanted side effects occur in a patient with a dose, lower doses (or effectively lower doses achieved by a different, more localized route of administration) may be used.

As used herein, the term "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease.

The term "cancer" according to the present disclosure also comprises cancer metastases. By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the present disclosure relates to "distant metastasis" which relates to a metastasis which is remote from the primary tumor and the regional lymph node system.

Terms such as "reduce", "inhibit", "interfere", and "negatively modulate" as used herein means the ability to cause an overall decrease, for example, of about 5% or greater, about 10% or greater, about 15% or greater, about 20% or greater, about 25% or greater, about 30% or greater, about 40% or greater, about 50% or greater, or about 75% or greater, in the level. The term "inhibit" or similar phrases includes a complete or essentially complete inhibition, i.e. a reduction to zero or essentially to zero.

Terms such as "increase" or "enhance" in one embodiment relate to an increase or enhancement by at least about 10%, at least about 20%, at least about 30%, at least about 40%, at least about 50%, at least about 80%, or at least about 100%.

"Physiological pH" as used herein refers to a pH of 7.5 or about 7.5.

As used in the present disclosure, "% by weight" refers to weight percent, which is a unit of concentration measuring the amount of a substance in grams (g) expressed as a percent of the total weight of the total composition in grams (g).

The term "freezing" relates to the solidification of a liquid, usually with the removal of heat.

The term "lyophilizing" or "lyophilization" refers to the freeze-drying of a substance by freezing it and then reducing the surrounding pressure (e.g., below 15 Pa, such as below 10 Pa, below 5 Pa, or 1 Pa or less) to allow the frozen medium in the substance to sublimate directly from the solid phase to the gas phase. Thus, the terms "lyophilizing" and "freeze-drying" are used herein interchangeably.

The term "recombinant" in the context of the present disclosure means "made through genetic engineering". In one embodiment, a "recombinant object" in the context of the present disclosure is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

According to the present disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" refers to large peptides, in particular peptides having at least about 151 amino acids, but the terms "peptide" and "protein" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides and can also refer to therapeutically active fragments thereof. It can also include therapeutically active variants of a protein. Examples of therapeutically active proteins include, but are not limited to, antigens for vaccination and immunostimulants such as cytokines.

The term "portion" refers to a fraction. With respect to a particular structure such as an amino acid sequence or protein the term "portion" thereof may designate a continuous or a discontinuous fraction of said structure.

The terms "part" and "fragment" are used interchangeably herein and refer to a continuous element. For example, a part of a structure such as an amino acid sequence or protein refers to a continuous element of said structure. When used in context of a composition, the term "part" means a portion of the composition. For example, a part of a composition may any portion from 0.1% to 99.9% (such as 0.1%, 0.5%, 1%, 5%, 10%, 50%, 90%, or 99%) of said composition.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable, e.g., by translation of a truncated open reading frame that lacks the 3'-end of the open reading frame. A fragment shortened at the N-terminus (C-terminal fragment) is obtainable, e.g., by translation of a truncated open reading frame that lacks the 5'-end of the open reading frame, as long as the truncated open reading frame comprises a start codon that serves to initiate translation. A fragment of an amino acid sequence comprises, e.g., at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

According to the present disclosure, a part or fragment of a peptide or protein preferably has at least one functional property of the peptide or protein from which it has been derived. Such functional properties comprise a pharmacological activity, the interaction with other peptides or proteins, an enzymatic activity, the interaction with antibodies, and the selective binding of nucleic acids. E.g., a pharmacological active fragment of a peptide or protein has at least one of the pharmacological activities of the peptide or protein from which the fragment has been derived. A part or fragment of a peptide or protein preferably comprises a sequence of at least 6, in particular at least 8, at least 10, at least 12, at least 15, at least 20, at least 30 or at least 50, consecutive amino acids of the peptide or protein. A part or fragment of a peptide or protein preferably comprises a sequence of up to 8, in particular up to 10, up to 12, up to 15, up to 20, up to 30 or up to 55, consecutive amino acids of the peptide or protein.

By "variant" herein is meant an amino acid sequence that differs from a parent amino acid sequence by virtue of at least one amino acid modification. The parent amino acid sequence may be a naturally occurring or wild type (WT) amino acid sequence, or may be a modified version of a wild type amino acid sequence. Preferably, the variant amino acid sequence has at least one amino acid modification compared to the parent amino acid sequence, e.g., from 1 to about 20 amino acid modifications, and preferably from 1 to about 10 or from 1 to about 5 amino acid modifications compared to the parent.

By "wild type" or "WT" or "native" herein is meant an amino acid sequence that is found in nature, including allelic variations. A wild-type amino acid sequence, peptide or protein has an amino acid sequence that has not been intentionally modified.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical" and "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, -2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference amino acid sequence consists of 200 amino acid residues, the degree of identity is given for at least about 100, at least about 120, at least about 140, at least about 160, at least about 180, or about 200 amino acid residues, in some embodiments continuous amino acid residues. In some embodiments, the degree of similarity or identity is given for the entire length of the reference sequence.

Homologous amino acid sequences exhibit according to the present disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to binding agents, one particular function is one or more binding activities displayed by the amino acid sequence from which the fragment or variant is derived. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., binding to a target antigen. In one embodiment, the modifications in the amino acid sequence of the parent molecule or sequence do not significantly affect or alter the characteristics of the molecule or sequence. In different embodiments, the function of the functional fragment or functional variant may be reduced but still significantly present, e.g., binding of the functional variant may be at least 50%, at least 60%, at least 70%, at least 80%, or at least 90% of the parent molecule or sequence. However, in other embodiments, function of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence.

Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the binding agents for use herein may be altered such that they vary in sequence from the naturally occurring or native sequences from which they were derived, while retaining the desirable activity of the native sequences.

"Isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell. In one embodiment, the binding agent, e.g., antibody, described herein is isolated. An "isolated binding agent" as used herein, is intended to refer to a binding agent which is substantially free of other binding agents having different antigenic specificities. In one embodiment, an isolated bispecific binding agent that specifically binds to EpCAM and CD137 is substantially free of monospecific antibodies that specifically bind to EpCAM or CD137. In a preferred embodiment, the binding agent used in the present disclosure is in substantially purified form.

The term "genetic modification" or simply "modification" includes the transfection of cells with nucleic acid. The term "transfection" relates to the introduction of nucleic acids, in particular RNA, into a cell. For purposes of the present disclosure, the term "transfection" also includes the introduction of a nucleic acid into a cell or the uptake of a nucleic acid by such cell, wherein the cell may be present in a subject, e.g., a patient. Thus, according to the present disclosure, a cell for transfection of a nucleic acid described herein can be present in vitro or in vivo, e.g. the cell can form part of an organ, a tissue and/or an organism of a patient. According to the present disclosure, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, nucleic acid encoding antigen is transiently transfected into cells. RNA can be transfected into cells to transiently express its coded protein.

According to the present disclosure, an analog of a peptide or protein is a modified form of said peptide or protein from which it has been derived and has at least one functional property of said peptide or protein. E.g., a pharmacological active analog of a peptide or protein has at least one of the pharmacological activities of the peptide or protein from which the analog has been derived. Such modifications include any chemical modification and comprise single or multiple substitutions, deletions and/or additions of any molecules associated with the protein or peptide, such as carbohydrates, lipids and/or proteins or peptides. In one embodiment, "analogs" of proteins or peptides include those modified forms resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "analog" also extends to all functional chemical equivalents of said proteins and peptides.

"Activation" or "stimulation", as used herein, refers to the state of an immune effector cell such as T cell that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which immune effector cells are stimulated by an antigen, proliferate, and the specific immune effector cell recognizing said antigen is amplified. Preferably, clonal expansion leads to differentiation of the immune effector cells.

An "antigen" according to the present disclosure covers any substance or molecular structure that can bind to an antibody or T-cell receptor. The presence of an antigen in a body may elicit an immune response. Thus, "antigen" covers any substance against which an immune response or an immune mechanism is directed. This also includes situations wherein the antigen is processed into antigen peptides and an immune response or an immune mechanism is directed against one or more antigen peptides, in particular if presented in the context of MHC molecules. In particular, an "antigen" relates to any substance, preferably a peptide or protein, that reacts specifically with antibodies or T-lymphocytes (T-cells). According to the present disclosure, the term "antigen" comprises any molecule which comprises at least one epitope, such as a T cell epitope. Preferably, an antigen in the context of the present disclosure is a molecule which, optionally after processing, induces an immune reaction, which is preferably specific for the antigen (including cells expressing the antigen). In one embodiment, an antigen is a disease-associated antigen, such as a tumor antigen, a viral antigen, or a bacterial antigen, or an epitope derived from such antigen.

The term "epitope" refers to an antigenic determinant in a molecule such as an antigen, i.e., to a part in or fragment of the molecule that is recognized by the immune system, for example, that is recognized by antibodies T cells or B cells, in particular when presented in the context of MHC molecules. In one embodiment, "epitope" means a protein determinant capable of specific binding to an antibody. Epitopes usually consist of surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen-binding peptide (in other words, the amino acid residue is within the footprint of the specifically antigen-binding peptide).

An epitope of a protein preferably comprises a continuous or discontinuous portion of said protein and is preferably between about 5 and about 100, preferably between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope in the context of the present disclosure is a T cell epitope.

The term "optional" or "optionally" as used herein means that the subsequently described event, circumstance or condition may or may not occur, and that the description includes instances where said event, circumstance, or condition occurs and instances in which it does not occur.

As used herein, the terms "linked", "fused", or "fusion" are used interchangeably. These terms refer to the joining together of two or more elements or components or domains.

The term "disease" (also referred to as "disorder" herein) refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably. Similarly, the term "method for preventing" in the context of progression of a disease, such as progression of a tumor or cancer, relates to any method that is intended to prevent the disease from progressing in an individual.

The terms "individual" and "subject" are used herein interchangeably. They refer to a human or another mammal (e.g., mouse, rat, rabbit, dog, cat, cattle, swine, sheep, horse or primate), or any other non-mammal-animal, including birds (chicken), fish or any other animal species that can be afflicted with or is susceptible to a disease or disorder (e.g., cancer). Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment of the disclosure, a nucleic acid is expressed in cells of a subject treated to provide the encoded peptide or protein. In one embodiment, the nucleic acid is transiently expressed in cells of the subject. Thus, in one embodiment, the nucleic acid is not integrated into the genome of the cells. In one embodiment, the nucleic acid is RNA, preferably in vitro transcribed RNA.

The nucleic acids described herein may be recombinant and/or isolated molecules.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA described herein may have modified nucleosides. In some embodiments, the RNA comprises a modified nucleoside in place of at least one (e.g., every) uridine.

In some embodiments, the modified nucleoside is independently selected from pseudouridine (ψ), N1-methyl-pseudouridine (m1ψ), and 5-methyl-uridine (m5U).

In some embodiments, the modified nucleoside replacing one or more uridine in the RNA may be any one or more of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($cm^5U$), 1-taurinomethyl-pseudouridine, 5-taurinomethyl-2-thio-uridine ($cm^5\ s^2U$), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thiodihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1-methyl-3-(3-amino-3-carboxypropyl)pseudouridine (acp$^3$ ψ) 5-(isopentenylaminomethyl)uridine (inm$^5$U), 5-(isopentenylaminomethyl)-2-thio-uridine (inm$^5$s$^2$U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, the RNA comprises a cap0, cap1, or cap2. According to the present disclosure, the term "cap0" means the structure "m$^7$GpppN", wherein N is any nucleoside bearing an OH moiety at position 2'. According to the present disclosure, the term "cap1" means the structure "m$^7$GpppNm", wherein Nm is any nucleoside bearing an OCH$_3$ moiety at position 2'. According to the present disclosure, the term "cap2" means the structure "m$^7$GpppNmNm", wherein each Nm is independently any nucleoside bearing an OCH$_3$ moiety at position 2'.

In some embodiments, the RNA comprises a 5'-cap structure selected from the group consisting of m$_2$$^{7,2'O}$G(5')ppSp(5')G (in particular its D1 diastereomer), m$_2$$^{7,3'O}$G(5')ppp(5')G, and m$_2$$^{7,3'-O}$Gppp(m$_1$$^{2'-O}$) ApG.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, the RNA according to the present disclosure comprises a 3'-poly(A) sequence. As used herein, the term "poly(A) sequence" or "poly-A tail" refers to an uninterrupted or interrupted sequence of adenylate residues which is typically located at the 3' end of an RNA molecule. Poly(A) sequences are known to those of skill in the art and may follow the 3' UTR in the RNAs described herein. The poly(A) sequence may be of any length. In some embodiments, a poly(A) sequence comprises or consists of at least 20, at least 30, at least 40, at least 80, or at least 100 and up to 500, up to 400, up to 300, up to 200, or up to 150 nucleotides, and, in particular, about 110 nucleotides. In some embodiments, the poly(A) sequence only consists of A nucleotides. In some embodiments, the poly(A) sequence essentially consists of A nucleotides, but is interrupted by a random sequence of the four nucleotides (A, C, G, and U), as disclosed in WO 2016/005324 A1, hereby incorporated by reference. Such random sequence may be 5 to 50, 10 to 30, or 10 to 20 nucleotides in length. A poly(A) cassette present in the coding strand of DNA that essentially consists of dA nucleotides, but is interrupted by a random sequence having an equal distribution of the four nucleotides (dA, dC, dG, dT) and having a length of e.g. 5 to 50 nucleotides shows, on DNA level, constant propagation of plasmid DNA in E. coli and is still associated, on RNA level, with the beneficial properties with respect to supporting RNA stability and translational efficiency. In some embodiments, no nucleotides other than A nucleotides flank a poly(A) sequence at its 3' end, i.e., the poly(A) sequence is not masked or followed at its 3' end by a nucleotide other than A.

In the context of the present disclosure, the term "transcription" relates to a process, wherein the genetic code in a DNA sequence is transcribed into RNA. Subsequently, the RNA may be translated into peptide or protein.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Similarly, RNA such as mRNA encodes a protein if translation of the RNA produces the protein in a cell or other biological system.

RNA may be naked or packaged, e.g., formulated in particles such as protein and/or lipid particles, e.g., lipid nanoparticles.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

Fc regions may have at their C-terminus a lysine. The origin of this lysine is a naturally occurring sequence found in humans from which these Fc regions are derived. During cell culture production of recombinant antibodies, this terminal lysine can be cleaved off by proteolysis by endogenous carboxypeptidase(s), resulting in a constant region having the same sequence but lacking the C-terminal lysine. For manufacturing purposes of antibodies, the DNA encoding this terminal lysine can be omitted from the sequence such that antibodies are produced without the lysine. Antibodies produced from nucleic acid sequences that either do, or do not encode a terminal lysine are substantially identical in sequence and in function since the degree of processing of the terminal lysine is typically high when e.g. using antibodies produced in CHO-based production systems (Dick, L. W. et al. Biotechnol. Bioeng. 2008; 100: 1132-1143). Hence, it is understood that proteins in accordance with the invention, such as antibodies, can be generated with or without encoding or having a terminal lysine.

ASPECTS AND EMBODIMENTS OF THE PRESENT DISCLOSURE

Binding Agent Binding to EpCAM and CD137

In a first aspect, the present disclosure provides a binding agent comprising a first binding region binding to EpCAM and a second binding region binding to CD137.

The binding agent disclosed herein can in principle be an antibody of any isotype. The choice of isotype typically will be guided by the desired Fc-mediated effector functions, such as ADCC induction, or the requirement for an antibody devoid of Fc-mediated effector function ("inert" antibody). Exemplary isotypes are IgG1, IgG2, IgG3, and IgG4. Either of the human light chain constant regions, kappa or lambda, may be used. The effector function of the antibodies described herein may be changed by isotype switching to, e.g., an IgG1, IgG2, IgG3, IgG4, IgD, IgA, IgE, or IgM antibody for various therapeutic uses. In one embodiment, both heavy chains of an antibody described herein are of the IgG1 isotype, for instance an IgG1,κ. Optionally, the heavy chain may be modified in the hinge and/or CH3 region as described elsewhere herein.

Preferably, each of the antigen-binding regions comprises a heavy chain variable region (VH) and a light chain variable region (VL), and wherein said variable regions each comprise three CDR sequences, CDR1, CDR2 and CDR3, respectively, and four framework sequences, FR1, FR2, FR3 and FR4, respectively. Furthermore, preferably, the antibody comprises two heavy chain constant regions (CH), and two light chain constant regions (CL).

In one embodiment, the binding agent is a full-length antibody, such as a full-length IgG1 antibody. For example, in one embodiment, the binding agent, e.g., a bispecific antibody, comprises two half-molecules each comprising an antigen-binding region.

Many different formats of bispecific antibodies are known in the art, and were reviewed by Kontermann; Drug Discov Today, 2015 July; 20(7):838-47 and; MAbs, 2012 March-April; 4(2):182-97. All these formats are encompassed herein. A bispecific antibody according to the present disclosure is not limited to any particular bispecific format or method of producing it.

Examples of bispecific antibody molecules which may be used in the present disclosure comprise (i) a single antibody that has two arms comprising different antigen-binding regions; (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')₂ fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the binding agent described herein is a diabody or a cross-body. In one embodiment, the binding agent is a bispecific antibody obtained via a controlled Fab-arm exchange (such as described in WO2011131746 (Genmab)).

Examples of different classes of binding agents include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc regions or parts thereof; (v) Fab fusion molecules, wherein different Fab-fragments are fused together, fused to heavy-chain constant-domains, Fc regions or parts thereof; and (vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc regions or parts thereof.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. J. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcAAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2): 208-18), approaches with common light chain (Crucell/Merus, U.S. Pat. No. 7,262,028), κλ Bodies (NovImmune, WO2012023053) and CovX-body (CovX/Pfizer; Doppalapudi, V. R., et al 2007. Bioorg. Med. Chem. Lett. 17, 501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, U.S. Ser. No. 00/795,1918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to ScFv/Fc Fusions (Pearce et al., Biochem Mol Biol Int. 1997 September; 42(6):1179-88), SCORPION molecules (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-DART) molecules (MacroGenics, WO2008157379, WO2010080538) and Dual(ScFv)2-Fab molecules (National Research Center for Antibody Medicine—China).

Examples of Fab fusion bispecific antibodies include but are not limited to F(ab)2 molecules (Medarex/AMGEN; Deo et al J Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 Dec. 15; 165(12):7050-7.) and Fab-Fv molecules (UCB-Celltech, WO 2009040562 A1).

Examples of ScFv-, diabody-based and domain antibodies include but are not limited to Bispecific T Cell Engager (BiTE) molecules (Micromet, WO2005061547), Tandem Diabody molecules (TandAb) (Affimed) Le Gall et al., Protein Eng Des Sel. 2004 April; 17(4):357-66.), Dual Affinity Retargeting Technology (DART) molecules (MacroGenics, WO2008157379, WO2010080538), Single-chain Diabody molecules (Lawrence, FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6): 667-75.), dual targeting nanobodies (Ablynx, Hmila et al., FASEB J. 2010) and dual targeting heavy chain only domain antibodies.

In one aspect, the bispecific antibody of the disclosure comprises a first Fc sequence comprising a first CH3 region, and a second Fc sequence comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference.

As described further herein, a stable bispecific EpCAMxCD137 antibody can be obtained at high yield using a particular method on the basis of one homodimeric starting EpCAM antibody and one homodimeric starting CD137 antibody containing only a few, conservative, asymmetrical mutations in the CH3 regions. Asymmetrical mutations mean that the sequences of said first and second CH3 regions contain amino acid substitutions at non-identical positions.

In one embodiment, the bispecific antibody as defined in any of the embodiments disclosed herein, comprises a first CH3 region which has an amino acid substitution at a position selected from the group consisting of: 366, 368, 370, 399, 405, 407 and 409 in a human IgG1 heavy chain, and a second CH3 region which has an amino acid substitution at a position selected from the group consisting of: 366, 368, 370, 399, 405, 407 and 409 in a human IgG1 heavy chain, and wherein the first and second CH3 regions are not substituted in the same positions.

In one embodiment, the bispecific antibody as defined in any of the embodiments disclosed herein, comprises the sequences of said first and second CH3 regions containing asymmetrical mutations, i.e. mutations at different positions in the two CH3 regions, e.g. a mutation at position 405 in one of the CH3 regions and a mutation at position 409 in the other CH3 region. In one embodiment, the mutation at position 405 is F405L. In one embodiment, the mutation at position 409 is K409R.

In one embodiment, the bispecific antibody comprises a first and second heavy chain, wherein each of said first and second heavy chains comprises at least a hinge region, a CH2 and a CH3 region, wherein (i) the amino acid in the position corresponding to F405 in human IgG1 heavy chain is L in said first heavy chain, and the amino acid in the position corresponding to K409 in human IgG1 heavy chain is R in said second heavy chain, or (ii) the amino acid in the position corresponding to K409 in human IgG1 heavy chain is R in said first heavy chain, and the amino acid in the position corresponding to F405 in human IgG1 heavy chain is L in said second heavy chain.

Traditional methods such as the hybrid hybridoma and chemical conjugation methods (Marvin and Zhu (2005) Acta Pharmacol Sin 26:649) can be used in the preparation of the bispecific antibodies described herein. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific, product, upon co-expression of different antibody constructs can also be used, e.g., the method described by Lindhofer et al. (1995 J Immunol 155:219). Fusion of rat and mouse hybridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing bispecific EpCAMxCD137 antibodies of the present disclosure includes the methods described in WO2011131746 and WO2013060867 (Genmab) comprising the following steps:
a) providing a first antibody comprising an Fc region, said Fc region comprising a first CH3 region;
b) providing a second antibody comprising a second Fc region, said Fc region comprising a second CH3 region, wherein the first antibody is a EpCAM antibody and the second antibody is a CD137 antibody, or vice versa; wherein the sequences of said first and second CH3 regions are different and are such that the heterodimeric interaction between said first and second CH3 regions is stronger than each of the homodimeric interactions of said first and second CH3 regions;
c) incubating said first antibody together with said second antibody under reducing conditions; and
d) obtaining said bispecific EpCAMxCD137 antibody.

Similarly, there is provided a method for producing an antibody according to the disclosure, comprising the steps of:
a) culturing a host cell producing a first antibody comprising an antigen-binding region capable of binding to human EpCAM as defined herein and purifying said first antibody from the culture;
b) culturing a host cell producing a second antibody comprising an antigen-binding region capable of binding to human CD137 as defined herein and purifying said second antibody from the culture;
c) incubating said first antibody together with said second antibody under reducing conditions sufficient to allow the cysteines in the hinge region to undergo disulfide-bond isomerization, and
d) obtaining said bispecific antibody.

In one embodiment of the disclosure, the said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bonds with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a further embodiment, step c) comprises restoring the conditions to become non-reducing or less reducing, for example by removal of a reducing agent, e.g. by desalting.

As described above, in one embodiment, the sequences of the first and second CH3 regions of the homodimeric starting antibodies are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference in their entirety.

In particular, a stable bispecific EpCAMxCD137 antibody can be obtained at high yield using the above method on the basis of two homodimeric starting antibodies which bind EpCAM and CD137, respectively, and contain only a few, asymmetrical mutations in the CH3 regions. Asymmetrical mutations mean that the sequences of said first and second CH3 regions contain amino acid substitutions at non-identical positions.

In some embodiments, the binding agent according to the present disclosure comprises, in addition to the antigen-binding regions, an Fc region consisting of the Fc sequences of the two heavy chains.

The first and second Fc sequences may each be of any isotype, including, but not limited to, IgG1, IgG2, IgG3 and IgG4, and may comprise one or more mutations or modifications. In one embodiment, each of the first and second Fc sequences is of the IgG1 isotype or derived therefrom, optionally with one or more mutations or modifications. In one embodiment, each of the first and second Fc sequences is of the IgG4 isotype or derived therefrom, optionally with one or more mutations or modifications. In another embodiment, one of the Fc sequences is of the IgG1 isotype and the other of the IgG4 isotype, or is derived from such respective isotypes, optionally with one or more mutations or modifications.

In one embodiment, one or both Fc sequences are effector-function-deficient. For example, the Fc sequence(s) may be of an IgG1 isotype, or a non-IgG1 isotype, e.g. IgG2, IgG3, or IgG4, which has been mutated such that the ability to mediate effector functions, such as ADCC, has been reduced or even eliminated.

The term "effector functions" as used herein includes any functions mediated by components of the immune system that result, for example, in the killing of diseased cells such as tumor cells, or in the inhibition of tumor growth and/or inhibition of tumor development, including inhibition of tumor dissemination and metastasis. Preferably, the effector functions in the context of the present disclosure are T cell mediated effector functions. Such functions comprise ADCC, ADCP or CDC.

Antibody-Dependent Cell-Mediated Cytotoxicity (ADCC)

Antibody-dependent cell-mediated cytotoxicity (ADCC) is the killing of an antibody-coated target cell by a cytotoxic effector cell through a nonphagocytic process, characterised by the release of the content of cytotoxic granules or by the expression of cell death-inducing molecules. ADCC is independent of the immune complement system that also lyses targets but does not require any other cell. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, monocytes, macrophages, neutrophils, eosinophils and dendritic cells. ADCC is a rapid effector mechanism whose efficacy is dependent on a number of parameters (density and stability of the antigen on the surface of the target cell; antibody affinity and FcR-binding affinity). ADCC involving human IgG1, the most used IgG subclass for therapeutic antibodies, is highly dependent on the glycosylation profile of its Fc portion and on the polymorphism of Fcγ receptors.

Antibody-Dependent Cellular Phagocytosis (ADCP)

ADCP is one crucial mechanism of action of many antibody therapies. It is defined as a highly regulated process by which antibodies eliminate bound targets via connecting its Fc domain to specific receptors on phagocytic cells, and eliciting phagocytosis. Unlike ADCC, ADCP can be mediated by monocytes, macrophages, neutrophils, and dendritic cells, through FcγRIIa, FcγRI, and FcγRIIIa, of which FcγRIIa (CD32a) on macrophages represent the predominant pathway.

Complement-Dependent Cytotoxicity (CDC)

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the CH2 domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Antibodies described herein may comprise modifications in the Fc region. When an antibody comprises such modifications, it may become an inert, or non-activating, antibody. The term "inertness", "inert" or "non-activating" as used herein, refers to an Fc region which is at least not able to bind any Fcγ receptors, induce Fc-mediated cross-linking of FcRs, or induce FcR-mediated cross-linking of target antigens via two Fc regions of individual antibodies, or is not able to bind C1q. The inertness of an Fc region of a humanized or chimeric EpCAM or CD137 antibody is advantageously tested using the antibody in a monospecific format.

Several variants can be constructed to make the Fc region of an antibody inactive for interactions with Fcγ (gamma) receptors and C1q for therapeutic antibody development. Examples of such variants are described herein.

Thus, in one embodiment of the antibody described herein, said antibody comprises a first and a second heavy chain, wherein one or both heavy chains are modified so that the antibody induces Fc-mediated effector function to a lesser extent relative to an antibody which is identical, except for comprising non-modified first and second heavy chains Said Fc-mediated effector function may be measured by determining, by binding to Fcγ receptors, by binding to C1q, or by induction of Fc-mediated cross-linking of FcRs.

In another such embodiment, the heavy and light chain constant sequences have been modified so that binding of C1q to said antibody is reduced compared to an unmodified antibody by at least 70%, at least 80%, at least 90%, at least 95%, at least 97%, or 100%, wherein C1q binding is determined by ELISA.

Thus, amino acids in the Fc region that play a dominant role in the interactions with C1q and the Fcγ receptors may be modified.

Examples of amino acid positions that may be modified, e.g. in an IgG1 isotype antibody, include positions L234, L235, G236, D265 and P331. Combinations thereof, such as L234F/L235E/D265A, or L234F/L235E/G236R can cause a profound decrease in binding to human CD64, CD32, CD16 and C1q.

L234F and L235E amino acid substitutions can result in Fc regions with abrogated interactions with Fcγ receptors and C1q (Canfield et al., 1991, J. Exp. Med. (173):1483-91; Duncan et al., 1988, Nature (332):738-40). Hence, in one embodiment, the amino acids in the positions corresponding to L234 and L235, may be F and E, respectively. A D265A or G236R amino acid substitution can decrease binding to all Fcγ receptors and prevent ADCC (Shields et al., 2001, J. Biol. Chem. (276):6591-604; Wilkinson et al., 2021, PloS one (16(12)) e0260954). Hence, in one embodiment, the amino acid in the position corresponding to D265 may be A or the amino acid in the position corresponding to G236 may be R.

In one embodiment of the disclosure, in both said first and second heavy chains the amino acids in the positions corresponding to positions L234 and L235 in a human IgG1 heavy chain, are F and E, respectively.

In one embodiment, in one or both of said first and second heavy chains the amino acids in the positions corresponding to positions L234, L235, and D265 in a human IgG1 heavy chain, are F, E, and A, respectively.

In one embodiment, in one or both of said first and second heavy chains the amino acids in the positions corresponding to positions L234, L235, and G236 in a human IgG1 heavy chain, are F, E, and R, respectively.

The L234F-L235E-D265A non-activating mutations (also referred to herein as FEA or FEA format), have been shown to have an excellent safety profile and ability to strongly suppress Fc-mediated effector function. Nevertheless, it was observed that for IgG1 antibodies that are potent inducers of complement-dependent cytotoxicity (CDC), harboring the FEA mutations can show some residual CDC. Furthermore, it was observed that recombinantly expressed antibodies with the FEA format may exhibit increased glycosylation heterogeneity as a result of additional processing of their N-glycans as compared with a wild-type IgG1 Fc region and these antibodies were also shown to be more susceptible to aggregation induced by low pH conditions. Meanwhile, when the mutations L234F, L235E and G236R are combined (also referred to herein as FER, or FER format) in IgG1 antibodies this resulted in an improved inert format capable of avoiding potential residual CDC activity, providing wild-type like glycosylation and having improved tolerance to low pH conditions. Thereby, the FER format is a highly advantageous non-activating antibody format that is well suitable for clinical development and clinical use. For bispecific antibodies, this FER inert format may also be combined in a heterodimeric format with respect to inert format substitutions, for example, a bispecific antibody may be composed of one chain carrying the inert format substitutions, whereas the other chain may comprise different inert format substitutions, e.g. FEA. Hence, the FER inert format is well suitable to be combined e.g. with existing candidate antibodies which have already undergone development for clinical use without the need to redesign and redo all the assays required, thereby allowing to quickly generate bispecific antibodies therewith utilizing technologies such as controlled Fab-arm exchange.

In a particularly preferred embodiment, in one of said first and second heavy chains the amino acids in the positions corresponding to positions L234, L235, and D265 in a human IgG1 heavy chain, are F, E, and A, respectively and in the other of said first and second heavy chains the amino acids in the positions corresponding to positions L234, L235, and G236 in a human IgG1 heavy chain, are F, E, and R, respectively.

In a further particularly preferred embodiment, the binding agent is a bispecific antibody comprising a first and second heavy chain, wherein the positions corresponding to positions L234 and L235 in a human IgG1 heavy chain according to EU numbering of both the first heavy chain and the second heavy chain are F and E, respectively, and wherein (i) the position corresponding to F405 in a human IgG1 heavy chain according to EU numbering of the first heavy chain is L, and the position corresponding to K409 in a human IgG1 heavy chain according to EU numbering of the second heavy chain is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

In a further particularly preferred embodiment, the binding agent is a bispecific antibody comprising a first and second heavy chain, wherein (1) the positions corresponding to positions L234, L235, and D265 in a human IgG1 heavy chain according to EU numbering of both the first heavy chain and the second heavy chain are F, E, and A, respectively, (2) the positions corresponding to positions L234, L235, and G236 in a human IgG1 heavy chain according to EU numbering of both the first heavy chain and the second heavy chain are F, E, and R, respectively, or (3) the positions corresponding to positions L234, L235, and D265 in a human IgG1 heavy chain according to EU numbering of one of the first heavy chain and the second heavy chain are F, E, and A, respectively, and the positions corresponding to positions L234, L235, and G236 in a human IgG1 heavy chain according to EU numbering of the other of the first heavy chain and the second heavy chain are F, E, and R, respectively, and wherein (i) the position corresponding to F405 in a human IgG1 heavy chain according to EU numbering of the first heavy chain is L, and the position corresponding to K409 in a human IgG1 heavy chain according to EU numbering of the second heavy chain is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

Antibody variants having the combination of three amino acid substitutions L234F, L235E and D265A and in addition the K409R or the F405L mutation are herein termed with the suffix "FEAR" or "FEAL", respectively.

Antibody variants having the combination of three amino acid substitutions L234F, L235E and G236R and in addition the K409R or the F405L mutation are herein termed with the suffix "FERR" or "FERL", respectively.

In a preferred embodiment, the bispecific antibody described herein comprises:
(i) a half-molecule antibody derived from IgG1-EpCAM-FEAL, and a half-molecule antibody derived from IgG1-CD137-FEAR,
(ii) a half-molecule antibody derived from IgG1-EpCAM-FEAR, and a half-molecule antibody derived from IgG1-CD137-FEAL,
(iii) a half-molecule antibody derived from IgG1-EpCAM-FERL, and a half-molecule antibody derived from IgG1-CD137-FEAR, or
(iv) a half-molecule antibody derived from IgG1-EpCAM-FEAR, and a half-molecule antibody derived from IgG1-CD137-FERL.

In a further embodiment, the binding agents or antibodies described herein are linked or conjugated to one or more therapeutic moieties, such as a cytokine, an immune-suppressant, an immune-stimulatory molecule and/or a radio-isotope. Such conjugates are referred to herein as "immunoconjugates" or "drug conjugates" Immunoconjugates which include one or more cytotoxins are referred to as "immuno-toxins".

In one embodiment, the first and/or second Fc sequence is conjugated to a drug or a prodrug or contains an acceptor group for the same. Such acceptor group may e.g. be an unnatural amino acid.

In one embodiment of the binding agent binding to EpCAM and CD137, EpCAM is human EpCAM, in particular human EpCAM comprising the sequence set forth in SEQ ID NO: 59. In one embodiment of the binding agent binding to EpCAM and CD137, CD137 is human CD137, in particular human CD137 comprising the sequence set forth in SEQ ID NO: 62. In one embodiment, EpCAM is human EpCAM and CD137 is human CD137. In one embodiment, EpCAM is human EpCAM comprising the sequence set forth in SEQ ID NO: 59 and CD137 is human CD137 comprising the sequence set forth in SEQ ID NO: 62.

In one embodiment of the binding agent,
a) the first binding region binding to human EpCAM comprises a heavy chain variable region (VH) comprising the CDR1, CDR2, and CDR3 sequences of SEQ ID NO: 1, and a light chain variable region (VL) comprising the CDR1, CDR2, and CDR3 sequences of SEQ ID NO: 5;
and
b) the second binding region binding to human CD137 comprises a heavy chain variable region (VH) comprising the CDR1, CDR2, and CDR3 sequences of SEQ ID NO: 11, and a light chain variable region (VL) comprising the CDR1, CDR2, and CDR3 sequences of SEQ ID NO: 15.

In one embodiment of the binding agent,
a) the first binding region binding to human EpCAM comprises a heavy chain variable region (VH) comprising the CDR1, CDR2, and CDR3 sequences set forth in: SEQ ID NO: 2, 3, and 4, respectively, and a light chain variable region (VL) comprising the CDR1, CDR2, and CDR3 sequences set forth in: SEQ ID NO: 6, 7, and 8, respectively;
and
b) the second binding region binding to human CD137 comprises a heavy chain variable region (VH) comprising the CDR1, CDR2, and CDR3 sequences set forth in: SEQ ID NO: 12, 13, and 14, respectively, and a light chain variable region (VL) comprising the CDR1, CDR2, and CDR3 sequences set forth in: SEQ ID NO: 16, 17, and 18, respectively.

In one embodiment of the binding agent,
a) the first binding region binding to human EpCAM comprises a heavy chain variable region (VH) comprising an amino acid sequence having at least 90%, at least 95%, at least 97%, at least 99%, or 100% sequence identity to SEQ ID NO: 1 and a light chain variable region (VL) region comprising an amino acid sequence having at least 90%, at least 95%, at least 97%, at least 99%, or 100% sequence identity to SEQ ID NO: 5, and
b) the second binding region binding to human CD137 comprises a heavy chain variable region (VH) comprising an amino acid sequence having at least 90%, at least 95%, at least 97%, at least 99%, or 100% sequence identity to SEQ ID NO: 11 and a light chain variable region (VL) region and comprising an amino acid sequence having at least 90%, at least 95%, at least 97%, at least 99%, or 100% sequence identity to SEQ ID NO: 15.

In one embodiment of the binding agent,
a) the first binding region binding to human EpCAM comprises a heavy chain variable region (VH) comprising the amino acid sequence set forth in SEQ ID NO: 1 and a light chain variable region (VL) region comprising the amino acid sequence set forth in SEQ ID NO: 5, and
b) the second binding region binding to human CD137 comprises a heavy chain variable region (VH) comprising the amino acid sequence set forth in SEQ ID NO: 11 and a light chain variable region (VL) region comprising the amino acid sequence set forth in SEQ ID NO: 15.

The binding agent may in particular be an antibody, such as a multispecific antibody, e.g., a bispecific antibody. Also, the binding agent may be in the format of a full-length antibody or an antibody fragment.

It is further preferred that the binding agent is a human antibody or a humanized antibody.

Each variable region may comprise three complementarity determining regions (CDR1, CDR2, and CDR3) and four framework regions (FR1, FR2, FR3, and FR4).

The complementarity determining regions (CDRs) and the framework regions (FRs) may be arranged from amino-terminus to carboxy-terminus in the following order: FR1, CDR1, FR2, CDR2, FR3, CDR3, FR4.

In one embodiment, the binding agent comprises
i) a polypeptide comprising a first heavy chain variable region (VH) (VH of said first binding region) and a first heavy chain constant region (CH), and
ii) a polypeptide comprising a second heavy chain variable region (VH) (VH of said second binding region) and a second heavy chain constant region (CH).

In one embodiment, the binding agent comprises
i) a polypeptide comprising a first light chain variable region (VL) (VL of said first binding region) and further comprising a first light chain constant region (CL), and
ii) a polypeptide comprising a second light chain variable region (VL) (VL of said second binding region) and further comprising a second light chain constant region (CL).

In one embodiment, the binding agent is an antibody comprising a first binding arm and a second binding arm, wherein the first binding arm comprises
i) a polypeptide comprising said first heavy chain variable region (VH) and said first heavy chain constant region (CH), and
ii) a polypeptide comprising said first light chain variable region (VL) and said first light chain constant region (CL);
and the second binding arm comprises
iii) a polypeptide comprising said second heavy chain variable region (VH) and said second heavy chain constant region (CH), and
iv) a polypeptide comprising said second light chain variable region (VL) and said second light chain constant region (CL).

In one embodiment, the binding agent comprises i) a first heavy chain and light chain comprising said antigen-binding region capable of binding to EpCAM, the first heavy chain comprising a first heavy chain constant region and the first light chain comprising a first light chain constant region; and ii) a second heavy chain and light chain comprising said antigen-binding region capable of binding CD137, the second heavy chain comprising a second heavy chain constant region and the second light chain comprising a second light chain constant region.

Each of the first and second heavy chain constant regions (CHs) may comprise one or more of a constant heavy chain 1 (CH1) region, a hinge region, a constant heavy chain 2 (CH2) region and a constant heavy chain 3 (CH3) region, preferably at least a hinge region, a CH2 region and a CH3 region.

Each of the first and second heavy chain constant regions (CHs) may comprise a CH3 region, wherein the two CH3 regions comprise asymmetrical mutations. Asymmetrical mutations mean that the sequences of said first and second CH3 regions contain amino acid substitutions at non-identical positions. For example, one of said first and second CH3 regions contains a mutation at the position corresponding to position 405 in a human IgG1 heavy chain according to EU numbering, and the other of said first and second CH3 regions contains a mutation at the position corresponding to position 409 in a human IgG1 heavy chain according to EU numbering.

In said first heavy chain constant region (CH) at least one of the amino acids in a position corresponding to a position selected from the group consisting of T366, L368, K370, D399, F405, Y407, and K409 in a human IgG1 heavy chain according to EU numbering may have been substituted, and in said second heavy chain constant region (CH) at least one of the amino acids in a position corresponding to a position selected from the group consisting of T366, L368, K370, D399, F405, Y407, and K409 in a human IgG1 heavy chain according to EU numbering may have been substituted. In particular embodiments, the first and the second heavy chains are not substituted in the same positions (i.e., the first and the second heavy chains contain asymmetrical mutations).

In one embodiment of the binding agent, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain, and the amino acid in the position corresponding to F405 in a human IgG1 heavy chain according to EU numbering is L in said second heavy chain.

In one embodiment, the binding agent induces Fc-mediated effector function to a lesser extent compared to another antibody comprising the same first and second antigen binding regions and two heavy chain constant regions (CHs) comprising human IgG1 hinge, CH2 and CH3 regions.

In one particular embodiment of the binding agent, said first and second heavy chain constant regions (CHs) are modified so that the antibody induces Fc-mediated effector function to a lesser extent compared to an antibody which is identical except for comprising non-modified first and second heavy chain constant regions (CHs). In particular, each or both of said non-modified first and second heavy chain constant regions (CHs) may comprise, consists of or consist essentially of the amino acid sequence set forth in SEQ ID NO: 47.

The Fc-mediated effector function may be determined by measuring binding of the binding agent to Fcγ receptors, binding to C1q, or induction of Fc-mediated cross-linking of Fcγ receptors. In particular, the Fc-mediated effector function may be determined by measuring binding of the binding agent to C1q.

The first and second heavy chain constant regions of the binding agent may have been modified so that binding of C1q to said antibody is reduced compared to a wild-type antibody, preferably reduced by at least 70%, at least 80%, at least 90%, at least 95%, at least 97%, or 100%, wherein C1q binding is preferably determined by ELISA.

In one embodiment of the binding agent, in at least one of said first and second heavy chain constant regions (CHs), one or more amino acids in the positions corresponding to positions L234, L235, G236, D265, N297, and P331 in a human IgG1 heavy chain according to EU numbering, are not L, L, G, D, N, and P, respectively.

In one embodiment of the binding agent, the positions corresponding to positions L234 and L235 in a human IgG1 heavy chain according to EU numbering may be F and E, respectively, in said first and second heavy chains.

In particular, the positions corresponding to positions L234, L235, and G236 in a human IgG1 heavy chain according to EU numbering may be F, E, and R, respectively, in said first and/or second heavy chain constant regions (HCs) and/or the positions corresponding to positions L234, L235, and D265 in a human IgG1 heavy chain according to EU numbering may be F, E, and A, respectively, in said first and/or second heavy chain constant regions (HCs). In one embodiment, the positions corresponding to positions L234, L235, and G236 in a human IgG1 heavy chain according to EU numbering may be F, E, and R, respectively, in one of said first and second heavy chain constant regions (HCs) and the positions corresponding to positions L234, L235, and D265 in a human IgG1 heavy chain according to EU numbering may be F, E, and A, respectively, in the other of said first and second heavy chain constant regions (HCs). In one embodiment, the positions corresponding to positions L234, L235, and G236 in a human IgG1 heavy chain according to EU numbering may be F, E, and R, respectively, in said first heavy chain constant region (HCs) and the positions corresponding to positions L234, L235, and D265 in a human IgG1 heavy chain according to EU numbering may be F, E, and A, respectively, in said second heavy chain constant regions (HCs)

In one embodiment of the binding agent, the positions corresponding to positions L234 and L235 in a human IgG1 heavy chain according to EU numbering of both the first and second heavy chain constant regions are F and E, respectively, wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

In one embodiment of the binding agent, the positions corresponding to positions L234, L235, and D265 in a human IgG1 heavy chain according to EU numbering of both the first and second heavy chain constant regions are F, E, and A, respectively, the positions corresponding to positions L234, L235, and G236 in a human IgG1 heavy chain according to EU numbering of both the first and second heavy chain constant regions are F, E, and R, respectively, or the positions corresponding to positions L234, L235, and D265 in a human IgG1 heavy chain according to EU numbering of one of the first and second heavy chain constant regions are F, E, and A, respectively, and the positions corresponding to positions L234, L235, and G236 in a human IgG1 heavy chain according to EU numbering of the other of the first and second heavy chain constant regions are F, E, and R, respectively, wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

In one embodiment, the binding agent comprises a kappa (κ) light chain constant region.

In one embodiment, the binding agent comprises a lambda (λ) light chain constant region.

In one embodiment of the binding agent, the first light chain constant region is a kappa (κ) light chain constant region or a lambda (λ) light chain constant region.

In one embodiment of the binding agent, the second light chain constant region is a lambda (λ) light chain constant region or a kappa (κ) light chain constant region.

In one embodiment of the binding agent, the first light chain constant region is a kappa (κ) light chain constant region and the second light chain constant region is a kappa (κ) light chain constant region. In one embodiment of the binding agent, the first light chain constant region is a lambda (λ) light chain constant region and the second light chain constant region is a lambda (λ) light chain constant region.

In one embodiment of the binding agent, the first light chain constant region is a kappa (κ) light chain constant region and the second light chain constant region is a lambda (λ) light chain constant region or the first light chain constant region is a lambda (λ) light chain constant region and the second light chain constant region is a kappa (κ) light chain constant region.

In one embodiment, the binding agent (in particular, antibody) is of an isotype selected from the group consisting of IgG1, IgG2, IgG3, and IgG4. In particular, the binding agent may be a full-length IgG1 antibody. In preferred embodiments, the binding agent (in particular, antibody) is of the IgG1m(f) allotype.

Use of the Binding Agent Binding to EpCAM and CD137

The binding agent disclosed herein may be used in the treatment of tumors or cancer. In one embodiment, the tumor or cancer is a tumor or cancer expressing EpCAM. In one embodiment, EpCAM is human EpCAM, in particular human EpCAM comprising the sequence set forth in SEQ ID NO: 59.

The subject to be treated according to the present disclosure is preferably a human subject.

In one preferred embodiment, the tumor or cancer to be treated is a solid tumor or cancer. The tumor or cancer may be a metastatic tumor or cancer.

Preferably, the tumor or cancer may be selected from the group consisting of melanoma, ovarian cancer, lung cancer (e.g., non-small cell lung cancer (NSCLC)), colorectal cancer, head and neck cancer, gastric cancer, breast cancer, renal cancer, urothelial cancer, bladder cancer, esophageal cancer, pancreatic cancer, hepatic cancer, thymoma and thymic carcinoma, brain cancer, glioma, adrenocortical carcinoma, thyroid cancer, other skin cancers, sarcoma, multiple myeloma, leukemia, lymphoma, myelodysplastic syndromes, endometrial cancer, prostate cancer, penile cancer, cervical cancer, Hodgkin's lymphoma, non-Hodgkin's lymphoma, Merkel cell carcinoma and mesothelioma. More preferably, the tumor or cancer is selected from the group consisting of melanoma, lung cancer, colorectal cancer, pancreatic cancer, and head and neck cancer.

In particular embodiments, the tumor or cancer is selected from the group consisting of lung cancer (e.g. non-small cell lung cancer (NSCLC), urothelial cancer (cancer of the bladder, ureter, urethra, or renal pelvis), endometrial cancer (EC), breast cancer (e.g. triple negative breast cancer (TNBC)), squamous cell carcinoma of the head and neck (SCCHN) (e.g. cancer of the oral cavity, pharynx or larynx) and cervical cancer.

In some embodiments, the amount of binding agent administered in each dose and/or in each treatment cycle is
 about 0.3-5 mg/kg body weight or about 25-400 mg in total; and/or
 about $2.1 \times 10^{-9}$-$3.4 \times 10^{-8}$ mol/kg body weight or about $1.7 \times 10^{-7}$-$2.7 \times 10^{-6}$ mol in total.

According to these embodiments, the dose defined in mg/kg may be converted to flat dose, and vice versa, based on the median body weight of the subjects to whom the binding agent is administered being 80 kg.

The amount of binding agent administered in each dose and/or in each treatment cycle may in particular be about 0.3-4.0 mg/kg body weight or about 25-320 mg in total; and/or
 about $2.1 \times 10^{-9}$-$2.7 \times 10^{-8}$ mol/kg body weight or about $1.7 \times 10^{-7}$-$2.2 \times 10^{-6}$ mol in total.

The amount of binding agent administered in each dose and/or in each treatment cycle may in particular be about 0.38-4.0 mg/kg body weight or about 30-320 mg in total; and/or about $2.6 \times 10^{-9}$-$2.7 \times 10^{-8}$ mol/kg body weight or about $2.4 \times 10^{-7}$-$2.2 \times 10^{-6}$ mol in total.

The amount of binding agent administered in each dose and/or in each treatment cycle may in particular be about 0.5-3.3 mg/kg body weight or about 40-260 mg in total; and/or
 about $3.4 \times 10^{-9}$-$2.2 \times 10^{-8}$ mol/kg body weight or about $2.7 \times 10^{-7}$-$1.8 \times 10^{-6}$ mol in total.

The amount of binding agent administered in each dose and/or in each treatment cycle may in particular be about 0.6-2.5 mg/kg body weight or about 50-200 mg in total; and/or
 about $4.3 \times 10^{-9}$-$1.7 \times 10^{-8}$ mol/kg body weight or about $3.4 \times 10^{-7}$-$1.4 \times 10^{-6}$ mol in total.

The amount of binding agent administered in each dose and/or in each treatment cycle may in particular be about 0.8-1.8 mg/kg body weight or about 60-140 mg in total; and/or
 about $5.1 \times 10^{-9}$-$1.2 \times 10^{-8}$ mol/kg body weight or about $4.1 \times 10^{-7}$-$9.5 \times 10^{-7}$ mol in total.

The amount of binding agent administered in each dose and/or in each treatment cycle may in particular be about 0.9-1.8 mg/kg body weight or about 70-140 mg in total; and/or
 about $6.0 \times 10^{-9}$-$1.2 \times 10^{-8}$ mol/kg body weight or about $4.8 \times 10^{-7}$-$9.5 \times 10^{-7}$ mol in total.

The amount of binding agent administered in each dose and/or in each treatment cycle may in particular be about 1-1.5 mg/kg body weight or about 80-120 mg in total; and/or
 about $6.8 \times 10^{-9}$-$1.0 \times 10^{-8}$ mol/kg body weight or about $5.5 \times 10^{-7}$-$8.2 \times 10^{-7}$ mol in total.

The amount of binding agent administered in each dose and/or in each treatment cycle may in particular be about 1.1-1.4 mg/kg body weight or about 90-110 mg in total; and/or
 about $7.7 \times 10^{-9}$-$9.4 \times 10^{-9}$ mol/kg body weight or about $6.1 \times 10^{-7}$-$7.5 \times 10^{-7}$ mol in total.

The amount of binding agent administered in each dose and/or in each treatment cycle may in particular be about 1.2-1.3 mg/kg body weight or about 95-105 mg in total; and/or
 about $6.8 \times 10^{-9}$-$8.9 \times 10^{-9}$ mol/kg body weight or about $6.5 \times 10^{-7}$-$7.2 \times 10^{-7}$ mol in total.

The amount of binding agent administered in each dose and/or in each treatment cycle may in particular be about 0.8-1.5 mg/kg body weight or about 65-120 mg in total; and/or
 about $5.5 \times 10^{-9}$-$1.0 \times 10^{-8}$ mol/kg body weight or about $4.4 \times 10^{-7}$-$8.2 \times 10^{-7}$ mol in total.

The amount of binding agent administered in each dose and/or in each treatment cycle may in particular be about 0.9-1.3 mg/kg body weight or about 70-100 mg in total; and/or
 about $6.0 \times 10^{-9}$-$8.5 \times 10^{-9}$ mol/kg body weight or about $4.8 \times 10^{-7}$-$6.8 \times 10^{-7}$ mol in total.
 about 0.9-1.1 mg/kg body weight or about 75-90 mg in total; and/or
 about $6.4 \times 10^{-9}$-$7.7 \times 10^{-9}$ mol/kg body weight or about $5.1 \times 10^{-7}$-$6.1 \times 10^{-7}$ mol in total.

Further, the amount of binding agent administered in each dose and/or in each treatment cycle may in particular be 0.3-4.0 mg/kg body weight or 25-320 mg in total; and/or $2.1 \times 10^{-9}$-$2.7 \times 10^{-8}$ mol/kg body weight or $1.7 \times 10^{-7}$-$2.2 \times 10^{-6}$ mol in total.

The amount of binding agent administered in each dose and/or in each treatment cycle may in particular be 0.38-4.0 mg/kg body weight or 30-320 mg in total; and/or $2.6 \times 10^{-9}$-$2.7 \times 10^{-8}$ mol/kg body weight or $2.4 \times 10^{-7}$-$2.2 \times 10^{-6}$ mol in total.

The amount of binding agent administered in each dose and/or in each treatment cycle may in particular be 0.5-3.3 mg/kg body weight or 40-260 mg in total; and/or $3.4 \times 10^{-9}$-$2.2 \times 10^{-8}$ mol/kg body weight or $2.7 \times 10^{-7}$-$1.8 \times 10^{-6}$ mol in total.

The amount of binding agent administered in each dose and/or in each treatment cycle may in particular be 0.6-2.5 mg/kg body weight or 50-200 mg in total; and/or $4.3 \times 10^{-9}$-$1.7 \times 10^{-8}$ mol/kg body weight or $3.4 \times 10^{-7}$-$1.4 \times 10^{-6}$ mol in total.

The amount of binding agent administered in each dose and/or in each treatment cycle may in particular be 0.8-1.8 mg/kg body weight or 60-140 mg in total; and/or $5.1 \times 10^{-9}$-$1.2 \times 10^{-8}$ mol/kg body weight or $4.1 \times 10^{-7}$-$9.5 \times 10^{-7}$ mol in total.

The amount of binding agent administered in each dose and/or in each treatment cycle may in particular be 0.9-1.8 mg/kg body weight or 70-140 mg in total; and/or $6.0 \times 10^{-9}$-$1.2 \times 10^{-8}$ mol/kg body weight or $4.8 \times 10^{-7}$-$9.5 \times 10^{-7}$ mol in total.

The amount of binding agent administered in each dose and/or in each treatment cycle may in particular be 1-1.5 mg/kg body weight or 80-120 mg in total; and/or $6.8 \times 10^{-9}$-$1.0 \times 10^{-8}$ mol/kg body weight or $5.5 \times 10^{-7}$-$8.2 \times 10^{-7}$ mol in total.

The amount of binding agent administered in each dose and/or in each treatment cycle may in particular be 1.1-1.4 mg/kg body weight or 90-110 mg in total; and/or $7.7 \times 10^{-9}$-$9.4 \times 10^{-9}$ mol/kg body weight or $6.1 \times 10^{-7}$-$7.5 \times 10^{-7}$ mol in total.

The amount of binding agent administered in each dose and/or in each treatment cycle may in particular be 1.2-1.3 mg/kg body weight or 95-105 mg in total; and/or $6.8 \times 10^{-9}$-$8.9 \times 10^{-9}$ mol/kg body weight or $6.5 \times 10^{-7}$-$7.2 \times 10^{-7}$ mol in total.

The amount of binding agent administered in each dose and/or in each treatment cycle may in particular be 0.8-1.5 mg/kg body weight or 65-120 mg in total; and/or $5.5 \times 10^{-9}$-$1.0 \times 10^{-8}$ mol/kg body weight or $4.4 \times 10^{-7}$-$8.2 \times 10^{-7}$ mol in total.

The amount of binding agent administered in each dose and/or in each treatment cycle may in particular be 0.9-1.3 mg/kg body weight or 70-100 mg in total; and/or $6.0 \times 10^{-9}$-$8.5 \times 10^{-9}$ mol/kg body weight or $4.8 \times 10^{-7}$-$6.8 \times 10^{-7}$ mol in total.

The amount of binding agent administered in each dose and/or in each treatment cycle may in particular be 0.9-1.1 mg/kg body weight or 75-90 mg in total; and/or $6.4 \times 10^{-9}$-$7.7 \times 10^{-9}$ mol/kg body weight or $5.1 \times 10^{-7}$-$6.1 \times 10^{-7}$ mol in total.

The amount of binding agent administered in each dose and/or in each treatment cycle may be
- about 1.1 mg/kg body weight or about 80 mg in total; and/or
- about $6.8 \times 10^{-9}$ mol/kg body weight or about $5.5 \times 10^{-7}$ mol in total.

The amount of binding agent administered in each dose and/or in each treatment cycle may be 1.1 mg/kg body weight or 80 mg in total; and/or $6.8 \times 10^{-9}$ mol/kg body weight or $5.5 \times 10^{-7}$ mol in total.

It is currently preferred that the amount of binding agent administered in each dose and/or in each treatment cycle is
- about 1.25 mg/kg body weight or about 100 mg in total; and/or
- about $8.5 \times 10^{-9}$ mol/kg body weight or about $6.8 \times 10^{-7}$ mol in total.

It is equally preferred that the amount of binding agent administered in each dose and/or in each treatment cycle is
- 1.25 mg/kg body weight or 100 mg in total; and/or
- $8.5 \times 10^{-9}$ mol/kg body weight or $6.8 \times 10^{-7}$ mol in total.

The binding agent may be administered in any manner and by any route known in the art. In a preferred embodiment, the binding agent is administered systemically, such as parenterally, in particular intravenously.

The binding agent may be administered in the form of any suitable pharmaceutical composition as described herein. In a preferred embodiment, the binding agent is administered in the form of an infusion.

The binding agent may be administered by using intravenous (IV) infusion, such as by intravenous infusion over a minimum of 30 minutes, such as over a minimum of 60 minutes e.g., by using intravenous infusion over 30 to 120 minutes. Preferably, the binding agent is administered by using intravenous (IV) infusion over 30 minutes.

The binding agent described herein may be administered per se or in the form of nucleic acid encoding the binding agent.

The binding agent or nucleic acid encoding the binding agent may be administered in any suitable form (e.g., naked as such or packaged in the form of suitable particles comprising the binding agent or nucleic acid). However, it is preferred that the binding agent or nucleic acid, are administered in the form of any suitable pharmaceutical composition as described herein.

The binding agent may be co-administered together with one or more additional therapeutic agents. In some embodiments, the one or more additional therapeutic agents comprise one or more chemotherapeutic agents, in particular, those chemotherapeutic agents which are commonly used in the treatment of a tumor or cancer as described herein. For example, the one or more chemotherapeutic agents include platinum-based compounds (e.g., cisplatin, oxaliplatin, and carboplatin), taxane-based compounds (e.g., paclitaxel and nab-paclitaxel), nucleoside analogs (e.g., 5-fluorouracil and gemcitabine), and combinations thereof (e.g., cisplatin/carboplatin+5-fluorouracil or nab-paclitaxel+gemcitabine).

A composition or pharmaceutical composition may be formulated with a carrier, excipient and/or diluent as well as any other components suitable for pharmaceutical compositions, including known adjuvants, in accordance with conventional techniques such as those disclosed in Remington: The Science and Practice of Pharmacy, 19th Edition, Gennaro, Ed., Mack Publishing Co., Easton, PA, 1995. The pharmaceutically acceptable carriers or diluents as well as any known adjuvants and excipients should be suitable for the binding agent and/or nucleic acid and/or, if present, one or more additional therapeutic agents and the chosen mode of administration. Suitability for carriers and other components of pharmaceutical compositions is determined based on the lack of significant negative impact on the desired biological properties of the chosen compound or pharmaceutical composition.

A composition, in particular a pharmaceutical composition, may include diluents, fillers, salts, buffers, detergents (e.g., a nonionic detergent, such as Tween-20 or Tween-80), stabilizers (e.g., sugars or protein-free amino acids), preservatives, solubilizers, and/or other materials suitable for inclusion in a pharmaceutical composition.

The pharmaceutical compositions of the present disclosure may comprise one or more pharmaceutically acceptable carriers, excipients and/or diluents. Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regards to the intended route of administration and standard pharmaceutical practice.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Examples of suitable aqueous and non-aqueous carriers which may be employed in the (pharmaceutical) compositions include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the (pharmaceutical) compositions is contemplated.

The term "excipient" as used herein refers to a substance which may be present in a (pharmaceutical) composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water Suitable preservatives for use in the pharmaceutical compositions of the present disclosure include, without limitation, benzalkonium chloride, chlorobutanol, paraben and thimerosal.

A (pharmaceutical) composition may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

A (pharmaceutical) composition may also comprise isotonicity agents, such as sugars, polyalcohols, such as mannitol, sorbitol, glycerol or sodium chloride in the composition.

A (pharmaceutical) composition may also contain one or more adjuvants appropriate for the chosen route of administration such as preservatives, wetting agents, emulsifying agents, dispersing agents, preservatives or buffers, which may enhance the shelf life or effectiveness of the composition. The composition as used herein may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho esters, and polylactic acid alone or with a wax, or other materials well known in the art. Methods for the preparation of such formulations are generally known to those skilled in the art, see e.g. Sustained and Controlled Release Drug Delivery Systems, J. R. Robinson, ed., Marcel Dekker, Inc., New York, 1978.

"Pharmaceutically acceptable salts" comprise, for example, acid addition salts which may, for example, be formed by using a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, suitable pharmaceutically acceptable salts may include alkali metal salts (e.g., sodium or potassium salts); alkaline earth metal salts (e.g., calcium or magnesium salts); ammonium ($NH_4^+$); and salts formed with suitable organic ligands (e.g., quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalene-sulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)). Salts which are not pharmaceutically acceptable may be used for preparing pharmaceutically acceptable salts and are included in the present disclosure.

In one embodiment, the binding agent used herein may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except in so far as any conventional media or agent is incompatible with the active compound, use thereof in the compositions is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate.

The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compounds in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

In certain embodiments the binding agent is formulated in a composition or formulation comprising histidine, sucrose and Polysorbate-80, and having a pH from about 5 to about 6, such as from 5 to 6. In particular, the binding agent may be in a composition or formulation comprising about 20 mM histidine, about 250 mM Sucrose, about 0.02% Polysorbate-80, and having a pH of about 5.5, such as a composition or formulation comprising 20 mM histidine, 250 mM Sucrose, 0.02% Polysorbate-80, and having a pH of 5.5. The formulation may in particular embodiments comprise about 10 to about 30 mg binding agent/mL, such as 10-30 mg binding agent/mL, in particular about 20 mg binding agent/mL, such as 20 mg binding agent/mL.

The binding agent may be provided in a composition as defined above and may then be diluted in 0.9% NaCl (saline) prior to administration.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The description (including the following examples) is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Generation of EpCAMx4-1BB Bispecific Antibodies by 2-MEA-Induced Fab-Arm Exchange The following antibodies were used in the examples:
EpCAM Antibodies VH and VL sequences of UBS-54 have been disclosed in patent no EP 1 479 696 A1 (Crucell Holland BV), and the antibodies based on these sequences are referred to herein as "IgG1-EpCAM-UBS-54". VH and VL sequences of A37 have been disclosed in patent no EP 1 479 696 A1 (Crucell Holland BV), and the antibodies based on these sequences are referred to herein as "IgG1-EpCAM-A37". VH and VL sequences of C52 have been disclosed in EP 1 479 696 A1 (Crucell Holland BV), and the antibodies based on these sequences are referred to herein as "IgG1-EpCAM-052". The entire kappa light chain and heavy chain sequence of 323/A3 has been disclosed in patent no U.S. Pat. No. 7,648,703 B2 (GlaxoSmithKline LLC), and the antibodies based on the VH and VL sequences of 323/A3 are referred to herein as "IgG1-EpCAM-323-A3".
4-1BB Antibodies CD137 antibody clone 005 as described in Example 1 and Table 1 of WO2018/011421 (Genmab A/S; BioNTech AG). CD137 antibody clone 005 is referred to herein as "IgG1-CD137-005". CD137 antibody clone 009 as described in Example 1 and Table 1 of WO2018/011421(Genmab A/S; BioNTech AG). CD137 antibody clone 009 is referred to herein as "IgG1-CD137-009". CD137-009 humanized antibody (HC7 and LC2) as described in Example 7 and Table 1 of WO2018/011421 (Genmab A/S; BioNTech AG). Name 4-1BB-009-HC7LC2 is referred to herein as "IgG1-CD137-009-HC7LC2".
Antibody Expression Antibody sequences were cloned into pcDNA3.3 expression vectors (Invitrogen, US) and expressed as IgG1, κ or IgG1, λ, with or without Fc-silencing and/or DuoBody® technology amino acid substitutions in the Fc domain (see below). All antibodies were produced under serum-free conditions by co-transfecting relevant heavy and light chain expression vectors in Expi293FTM cells (Thermo Fisher Scientific, US; cat. no. A14527) using ExpiFectamine™ 293 (Thermo Fisher Scientific; cat. no. A14525), essentially as described by the manufacturer.
Generation of Bispecific Antibodies Bispecific antibodies were generated in vitro using the DuoBody® platform technology, i.e. 2-MEA-induced controlled Fab-arm exchange (cFAE) as described in WO2011147986, WO2011131746 and WO2013060867 (Genmab), Labrijn et al., PNAS 2013, 110: 5145-50 and Gramer et al., MAbs 2013, 5: 962-973. To enable the generation of bispecific antibodies by this method, IgG1 molecules carrying a single mutation in the CH3 domain were generated: in one parental IgG1 antibody the F405L mutation, in the other parental IgG1 antibody the K409R mutation. In addition to these mutations, the parental IgG1 antibodies included substitutions that result in an Fc domain that is unable to interact with IgG Fc receptors (Fc gamma receptors) and/or complement factors such as C1q: L234F, L235E, D265A (FEA; US 2015/0337049) or L234F, L235E, G236R (FER).

The combination of Fc-silencing and DuoBody® technology mutations were designated as follows:
L234F, L235E, D265A, and F405L: FEAL
L234F, L235E, D265A, and K409R: FEAR
L234F, L235E, G236R, and F405L: FERL Mouse bispecific antibodies were generated in vitro by 2-MEA-induced controlled Fab-arm exchange (cFAE) as described in Labrijn et al., Sci Rep 2017, 7:2476. To enable the generation of bispecific antibodies by this method, mouse IgG2a molecules (IgG2amm) carrying double matched point mutations in the CH3 domain were generated: in one parental IgG2amm antibody the F405L/R411T (LT) mutations, in the other parental IgG2amm antibody the T370K/K409R (KR) mutations. In addition to these mutations, the parental IgG2amm antibodies included substitutions that result in an Fc domain that is unable to interact with IgG Fc receptors (Fc gamma receptors) and/or complement factors such as C1q: L234A, L235A as described in Labrijn et al., Sci Rep 2017, 7:2476.

For mouse bispecific antibodies the combination of silencing and cFAE mutations were designated as follows:
L234A, L235A, F405L/R411T: AALT
L234A, L235A, T370K/K409R: AAKR The heavy chain (HC) and light chain (LC) sequences of the parental antibodies are set forth in the following SEQ ID NOs:

```
SEQ ID NO: 25 (HC) and SEQ ID NO: 26 (LC)
IgG1-EpCAM-UBS-54-FEAR.

SEQ ID NO: 29 (HC) and SEQ ID NO: 10 (LC)
IgG1-EpCAM-A37-FEAR.

SEQ ID NO: 9 (HC) and SEQ ID NO: 10 (LC)
IgG1-EpCAM-A37-FERL.

SEQ ID NO: 27 (HC) and SEQ ID NO: 28 (LC)
IgG1-EpCAM-C52-FEAR.

SEQ ID NO: 24 (HC) and SEQ ID NO: 22 (LC)
IgG1-EpCAM-323-A3.

SEQ ID NO: 21 (HC) and SEQ ID NO: 22 (LC)
IgG1-EpCAM-323-A3-FEAL.

SEQ ID NO: 23 (HC) and SEQ ID NO: 22 (LC)
IgG1-EpCAM-323-A3-FEAR.

SEQ ID NO: 33 (HC) and SEQ ID NO: 34 (LC)
IgG1-CD137-005-FEAR.

SEQ ID NO: 31 (HC) and SEQ ID NO: 32 (LC)
IgG1-CD137-009-FEAR.

SEQ ID NO: 19 (HC) and SEQ ID NO: 20 (LC)
IgG1-CD137-009-HC7LC2-FEAR.

SEQ ID NO: 30 (HC) and SEQ ID NO: 20 (LC)
IgG1-CD137-009-HC7LC2-FEAL.

SEQ ID NO: 39 (HC) and SEQ ID NO: 40 (LC)
IgG2amm-EpCAM-323-A3-AAKR.
```

-continued
```
SEQ ID NO: 41 (HC) and SEQ ID NO: 40 (LC)
IgG2amm-EpCAM-323-A3-AALT.

SEQ ID NO: 42 (HC) and SEQ ID NO: 43 (LC)
IgG2amm-m4-1BB-3H3-AAKR.
```

To generate bispecific antibodies, the two parental antibodies were mixed in equal molar ratios in PBS buffer (Phosphate Buffered Saline; 8.7 mM $HPO_4^{2-}$, 1.8 mM $H_2PO_4^-$, 163.9 mM Na+, 140.3 mM Cl—, pH 7.4). 2-mercaptoethylamine-HCl (2-MEA) was added to a final concentration of 75 mM and the reaction mixture was incubated at 31° C. for 5 h. The 2-MEA was removed by dialysis into PBS buffer using 10 kDa molecular-weight cutoff Slide-A-Lyzer carriages (Thermo Fisher Scientific) according to the manufacturer's protocol. Samples were stored overnight at 4° C. to allow for the re-oxidation of the disulfide bonds and formation of intact bispecific antibodies. The efficacy of cFAE was >95% as assessed by electrospray ionization mass spectrometry mass spectrometry (ESI-MS) as described by Gramer et al. (MAbs. 2013 Nov. 1; 5(6): 962-973.).

Non-Binding Control Antibody b12

IgG1-b12 is an HIV-1 gp120 specific antibody (Barbas, CF. J Mol Biol. 1993 Apr. 5; 230(3):812-23) that is used in some of the examples as negative, non-binding control antibody for monospecific and bispecific antibodies.

The heavy chain (HC) and light chain (LC) sequences of the parental antibodies are set forth in the following SEQ ID NOs:

```
SEQ ID NO: 36 (HC) and SEQ ID NO: 37 (LC)
IgG1-b12-FEAL.

SEQ ID NO: 35 (HC) and SEQ ID NO: 37 (LC)
IgG1-b12-FEAR.

SEQ ID NO: 38 (HC) and SEQ ID NO: 37 (LC)
IgG1-b12-FERL.

SEQ ID NO: 44 (HC) and SEQ ID NO: 45 (LC)
IgG2amm-b12-AALT.

SEQ ID NO: 46 (HC) and SEQ ID NO: 45 (LC)
IgG2amm-b12-AAKR.
```

Example 2—Determination of the Binding Affinities of EpCAM-Specific Antibodies Using Biolayer Interferometry Methods Target binding affinity of EpCAM-specific antibodies was determined by label-free biolayer interferometry (BLI) on an Octet HTX instrument (FortéBio).

Experiments were carried out while shaking at 1,000 RPM at 30° C. Anti-Penta-HIS (HIS1K) biosensors (FortéBio, cat. no. 18-5120) were pre-conditioned by exposure to 10 mM glycine (Sigma-Aldrich, cat. no. 15527) buffer pH 1.5 for 5 s, followed by neutralization in Sample Diluent (FortéBio, cat. no. 18-1104) for 5 s; both steps were repeated 2 times. The anti-Penta-HIS biosensors were loaded with 100 nM (2.8 μg/mL) recombinant human EpCAM (R&D systems, cat no 9277-EP) or recombinant cynomolgus monkey EpCAM (R&D systems, cat. no. 10451-EP) for 600 s. After a baseline measurement in Sample Diluent (300 s), the association (200 s) and dissociation (1,000 s) of the functionally monovalent antibodies was determined using a concentration range of 1.56-100 nM, with two-fold dilution steps in Sample Diluent. Functionally monovalent EpCAM antibodies are bispecific molecules that contains one EpCAM-specific Fab arm and a non-binding control Fab (based on HIV gp120-specific b12 antibody described in Example 1), thereby ensuring that binding to EpCAM in this assay is functionally monovalent. The molecular mass based on the amino acid sequence of the used antibodies (146.0-148.6 kDa) was used for calculations. For each antibody a reference sensor was used, which was incubated with Sample Diluent instead of antibody.

Data were acquired using Data Acquisition Software V12.0 (FortéBio) and analyzed with Data Analysis Software v12 (FortéBio). Data traces were corrected per antibody by subtraction of the reference sensor. The Y-axis was aligned to the last 10 s of the baseline. Interstep Correction alignment to dissociation and Savitzky-Golay filtering were applied. Data traces with a response <0.05 nm were excluded from analysis. The data was fitted with the 1:1 Global Full fit model, using a window of interest for association of 200 s and dissociation times set at 50 s and 200 s (indicated in Table 4 and Table 5). The dissociation time that was used for the reported data was chosen based upon visual inspection of the curve-fits and highest $R^2$ value. Data corresponding to curve fits with a $R^2<0.98$ were excluded from analyses.

"$K_D$" (M) refers to the equilibrium dissociation constant of the antibody-antigen interaction, and is obtained by dividing $k_d$ by $k_a$. "$k_d$" (sec$^{-1}$) refers to the dissociation rate constant of the antibody-antigen interaction. This is sometimes also referred to as the $k_{off}$ value or off-rate. "$k_a$" (M$^-$×sec$^{-1}$) refers to the association rate constant of the antibody-antigen interaction. This is sometimes also referred to as the $k_{on}$ value or on-rate.

Results

Table 4 shows the association rate constant $k_a$ (1/Ms), dissociation rate constant $k_d$ (1/s) and equilibrium dissociation constant $K_D$ (M) of bispecific, functionally monovalent EpCAM antibodies for recombinant human EpCAM, as determined by biolayer interferometry. Affinities of the antibodies to human EpCAM ranged from 3.2-55 nM.

Table 5 shows the association rate constant $k_a$ (1/Ms), dissociation rate constant $k_d$ (1/s) and equilibrium dissociation constant $K_D$ (M) of the EpCAM antibodies for cynomolgus monkey EpCAM, as determined with biolayer interferometry. Only BisG1-b12-FEAL/EpCAM-A37-FEAR showed reliable results for binding to cynomolgus monkey EpCAM, with an affinity of 41 nM. Although for BisG1-b12-FEAL/EpCAM-A37-FEAR a difference in kinetics of binding to cynomolgus monkey compared to human EpCAM was observed (faster on- and off-rate for binding to cynomolgus monkey EpCAM), there was only a 2-fold difference in affinity ($K_D$).

TABLE 4

Binding affinities of bispecific, functionally monovalent EpCAM antibodies to human EpCAM extracellular domain as determined by label-free biolayer interferometry.

| Antibody | Response | Fit time (s) | Full $R^2$ | On-rate $k_a$ (1/Ms) | Off-rate $k_d$ (1/s) | $K_D$ (M) |
|---|---|---|---|---|---|---|
| BisG1-b12-FEAL/EpCAM-UBS-54-FEAR | 0.60 | 50 | 1.00 | $5.3 \times 10^5$ | $3.0 \times 10^{-2}$ | $5.5 \times 10^{-8}$ |
| BisG1-b12-FEAL/EpCAM-A37-FEAR | 1.44 | 50 | 1.00 | $3.2 \times 10^5$ | $6.3 \times 10^{-3}$ | $2.0 \times 10^{-8}$ |
| BisG1-b12-FEAL/EpCAM-C52-FEAR | 0.73 | 50 | 1.00 | $4.6 \times 10^5$ | $2.2 \times 10^{-2}$ | $4.8 \times 10^{-8}$ |
| BisG2amm-EpCAM-323-A3-AALT/m4-1BB-3H3-AAKR | 1.21 | 200 | 1.00 | $3.4 \times 10^5$ | $1.1 \times 10^{-3}$ | $3.2 \times 10^{-9}$ |

TABLE 5

Binding affinities of bispecific, functionally monovalent EpCAM antibodies to cynomolgus monkey EpCAM extracellular domain as determined by label-free biolayer interferometry.

| Antibody | Response | Fit time (s) | Full $R^2$ | On-rate $k_a$ (1/Ms) | Off-rate $k_d$ (1/s) | $K_D$ (M) |
|---|---|---|---|---|---|---|
| BisG1-b12-FEAL/EpCAM-UBS-54-FEAR | 0.11 | 50 | 0.90 | Full $R^2$ < 0.98 | | |
| BisG1-b12-FEAL/EpCAM-A37-FEAR | 0.59 | 50 | 1.00 | $5.5 \times 10^5$ | $2.3 \times 10^{-2}$ | $4.1 \times 10^{-8}$ |
| BisG1-b12-FEAL/EpCAM-C52-FEAR | 0.28 | 50 | 0.97 | Full $R^2$ < 0.98 | | |
| BisG2amm-EpCAM-323-A3-AALT/m4-1BB-3H3-AAKR | 0.02 | N/A | N/A | Response < 0.05 | | |

Example 3—Cross-Block of EpCAM Antibodies as Determined by Biolayer Interferometry Methods Antibody cross-block analysis (epitope binning) in classical sandwich format was performed by BLI on an Octet HTX instrument (FortéBio). Experiments were carried out while shaking at 1,000 RPM and at 30° C.

Amine Reactive 2nd Generation (AR2G) biosensors (FortéBio, cat. no. 18-5092) were activated for 300 s with a solution of 20 mM EDC (N-[3-Dimethylaminopropyl]-N'-ethylcarbodiimide hydrochloride; FortéBio, 18-1033) and 10 mM s-NHS (N-Hydroxysulfosuccinimide sodium salt; FortéBio, 18-1067). The activated AR2G sensors were loaded with 20 µg/mL first EpCAM antibody in 10 mM Sodium Acetate pH 6.0 (FortéBio, cat. no. 18-1070) for 600 s and quenched with 1 M ethanolamine pH 8.5 (FortéBio cat. no. 18-1071) for 300 s.

After a baseline measurement (50 s) in Sample Diluent (FortéBio, cat. no. 18-1104), the AR2G biosensors containing immobilized antibodies were loaded for 300 s with recombinant human EpCAM (100 nM or 2.8 µg/mL diluted in Sample Diluent; R&D systems, cat no 9277-EP). The theoretical molecular mass of human EpCAM based on the amino acid sequence (28 kDa) was used for calculations. The association (300 s) of a second EpCAM antibody (10 µg/mL in Sample Diluent) was determined. Data were acquired using Data Acquisition Software v12.0.1.8 (FortéBio) and analyzed with Data Analysis HT Software v12.0.1.55 (FortéBio). Data traces were corrected by subtraction of a reference curve (Sample Diluent instead of second antibody) in order to correct for the dissociation of human EpCAM from the immobilized first antibody. The Y-axis was aligned to the start of the association step and Savitzky-Golay filtering was applied. The corrected association responses of the second antibodies were plotted in a matrix format. In general, responses >0.1 nm for the second antibody was considered an indication of second antibody binding, and thus an indication for no or incomplete binding competition between the first and second antibody. By contrast, responses between −0.1 and 0.1 nm were considered to be blocking antibody pairs.

Results

Cross-block binding competition experiments were performed for antibodies IgG1-EpCAM-323-A3-FEAR, IgG1-EpCAM-052-FEAR, IgG1-EpCAM-UBS-54-FEAR and IgG1-EpCAM-A37-FEAR. All EpCAM antibodies blocked binding of the other EpCAM antibodies to recombinant human EpCAM (Table 6).

Example 4—Expression of EpCAM on Human Tumor Cell Lines

Methods

To allow ranking of tumor cell lines with respect to EpCAM expression, relative EpCAM surface expression levels were evaluated using flow cytometry on the following human tumor cell lines: T84 (lung metastasis of colon adenocarcinoma; ATCC, cat.no. CLL-248), DiFi (rectal carcinoma; kindly provided by the Thomas Valerius Christian Albrechts University, Kiel, Germany), HPAF-II (pancreatic adenocarcinoma; ATCC, cat.no. CRL-1997), NCI-N87 (gastric carcinoma; ATCC, cat.no. CRL-5822), Calu-3 (non-small cell lung carcinoma; ATCC, cat.no. HTB-55), NCI-H747 (colorectal adenocarcinoma; ATCC, cat.no. CLL-252), and A549 (non-small cell lung adenocarcinoma; ATCC, cat.no. CLL-185).

Cells ($5 \times 10^4$ cells/well) were incubated in polystyrene 96-well round-bottom plates (Greiner bio-one, cat. no. 650180) with an allophycocyanin (APC)-conjugated anti-EpCAM antibody (clone EBA-1, IgG1λ; BD Bioscience, cat. no. 347200), an APC-conjugated non-binding control antibody (Clone 11711, IgG1k; R&D Systems, cat. IC002A) or no antibody in 50 µL FACS buffer (phosphate-buffered saline [PBS; Lonza, cat. no. BE17-517Q] supplemented with 0.1% bovine serum albumin [BSA, fraction V, Roche, cat, no. 10735086001] and 0.02% $NaN_3$ [Bio-world, cat. no. 4192 0044-3]) at 4° C. for 30 min. Cells were washed in FACS buffer and analyzed by flow cytometry on a FACS-Celesta flow cytometer (BD Biosciences, USA). A geometric mean fluorescence intensity (GeoMFI) was calculated for each cell line by subtracting the Geomean MFI of the cells incubated with the non-binding control antibody from the Geomean MFI of the cells stained with anti-EpCAM antibody using Graphpad Prism Software and Microsoft Office Excel.

Results

Figure 1:
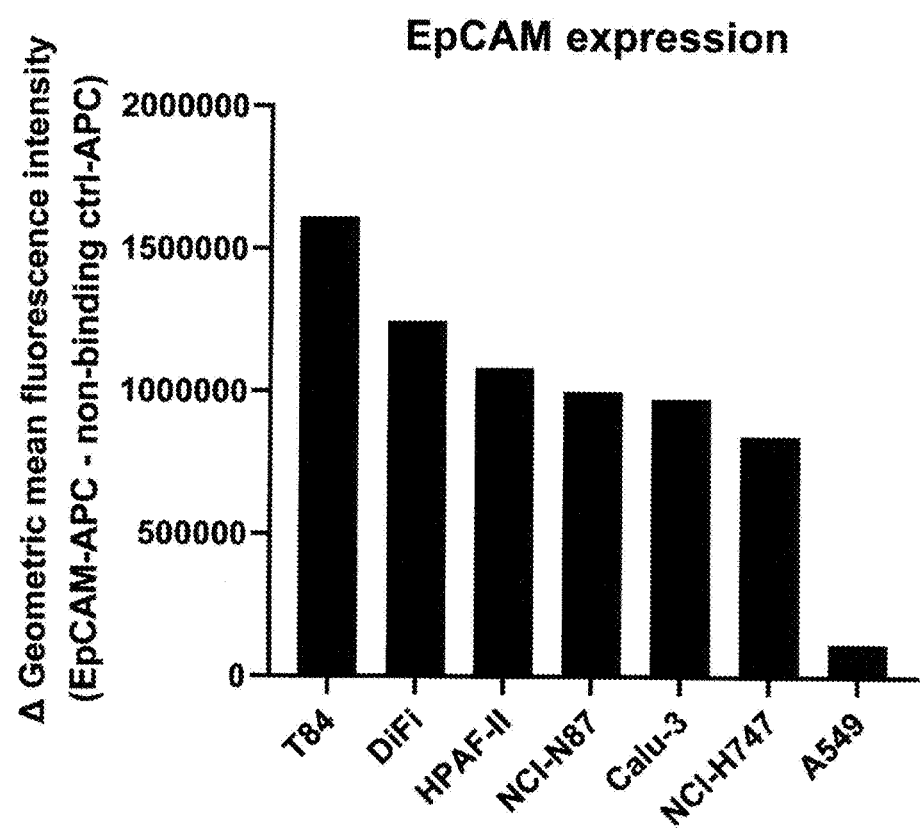
FIG. 1: Relative EpCAM expression on tumor cells

FIG. 1 shows the relative EpCAM expression on tumor cell lines, as determined using flow cytometry, confirming EpCAM expression on all tested cell lines. The tumor cell lines were ranked based on EpCAM expression as following: T84>DiFi>HPAF-II>NCI-N87>Calu-3>NCI-H747>>A549.

Example 5—Binding of EpCAM Antibodies to EpCAM-Positive Human Tumor Cells

Methods

Binding to the EpCAM-expressing human tumor cell lines DiFi, HPAF-II and A549 by bivalent EpCAM antibodies or bispecific antibodies carrying one EpCAM-binding arm was analyzed by flow cytometry. Cells ($3-5 \times 10^4$ cells/well) were incubated in polystyrene 96-well round-bottom

TABLE 6

Antibody cross-block as determined by biolayer interferometry.

|  | IgG1-EpCAM-323-A3-FEAR | IgG1-EpCAM-C52-FEAR | IgG1-EpCAM-UBS-54-FEAR | IgG1-EpCAM-A37-FEAR |
| --- | --- | --- | --- | --- |
| IgG1-EpCAM-323-A3-FEAR | 0.00 | −0.01 | 0.00 | −0.01 |
| IgG1-EpCAM-C52-FEAR | −0.02 | −0.02 | −0.01 | 0.00 |
| IgG1-EpCAM-UBS-54-FEAR | −0.01 | 0.00 | −0.02 | 0.00 |
| IgG1-EpCAM-A37-FEAR | −0.02 | −0.03 | −0.03 | −0.04 |

The first column shows the immobilized antibodies (first antibody) and the first row shows the antibodies in solution (second antibody). Corrected association responses of the antibodies in solution are shown. Cross-block of antibodies is indicated by the dark grey color.

plates (Greiner bio-one, cat. no. 650180) with serial dilutions of bivalent or monovalent EpCAM antibodies (FIG. 2A-D: range 0.005 ng/mL to 50 µg/mL in 5-fold dilution steps; FIG. 2 E: range 0.5 ng/mL to 30 µg/mL in 3-fold dilution steps) in 50 µl PBS (FIG. 2A-C; Hyclone GE Healthcare, cat. no. SH3A3830.03) or FACS buffer (FIG. 2 D, E) at 4° C. for 30 min. After washing once (A-D) or twice (E) in FACS buffer, cells were incubated with 50 µL R-Phycoerythrin (R-PE) AffiniPure F(ab')$_2$ fragment goat-anti-human IgG (Jackson ImmunoResearch, cat.no. 109-116-098; diluted 1:500 in FACS buffer [A-D] or 1:200 in FACS buffer [E]) at 4° C. for 30 min in the dark. Next, cells were washed once (A-D) or twice (E) in FACS buffer, re-suspended in 100 µL FACS buffer and analyzed on a BD LSRFortessa FACS (BD Biosciences, USA), Celesta (BD Biosciences, USA) or iQue (Sartorius, Germany). Binding curves were analyzed using non-linear regression (sigmoidal dose-response with variable slope) using GraphPad Prism V7.02 software (GraphPad Software, San Diego, CA, USA).

Results

Figure 2:
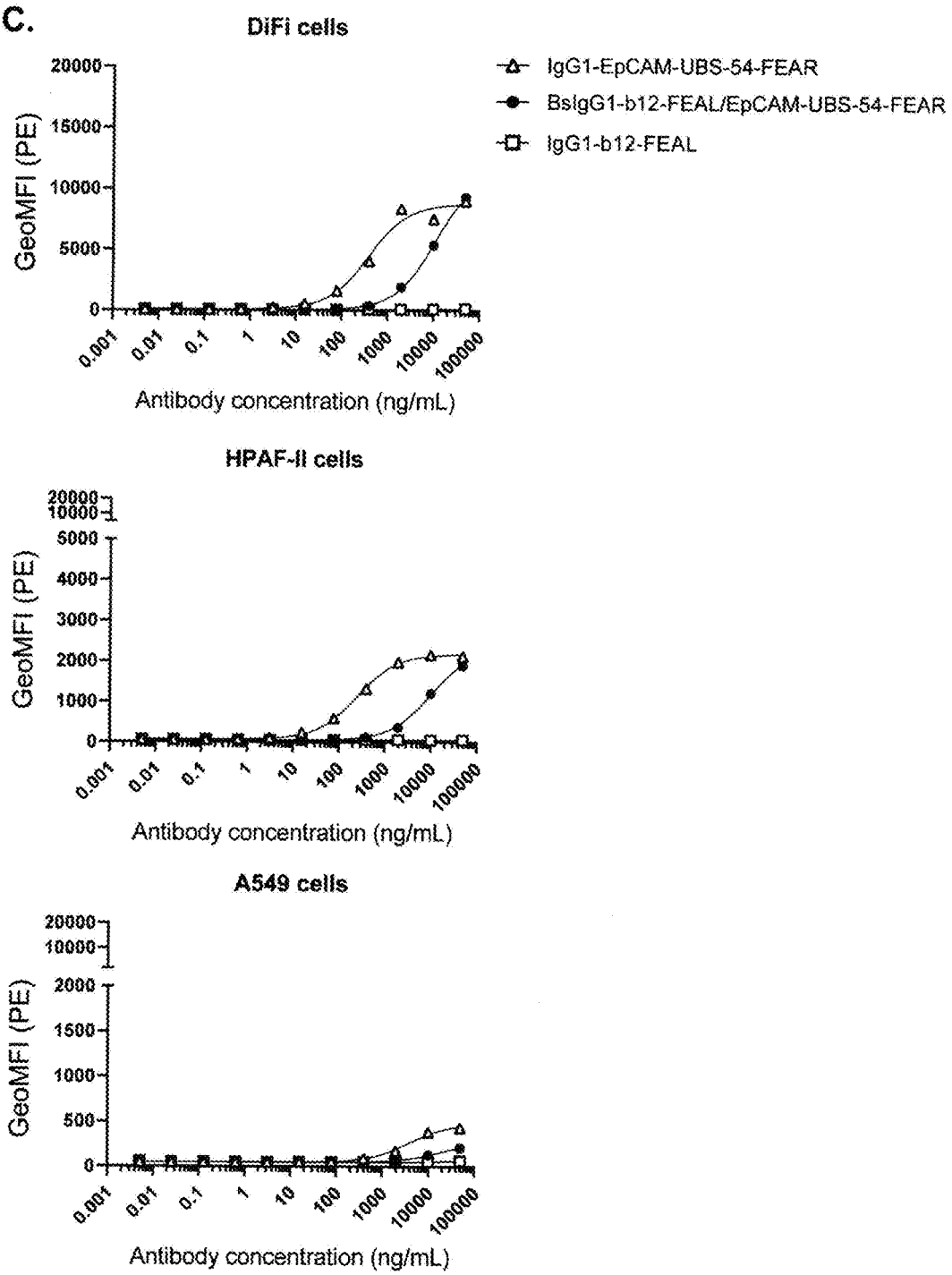
FIG. 2: Binding of bivalent EpCAM antibodies and their monovalent counterparts to DiFi, HPAF-H or A549 cells. Mono- and bivalent binding of EpCAM antibodies to DiFi, HPAF-II or A549 cell lines was determined by flow cytometry. IgG1-b12-FEAL was included as negative control in all experiments (open squares). Data shown is mean fluorescence intensity (MFI; R-Phycoerythrin [PE])±standard deviation (SD) of duplicate measurements of one representative experiment. A. Binding of bsIgG1-b12-FEALxEpCAM-A37-FEAR (closed circles) and IgG1-EpCAM-A37-FEAR (open triangles) antibodies to DiFi, HPAF-II or A549 cells. B. Binding of bsIgG1-b12-FEALxEpCAM-052-FEAR (closed circles) and IgG1-EpCAM-052-FEAR (open triangles) antibodies to DiFi, HPAF-II or A549 cells. C. Binding of bsIgG1-b12-FEALxEpCAM-UBS-54-FEAR (closed circles) and IgG1-EpCAM-UBS-54-FEAR (open triangles) antibodies to DiFi, HPAF-II or A549 cells. D. Binding of IgG1-EpCAM-323-A3-FEAR (open triangles) antibodies to DiFi or HPAF-II cells. E. Binding of bsIgG1-CD137-009-HC7LC2-FEAL/EpCAM-A37-FEAR and bsIgG1-EpCAM-A37-FERL/CD137-009-HC7LC2-FEAR and non-binding control bispecific antibodies bsIgG1-b12-FERL/CD137-HC7LC2-FEAR and bsIgG1-b12-FERL/b12-FEAR to DiFi cells.

FIG. 2 shows that monospecific, bivalent (monoclonal) EpCAM antibodies (A) IgG1-EpCAM-A37-FEAR, (B) IgG1-EpCAM-052-FEAR and (C) IgG1-EpCAM-UBS-54-FEAR display dose-dependent binding to human EpCAM-expressing DiFi, HPAF-II and A549 tumor cells. Bispecific, monovalent EpCAMxb12 antibodies (A) bsIgG1-b12-FEALxEpCAM-A37-FEAR, (B) bsIgG1-b12-FEALxEpCAM-052-FEAR and (C) bsIgG1-b12-FEALxEpCAM-UBS-54-FEAR display binding at higher antibody concentrations compared to IgG1-EpCAM-A37-FEAR, IgG1-EpCAM-052-FEAR or IgG1-EpCAM-UBS-54-FEAR, respectively. The maximum binding to DiFi, HPAF-II and A549 tumor cells was comparable to that of their respective monospecific, bivalent EpCAM counterparts. Furthermore, monospecific, bivalent EpCAM antibody IgG1-323-A3-FEAR displayed dose-dependent binding to DiFi and HPAF-II tumor cells (D). The negative control antibody that was included in these experiments, IgG1-b12-FEAL, did not show binding to DiFi, HPAF-II, and A549 tumor cells.

Next, the capacity to bind DiFi tumor cells was studied for two bispecific EpCAMx4-1BB antibodies that contained the same variable domains but differed in their Fc-domain: one containing an Fc-domain harboring the L234F/L235E/D265A (FEA) inertness mutations in both heavy chains (HC), and one containing the FEA inertness mutations in the HC of the 4-1BB-binding arm and the L234F/L235E/G236R (FER) inertness mutations in the HC of the EpCAM-binding arm. The two bispecific antibodies showed comparable binding as demonstrated by the EC50 values (3.841 nM vs 3.961 nM, respectively; FIG. 2E). The negative control antibodies that were included in these experiments, bsIgG1-b12-FERL/CD137-009-HC7LC2-FEAR and bsIgG1-b12-FERL/b12-FEAR, did not show binding to DiFi tumor cells, indicating that binding of the EpCAMx4-1BB bispecific antibodies is specific for EpCAM.

Example 6—Binding of EpCAM Antibodies to CHO Cells Transfected with Human, Cynomolgus Monkey or Mouse EpCAM Chinese Hamster Ovary (CHO)-S cells (1.0×10$^6$ cells/mL; ThermoFisher Scientific, cat. no. R800-07) were cultured in Freestyle™ CHO Expression Medium (ThermoFisher Scientific, cat. no. 12651022). Prior to transfection with constructs encoding full-length human (SEQ ID: 59), cynomolgus monkey (SEQ ID: 60) or mouse EpCAM (SEQ ID: 61; for all constructs 1.25 µg/mL), the medium was supplemented with 50 units penicillin and 50 µg/mL streptomycin (Pen/Strep; Lonza, cat. no. DE17-603E). Transfection was performed using Freestyle Max™ transfection reagent (ThermoFisher Scientific, cat. no. 16447100) and OptiPRO™ SFM medium (ThermoFisher Scientific, cat. no. 12309019), according to the manufacturer's instructions. After transfection, cells were incubated 24 h at 37° C., 85% humidity, 8% CO$_2$ while shaking, and then frozen in Freestyle™ CHO Expression Medium supplemented with 10% DMSO until further use.

Binding of EpCAM antibodies to CHO-S cells transiently transfected with full length human, cynomolgus monkey or mouse EpCAM was analyzed by flow cytometry. Cells were thawed in Roswell Memorial Park Institute 1640 medium (RPMI; Lonza, cat. no. 12-115F) supplemented with 10% Donor Bovine Serum with Iron (DBSI; Life technologies, cat. no. 20371). Cells were incubated (3×10$^4$ cells/well) in polystyrene 96-well round-bottom plates (Greiner bio-one, cat. no. 650180) with serial dilutions of EpCAM antibodies (range 0.0001 to 50 µg/mL in 5-fold dilution steps) in 50 µL PBS/0.1% BSA/0.02% azide (FACS buffer) at 4° C. for 30 min. After washing twice in FACS buffer, cells were incubated in 50 µL R-Phycoerythrin (PE)-conjugated goat-anti-human IgG F(ab')2 (1:500 in FACS buffer; Jackson ImmunoResearch Laboratories, cat. no. 109-116-098) at 4° C. for 30 min. Cells were washed twice in FACS buffer, re-suspended in 20 µL FACS buffer supplemented with TO-PRO™-3 Iodide (diluted 1:20000; Invitrogen, cat. no. T3605) and analyzed on an iQue screener (Intellicyt Corporation, USA). Binding curves were analyzed by non-linear regression (sigmoidal dose-response with variable slope) using GraphPad Prism V8.4.1 software (GraphPad Software, San Diego, CA, USA). FIG. 3A shows dose-dependent binding of bivalent EpCAM-binding antibodies IgG1-EpCAM-UBS-54-FEAR, IgG1-EpCAM-A37-FEAR, IgG1-EpCAM-052-FEAR and IgG1-EpCAM-323-A3 to CHO-S cells transfected with full length human, cynomolgus monkey and mouse EpCAM Similarly, FIG. 3B shows dose-dependent binding of monovalent EpCAM-binding antibodies bsIgG1-b12-FEAL/EpCAM-UBS-54-FEAR, bsIgG1-EpCAM-A37-FERL/b12-FEAR, bsIgG1-b12-FEAL/EpCAM-052-FEAR, and bsIgG1-b12-FEAL/EpCAM-323-A3-FEAR to CHO-S cells transfected with full length human, cynomolgus monkey and mouse EpCAM. By contrast, no binding of either monovalent or bivalent EpCAM antibodies to non-transfected CHO-WT cells was observed.

Example 7—Cell-Based Reporter Assay to Determine 4-1BB Agonist Activity of an EpCAMx4-1BB Bispecific Antibody and the Dependence of Agonist Activity on Target Crosslinking To determine the 4-1BB agonist activity of Fc-inert EpCAMx4-1BB bispecific antibodies, a reporter cell line expressing luciferase under the control of NF-κB response elements (HEK293_NFK_gfp_luc cells) was transduced with human 4-1BB (HEK293_NFK_h4-1BB_gfp_luc cells). To determine the dependence of 4-1BB agonist activity on target crosslinking, the reporter assay was conducted either using the reporter cell line alone, or in co-culture with EpCAM-expressing OV-90-SC12 cells. HEK293_NFK_h4-1BB_gfp_luc cells were generated by transposon-mediated transfection of human 4-1BB into HEK293_NFK_gfp_luc cells (BioCat GmbH, cat. no. TR860A-1) followed by blasticidin selection. Cells were seeded in 96-well white flat-bottom plates (Fisher Scientific, cat. no. 10072151) at $3\times10^4$ cells/well and cultured overnight in DMEM (Thermo Fisher Scientific, cat. no. 31966-047) supplemented with 10% non heat-inactivated FBS (Biochrom, cat. no. S0115). On the next day, serial dilutions of BsIgG1-CD137-005-FEAR/EpCAM-323-A3-FEAL were prepared in DMEM with 0.5% non heat-inactivated FBS and added to the wells containing HEK293_NKF_h4-1BB_gfp_luc cells (3-fold dilution series, final concentration range 8.2-0.01 µg/mL). OV-90-SC12 cells (a subclone of OV-90, ATCC, cat. no. CRL-11730) in DMEM with 0.5% non heat-inactivated FBS ($3\times10^4$ cells/well) or medium only were added to the wells, and the plates were incubated overnight. On the next day, culture supernatants were discarded, and 50 µL RPMI 1640 medium (Life Technologies GmbH, cat. no. 61870-010), along 50 µl with Bio-Glo™ luciferase assay substrate (Promega, cat. no. G7940) was added to each well. The plates were incubated for 10 min, protected from light Luminescence was measured using a Tecan Infinite F200 Pro plate reader.

4-1BB agonist activity of BsIgG1-CD137-005-FEAR/EpCAM-323-A3-FEAL was analyzed at 3-fold serial dilutions from 8.2-0.01 µg/mL (FIG. 4). A dose-dependent increase in luciferase luminescence was observed only in the presence of EpCAM-expressing OV-90-SC12 cells. These results showed that the Fc-inert EpCAMx4-1BB bispecific antibody exhibits conditional 4-1BB agonist activity in vitro.

Example 8—Capacity to Induce CD4+ and CD8+ T-Cell Proliferation in PBMC-Tumor Cell Co-Cultures by EpCAMx4-1BB Bispecific Antibodies Containing Inertness Mutations Methods The ability of EpCAMx4-1BB bispecific antibodies to increase PBMC proliferation through 4-1BB co-stimulation was assessed in in vitro co-cultures of EpCAM-expressing tumor cell lines and primary human peripheral blood mononuclear cells (PBMCs), which were isolated from healthy human donor buffy coats (Sanquin, Amsterdam, The Netherlands) using a Ficoll gradient (Corning; lymphocyte separation medium, cat. no. 25-072-CI). The ability to enhance PBMC proliferation was assessed both for EpCAMx4-1BB bispecific antibodies with an Fc-domain containing the FEA inertness mutations in both heavy chains (HC), and for EpCAMx4-1BB bispecific antibodies with an Fc-domain containing the FEA inertness mutations in the HC of the 4-1BB-binding arm, and the FER inertness mutations in the HC of the EpCAM-binding arm.

In a first set of experiments (FIGS. 5-7), EpCAM-expressing tumor cells (DiFi, T84, HPAF-II, NCI-N87, Calu-3 or NCI-H747; as described herein above) were seeded at a density of 6,250 cells/well into polystyrene 96-well flat-bottom plates (Greiner bio-one, cat. no. 655180) in T-cell medium (Iscove's Modified Dulbecco's Medium [IMDM; Lonza, cat. no. 12-722F] supplemented with 5% Human Serum [Sanquin Blood Bank, cat. no. B0626] and 1% Pen/Strep, Lonza, cat. no. DE17-603E) and left to adhere at 37° C. for 4 h. PBMCs were labelled with 0.5 µM Cell-Trace™ CFSE (carboxyfluorescein succinimidyl ester; ThermoFisher Scientific; cat. no. C34554A) in PBS (phosphate-buffered saline, Hyclone, cat. no. SH3A383003) at 37° C. for 20 min. After washing, resting the PBMCs for 0.5-1.5 h in T-cell medium and washing again, the PBMCs were mixed with anti-CD3 antibody (0.1 µg/mL; clone UCHT1; Stemcell, cat. no. 60011) and added to tumor cells at a ratio of 16:1 (100,000 cells/well). Bispecific EpCAMx4-1BB, EpCAMxb12 or non-binding control antibodies were added (final concentration serial dilution: 8-25,000 ng/mL in 5-fold dilutions [FIGS. 5 and 7], or at a single concentration of 10 µg/mL [FIG. 6]) and plates were incubated at 37° C. for 96 h. Next, 150 µl supernatants containing PBMCs were transferred to 96-well round-bottom plates. After washing the cells in PBS, PBMCs were stained with 50 µL BD Horizon™ Fixable Viability Stain 510 (FVS510; 1:5000 dilution in PBS; BD Biosciences; cat. no. 564406) for 20 min at RT protected from light. In experiments where proliferation was evaluated in CD4+ and CD8+ T-cell subsets, cells were additionally stained with brilliant violet (BV)785-labeled anti-CD19 (clone SJ25C1, 1:50; BioLegend, cat. no. 363028), APC-eF780-labeled anti-CD4 (clone OKT4, 1:50; eBioscience, cat. no. 47-0048-42), AF700-labeled anti-CD8 (clone RPA-T8, 1:100; BioLegend, cat. no. 301028), and BV605-labeled anti-CD14 (clone: M5E2, 1:200; BioLegend, cat. no. 301834) antibodies in 50 µL FACS buffer at 4° C. for 30 min protected from light. After washing the cells, cells were resuspended in 30-60 L FACS buffer (PBS [Lonza, BE17-517Q] supplemented with 0.1% bovine serum albumin [BSA, fraction V, Roche, cat, no. 10735086001], 0.02% NaN3 [Bio-world, cat. no. 41920044-3] and 2 mM EDTA [Sigma-Aldrich, cat. no. BCCB3789]) and analyzed on an iQue flow cytometer using Intellicyt software (FIGS. 5 and 7) or BD Symphony flow cytometer using FlowJo software (FIG. 6).

A second set of experiments was essentially performed as described above, with the following exceptions. Final concentration serial dilution of bispecific EpCAMx4-1BB, EpCAMxb12 or non-binding control antibodies was 0.32-25,000 ng/mL (FIG. 8). After staining the cells with 50 µL BD Horizon™ Fixable Viability Stain 510 (1:5000 dilution in PBS), the plates were incubated for 30 min at RT protected from light. The cells were additionally stained with brilliant violet (BV)785-labeled anti-CD19 (clone SJ25C1, 1:80), APC-eF780-labeled anti-CD4 (clone OKT4, 1:100), AF700-labeled anti-CD8 (clone RPA-T8, 1:100; BioLegend, cat. no. 301028), and PE-Cy7-labeled anti-CD14 (clone: M5E2; 1:50; BD, cat. no. 557742) antibodies in 50 µL FACS buffer at 4° C. for 30 min protected from light. After washing, the cells were resuspended in 80 µL FACS buffer and analyzed on an iQue flow cytometer using BD Symphony flow cytometer using FlowJo software (FIG. 8). For evaluation of PBMC proliferation, cells were gated for lymphocytes (based on FSC/SSC) and viable cells (FVS510- population). For evaluation of CD4+ or CD8+ T cells, PBMCs were gated for lymphocytes (based on FSC/SSC), viable cells (FVS510- population), T cells (CD14-CD19-population) and finally CD4+ or CD8+ T cells (CD4+CD8- or CD4-CD8+ populations, respectively). CFSE-stained cells were measured to assess PBMC, CD4+ or CD8+ T-cell proliferation. The Division Index, representing the average number of divisions per cell, was calculated using Microsoft Office Excel and visualized using Graphpad Prism, using the following formula:

$\Sigma(x_i/2i*i)/\Sigma(x_i/2i)$, where $i$ is the number of the peak with the undivided peak is 0, the first divided is 1 etc., and $x_i$ is the number of cells in the corresponding peak.

Results

The ability of EpCAMx4-1BB bispecific antibodies to increase T-cell proliferation through 4-1BB co-stimulation was assessed in in vitro co-cultures of the EpCAM-expressing DiFi tumor cell line and PBMCs. FIG. 5 shows that bsIgG1-CD137-009-HC7LC2-FEAL/EpCAM-UBS54-FEAR (A), bsIgG1-CD137-009-HC7LC2-FEAL/EpCAM- A37-FEAR (B), bsIgG1-CD137-009-HC7LC2-FEAL/Ep-CAM-052-FEAR (C) and bsIgG1-CD137-009-HC7LC2-FEAL/EpCAM-323-A3-FEAR (D) enhanced dose-dependent proliferation of CFSE-labeled cells (shown as increase in the division index). The maximum increase in division index induced by all four EpCAMx4-1BB antibodies was comparable. By contrast, the bispecific EpCAMxb12 antibodies bsIgG1-b12-FEAL/EpCAM-UBS54-FEAR (A), bsIgG1-b12-FEAL/EpCAM-A37-FEAR (B), bsIgG1-b12-FEAL/EpCAM-052-FEAR (C) and bsIgG1-b12-FEAL/Ep-CAM-323-A3-FEAR (D) did not enhance proliferation, as the division index was comparable to isotype control antibody IgG1-b12-FEAL.

Furthermore, the effect of EpCAMx4-1BB bispecific antibodies on proliferation of CD4+ and CD8+ T cells was evaluated by gating specifically on these T-cell subsets. FIG. 6 shows that the EpCAMx4-1BB bispecific antibodies bsIgG1-CD137-009-HC7LC2-FEAL/EpCAM-UBS54-FEAR, bsIgG1-CD137-009-HC7LC2-FEAL/EpCAM-A37-FEAR and bsIgG1-CD137-009-HC7LC2-FEAL/EpCAM-052-FEAR enhanced proliferation of both (A) CD4+ and (B) CD8+ T cells (shown as increase in the division index). By contrast, the bispecific EpCAMxb12 antibodies bsIgG1-b12-FEAL/EpCAM-UBS54-FEAR, bsIgG1-b12-FEAL/Ep-CAM-A37-FEAR, bsIgG1-b12-FEAL/EpCAM-052-FEAR did not affect CD4+ or CD8+ T-cell proliferation, as the division index was comparable to isotype control antibody IgG1-b12-FEAL.

Next, a selection of tumor cell lines with a range of EpCAM expression levels (described in Example 4) was used to further evaluate the effect of EpCAMx4-1BB antibodies on PBMC proliferation. FIG. 7 shows that EpCAMx4-1BB bispecific antibodies bsIgG1-CD137-009-HC7LC2-FEAL/EpCAM-A37-FEAR and bsIgG1-CD137-009-HC7LC2-FEAL/EpCAM-323-A3-FEAR enhanced PBMC proliferation (shown as increase in the division index) in the presence of T84, DiFi, HPAF-II, NCI-N87, Calu-3 or NCI-H747 tumor cells. By contrast, the bispecific EpCAMxb12 antibodies bsIgG1-b12-FEAL/EpCAM-A37-FEAR and bsIgG1-b12-FEAL/EpCAM-323-A3-FEAR did not affect proliferation in any of the PBMC-tumor cell co-cultures, as the division index was comparable to isotype control antibody IgG1-b12-FEAL. These results indicated that EpCAMx-4-1BB bsAb were able to increase proliferation of activated PBMC in all tumor cells lines tested, with no clear impact of EpCAM expression in the range tested here.

The ability of EpCAMx4-1BB bispecific antibodies either with an Fc-domain containing the FEA mutations in both HCs, or with an Fc-domain with the FEA mutations in one HC and the FER mutations in the other HC, to enhance proliferation of activated CD4+ and CD8+ T cells was compared (FIG. 8). A highly comparable level of CD4+ and CD8+ T-cell proliferation was observed after 96 h of incubation of co-cultures of PBMC and DiFi tumor cells with a concentration series of either bsIgG1-EpCAM-A37-FERL/CD137-009-HC7LC2-FEAR or bsIgG1-EpCAM-A37-FEAR/CD137-009-HC7LC2-FEAL. This indicates that the capacity to enhance T-cell proliferation by EpCAMx4-1BB bispecific antibodies was not altered when the FEA inertness mutations were exchanged with the FER inertness mutations in one of the two HC.

In conclusion, EpCAMx4-1BB bispecific antibodies enhanced proliferation of activated PBMCs in co-cultures with tumor cells with a range of EpCAM expression levels, including proliferation of both CD4+ and CD8+ T cells. The capacity to enhance T-cell proliferation was comparable for EpCAMx4-1BB bispecific antibodies that either contained the FEA inertness mutations in both HCs or that contained the FEA inertness mutations in one HC and the FER inertness mutations in the other HC.

Example 9—Ex Vivo TIL Expansion Assay to Determine the Capacity of EpCAMx4-1BB Bispecific Antibodies to Induce Proliferation of Tumor-Infiltrating T Cells and NK Cells To determine the effect of EpCAMx4-1BB bispecific antibodies on TIL subsets, ex vivo TIL expansion assays were conducted using surgically resected primary tumor tissue from human non-small cell lung cancer patients.

Cryopreserved tumor tissue fragments were thawed and dissected into fragments of approximately 1 mm$^3$. The fragments were seeded in 24-well plates (Greiner, cat. no. 662160; 2 fragments per well, 12-16 wells per condition) in X-VIVO™ 15 medium (Lonza, cat. no. BE02-060Q) supplemented with 2% human serum albumin (CLS Behring, PZN-00504775), 1% penicillin/streptomycin (Thermo Fisher Scientific, cat. no. 15140-122), 1% amphotericin B (Thermo Fisher Scientific, cat. no. 152-900-26), and 50 U/mL interleukin (IL)-2 (Proleukin-S, Novartis Pharma GmbH, PZN-02238131). Bispecific antibodies (BsIgG1-CD137-009-HC7LC2-FEAL/EpCAM-323-A3-FEAR or BsIgG1-CD137-009-HC7LC2-FEAL/EpCAM-A37-FEAR) were added to the wells (0.2 or 5 µg/mL final concentration). The fragments were cultured for 3 days. Fresh culture medium containing IL-2 and antibodies (same concentrations as above) was added on day 3. During the remaining culture period, TIL growth and formation of TIL microclusters were regularly monitored through a microscope. On day 7, cells were pooled by transferring contents of two wells of the original 24-well plate into one well of a fresh 6-well plate (Greiner, cat. no. 657160). Fresh culture medium containing IL-2 (33 U/mL final concentration) was added. On day 10, half of the culture supernatant in each well was replaced by fresh culture medium containing IL-2 (15 U/mL final concentration). On day 14, cells were harvested and pooled by treatment condition for flow cytometry analysis.

Aliquots of 100 µL from each treatment group of harvested cells were stained with the following anti-human antibodies: V500-conjugated anti-CD45 (BD Biosciences, cat. no. 560777), Brilliant Violet (BV)786-conjugated anti-CD56 (BD Biosciences, cat. no. 740979), Pacific Blue-conjugated anti-CD3 (BD Biosciences, cat. No. 558117), PerCP-eFluor780-conjugated anti-CD4 (Thermo Fisher Scientific, cat. no. 46-0047-42), and BV605-conjugated anti-CD8a (BD Biosciences, cat. no. 564116). In addition, cells were stained with fixable viability dye eFluor780 (Thermo Fisher Scientific, cat. no. 65-0865-14). Prior to acquisition, 30 µL of reference beads (CountBright™ Absolute Counting Beads, Invitrogen, cat. no. C36950) were added to each sample. Data were collected on a FACS Celesta flow cytometer (BD Biosciences).

Flow cytometry data were analyzed using Flowjo Software version 10.7.1. Absolute cell numbers were determined using the formula:

Cell number=Event count (cell)/Event count (beads)×bead concentration×sample volume In ex vivo TIL expansion assays, numbers of all TIL (CD45+), as well as CD4+ T cells, CD8+ T cells, and NK cells were increased in cultures treated with EpCAMx4-1BB bispecific antibodies compared to no antibody control (FIG. 9). The increase in cell numbers was more pronounced in cultures treated with 0.2 µg/mL EpCAMx4-1BB bispecific antibodies, compared to 5 µg/mL. These results showed that EpCAMx4-1BB bispecific antibodies can enhance expansion of CD8+ T cells, CD4+ T cells and NK cells from human tumor specimens ex vivo.

Example 10—Treatment of MC38 Tumor-Bearing Mice to Determine In Vivo Anti-Tumor Activity of an EpCAMx4-1BB Bispecific Antibody To assess the anti-tumor activity of an EpCAMx4-1BB bispecific antibody, an in vivo model of human EpCAM-transgenic mice (Jackson Laboratory, strain B6.FVB-Tg (TACSTD1)02Leij/J) bearing human EpCAM-overexpressing MC38 tumors (MC38_hEpCAM) was used. MC38_hEpCAM cells were generated by retroviral transduction of human EpCAM into MC38 cells (Kerafast, cat. no. Event count (beads)ENH204-FP).

Age and gender-matched mice were subcutaneously inoculated with $5 \times 10^5$ MC38_hEpCAM cells in 100 µL PBS (Thermo Fisher Scientific, cat. no. 141-902-50). Tumor growth was evaluated at least twice per week using a caliper and tumor volumes were calculated from caliper measurements as ([length]×[width]$^2$)/2, where length is the longest tumor dimension and width is the longest tumor dimension perpendicular to the length. When tumors reached a median size of approximately 30 mm$^3$, treatment with BsIgG2amm-EpCAM-323-A3-AALT/m4-1BB-3H3-AAKR or the isotype control antibody IgG2amm-b12-AAKR was commenced. Mice were treated with 100 µg of the respective antibody intraperitoneally in 200 µL PBS on days 12, 17, 21, 24, 28, and 31 after tumor inoculation. Body weight of mice was measured three times per week. Individual animals were euthanized when the tumor volume exceeded 1,500 mm$^3$ or when mice reached other humane endpoints (e.g. body weight loss ≥20%, ulceration of tumors (>75%) or occurrence of clinical signs of illness).

Growth of MC38_hEpCAM tumors was significantly reduced in mice treated with BsIgG2amm-EpCAM-323-A3-AALT/m4-1BB-3H3-AAKR, compared to isotype control-treated mice (FIG. 10). In addition, survival of BisIgG2amm-EpCAM-323-A3-AALT/m4-1BB-3H3-AAKR-treated mice was also significantly improved. These results showed that the EpCAMx4-1BB bispecific antibody exhibits antitumor activity in vivo.

Example 11—Comparison of EpCAMx4-1BB Bispecific Antibodies with Combination of EpCAM- and 4-1BB-Specific Antibodies in PBMC-Tumor Cell Co-Cultures The ability to enhance CD4+ and CD8+ T-cell proliferation and activation (defined by expression of T-cell activation markers CD25 and 4-1BB) in PBMC-tumor cell co-cultures was compared between an EpCAMx4-1BB bispecific antibody and the combination of IgG1-EpCAM-A37-FERL and IgG1-CD137-009-HC7LC2-FEAR antibodies or the combination of bsIgG1-EpCAM-A37-FERL/b12-FEAR and bsIgG1-b12-FERL/CD137-HC7LC2-FEAR antibodies.

Methods

The ability of EpCAMx4-1BB bispecific antibodies to enhance CD4+ and CD8+ T-cell proliferation and activation was assessed in in vitro co-cultures of EpCAM-expressing DiFi tumor cells and PBMCs, which were purified from healthy human donor buffy coats (Sanquin, Amsterdam, The Netherlands). In the first set of experiments, the ability to enhance CD4+ and CD8+ T-cell proliferation of bsIgG1-EpCAM-A37-FERL/CD137-009-HC7LC2-FEAR was compared to the combination of bivalent monoclonal antibodies IgG1-EpCAM-A37-FERL and IgG1-CD137-009-HC7LC2-FEAR (FIG. 11). These experiments were essentially performed as described in Example 8, with the following exceptions. PBMCs were labelled with 0.5 µM CellTrace™ Violet (CTV; 1:10,000, ThermoFisher Scientific; cat. no. C34557) in PBS at 37° C. for 20 min protected from light. Final concentrations of IgG1-EpCAM-A37-FERL, IgG1-CD137-009-HC7LC2-FEAR (either alone or in combination), and bsIgG1-EpCAM-A37-FERL/CD137-009-HC7LC2-FEAR were 0.3 or 3 µg/mL (for combination: 0.3 or 3 µg/mL of each antibody). After incubation with the antibodies for 96 h and washing, cells were stained with 50 µL BD Horizon™ Fixable Viability Stain 510 (FVS510; 1:1000 dilution in PBS; BD Biosciences; cat. no. 564406) at 4° C. for 30 min protected from light. Next, cells were stained with BV785-labeled anti-CD19 (clone SJ25C1, 1:80; BioLegend, cat. no. 363028), APC-eF780-labeled anti-CD4 (clone OKT4, 1:100; eBioscience, cat. no. 47-0048-42), AF700-labeled anti-CD8 (clone RPA-T8, 1:100; BioLegend, cat. no. 301028), and PE-Cy7-labeled anti-CD14 (clone: M5E2, 1:50; BD Biosciences, cat. no. 557742) antibodies in 50 µL FACS buffer at 4° C. for 30 min protected from light. After washing, the cells were resuspended in 80 µL FACS buffer and were acquired on a BD FACSCelesta™ Cell Analyzer (BD Biosciences) and analyzed using FlowJo software. For evaluation of CD4+ or CD8+ T cells, PBMCs were gated for lymphocytes and single cells (based on FSC/SSC), viable cells (FVS510-population), T cells (CD14−CD19− population) and finally CD4+ or CD8+ T cells (CD4+CD8− or CD4-CD8+ populations, respectively). CTV-stained cells were measured to assess CD4+ or CD8+ T-cell proliferation. The percentage divided cells were determined as the percentage of cells that had undergone cell division (based on CTV-dilution) out of the total CD4+ or CD8+ T-cell population. Expansion index values were calculated as follows:

Expansion index=Total number of cells/number of cells at start of culture=($G0+G1+G2+G3+G4+G5+G6+G7$)/($G0+G1$:2+$G2$:4+$G3$:8+$G4$:16+$G5$:32+$G6$:64+$G7$:128)

Gn=number of cells in generation n peak (with n=0 to 7)

In the second set of experiments, the ability of EpCAMx4-1BB bispecific antibodies to enhance CD4+ and CD8+ T-cell proliferation and activation was compared to the combination of monovalent EpCAM- and 4-1BB-specific bsIgG1-EpCAM-A37-FERL/b12-FEAR and bsIgG1-b12-FERL/CD137-HC7LC2-FEAR (FIG. 12 and FIG. 13). These experiments were essentially performed as described in Example 8, with the following exceptions. PBMCs were labelled with 0.5 µM CellTrace™ Violet (CTV, 1:10,000, ThermoFisher Scientific; cat. no. C34557) in PBS at 37° C. for 20 min protected from light. Final concentration of serial dilution of bispecific EpCAMx4-1BB was 0.0005-3 µg/mL. Final concentration of the combination of bsIgG1-EpCAM-A37-FERL/b12-FEAR and bsIgG1-b12-FERL/CD137-HC7LC2-FEAR was 3 µg/mL of each antibody. After incubation with the antibodies for 96 h and washing, PBMCs were stained with 50 µL BD Horizon™ Fixable Viability Stain 575V (FVS575; 1:1000 dilution in PBS; BD Biosciences; cat. no. 565694) at 4° C. for 30 min protected from light. Next, cells were stained with BV785-labeled anti-CD19 (clone SJ25C1, 1:80; BioLegend, cat. no. 363028), APC-eF780-labeled anti-CD4 (clone OKT4, 1:100; eBioscience, cat. no. 47-0048-42), AF700-labeled anti-CD8

(clone RPA-T8, 1:100; BioLegend, cat. no. 301028), APC-labeled anti-4-1BB (clone: 4B4-1, 1: 40, Biolegend, cat. no. 309810), PE-labeled anti-CD25 (clone: M-A251, 1:200, Biolegend, cat. no. 356104) and PE-Cy7-labeled anti-CD14 (clone: M5E2, 1:50; BD Biosciences, cat. no. 557742) antibodies in 50 µL FACS buffer at 4° C. for 30 min protected from light. After washing, the cells were resuspended in 80 µL FACS buffer and were acquired on a BD LSRFortessa FACS (BD Biosciences, USA) and analyzed using FlowJo software. For evaluation of CD4+ or CD8+ T cells, PBMCs were gated for lymphocytes and single cells (based on FSC/SSC), viable cells (FVS575– population), T cells (CD14–CD19– population) and finally CD4+ or CD8+ T cells (CD4+CD8– or CD4–CD8+ populations, respectively). CTV-stained cells were measured to assess CD4+ or CD8+ T-cell proliferation. As the expansion index could not be calculated for these experiments, the percentage of divided cells were reported instead and were determined as the percentage of cells that had undergone cell division (based on CTV-dilution) out of the total CD4+ or CD8+ T-cell population. % CD25+ or % 4-1BB+ cells or geomean fluorescent intensity (FI) of the CD25+ or 4-1BB+ population were determined within the CD4+ and CD8+ T-cell populations.

Results

The ability of EpCAMx4-1BB bispecific antibodies to enhance CD4+ and CD8+ T-cell proliferation and activation was assessed in in vitro co-cultures of EpCAM-expressing DiFi tumor cells and PBMCs.

Proliferation and activation of T cells treated with EpCAMx4-1BB bispecific antibodies was compared to EpCAM-specific and 4-1BB-specific antibodies (monovalent or bivalent, either alone or in combination).

FIG. 11 shows that bsIgG1-EpCAM-A37-FERL/CD137-009-HC7LC2-FEAR enhanced proliferation of CTV-labeled CD4+ and CD8+ T cells compared to bivalent monoclonal antibodies IgG1-EpCAM-A37-FERL and IgG1-CD137-009-HC7LC2-FEAR (either alone or in combination), as shown by an increase in the expansion index. Across all PBMC donors tested, bsIgG1-EpCAM-A37-FERL/CD137-009-HC7LC2-FEAR consistently showed the highest increase in CD4+ and CD8+ T-cell proliferation (data not shown).

FIG. 12 shows that bsIgG1-EpCAM-A37-FERL/CD137-009-HC7LC2-FEAR dose-dependently enhanced proliferation of CTV-labeled CD4+ and CD8+ T cells, as shown by an increase in the percentage of divided cells. By contrast, the combination of monovalent EpCAM- and 4-1BB-specific antibodies bsIgG1-EpCAM-A37-FERL/b12-FEAR and bsIgG1-b12-FERL/CD137-HC7LC2-FEAR did not enhance CD4+ or CD8+ T-cell proliferation, as the percentage of divided cells was comparable to anti-CD3-stimulated PBMCs that were co-cultured with DiFi tumor cells without addition of antibody.

FIG. 13 shows that bsIgG1-EpCAM-A37-FERL/CD137-009-HC7LC2-FEAR dose-dependently enhanced activation of CD4+ and CD8+ T cells, as shown by the increase in expression of the T-cell activation markers CD25 and 4-1BB. Both the percentage of CD4+ and CD8+ T cells expressing CD25 and 4-1BB, as well as the geometric mean FI of the CD25+ or 4-1BB+ population were increased by bsIgG1-EpCAM-A37-FERL/CD137-009-HC7LC2-FEAR. By contrast, the combination of the monovalent EpCAM- and 4-1BB-specific antibodies bsIgG1-EpCAM-A37-FERL/b12-FEAR and bsIgG1-b12-FERL/CD137-HC7LC2-FEAR did not enhance activation of CD4+ and CD8+ T cells, as the percentage of cells expressing CD25 and 4-1BB as well as the geomean FI of the CD25+ or 4-1BB+ population were comparable to anti-CD3-stimulated PBMCs that were co-cultured with DiFi tumor cells without addition of antibody.

In conclusion, the EpCAMx4-1BB bispecific antibody showed enhanced CD4+ and CD8+ T-cell proliferation and activation in PBMC-tumor cell co-cultures compared to the combination of bivalent or monovalent EpCAM- and 4-1BB-specific antibodies.

Example 12—Effect of EpCAMx4-1BB Bispecific Antibodies on T-Cell Proliferation and Activation in PBMC-Tumor Cell Co-Cultures Using Cancer Patient-Derived PBMCs The ability of an EpCAMx4-1BB bispecific antibody to enhance CD4+ and CD8+ T-cell proliferation and activation (defined by expression of T-cell activation markers CD25 and 4-1BB) in PBMC-tumor cell co-cultures was evaluated using PBMCs derived from cancer patients.

Methods

The ability of EpCAMx4-1BB bispecific antibodies to enhance CD4+ and CD8+ T-cell proliferation and activation was assessed in in vitro co-cultures of EpCAM-expressing DiFi tumor cells and cancer patient-derived PBMCs (Discovery Life Sciences). These experiments were essentially performed as described in Example 8, with the following exceptions.

PBMCs were derived from a colorectal cancer patient receiving chemotherapy and other treatments and exhibited stable disease at the time of blood collection. PBMCs were labelled with 0.5 µM CellTrace™ Violet (CTV; 1:10,000, ThermoFisher Scientific; cat. no. C34557) in PBS at 37° C. for 20 min protected from light. Final concentrations of bsIgG1-EpCAM-A37-FERL/CD137-009-HC7LC2-FEAR were 0.0004-3 µg/mL and of the combination of bsIgG1-EpCAM-A37-FERL/b12-FEAR and bsIgG1-b12-FERL/CD137-009-HC7LC2-FEAR, it was 3 µg/mL of each antibody. After incubation with the antibodies for 96 h (37° C., 5% $CO_2$) and washing with PBS, cells were stained with 50 µL BD Horizon™ Fixable Viability Stain 510 (FVS510; 1:1000 dilution in PBS; BD Biosciences; cat. no. 564406) at 4° C. for 30 min protected from light. Next, cells were stained with BV785-labeled anti-CD19 (clone SJ25C1, 1:80; BioLegend, cat. no. 363028), APC-eF780-labeled anti-CD4 (clone OKT4, 1:100; eBioscience, cat. no. 47-0048-42), AF700-labeled anti-CD8 (clone RPA-T8, 1:100; BioLegend, cat. no. 301028), APC-labeled anti-4-1BB (clone: 4B4-1, 1: 40, Biolegend, cat. no. 309810), PE-labeled anti-CD25 (clone: M-A251, 1:200, Biolegend, cat. no. 356104) and PE-Cy7-labeled anti-CD14 (clone: M5E2, 1:50; BD Biosciences, cat. no. 557742) antibodies in 50 µL FACS buffer at 4° C. for 30 min protected from light. After washing, the cells were resuspended in 80 µL FACS buffer and were acquired on a BD LSRFortessa FACS (BD Biosciences, USA) and analyzed using FlowJo software. For evaluation of CD4+ or CD8+ T cells, PBMCs were gated for lymphocytes and single cells (based on FSC/SSC), viable cells (FVS510– population), T cells (CD14–CD19– population) and finally CD4+ or CD8+ T cells (CD4+CD8– or CD4–CD8+ populations, respectively). CTV-stained cells were measured to assess CD4+ or CD8+ T-cell proliferation. The percentage divided cells were determined as the percentage of cells that had undergone cell division (based on CTV-dilution) out of the total CD4+ or CD8+ T-cell population. % CD25+ or % 4-1BB+ cells or geomean fluorescence intensity (FI) of the CD25+ or 4-1BB+ population were determined within the CD4+ and CD8+ T-cell populations.

Results

The ability of EpCAMx4-1BB bispecific antibodies to enhance CD4+ and CD8+ T-cell proliferation and activation was assessed in in vitro co-cultures of EpCAM-expressing DiFi tumor cells and colorectal cancer patient-derived PBMCs and compared to the combination of monovalent EpCAM-specific and 4-1BB-specific antibodies.

FIG. 14 shows that bsIgG1-EpCAM-A37-FERL/CD137-009-HC7LC2-FEAR dose-dependently enhanced proliferation of CTV-labeled CD4+ and CD8+ T cells, as shown by an increase in the percentage of divided cells. By contrast, the combination of monovalent EpCAM- and 4-1BB-specific antibodies bsIgG1-EpCAM-A37-FERL/b12-FEAR and bsIgG1-b12-FERL/CD137-009-HC7LC2-FEAR did not enhance CD4+ or CD8+ T-cell proliferation at 3 µg/mL.

FIG. 15 shows that bsIgG1-EpCAM-A37-FERL/CD137-009-HC7LC2-FEAR dose-dependently enhanced activation of CD4+ and CD8+ T cells, as shown by the increase in T-cell activation markers CD25 and 4-1BB. Both the percentage of CD4+ and CD8+ T cells expressing CD25 or 4-1BB, as well as the geometric mean FI in the CD25+ or 4-1BB+ population were increased by bsIgG1-EpCAM-A37-FERL/CD137-009-HC7LC2-FEAR. By contrast, the combination of monovalent EpCAM- and 4-1BB-specific antibodies bsIgG1-EpCAM-A37-FERL/b12-FEAR and bsIgG1-b12-FERL/CD137-009-HC7LC2-FEAR did not enhance activation of CD4+ and CD8+ T cells, as the percentage of cells expressing CD25 or 4-1BB as well as the geomean FI of both markers were comparable to anti-CD3-stimulated PBMCs that were co-cultured with DiFi tumor cells without addition of antibody.

In conclusion, the EpCAMx4-1BB bispecific antibody showed enhanced CD4+ and CD8+ T-cell proliferation and activation in co-cultures of cancer patient-derived PBMCs and DiFi tumor cells compared to the combination of monovalent EpCAM- and 4-1BB-specific antibodies.

Example 13—In Vitro Killing Assay to Determine the Capacity of EpCAMx4-1BB Bispecific Antibodies to Enhance T-Cell Mediated Cytotoxicity Towards Tumor Cells The effect of DuoBody EpCAMx4-1BB on the cytotoxic activity of human $CD8^+$ T cells was investigated in co-culture with tumor cells as target cells. Expression of the cytotoxicity-associated molecules Granzyme B (GzmB) and CD107a by the $CD8^+$ T cells was assessed by flow cytometry. Target cell killing was evaluated by real-time cell analysis using the xCELLigence system. The human breast cancer cell line MDA-MB-231 (ATCC®, HTB-26™) was stably transduced with the model antigen claudin-6 and with human EpCAM (MDA-MB-231_hCLDN6_hEpCAM cells) and served as a target cell line.

Methods

MDA-MB-231_hCLDN6_hEpCAM cells were seeded at $1.5 \times 10^4$ cells per well in 96-well flat-bottom plates (Greiner, Cat no. #655180) and xCELLigence E-plates (Agilent, Cat no. #05232368001) in 100 µL Dulbecco's Modified Eagle Medium (DMEM, Thermo Fisher Scientific, Cat no. #31966-047) supplemented with 10% fetal bovine serum (FBS; Sigma-Aldrich, Cat no. #F7524). Cells were allowed to settle for 30 min at RT. The 96-well flat bottom plates (for flow cytometry analysis) and E-plates (for real-time cell analysis) were incubated for 1 d in the incubator or the xCELLigence real-time cell analysis instrument (Acea Biosciences), respectively (37° C., 5% $CO_2$ in both cases).

$CD8^+$ T cells were purified from PBMCs derived from HLA-A*02:01 positive healthy human donors by magnetic-activated cell sorting (MACS) using CD8 microbeads (Miltenyi Biotec, Cat no. #130-045-201). The purified $CD8^+$ T cells were electroporated with RNA encoding the alpha and beta chains of a CLDN6-specific TCR (TCR #12α, TCR #12β; 10 µg RNA each) at 500 V, 3 ms and 1 pulse Immediately after electroporation, prewarmed IMDM GlutaMAX (Life Technologies GmbH, Cat no. #31980030) supplemented with 5% pooled human serum (PHS; One Lambda Inc., Cat no. #A25761) was added to the cells. Electroporated T cells were transferred to a 6-well plate and incubated overnight (37° C., 5% $CO_2$). Electroporation efficiency was >85% as determined by flow cytometry on the next day.

After overnight incubation, the $CD8^+$ T cells were resuspended in DMEM with 10% FBS. The $CD8^+$ T cells were added to the wells (both 96-well plate and E-plate) containing the MDA-MB-231_hCLDN6_hEpCAM cells seeded on the previous day. $7.5 \times 10^4$ $CD8^+$ T cells were added per well, resulting in an effector:target ratio of 5:1. As a control, MDA-MB-231_hCLDN6_hEpCAM cells were cultured without the addition of T cells. bsIgG1-EpCAM-A37-FERL/CD137-009-HC7LC2-FEAR or control antibodies were diluted in DMEM with 10% FBS and added to the wells. As controls, Fc-inert monovalent bispecific antibodies containing one EpCAM-specific Fab arm or one 4-1BB-specific Fab arm paired with one non-binding Fab arm (bsIgG1-EpCAM-A37-FERL/b12-FEAR and bsIgG1-b12-FERLxCD137-009-HC7LC2-FEAR, respectively) and the Fc-inert non-binding antibody bsIgG1-b12-FERL/b12-FEAR were used. bsIgG1-EpCAM-A37-FERL/CD137-009-HC7LC2-FEAR was tested over a final concentration range of 0.0032 to 3.2 µg/mL, whereas the control antibodies were tested at a single final concentration of 3.2 µg/mL. The final volume was 200 µL/well.

A fluorochrome-labeled anti-CD107a antibody (Biolegend, Cat no. #328611; final dilution 1:2,500) was added to the wells of the 96-well plate but not to the E-plate. Cells in the 96-well plate were cultured in an incubator (37° C., 5% $CO_2$) for 2 d. During the last 4 h of the culture, 20 µL of Golgi-Plug (BD Biosciences, Cat no. #555029, final dilution 1:1,100) was added. At the end of the culture, the cells were stained with fluorochrome-labeled anti-CD8a antibody (BD Biosciences, Cat no. #564116, dilution 1:400 in Dulbecco's phosphate-buffered saline [DPBS, Thermo Fisher, Cat no. #14190250] with 2% EDTA [Sigma-Aldrich, Cat no. #03690] and 5% FBS [Sigma-Aldrich, Cat no. #F7524]), fixed in 2% Histofix (Carl Roth GmbH, Cat no. #P087.4, diluted in PBS), and stained intracellularly with fluorochrome-labeled anti-GzmB antibody (BD Biosciences, Cat no. #561142; dilution 1:300 in permeabilization buffer [Thermo Fisher, Cat no. #00-8333-56]). Flow cytometry data were acquired on a BD FACS Celesta flow cytometer (BD Biosciences) and analyzed with FlowJo (Tree Star Inc.).

Cells in the E-plate were cultured in an xCELLigence real-time cell analysis instrument for 5 to 6 d without disturbance, with impedance measurements at 2 to 3-hour intervals. The impedance measurements were expressed as cell index values. Cell indices correlate with the total area of adherent tumor-cell monolayers. Therefore, lower cell indices in T-cell/tumor-cell co-cultures as compared to tumor cells only indicate tumor cell killing Cell indices for each condition were normalized to the time point at which T-cell/tumor-cell co-cultures were initiated. Normalized cell index curves over time were visualized using GraphPad Prism.

For pooled evaluation of real-time cell analysis data across donors and over the entire assay period, area under the curve (AUC) was calculated using GraphPad Prism. Normalized cell index data from the beginning to the end of the co-culture were used for the AUC analyses. The AUC for each treatment group was normalized to the AUC of the co-cultures treated with bsIgG1-b12-FERL/b12-FEAR.

Results

FIG. 16A shows that CD8$^+$ T cells upregulated CD107a and GzmB expression when co-cultured with tumor cells expressing their cognate antigen. FIG. 16 shows that bsIgG1-EpCAM-A37-FERL/CD137-009-HC7LC2-FEAR dose-dependently enhanced CD107a and GzmB expression, whereas the monovalent control antibodies bsIgG1-Ep-CAM-A37-FERL/b12-FEAR and bsIgG1-b12-FERL/CD137-009-HC7LC2-FEAR did not increase expression levels over the non-binding control antibody bsIgG1-b12-FERL/b12-FEAR. Table 7 shows that EC$_{50}$ values for the bsIgG1-EpCAM-A37-FERL/CD137-009-HC7LC2-FEAR-mediated increase in CD107a and GzmB expression were in the subnanomolar range: 0.18±0.10 nM for CD107a and 0.12±0.02 nM for GzmB (average±SD of n=5 to 6 donors). At bsIgG1-EpCAM-A37-FERL/CD137-009-HC7LC2-FEAR concentrations of 0.2 and 0.8 µg/mL, the increase in CD107a and GzmB expression levels was statistically significant compared to both monovalent control antibodies.

FIG. 17 shows that Antigen-stimulated CD8$^+$ T cells exhibited cytotoxic activity against MDA-MB-231_hCLDN6_hEpCAM cells, as indicated by lower cell index values of CD8$^+$ T-cell/tumor-cell co-cultures treated with the non-binding control antibody bsIgG1-b12-FERL/b12-FEAR as compared to tumor cells cultured alone. bsIgG1-EpCAM-A37-FERL/CD137-009-HC7LC2-FEAR dose-dependently enhanced CD8$^+$ T-cell mediated cytotoxic activity compared to bsIgG-b12-FERL/b12-FEAR, with the maximum effect observed at concentrations ≥0.2 µg/mL. In contrast, the monovalent control antibodies bsIgG1-Ep-CAM-A37-FERL/b12-FEAR and bsIgG1-b12-FERL/CD137-009-HC7LC2-FEAR had no considerable effect on cytotoxic activity. At bsIgG1-EpCAM-A37-FERL/CD137-009-HC7LC2-FEAR concentrations of 0.2 and 0.8 µg/mL, the increase in cytotoxic activity was statistically significant compared to both monovalent control antibodies.

TABLE 7

EC$_{50}$ values for CD107a and GzmB expression by CD8$^+$ T cells

| Donor no. | EC$_{50}$ CD107a GMFI (µg/mL) | EC$_{50}$ GzmB GMFI (µg/mL) |
|---|---|---|
| 1 | 0.0503 | 0.0179 |
| 2 | 0.0300 | 0.0176 |
| 3 | 0.0217 | 0.0204 |
| 4 | 0.0120 | 0.0121 |
| 5 | N/A$^a$ | 0.0201 |
| 6 | 0.0210 | 0.0224 |

TABLE 7-continued

EC$_{50}$ values for CD107a and GzmB expression by CD8$^+$ T cells

| Donor no. | EC$_{50}$ CD107a GMFI (µg/mL) | EC$_{50}$ GzmB GMFI (µg/mL) |
|---|---|---|
| Average ± SD (µg/mL) | 0.0270 ± 0.0145 | 0.0184 ± 0.0036 |
| Average ± SD (nM) | 0.1834 ± 0.0986 | 0.1226 ± 0.0237 |

$^a$EC$_{50}$ values were not determined, because no sigmoidal dose-response curve was obtained.
EC$_{50}$ = half-maximal effective concentration;
GMFI = geometric mean fluorescence intensity;
GzmB = granzyme B;
N/A = not applicable;
SD = standard deviation.

Example 14—Binding of EpCAMx4-1BB Bispecific Antibodies with Different Fc-Inertness Mutations (FER/FEA, FEA/FEA, FER/FER) to FcγRs and FcRn The effect of different combinations of Fc-inertness mutations (FER/FEA, FEA/FEA, FER/FER) in EpCAMx4-1BB bispecific antibodies on FcγR and FcRn binding was analyzed by surface plasmon resonance (SPR).

Methods

Binding of EpCAMx4-1BB bispecific antibodies with various Fc-inertness mutations (FER/FEA, FEA/FEA, FER/FER) to immobilized human recombinant FcγR variants (FcγRIa, FcγRIIa, FcγRIIb, and FcγRIIIa) was analyzed by SPR using a Biacore 8K SPR system. Biacore Series S Sensor Chips CM5 (Cytiva, cat. no. 29104988) were covalently coated with anti-histidine (His) antibody using amine coupling and His-capture kits (Cytiva, cat. no. BR100050 and cat. no. 29234602) according to the manufacturer's instructions.

Aliquots of His-tagged FcγR proteins (Table 8) were diluted in HBS-EP+ (Cytiva, cat. no. BR100669) and used for capturing onto the surface of the anti-His-coated sensor chips with a flow rate of 10 µL/min and a contact time of 60 s. This resulted in captured levels of approximately 215-365 resonance units (RU).

After three start-up cycles of HBS-EP+ buffer, antibodies (IgG1-EpCAM-A37-FERL, IgG1-CD137-009-HC7LC2-FEAR, bsIgG1-EpCAM-A37-FERL/CD137-009-HC7LC2-FEAR, bsIgG1-CD137-009-HC7LC2-FEAL/EpCAM-A37-FEAR, bsIgG1-EpCAM-A37-FERL/CD137-009-HC7LC2-FERR, IgG1-b12) were injected to generate binding curves, using antibody ranges as indicated in Table 9. Each sample that was analyzed on a surface with captured FcγR (active surface) was also analyzed on a parallel flow cell without captured FcγR (reference surface), which was used for background correction.

At the end of each cycle, the surface was regenerated using 10 mM Glycine-HCl pH 1.5 (Cytiva, cat. no. BR100354). Sensorgrams were generated using Biacore Insight Evaluation software (Cytiva) and a four-parameter logistic fit was applied on endpoint measurements (binding plateau versus post-capture baseline) to calculate relative binding of the EpCAMx4-1BB bispecific antibodies against the IgG1-b12 antibody that has a wild-type Fc region.

TABLE 8

Recombinant human FcγR proteins used for SPR

| Name | Description | SinoBiological Cat. no. | Coating concentration |
|---|---|---|---|
| FcγRIa | CD64 Protein, Human, Recombinant (His Tag), Biotinylated | 10256-H08S-B | 70 nM |
| FcγRIIa-H131 | CD32A Protein, Human, Recombinant (167 His, His Tag) | 10374-H08H1 | 160 nM |
| FcγRIIa-R131 | CD32A Protein, Human, Recombinant (167 Arg, His & AVI Tag), | 10364-H27H | 70 nM |
| FcγRIIb | CD32B/Fcgr2b Protein, Human, Recombinant (His & AVI Tag) | 10259-H27H | 70 nM |
| FcγRIIIa-V158 | CD 16a Protein, Human, Recombinant (176 Val, His & AVI Tag) | 10389-H27H1 | 110 nM |
| FcγRIIIa-F158 | CD16a Protein, Human, Recombinant (ECD, 176 Phe, His & AVI Tag) | 10389-H27H | 150 nM |

TABLE 9

Test conditions for individual FcγRs in SPR

| | Antibody concentration range tested | | |
|---|---|---|---|
| FcγR | Start concentration (nM) | Lowest concentration (nM) | Fold dilution |
| FcγRIa | 3,000 | 0.02 | 1:3 |
| FcγRIIa-H131 | 10,000 | 0.42 | 1:2.5 |
| FcγRIIa-R131 | 10,000 | 0.42 | 1:2.5 |
| FcγRIIb | 10,000 | 4.88 | 1:2 |
| FcγRIIIa-V158 | 10,000 | 0.06 | 1:3 |
| FcγRIIIa-F158 | 10,000 | 0.42 | 1:2.5 |

In a separate experiment, binding to neonatal Fc receptor (FcRn) was tested by SPR, using a kinetics assay with the following changes to the methods described above. His-tagged FcRn (SinoBiological, cat. no. CT009-H08H-B) was diluted to 5 nM (for pH 6.0) or 7.3 nM (for pH 7.4) in PBS-P+ buffer (Cytiva, cat. no. 28995084). The antibody concentration curve for IgG1-b12 was 0-100 nM, while for bsIgG1-EpCAM-A37-FERL/CD137-009-HC7LC2-FEAR, IgG1-EpCAM-A37-FERL and IgG1-CD137-009-HC7LC2-FEAR it was 0-500 nM. Experiments were performed three times at pH 6.0 (under acidic conditions, at which IgG binds to FcRn) and two times at pH 7.4 (binding to IgG is not expected at this pH).

Results

FIG. 18 shows that no binding of bsIgG1-EpCAM-A37-FERL/CD137-009-HC7LC2-FEAR, bsIgG1-CD137-009-HC7LC2-FEAL/EpCAM-A37-FEAR, bsIgG1-EpCAM-A37-FERL/CD137-009-HC7LC2-FERR to FcγRIa, FcγRIIa (either the H131 or R131 variant), FcγRIIb and FcγRIIIa (either the F158 or V158 variant) was detected. In addition, monoclonal antibodies IgG1-EpCAM-A37-FERL and IgG1-CD137-009-HC7LC2-FEAR also did not show any binding to these FcγRs. In contrast, the positive control antibody IgG1-b12 showed dose-dependent binding to all tested FcγRs.

Table 10 shows that binding of bsIgG1-EpCAM-A37-FERL/CD137-009-HC7LC2-FEAR, IgG1-EpCAM-A37-FERL and IgG1-CD137-009-HC7LC2-FEAR to FcRn was retained with mean binding affinities ($K_D$) of 312 nM, 230 nM and 375 nM, respectively. The affinity of IgG1-b12, with a wild-type IgG1 backbone, was determined at 29 nM ($K_D$). At pH 7.4, no binding to FcRn was observed for any of the tested antibodies.

In conclusion, none of the EpCAMx4-1BB bispecific antibodies, containing different inertness mutations (FER/FEA, FEA/FEA or FER/FER), showed binding to FcγRs by SPR, while binding to FcRn was retained.

TABLE 10

Binding of antibodies with different Fc-inertness mutations (FER/FEA, FEA or FER) to FcRn

| Antibody | Association constant ($k_a$) ($M^{-1}s^{-1}$) | Dissociation constant ($k_d$) ($s^{-1}$) | Mean binding affinity ($K_D$) |
|---|---|---|---|
| bsIgG1-EpCAM-A37-FERL/ CD137-009-HC7LC2-FEAR | 1.59E+05 | 4.89E−02 | 312 nM |
| IgG1-EpCAM-A37-FERL | 1.80E+05 | 4.13E−02 | 230 nM |
| IgG1-CD137-009-HC7LC2-FEAR | 1.43E+05 | 5.39E−02 | 375 nM |
| IgG1-b12 | 1.10E+06 | 3.22E−02 | 29 nM |

Example 15—Non-Clinical Toxicology Study of bsIgG1-EpCAM-A37-FERL/CD137-009-HC7LC2-FEAR in Cynomolgus Monkeys A toxicology assessment for bsIgG1-EpCAM-A37-FERL/CD137-009-HC7LC2-FEAR was performed in cynomolgus monkeys. Toxicity was assessed by examining clinical signs, body weight, ECGs, toxicokinetics, immunophenotyping, clinical chemistry parameters (including lipase and amylase), gross necropsy, and histopathology. Preliminary results indicate that doses of up to 50 mg/kg were well tolerated when bsIgG1-EpCAM-A37-FERL/CD137-009-HC7LC2-FEAR was given intravenously up to 5 times in weekly intervals. Only a non-adverse transient increase in plasma IL-6, MCP-1, and MIP-1b levels 4 hours after the third and subsequent infusions which had resolved by 24 hours post-dose was observed. In conclusion, there were no adverse effects up to 50 mg/kg for any of the parameters tested and it therefore appears that bsIgG1-EpCAM-A37-FERL/CD137-009-HC7LC2-FEAR elicits an acceptable non-clinical safety profile, supporting its further testing in First-in-Human clinical trials.

SEQUENCE LISTING

```
Sequence total quantity: 98
SEQ ID NO: 1              moltype = AA  length = 115
FEATURE                   Location/Qualifiers
REGION                    1..115
                          note = VH
source                    1..115
                          mol_type = protein
                          organism = synthetic construct
SEQUENCE: 1
QVQLVQSGAE VKKPGSSVRV SCKASGGTFS SYAISWVRQA PGQGLEWMGG IIPIFGTANY   60
AQKFQGRVTI TADESTSTAY MELSSLRSED TAVYYCARDP FLHYWGQGTL VTVSS       115

SEQ ID NO: 2              moltype = AA  length = 8
FEATURE                   Location/Qualifiers
REGION                    1..8
                          note = VH_CDR1
source                    1..8
                          mol_type = protein
                          organism = synthetic construct
SEQUENCE: 2
GGTFSSYA                                                              8

SEQ ID NO: 3              moltype = AA  length = 8
FEATURE                   Location/Qualifiers
REGION                    1..8
                          note = VH_CDR2
source                    1..8
                          mol_type = protein
                          organism = synthetic construct
SEQUENCE: 3
IIPIFGTA                                                              8

SEQ ID NO: 4              moltype = AA  length = 8
FEATURE                   Location/Qualifiers
REGION                    1..8
                          note = VH_CDR3
source                    1..8
                          mol_type = protein
                          organism = synthetic construct
SEQUENCE: 4
ARDPFLHY                                                              8

SEQ ID NO: 5              moltype = AA  length = 108
FEATURE                   Location/Qualifiers
REGION                    1..108
                          note = VL
source                    1..108
                          mol_type = protein
                          organism = synthetic construct
SEQUENCE: 5
EIELTQSPGT LSLSPGERAT LSCRASQTIS NNYLAWYQQK RGQAPRLLIY AASSRATGIP   60
DRFSGTGSGT DFTLTISRLE PEDFAVYYCA QGELYPRQFG GGTKLEIK               108

SEQ ID NO: 6              moltype = AA  length = 7
FEATURE                   Location/Qualifiers
REGION                    1..7
                          note = VL_CDR1
source                    1..7
                          mol_type = protein
                          organism = synthetic construct
SEQUENCE: 6
QTISNNY                                                               7

SEQ ID NO: 7              moltype =     length =
SEQUENCE: 7
000

SEQ ID NO: 8              moltype = AA  length = 9
FEATURE                   Location/Qualifiers
REGION                    1..9
                          note = VL_CDR3
source                    1..9
                          mol_type = protein
                          organism = synthetic construct
SEQUENCE: 8
AQGELYPRQ                                                             9

SEQ ID NO: 9              moltype = AA  length = 444
```

```
FEATURE                 Location/Qualifiers
REGION                  1..444
                        note = Full heavy chain
source                  1..444
                        mol_type = protein
                        organism = synthetic construct
SEQUENCE: 9
QVQLVQSGAE VKKPGSSVRV SCKASGGTFS SYAISWVRQA PGQGLEWMGG IIPIFGTANY    60
AQKFQGRVTI TADESTSTAY MELSSLRSED TAVYYCARDP FLHYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP EFERGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFLLYSKLTV DKSRWQQGNV   420
FSCSVMHEAL HNHYTQKSLS LSPG                                         444

SEQ ID NO: 10           moltype = AA  length = 215
FEATURE                 Location/Qualifiers
REGION                  1..215
                        note = Full light chain
source                  1..215
                        mol_type = protein
                        organism = synthetic construct
SEQUENCE: 10
EIELTQSPGT LSLSPGERAT LSCRASQTIS NNYLAWYQQK RGQAPRLLIY AASSRATGIP    60
DRFSGTGSGT DFTLTISRLE PEDFAVYYCA QGELYPRQFG GGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 11           moltype = AA  length = 117
FEATURE                 Location/Qualifiers
REGION                  1..117
                        note = VH
source                  1..117
                        mol_type = protein
                        organism = synthetic construct
SEQUENCE: 11
EVQLVESGGG LVQPGRSLRL SCTASGFSLN DYWMSWVRQA PGKGLEWVGY IDVGGSLYYA    60
ASVKGRFTIS RDDSKSIAYL QMNSLKTEDT AVYYCARGGL TYGFDLWGQG TLVTVSS      117

SEQ ID NO: 12           moltype = AA  length = 8
FEATURE                 Location/Qualifiers
REGION                  1..8
                        note = VH_CDR1
source                  1..8
                        mol_type = protein
                        organism = synthetic construct
SEQUENCE: 12
GFSLNDYW                                                              8

SEQ ID NO: 13           moltype = AA  length = 7
FEATURE                 Location/Qualifiers
REGION                  1..7
                        note = VH_CDR2
source                  1..7
                        mol_type = protein
                        organism = synthetic construct
SEQUENCE: 13
IDVGGSL                                                               7

SEQ ID NO: 14           moltype = AA  length = 11
FEATURE                 Location/Qualifiers
REGION                  1..11
                        note = VH_CDR3
source                  1..11
                        mol_type = protein
                        organism = synthetic construct
SEQUENCE: 14
ARGGLTYGFD L                                                         11

SEQ ID NO: 15           moltype = AA  length = 110
FEATURE                 Location/Qualifiers
REGION                  1..110
                        note = VL
source                  1..110
                        mol_type = protein
                        organism = synthetic construct
SEQUENCE: 15
DIVMTQSPSS LSASVGDRVT ITCQASEDIS SYLAWYQQKP GKAPKRLIYG ASDLASGVPS    60
```

```
RFSASGSGTD YTFTISSLQP EDIATYYCHY YATISGLGVA FGGGTKVEIK          110

SEQ ID NO: 16           moltype = AA   length = 6
FEATURE                 Location/Qualifiers
REGION                  1..6
                        note = VL_CDR1
source                  1..6
                        mol_type = protein
                        organism = synthetic construct
SEQUENCE: 16
EDISSY                                                          6

SEQ ID NO: 17           moltype =      length =
SEQUENCE: 17
000

SEQ ID NO: 18           moltype = AA   length = 12
FEATURE                 Location/Qualifiers
REGION                  1..12
                        note = VL_CDR3
source                  1..12
                        mol_type = protein
                        organism = synthetic construct
SEQUENCE: 18
HYYATISGLG VA                                                   12

SEQ ID NO: 19           moltype = AA   length = 446
FEATURE                 Location/Qualifiers
REGION                  1..446
                        note = Full heavy chain
source                  1..446
                        mol_type = protein
                        organism = synthetic construct
SEQUENCE: 19
EVQLVESGGG LVQPGRSLRL SCTASGFSLN DYWMSWVRQA PGKGLEWVGY IDVGGSLYYA   60
ASVKGRFTIS RDDSKSIAYL QMNSLKTEDT AVYYCARGGL TYGFDLWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APEFEGGPSV   240
FLFPPKPKDT LMISRTPEVT CVVVAVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSRL TVDKSRWQQG   420
NVFSCSVMHE ALHNHYTQKS LSLSPG                                       446

SEQ ID NO: 20           moltype = AA   length = 217
FEATURE                 Location/Qualifiers
REGION                  1..217
                        note = Full light chain
source                  1..217
                        mol_type = protein
                        organism = synthetic construct
SEQUENCE: 20
DIVMTQSPSS LSASVGDRVT ITCQASEDIS SYLAWYQQKP GKAPKRLIYG ASDLASGVPS   60
RFSASGSGTD YTFTISSLQP EDIATYYCHY YATISGLGVA FGGGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                           217

SEQ ID NO: 21           moltype = AA   length = 445
FEATURE                 Location/Qualifiers
REGION                  1..445
                        note = Full heavy chain
source                  1..445
                        mol_type = protein
                        organism = synthetic construct
SEQUENCE: 21
QIQLVQSGPE LKKPGETVKI SCKASGYTFT NYGMNWVRQA SGEGLKWMGW INTYTGEPTY   60
GEDFKGRFAF SLETSASTAY LQINNLKNED TATYFCARFG NYVDYWGQGT TLTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEFEGGPSVF   240
LFPPKPKDTL MISRTPEVTC VVVAVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFLLYSKLT VDKSRWQQGN   420
VFSCSVMHEA LHNHYTQKSL SLSPG                                        445

SEQ ID NO: 22           moltype = AA   length = 219
FEATURE                 Location/Qualifiers
REGION                  1..219
                        note = Full light chain
source                  1..219
                        mol_type = protein
```

```
                        organism = synthetic construct
SEQUENCE: 22
DIVMTQAAFS NPVTLGTSAS ISCRSSKNLL HSNGITYLYW YLQKPGQSPH LLIYQMSNLA    60
SGVPDRFSSS GSGTDFTLRI SRVEAEDVGV YYCAQNLEIP RTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 23           moltype = AA  length = 445
FEATURE                 Location/Qualifiers
REGION                  1..445
                        note = Full heavy chain
source                  1..445
                        mol_type = protein
                        organism = synthetic construct
SEQUENCE: 23
QIQLVQSGPE LKKPGETVKI SCKASGYTFT NYGMNWVRQA SGEGLKWMGW INTYTGEPTY    60
GEDFKGRFAF SLETSASTAY LQINNLKNED TATYFCARFG NYVDYWGQGT TLTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEFEGGPSVF   240
LFPPKPKDTL MISRTPEVTC VVVAVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSRLT VDKSRWQQGN   420
VFSCSVMHEA LHNHYTQKSL SLSPG                                        445

SEQ ID NO: 24           moltype = AA  length = 445
FEATURE                 Location/Qualifiers
REGION                  1..445
                        note = Full heavy chain
source                  1..445
                        mol_type = protein
                        organism = synthetic construct
SEQUENCE: 24
QIQLVQSGPE LKKPGETVKI SCKASGYTFT NYGMNWVRQA SGEGLKWMGW INTYTGEPTY    60
GEDFKGRFAF SLETSASTAY LQINNLKNED TATYFCARFG NYVDYWGQGT TLTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 25           moltype = AA  length = 444
FEATURE                 Location/Qualifiers
REGION                  1..444
                        note = Full heavy chain
source                  1..444
                        mol_type = protein
                        organism = synthetic construct
SEQUENCE: 25
QVQLVQSGAE VKKPGSSVRV SCKASGGTFS SYAISWVRQA PGQGLEWMGG IIPIFGTANY    60
AQKFQGRVTI TADESTSTAY MELSSLRSED TAVYYCARDP FLHYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP EFEGGPSVFL   240
FPPKPKDTLM ISRTPEVTCV VVAVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSRLTV DKSRWQQGNV   420
FSCSVMHEAL HNHYTQKSLS LSPG                                         444

SEQ ID NO: 26           moltype = AA  length = 218
FEATURE                 Location/Qualifiers
REGION                  1..218
                        note = Full light chain
source                  1..218
                        mol_type = protein
                        organism = synthetic construct
SEQUENCE: 26
EIELTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTF TFGPGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 27           moltype = AA  length = 444
FEATURE                 Location/Qualifiers
REGION                  1..444
                        note = Full heavy chain
source                  1..444
                        mol_type = protein
                        organism = synthetic construct
SEQUENCE: 27
```

```
QVQLVQSGAE VKKPGASVKV SCKASGGTFS SYAISWVRQA PGQGLEWMGG IVPIFGTANY      60
AQKFQGRVTI TADESTSTAY MELSSLRSED TAVYYCARDP FLHYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDK THTCPPCPAP EFEGGPSVFL    240
FPPKPKDTLM ISRTPEVTCV VVAVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSRLTV DKSRWQQGNV    420
FSCSVMHEAL HNHYTQKSLS LSPG                                          444

SEQ ID NO: 28            moltype = AA  length = 215
FEATURE                  Location/Qualifiers
REGION                   1..215
                         note = Full light chain
source                   1..215
                         mol_type = protein
                         organism = synthetic construct
SEQUENCE: 28
EIELTQSPGT LSLSPGERAT LSCRASQSVS SSYLAWYQQK PGQAPRLLIY GASSRATGIP     60
DRFSGSGSGT DFTLTISRLE PEDFAVYYCA QGELYPRQFG GGTKLDIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 29            moltype = AA  length = 444
FEATURE                  Location/Qualifiers
REGION                   1..444
                         note = Full heavy chain
source                   1..444
                         mol_type = protein
                         organism = synthetic construct
SEQUENCE: 29
QVQLVQSGAE VKKPGSSVRV SCKASGGTFS SYAISWVRQA PGQGLEWMGG IIPIFGTANY     60
AQKFQGRVTI TADESTSTAY MELSSLRSED TAVYYCARDP FLHYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDK THTCPPCPAP EFEGGPSVFL    240
FPPKPKDTLM ISRTPEVTCV VVAVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSRLTV DKSRWQQGNV    420
FSCSVMHEAL HNHYTQKSLS LSPG                                          444

SEQ ID NO: 30            moltype = AA  length = 446
FEATURE                  Location/Qualifiers
REGION                   1..446
                         note = Full heavy chain
source                   1..446
                         mol_type = protein
                         organism = synthetic construct
SEQUENCE: 30
EVQLVESGGG LVQPGRSLRL SCTASGFSLN DYWMSWVRQA PGKGLEWVGY IDVGGSLYYA     60
ASVKGRFTIS RDDSKSIAYL QMNSLKTEDT AVYYCARGGL TYGFDLWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKRVEPKSC DKTHTCPPCP APEFEGGPSV    240
FLFPPKPKDT LMISRTPEVT CVVVAVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPG                                        446

SEQ ID NO: 31            moltype = AA  length = 443
FEATURE                  Location/Qualifiers
REGION                   1..443
                         note = Full heavy chain
source                   1..443
                         mol_type = protein
                         organism = synthetic construct
SEQUENCE: 31
QSLEESGGRL VTPGTPLTLT CTVSGFSLND YWMSWVRQAP GKGLEWIGYI DVGGSLYYAS     60
WAKGRFTISR TSTTVDLKMT SLTTEDTATY FCARGGLTYG FDLWGPGTLV TVSSASTKGP    120
SVFPLAPSSL STSGGTAALG CLVKDYFPEP VTVSWNSGAL TSGVHTFPAV LQSSGLYSLS    180
SVVTVPSSSL GTQTYICNVN HKPSNTKVDK RVEPKSCDKT HTCPPCPAPE FEGGPSVFLF    240
PPKPKDTLMI SRTPEVTCVV VAVSHEDPEV KFNWYVDGVE VHNAKTKPRE EQYNSTYRVV    300
SVLTVLHQDW LNGKEYKCKV SNKALPAPIE KTISKAKGQP REPQVYTLPP SREEMTKNQV    360
SLTCLVKGFY PSDIAVEWES NGQPENNYKT TPPVLDSDGS FFLYSRLTVD KSRWQQGNVF    420
SCSVMHEALH NHYTQKSLSL SPG                                           443

SEQ ID NO: 32            moltype = AA  length = 217
FEATURE                  Location/Qualifiers
REGION                   1..217
                         note = Full light chain
source                   1..217
                         mol_type = protein
```

```
                      organism = synthetic construct
SEQUENCE: 32
DIVMTQTPAS VSEPVGGTVT INCQASEDIS SYLAWYQQKP GQRPKRLIYG ASDLASGVPS    60
RFSASGSGTE YALTISDLES ADAATYYCHY YATISGLGVA FGGGTEVVVK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 33         moltype = AA  length = 448
FEATURE               Location/Qualifiers
REGION                1..448
                      note = Full heavy chain
source                1..448
                      mol_type = protein
                      organism = synthetic construct
SEQUENCE: 33
QSVEESGGRL VTPGTPLTLT CTASGFTISD FHVTWVRQAP GKGLEWIGTI ITSASTTAYA    60
TWARGRFTIS KSSTTVNLKI VSPTTEDTAT YFCARSTYTD TSGYYFDFWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVAVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS RLTVDKSRWQ   420
QGNVFSCSVM HEALHNHYTQ KSLSLSPG                                     448

SEQ ID NO: 34         moltype = AA  length = 220
FEATURE               Location/Qualifiers
REGION                1..220
                      note = Full light chain
source                1..220
                      mol_type = protein
                      organism = synthetic construct
SEQUENCE: 34
AQVLTQTASP VSAAVGGTVI INCQSSQSIY NGNRLSWYQQ KPGQPPKLLI YSASTLASGV    60
SSRFKGSGSG TQFTLAISDV QSDDAATYYC LGSYDCDSAD CFAFGGGTEV VVERTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                        220

SEQ ID NO: 35         moltype = AA  length = 456
FEATURE               Location/Qualifiers
REGION                1..456
                      note = Full heavy chain
source                1..456
                      mol_type = protein
                      organism = synthetic construct
SEQUENCE: 35
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APEFEGGPSV FLFPPKPKDT LMISRTPEVT CVVVAVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFFLYSRL   420
TVDKSRWQQG NVFSCSVMHE ALHNHYTQKS LSLSPG                            456

SEQ ID NO: 36         moltype = AA  length = 456
FEATURE               Location/Qualifiers
REGION                1..456
                      note = Full heavy chain
source                1..456
                      mol_type = protein
                      organism = synthetic construct
SEQUENCE: 36
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APEFEGGPSV FLFPPKPKDT LMISRTPEVT CVVVAVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFLLYSKL   420
TVDKSRWQQG NVFSCSVMHE ALHNHYTQKS LSLSPG                            456

SEQ ID NO: 37         moltype = AA  length = 215
FEATURE               Location/Qualifiers
REGION                1..215
                      note = Full light chain
source                1..215
                      mol_type = protein
                      organism = synthetic construct
SEQUENCE: 37
```

```
EIVLTQSPGT LSLSPGERAT FSCRSSHSIR SRRVAWYQHK PGQAPRLVIH GVSNRASGIS    60
DRFSGSGSGT DFTLTITRVE PEDFALYYCQ VYGASSYTFG QGTKLERKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 38              moltype = AA   length = 456
FEATURE                    Location/Qualifiers
REGION                     1..456
                           note = Full heavy chain
source                     1..456
                           mol_type = protein
                           organism = synthetic construct
SEQUENCE: 38
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APEFERGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFLLYSKL   420
TVDKSRWQQG NVFSCSVMHE ALHNHYTQKS LSLSPG                            456

SEQ ID NO: 39              moltype = AA   length = 445
FEATURE                    Location/Qualifiers
REGION                     1..445
                           note = Full heavy chain
source                     1..445
                           mol_type = protein
                           organism = synthetic construct
SEQUENCE: 39
QIQLVQSGPE LKKPGETVKI SCKASGYTFT NYGMNWVRQA SGEGLKWMGW INTYTGEPTY    60
GEDFKGRFAF SLETSASTAY LQINNLKNED TATYFCARFG NYVDYWGQGT TLTVSSAKTT   120
APSVYPLAPV CGDTTGSSVT LGCLVKGYFP EPVTLTWNSG SLSSGVHTFP AVLQSDLYTL   180
SSSVTVTSST WPSQSITCNV AHPASSTKVD KKIEPRGPTI KPCPPCKCPA PNAAGGPSVF   240
IFPPKIKDVL MISLSPMVTC VVVDVSEDDP DVQISWFVNN VEVLTAQTQT HREDYNSTLR   300
VVSALPIQHQ DWMSGKEFKC KVNNKALPAP IERTISKPKG SVRAPQVYVL PPPEEEMTKK   360
QVTLTCMVKD FMPEDIYVEW TNNGKTELNY KNTEPVLDSD GSYFMYSRLR VEKKNWVERN   420
SYSCSVVHEG LHNHHTTKSF SRTPG                                        445

SEQ ID NO: 40              moltype = AA   length = 219
FEATURE                    Location/Qualifiers
REGION                     1..219
                           note = Full light chain
source                     1..219
                           mol_type = protein
                           organism = synthetic construct
SEQUENCE: 40
DIVMTQAAFS NPVTLGTSAS ISCRSSKNLL HSNGITYLYW YLQKPGQSPH LLIYQMSNLA    60
SGVPDRFSSS GSGTDFTLRI SRVEAEDVGV YYCAQNLEIP RTFGGGTKLE IKRADAAPTV   120
SIFPPSSEQL TSGGASVVCF LNNFYPKDIN VKWKIDGSER QNGVLNSWTD QDSKDSTYSM   180
SSTLTLTKDE YERHNSYTCE ATHKTSTSPI VKSFNRNEC                         219

SEQ ID NO: 41              moltype = AA   length = 445
FEATURE                    Location/Qualifiers
REGION                     1..445
                           note = Full heavy chain
source                     1..445
                           mol_type = protein
                           organism = synthetic construct
SEQUENCE: 41
QIQLVQSGPE LKKPGETVKI SCKASGYTFT NYGMNWVRQA SGEGLKWMGW INTYTGEPTY    60
GEDFKGRFAF SLETSASTAY LQINNLKNED TATYFCARFG NYVDYWGQGT TLTVSSAKTT   120
APSVYPLAPV CGDTTGSSVT LGCLVKGYFP EPVTLTWNSG SLSSGVHTFP AVLQSDLYTL   180
SSSVTVTSST WPSQSITCNV AHPASSTKVD KKIEPRGPTI KPCPPCKCPA PNAAGGPSVF   240
IFPPKIKDVL MISLSPMVTC VVVDVSEDDP DVQISWFVNN VEVLTAQTQT HREDYNSTLR   300
VVSALPIQHQ DWMSGKEFKC KVNNKALPAP IERTISKPKG SVRAPQVYVL PPPEEEMTKK   360
QVTLTCMVTD FMPEDIYVEW TNNGKTELNY KNTEPVLDSD GSYLMYSKLT VEKKNWVERN   420
SYSCSVVHEG LHNHHTTKSF SRTPG                                        445

SEQ ID NO: 42              moltype = AA   length = 453
FEATURE                    Location/Qualifiers
REGION                     1..453
                           note = Full heavy chain
source                     1..453
                           mol_type = protein
                           organism = synthetic construct
SEQUENCE: 42
EMQLVESGGG LVQPGRSMKL SCAGSGFTLS DYGVAWVRQA PKKGLEWVAY ISYAGGTTYY    60
RESVKGRFTI SRDNAKSTLY LQMDSLRSED TATYYCTIDG YGGYSGSHWY FDFWGPGTMV   120
```

```
TVSSAKTTAP SVYPLAPVCG DTTGSSVTLG CLVKGYFPEP VTLTWNSGSL SSGVHTFPAV    180
LQSDLYTLSS SVTVTSSTWP SQSITCNVAH PASSSTKVDKK IEPRGPTIKP CPPCKCPAPN   240
AAGGPSVFIF PPKIKDVLMI SLSPMVTCVV VDVSEDDPDV QISWFVNNVE VLTAQTQTHR   300
EDYNSTLRVV SALPIQHQDW MSGKEFKCKV NNKALPAPIE RTISKPKGSV RAPQVYVLPP   360
PEEEMTKKQV TLTCMVKDFM PEDIYVEWTN NGKTELNYKN TEPVLDSDGS YFMYSRLRVE   420
KKNWVERNSY SCSVVHEGLH NHHTTKSFSR TPG                                453

SEQ ID NO: 43            moltype = AA  length = 213
FEATURE                  Location/Qualifiers
REGION                   1..213
                         note = Full light chain
source                   1..213
                         mol_type = protein
                         organism = synthetic construct
SEQUENCE: 43
DIQMTQSPSL LSASVGDRVT LNCRTSQNVY KNLAWYQQKL GEAPKLLIYN ANSLQAGIPS    60
RFSGSGSGTD FTLTISSLQP EDVATYFCQQ YYSGNTFGAG TNLELKRADA APTVSIFPPS   120
SEQLTSGGAS VVCFLNNFYP KDINVKWKID GSERQNGVLN SWTDQDSKDS TYSMSSTLTL   180
TKDEYERHNS YTCEATHKTS TSPIVKSFNR NEC                                213

SEQ ID NO: 44            moltype = AA  length = 456
FEATURE                  Location/Qualifiers
REGION                   1..456
                         note = Full heavy chain
source                   1..456
                         mol_type = protein
                         organism = synthetic construct
SEQUENCE: 44
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSSAKT TAPSVYPLAP VCGDTTGSSV TLGCLVKGYF PEPVTLTWNS GSLSSGVHTF   180
PAVLQSDLYT LSSSVTVTSS TWPSQSITCN VAHPASSTKV DKKIEPRGPT IKPCPPCKCP   240
APNAAGGPSV FIFPPKIKDV LMISLSPMVT CVVVDVSEDD PDVQISWFVN NVEVLTAQTQ   300
THREDYNSTL RVVSALPIQH QDWMSGKEFK CKVNNKALPA PIERTISKPK GSVRAPQVYV   360
LPPPEEEMTK KQVTLTCMVT DFMPEDIYVE WTNNGKTELN YKNTEPVLDS DGSYLMYSKL   420
TVEKKNWVER NSYSCSVVHE GLHNHHTTKS FSRTPG                             456

SEQ ID NO: 45            moltype = AA  length = 215
FEATURE                  Location/Qualifiers
REGION                   1..215
                         note = Full light chain
source                   1..215
                         mol_type = protein
                         organism = synthetic construct
SEQUENCE: 45
EIVLTQSPGT LSLSPGERAT FSCRSSHSIR SRRVAWYQHK PGQAPRLVIH GVSNRASGIS    60
DRFSGSGSGT DFTLTITRVE PEDFALYYCQ VYGASSYNEA QGTKLERKRA DAAPTVSIFP   120
PSSEQLTSGG ASVVCFLNNF YPKDINVKWK IDGSERQNGV LNSWTDQDSK DSTYSMSSTL   180
TLTKDEYERH NSYTCEATHK TSTSPIVKSF NRNEC                              215

SEQ ID NO: 46            moltype = AA  length = 456
FEATURE                  Location/Qualifiers
REGION                   1..456
                         note = Full heavy chain
source                   1..456
                         mol_type = protein
                         organism = synthetic construct
SEQUENCE: 46
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSSAKT TAPSVYPLAP VCGDTTGSSV TLGCLVKGYF PEPVTLTWNS GSLSSGVHTF   180
PAVLQSDLYT LSSSVTVTSS TWPSQSITCN VAHPASSTKV DKKIEPRGPT IKPCPPCKCP   240
APNAAGGPSV FIFPPKIKDV LMISLSPMVT CVVVDVSEDD PDVQISWFVN NVEVLTAQTQ   300
THREDYNSTL RVVSALPIQH QDWMSGKEFK CKVNNKALPA PIERTISKPK GSVRAPQVYV   360
LPPPEEEMTK KQVTLTCMVK DFMPEDIYVE WTNNGKTELN YKNTEPVLDS DGSYFMYSRL   420
RVEKKNWVER NSYSCSVVHE GLHNHHTTKS FSRTPG                             456

SEQ ID NO: 47            moltype = AA  length = 329
FEATURE                  Location/Qualifiers
REGION                   1..329
                         note = IgG1 constant region
source                   1..329
                         mol_type = protein
                         organism = synthetic construct
SEQUENCE: 47
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
```

```
MTKNQVSLTC  LVKGFYPSDI  AVEWESNGQP  ENNYKTTPPV  LDSDGSFFLY  SKLTVDKSRW   300
QQGNVFSCSV  MHEALHNHYT  QKSLSLSPG                                       329

SEQ ID NO: 48           moltype = AA   length = 329
FEATURE                 Location/Qualifiers
REGION                  1..329
                        note = IgG1-FEA constant region
source                  1..329
                        mol_type = protein
                        organism = synthetic construct
SEQUENCE: 48
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKRVEP  KSCDKTHTCP  PCPAPEFEGG   120
PSVFLFPPKP  KDTLMISRTP  EVTCVVVAVS  HEDPEVKFNW  YVDGVEVHNA  KTKPREEQYN   180
STYRVVSVLT  VLHQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFFLY  SKLTVDKSRW   300
QQGNVFSCSV  MHEALHNHYT  QKSLSLSPG                                       329

SEQ ID NO: 49           moltype = AA   length = 329
FEATURE                 Location/Qualifiers
REGION                  1..329
                        note = IgG1-FER constant region
source                  1..329
                        mol_type = protein
                        organism = synthetic construct
SEQUENCE: 49
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKRVEP  KSCDKTHTCP  PCPAPEFERG   120
PSVFLFPPKP  KDTLMISRTP  EVTCVVVDVS  HEDPEVKFNW  YVDGVEVHNA  KTKPREEQYN   180
STYRVVSVLT  VLHQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFFLY  SKLTVDKSRW   300
QQGNVFSCSV  MHEALHNHYT  QKSLSLSPG                                       329

SEQ ID NO: 50           moltype = AA   length = 329
FEATURE                 Location/Qualifiers
REGION                  1..329
                        note = IgG1-F405L constant region
source                  1..329
                        mol_type = protein
                        organism = synthetic construct
SEQUENCE: 50
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKRVEP  KSCDKTHTCP  PCPAPELLGG   120
PSVFLFPPKP  KDTLMISRTP  EVTCVVVDVS  HEDPEVKFNW  YVDGVEVHNA  KTKPREEQYN   180
STYRVVSVLT  VLHQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFLLY  SKLTVDKSRW   300
QQGNVFSCSV  MHEALHNHYT  QKSLSLSPG                                       329

SEQ ID NO: 51           moltype = AA   length = 329
FEATURE                 Location/Qualifiers
REGION                  1..329
                        note = IgG1-K409R constant region
source                  1..329
                        mol_type = protein
                        organism = synthetic construct
SEQUENCE: 51
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKRVEP  KSCDKTHTCP  PCPAPELLGG   120
PSVFLFPPKP  KDTLMISRTP  EVTCVVVDVS  HEDPEVKFNW  YVDGVEVHNA  KTKPREEQYN   180
STYRVVSVLT  VLHQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFFLY  SRLTVDKSRW   300
QQGNVFSCSV  MHEALHNHYT  QKSLSLSPG                                       329

SEQ ID NO: 52           moltype = AA   length = 329
FEATURE                 Location/Qualifiers
REGION                  1..329
                        note = IgG1-FEAR constant region
source                  1..329
                        mol_type = protein
                        organism = synthetic construct
SEQUENCE: 52
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKRVEP  KSCDKTHTCP  PCPAPEFEGG   120
PSVFLFPPKP  KDTLMISRTP  EVTCVVVAVS  HEDPEVKFNW  YVDGVEVHNA  KTKPREEQYN   180
STYRVVSVLT  VLHQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFFLY  SRLTVDKSRW   300
QQGNVFSCSV  MHEALHNHYT  QKSLSLSPG                                       329

SEQ ID NO: 53           moltype = AA   length = 329
```

| FEATURE | Location/Qualifiers |
|---|---|
| REGION | 1..329 |
| | note = IgG1-FEAL constant region |
| source | 1..329 |
| | mol_type = protein |
| | organism = synthetic construct |

SEQUENCE: 53
```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFLLY SKLTVDKSRW  300
QQGNVFSCSV MHEALHNHYT QKSLSLSPG                                   329
```

| SEQ ID NO: 54 | moltype = AA   length = 329 |
|---|---|
| FEATURE | Location/Qualifiers |
| REGION | 1..329 |
| | note = IgG1-FERL constant region |
| source | 1..329 |
| | mol_type = protein |
| | organism = synthetic construct |

SEQUENCE: 54
```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPEFERG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFLLY SKLTVDKSRW  300
QQGNVFSCSV MHEALHNHYT QKSLSLSPG                                   329
```

| SEQ ID NO: 55 | moltype = AA   length = 107 |
|---|---|
| FEATURE | Location/Qualifiers |
| REGION | 1..107 |
| | note = kappa light chain constant region |
| source | 1..107 |
| | mol_type = protein |
| | organism = synthetic construct |

SEQUENCE: 55
```
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107
```

| SEQ ID NO: 56 | moltype = AA   length = 106 |
|---|---|
| FEATURE | Location/Qualifiers |
| REGION | 1..106 |
| | note = lambda light chain constant region |
| source | 1..106 |
| | mol_type = protein |
| | organism = synthetic construct |

SEQUENCE: 56
```
GQPKAAPSVT LFPPSSEELQ ANKATLVCLI SDFYPGAVTV AWKADSSPVK AGVETTTPSK   60
QSNNKYAASS YLSLTPEQWK SHRSYSCQVT HEGSTVEKTV APTECS                 106
```

| SEQ ID NO: 57 | moltype = AA   length = 329 |
|---|---|
| FEATURE | Location/Qualifiers |
| REGION | 1..329 |
| | note = IgG2amm-AAKR |
| source | 1..329 |
| | mol_type = protein |
| | organism = synthetic construct |

SEQUENCE: 57
```
AKTTAPSVYP LAPVCGDTTG SSVTLGCLVK GYFPEPVTLT WNSGSLSSGV HTFPAVLQSD   60
LYTLSSSVTV TSSTWPSQSI TCNVAHPASS TKVDKKIEPR GPTIKPCPPC KCPAPNAAGG  120
PSVFIFPPKI KDVLMISLSP MVTCVVVDVS EDDPDVQISW FVNNVEVLTA QTQTHREDYN  180
STLRVVSALP IQHQDWMSGK EFKCKVNNKA LPAPIERTIS KPKGSVRAPQ VYVLPPPEEE  240
MTKKQVTLTC MVKDFMPEDI YVEWTNNGKT ELNYKNTEPV LDSDGSYFMY SRLRVEKKNW  300
VERNSYSCSV VHEGLHNHHT TKSFSRTPG                                   329
```

| SEQ ID NO: 58 | moltype = AA   length = 329 |
|---|---|
| FEATURE | Location/Qualifiers |
| REGION | 1..329 |
| | note = IgG2amm-AALT |
| source | 1..329 |
| | mol_type = protein |
| | organism = synthetic construct |

SEQUENCE: 58
```
AKTTAPSVYP LAPVCGDTTG SSVTLGCLVK GYFPEPVTLT WNSGSLSSGV HTFPAVLQSD   60
LYTLSSSVTV TSSTWPSQSI TCNVAHPASS TKVDKKIEPR GPTIKPCPPC KCPAPNAAGG  120
PSVFIFPPKI KDVLMISLSP MVTCVVVDVS EDDPDVQISW FVNNVEVLTA QTQTHREDYN  180
STLRVVSALP IQHQDWMSGK EFKCKVNNKA LPAPIERTIS KPKGSVRAPQ VYVLPPPEEE  240
MTKKQVTLTC MVTDFMPEDI YVEWTNNGKT ELNYKNTEPV LDSDGSYLMY SKLTVEKKNW  300
```

```
VERNSYSCSV VHEGLHNHHT TKSFSRTPG                                       329

SEQ ID NO: 59          moltype = AA  length = 314
FEATURE                Location/Qualifiers
source                 1..314
                       mol_type = protein
                       organism = Homo sapiens
SEQUENCE: 59
MAPPQVLAFG LLLAAATATF AAAQEECVCE NYKLAVNCFV NNNRQCQCTS VGAQNTVICS       60
KLAAKCLVMK AEMNGSKLGR RAKPEGALQN NDGLYDPDCD ESGLFKAKQC NGTSMCWCVN      120
TAGVRRTDKD TEITCSERVR TYWIIIELKH KAREKPYDSK SLRTALQKEI TTRYQLDPKF      180
ITSILYENNV ITIDLVQNSS QKTQNDVDIA DVAYYFEKDV KGESLFHSKK MDLTVNGEQL      240
DLDPGQTLIY YVDEKAPEFS MQGLKAGVIA VIVVVVIAVV AGIVVLVISR KKRMAKYEKA      300
EIKEMGEMHR ELNA                                                       314

SEQ ID NO: 60          moltype = AA  length = 314
FEATURE                Location/Qualifiers
REGION                 1..314
                       note = Cynomolgus monkey EpCAM
source                 1..314
                       mol_type = protein
                       organism = synthetic construct
SEQUENCE: 60
MAPPQVLAFG LLLAAATASF AAAQKECVCE NYKLAVNCFL NDNGQCQCTS IGAQNTVLCS       60
KLAAKCLVMK AEMNGSKLGR RAKPEGALQN NDGLYDPDCD ESGLFKAKQC NGTSTCWCVN      120
TAGVRRTDKD TEITCSERVR TYWIIIELKH KAREKPYDVQ SLRTALEEAI KTRYQLDPKF      180
ITNILYEDNV ITIDLVQNSS QKTQNDVDIA DVAYYFEKDV KGESLFHSKK MDLRVNGEQL      240
DLDPGQTLIY YVDEKAPEFS MQGLKAGVIA VIVVVVIAIV AGIVVLVISR KKRMAKYEKA      300
EIKEMGEIHR ELNA                                                       314

SEQ ID NO: 61          moltype = AA  length = 315
FEATURE                Location/Qualifiers
source                 1..315
                       mol_type = protein
                       organism = Mus musculus
SEQUENCE: 61
MAGPQALAFG LLLAVVTATL AAAQRDCVCD NYKLATSCSL NEYGECQCTS YGTQNTVICS       60
KLASKCLAMK AEMTHSKSGR RIKPEGAIQN NDGLFKAKQC EQGLFKAKQC NGTATCWCVN      120
TAGVRRTDKD TEITCSERVR TYWIIIELKH KERESPYDHQ SLQTALQEAF TSRYKLNQKF      180
IKNIMYENNV ITIDLMQNSS QKTQDDVDIA DVAYYFEKDV KGESLFHSSK SMDLRVNGEP      240
LDLDPGQTLI YYVDEKAPEF SMQGLTAGII AVIVVVSLAV IAGIVVLVIS TRKKSAKYEK      300
AEIKEMGEIH RELNA                                                      315

SEQ ID NO: 62          moltype = AA  length = 255
FEATURE                Location/Qualifiers
source                 1..255
                       mol_type = protein
                       organism = Homo sapiens
SEQUENCE: 62
MGNSCYNIVA TLLLVLNFER TRSLQDPCSN CPAGTFCDNN RNQICSPCPP NSFSSAGGQR       60
TCDICRQCKG VFRTRKECSS TSNAECDCTP GFHCLGAGCS MCEQDCKQGQ ELTKKGCKDC      120
CFGTFNDQKR GICRPWTNCS LDGKSVLVNG TKERDVVCGP SPADLSPGAS SVTPPAPARE      180
PGHSPQIISF FLALTSTALL FLLFFLTLRF SVVKRGRKKL LYIFKQPFMR PVQTTQEEDG      240
CSCRFPEEEE GGCEL                                                      255

SEQ ID NO: 63          moltype = AA  length = 254
FEATURE                Location/Qualifiers
REGION                 1..254
                       note = Cynomolgus monkey 4-1BB
source                 1..254
                       mol_type = protein
                       organism = synthetic construct
SEQUENCE: 63
MGNSCYNIVA TLLLVLNFER TRSLQDLCSN CPAGTFCDNN RSQICSPCPP NSFSSAGGQR       60
TCDICRQCKG VFKTRKECSS TSNAECDCIS GYHCLGAECS MCEQDCKQGQ ELTKKGCKDC      120
CFGTFNDQKR GICRPWTNCS LDGKSVLVNG TKERDVVCGP SPADLSPGAS SATPPAPARE      180
PGHSPQIIFF LALTSTVVLF LLFFLVLRFS VVKRSRKKLL YIFKQPFMRP VQTTQEEDGC      240
SCRFPEEEEG GCEL                                                       254

SEQ ID NO: 64          moltype = AA  length = 5
FEATURE                Location/Qualifiers
REGION                 1..5
                       note = VH_CDR1
source                 1..5
                       mol_type = protein
                       organism = synthetic construct
SEQUENCE: 64
SYAIS                                                                   5
```

| | | |
|---|---|---|
| SEQ ID NO: 65<br>FEATURE<br>REGION<br><br>source | moltype = AA  length = 17<br>Location/Qualifiers<br>1..17<br>note = VH_CDR2<br>1..17<br>mol_type = protein<br>organism = synthetic construct | |
| SEQUENCE: 65<br>GIIPIFGTAN YAQKFQG | | 17 |
| SEQ ID NO: 66<br>FEATURE<br>REGION<br><br>source | moltype = AA  length = 6<br>Location/Qualifiers<br>1..6<br>note = VH_CDR3<br>1..6<br>mol_type = protein<br>organism = synthetic construct | |
| SEQUENCE: 66<br>DPFLHY | | 6 |
| SEQ ID NO: 67<br>FEATURE<br>REGION<br><br>source | moltype = AA  length = 12<br>Location/Qualifiers<br>1..12<br>note = VL_CDR1<br>1..12<br>mol_type = protein<br>organism = synthetic construct | |
| SEQUENCE: 67<br>RASQTISNNY LA | | 12 |
| SEQ ID NO: 68<br>FEATURE<br>REGION<br><br>source | moltype = AA  length = 7<br>Location/Qualifiers<br>1..7<br>note = VL_CDR2<br>1..7<br>mol_type = protein<br>organism = synthetic construct | |
| SEQUENCE: 68<br>AASSRAT | | 7 |
| SEQ ID NO: 69<br>FEATURE<br>REGION<br><br>source | moltype = AA  length = 5<br>Location/Qualifiers<br>1..5<br>note = VH_CDR1<br>1..5<br>mol_type = protein<br>organism = synthetic construct | |
| SEQUENCE: 69<br>DYWMS | | 5 |
| SEQ ID NO: 70<br>FEATURE<br>REGION<br><br>source | moltype = AA  length = 16<br>Location/Qualifiers<br>1..16<br>note = VH_CDR2<br>1..16<br>mol_type = protein<br>organism = synthetic construct | |
| SEQUENCE: 70<br>YIDVGGSLYY AASVKG | | 16 |
| SEQ ID NO: 71<br>FEATURE<br>REGION<br><br>source | moltype = AA  length = 9<br>Location/Qualifiers<br>1..9<br>note = VH_CDR3<br>1..9<br>mol_type = protein<br>organism = synthetic construct | |
| SEQUENCE: 71<br>GGLTYGFDL | | 9 |
| SEQ ID NO: 72<br>FEATURE<br>REGION<br><br>source | moltype = AA  length = 11<br>Location/Qualifiers<br>1..11<br>note = VL_CDR1<br>1..11<br>mol_type = protein<br>organism = synthetic construct | |
| SEQUENCE: 72<br>QASEDISSYL A | | 11 |

```
SEQ ID NO: 73           moltype = AA   length = 7
FEATURE                 Location/Qualifiers
REGION                  1..7
                        note = VL_CDR2
source                  1..7
                        mol_type = protein
                        organism = synthetic construct
SEQUENCE: 73
GASDLAS                                                                    7

SEQ ID NO: 74           moltype =     length =
SEQUENCE: 74
000

SEQ ID NO: 75           moltype =     length =
SEQUENCE: 75
000

SEQ ID NO: 76           moltype = AA   length = 8
FEATURE                 Location/Qualifiers
source                  1..8
                        mol_type = protein
                        organism = synthetic construct
SEQUENCE: 76
GYTFTNYG                                                                   8

SEQ ID NO: 77           moltype = AA   length = 8
FEATURE                 Location/Qualifiers
source                  1..8
                        mol_type = protein
                        organism = synthetic construct
SEQUENCE: 77
INTYTGEP                                                                   8

SEQ ID NO: 78           moltype = AA   length = 9
FEATURE                 Location/Qualifiers
source                  1..9
                        mol_type = protein
                        organism = synthetic construct
SEQUENCE: 78
ARFGNYVDY                                                                  9

SEQ ID NO: 79           moltype = AA   length = 11
FEATURE                 Location/Qualifiers
source                  1..11
                        mol_type = protein
                        organism = synthetic construct
SEQUENCE: 79
KNLLHSNGIT Y                                                              11

SEQ ID NO: 80           moltype =     length =
SEQUENCE: 80
000

SEQ ID NO: 81           moltype = AA   length = 9
FEATURE                 Location/Qualifiers
source                  1..9
                        mol_type = protein
                        organism = synthetic construct
SEQUENCE: 81
AQNLEIPRT                                                                  9

SEQ ID NO: 82           moltype = AA   length = 5
FEATURE                 Location/Qualifiers
source                  1..5
                        mol_type = protein
                        organism = synthetic construct
SEQUENCE: 82
NYGMN                                                                      5

SEQ ID NO: 83           moltype = AA   length = 17
FEATURE                 Location/Qualifiers
source                  1..17
                        mol_type = protein
                        organism = synthetic construct
SEQUENCE: 83
WINTYTGEPT YGEDFKG                                                        17
```

```
SEQ ID NO: 84         moltype = AA  length = 7
FEATURE               Location/Qualifiers
source                1..7
                      mol_type = protein
                      organism = synthetic construct
SEQUENCE: 84
FGNYVDY                                                                    7

SEQ ID NO: 85         moltype = AA  length = 16
FEATURE               Location/Qualifiers
source                1..16
                      mol_type = protein
                      organism = synthetic construct
SEQUENCE: 85
RSSKNLLHSN GITYLY                                                         16

SEQ ID NO: 86         moltype = AA  length = 7
FEATURE               Location/Qualifiers
source                1..7
                      mol_type = protein
                      organism = synthetic construct
SEQUENCE: 86
QMSNLAS                                                                    7

SEQ ID NO: 87         moltype =     length =
SEQUENCE: 87
000

SEQ ID NO: 88         moltype = AA  length = 11
FEATURE               Location/Qualifiers
source                1..11
                      mol_type = protein
                      organism = synthetic construct
SEQUENCE: 88
QSLLHSNGYN Y                                                              11

SEQ ID NO: 89         moltype =     length =
SEQUENCE: 89
000

SEQ ID NO: 90         moltype = AA  length = 8
FEATURE               Location/Qualifiers
source                1..8
                      mol_type = protein
                      organism = synthetic construct
SEQUENCE: 90
MQALQTFT                                                                   8

SEQ ID NO: 91         moltype = AA  length = 16
FEATURE               Location/Qualifiers
source                1..16
                      mol_type = protein
                      organism = synthetic construct
SEQUENCE: 91
RSSQSLLHSN GYNYLD                                                         16

SEQ ID NO: 92         moltype = AA  length = 7
FEATURE               Location/Qualifiers
source                1..7
                      mol_type = protein
                      organism = synthetic construct
SEQUENCE: 92
LGSNRAS                                                                    7

SEQ ID NO: 93         moltype = AA  length = 8
FEATURE               Location/Qualifiers
source                1..8
                      mol_type = protein
                      organism = synthetic construct
SEQUENCE: 93
IVPIFGTA                                                                   8

SEQ ID NO: 94         moltype = AA  length = 7
FEATURE               Location/Qualifiers
source                1..7
                      mol_type = protein
                      organism = synthetic construct
SEQUENCE: 94
QSVSSSY                                                                    7
```

```
SEQ ID NO: 95        moltype =    length =
SEQUENCE: 95
000

SEQ ID NO: 96        moltype = AA  length = 17
FEATURE              Location/Qualifiers
source               1..17
                     mol_type = protein
                     organism = synthetic construct
SEQUENCE: 96
GIVPIFGTAN YAQKFQG                                                    17

SEQ ID NO: 97        moltype = AA  length = 12
FEATURE              Location/Qualifiers
source               1..12
                     mol_type = protein
                     organism = synthetic construct
SEQUENCE: 97
RASQSVSSSY LA                                                         12

SEQ ID NO: 98        moltype = AA  length = 7
FEATURE              Location/Qualifiers
source               1..7
                     mol_type = protein
                     organism = synthetic construct
SEQUENCE: 98
GASSRAT                                                               7
```

The invention claimed is:

1. A binding agent comprising a first antigen-binding region binding to EpCAM and a second antigen-binding region binding to CD137, wherein a) said first antigen-binding region binding to EpCAM comprises a first heavy chain variable region (VH) comprising HCDR1, HCDR2, and HCDR3 sequences and a first light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 6, 7, and 8, respectively; and b) said second antigen-binding region binding to CD137 comprises a second heavy chain variable region (VH) comprising HCDR1, HCDR2, and HCDR3 sequences and a second light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively;

wherein the binding agent is an antibody comprising a first binding arm comprising said first antigen-binding region binding to EpCAM and a second binding arm comprising said second antigen-binding region binding to CD137, wherein the first binding arm comprises i) a polypeptide comprising the first heavy chain variable region (VH) and a first heavy chain constant region (CH), and ii) a polypeptide comprising the first light chain variable region (VL) and a first light chain constant region (CL);

and the second binding arm comprises iii) a polypeptide comprising the second heavy chain variable region (VH) and a second heavy chain constant region (CH), and iv) a polypeptide comprising the second light chain variable region (VL) and a second light chain constant region (CL);

wherein positions L234, L235, and G236 in a human IgG1 heavy chain according to EU numbering are F, E, and R, respectively, in the first CH and positions L234, L235, and D265 in a human IgG1 heavy chain according to EU numbering are F, E, and A in the second CH; and wherein the amino acid in the position corresponding to F405 in a human IgG1 heavy chain according to EU numbering is L in the first CH and the amino acid in the position corresponding to K409 in a human IgG1 heavy chain according to EU numbering is R in the second CH; and wherein the binding agent exhibits conditional CD137 agonist activity in vitro.

2. The binding agent of claim 1, wherein
the first VH comprises the amino acid sequence as set forth in SEQ ID NO: 1 and the first VL comprises the amino acid sequence as set forth in SEQ ID NO: 5; and
the second VH comprises the amino acid sequence as set forth in SEQ ID NO: 11 and the second VL comprises the amino acid sequence as set forth in SEQ ID NO: 15.

3. The binding agent of claim 1, wherein
a) the constant region of said first heavy chain comprises the amino acid sequence set forth in SEQ ID NO: 54; and
b) the constant region of said second heavy chain comprises the amino acid sequence set forth in SEQ ID NO: 52.

4. The binding agent of claim 1, wherein:
i) the polypeptide comprising the first VH and the first CH comprises the amino acid sequence set forth in SEQ ID NO: 9,
ii) the polypeptide comprising the first VL and the first CL comprises the amino acid sequence set forth in SEQ ID NO: 10,
iii) the polypeptide comprising the second VH and the second CH comprises the amino acid sequence set forth in SEQ ID NO: 19; and iv) the polypeptide comprising the second VL and the second CL comprises the amino acid sequence set forth in SEQ ID NO: 20.

5. A binding agent comprising a first binding arm comprising a first antigen-binding region and a first heavy chain constant region comprising a constant heavy chain 2 (CH2) region and a second binding arm comprising a second antigen-binding region and a second heavy chain constant region comprising a constant heavy chain 2 (CH2) region, wherein at least one of said first and second antigen-binding regions binds to EpCAM and the other of said first and second antigen-binding regions binds to CD137, wherein
   a) said antigen-binding region binding to EpCAM comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 2, 3, and 4, respectively, and the LCDR1, LCDR2, and LCDR3 sequences comprise the sequences as set forth in SEQ ID NO: 6, 7, and 8, respectively; and
   b) said antigen-binding region binding to CD137 comprises a heavy chain variable region (VH) comprising HCDR1, HCDR2, and HCDR3 sequences and a light chain variable region (VL) comprising LCDR1, LCDR2, and LCDR3 sequences, wherein the HCDR1, HCDR2, and HCDR3 sequences comprise the sequences as set forth in SEQ ID NO: 12, 13, and 14, respectively, and the LCDR1, LCDR2, and LCDR3 sequences comprises the sequences as set forth in SEQ ID NO: 16, 17 and 18, respectively, and
   wherein the positions corresponding to positions L234, L235, and G236 in a human IgG1 heavy chain according to EU numbering are F, E, and R, respectively, in at least one of said first and second heavy chain constant regions;
   wherein the binding agent exhibits conditional CD137 agonist activity in vitro.

6. The binding agent of claim 5, wherein the positions corresponding to positions L234, L235, and G236 in a human IgG1 heavy chain according to EU numbering are F, E, and R, respectively, in one of said first or second heavy chain constant regions and the positions corresponding to positions L234, L235, and D265 in a human IgG1 heavy chain according to EU numbering are F, E, and A, respectively, in the other of said first or second heavy chain constant regions.

7. The binding agent of claim 5, wherein said antigen-binding region binding to EpCAM comprises a heavy chain variable region (VH) and a light chain variable region (VL), wherein the VH comprises the sequence as set forth in SEQ ID NO: 1 and the VL comprises the sequence as set forth in SEQ ID NO: 5.

8. The binding agent of claim 5, wherein said antigen-binding region binding to CD137 comprises a heavy chain variable region (VH) and a light chain variable region (VL), wherein the VH comprises the sequence as set forth in SEQ ID NO: 11 and the VL comprises the sequence as set forth in SEQ ID NO: 15.

9. A binding agent comprising a first binding arm comprising an antigen-binding region binding to EpCAM and a first heavy chain constant region comprising a constant heavy chain 2 (CH2) region and a second binding arm comprising an antigen-binding region binding to CD137 and a second heavy chain constant region comprising a constant heavy chain 2 (CH2) region, wherein
   the first binding arm comprises
      i) a polypeptide comprising a first heavy chain variable region (VH) and the first heavy chain constant region (CH), and
      ii) a polypeptide comprising a first light chain variable region (VL) and a first light chain constant region (CL), wherein
         the first VH comprises first HCDR1, HCDR2, and HCDR3 sequences and the first VL comprises first LCDR1, LCDR2, and LCDR3 sequences, wherein the first HCDR1, HCDR2, and HCDR3 sequences comprise the sequences as set forth in SEQ ID NO: 2, 3, and 4, respectively, and the first LCDR1, LCDR2, and LCDR3 sequences comprise the sequences as set forth in SEQ ID NO: 6, 7, and 8, respectively;
   and the second binding arm comprises
      iii) a polypeptide comprising a second heavy chain variable region (VH) and the second heavy chain constant region (CH), and
      iv) a polypeptide comprising a second light chain variable region (VL) and a second light chain constant region (CL), wherein
         the second VH comprises second HCDR1, HCDR2, and HCDR3 sequences and the second VL comprises second LCDR1, LCDR2, and LCDR3 sequences, wherein the second HCDR1, HCDR2, and HCDR3 sequences comprise the sequences as set forth in SEQ ID NO: 12, 13, and 14, respectively, and the second LCDR1, LCDR2, and LCDR3 sequences comprise the sequences as set forth in SEQ ID NO: 16, 17, and 18, respectively, and
      wherein the positions corresponding to positions L234, L235, and G236 in a human IgG1 heavy chain according to EU numbering are F, E, and R, respectively, in at least one of said first and second heavy chain constant regions;
      wherein the binding agent exhibits conditional CD137 agonist activity in vitro.

10. The binding agent of claim 9, wherein
the first VH comprises the amino acid sequence as set forth in SEQ ID NO: 1 and the first VL comprises the amino acid sequence as set forth in SEQ ID NO: 5; and
the second VH comprises the amino acid sequence as set forth in SEQ ID NO: 11 and the second VL comprises the amino acid sequence as set forth in SEQ ID NO: 15.

11. The binding agent of claim 5, wherein each of the first and second heavy chain constant regions (CHs) comprises a CH3 region and wherein the two CH3 regions comprise asymmetrical mutations, wherein the positions corresponding to positions L234, L235, and D265 in a human IgG1 heavy chain according to EU numbering are F, E, and A, respectively, in said second heavy chain constant region (HC) and the positions corresponding to positions L234, L235, and G236 in a human IgG1 heavy chain according to EU numbering are F, E, and R, respectively, in said first heavy chain constant region (HC), and wherein (i) the position corresponding to F405 in a human IgG1 heavy chain according to EU numbering of the first heavy chain constant region is L, and the position corresponding to K409 in a human IgG1 heavy chain according to EU numbering of the second heavy chain constant region is R, or (ii) the position corresponding to K409 in a human IgG1 heavy chain according to EU numbering of the first heavy chain constant region is R, and the position corresponding to F405 in a human IgG1 heavy chain according to EU numbering of the second heavy chain constant region is L.

12. A pharmaceutical composition comprising the binding agent of claim 1.

13. The binding agent of claim 1, wherein the first VH comprises the sequence as set forth in SEQ ID NO: 1.

14. The binding agent of claim 1, wherein the first VL comprises the sequence as set forth in SEQ ID NO: 5.

15. The binding agent of claim 1, wherein the first VH comprises the sequence as set forth in SEQ ID NO: 1 and the first VL comprises the sequence as set forth in SEQ ID NO: 5.

16. The binding agent of claim 1, wherein the second VH comprises the sequence as set forth in SEQ ID NO: 11.

17. The binding agent of claim 1, wherein the second VL comprises the sequence as set forth in SEQ ID NO: 15.

18. The binding agent of claim 1, wherein the second VH comprises the sequence as set forth in SEQ ID NO: 11 and the second VL comprises the sequence as set forth in SEQ ID NO: 15.

19. The binding agent of claim 1, wherein the first VH comprises the sequence as set forth in SEQ ID NO: 1; the first VL comprises the sequence as set forth in SEQ ID NO: 5; the second VH comprises the sequence as set forth in SEQ ID NO: 11; and the second VL comprises the sequence as set forth in SEQ ID NO: 15.

20. A method for treating a subject comprising administering to the subject the binding agent of claim 1.

21. A method for treating a subject comprising administering to the subject the binding agent of claim 5.

22. A method for treating a subject comprising administering to the subject the binding agent of claim 9.

23. The binding agent of claim 1, wherein the binding agent has the ability to enhance CD4+ and CD8+ T-cell proliferation and activation in a peripheral blood mononuclear cell (PBMC)-tumor cell co-culture as compared to an agent comprising either the first antigen-binding region binding to EpCAM or the second antigen-binding region binding to CD137 but not both.

24. The binding agent of claim 19, wherein the binding agent has the ability to enhance CD4+ and CD8+ T-cell proliferation and activation in a peripheral blood mononuclear cell (PBMC)-tumor cell co-culture as compared to an agent comprising either the first antigen-binding region binding to EpCAM or the second antigen-binding region binding to CD137 but not both.

* * * * *